(12) United States Patent
Shendelman et al.

(10) Patent No.: US 9,994,920 B2
(45) Date of Patent: Jun. 12, 2018

(54) GENETIC LOCI ASSOCIATED WITH SOYBEAN CYST NEMATODE RESISTANCE AND METHODS OF USE

(71) Applicant: PIONEER HI BRED INTERNATIONAL, INC, Johnston, IA (US)

(72) Inventors: Joshua M Shendelman, Ankeny, IA (US); John B Woodward, Ankeny, IA (US); Meizhu Yang, Johnston, IA (US)

(73) Assignee: PIONEER HI-BRED INTERNATIONAL, INC.IA (US)

( * ) Notice: Subject to any disclaimer, the term of this patent is extended or adjusted under 35 U.S.C. 154(b) by 0 days. days.

(21) Appl. No.: 15/001,290

(22) Filed: Jan. 20, 2016

(65) Prior Publication Data
US 2016/0130671 A1 May 12, 2016

Related U.S. Application Data

(63) Continuation of application No. 13/781,963, filed on Mar. 1, 2013, now abandoned.

(60) Provisional application No. 61/740,567, filed on Dec. 21, 2012.

(51) Int. Cl.
*C12Q 1/68* (2018.01)
*C12N 15/82* (2006.01)

(52) U.S. Cl.
CPC ....... *C12Q 1/6895* (2013.01); *C12Q 2600/13* (2013.01); *C12Q 2600/156* (2013.01); *C12Q 2600/158* (2013.01); *C12Q 2600/172* (2013.01)

(58) Field of Classification Search
None
See application file for complete search history.

(56) References Cited

U.S. PATENT DOCUMENTS

| | | | |
|---|---|---|---|
| 5,491,081 | A | 2/1996 | Webb |
| 6,096,944 | A | 8/2000 | Vierling et al. |
| 6,162,967 | A | 12/2000 | Webb |
| 6,300,541 | B1 | 10/2001 | Lightfoot et al. |
| 6,538,175 | B1 | 3/2003 | Webb |
| 7,154,021 | B2 | 12/2006 | Hauge et al. |
| 7,485,770 | B2 | 2/2009 | Hauge et al. |
| 7,872,171 | B2 | 1/2011 | Webb |
| 2002/0144310 | A1 | 10/2002 | Lightfoot et al. |
| 2006/0225150 | A1* | 10/2006 | Hauge ............. C07K 14/415 800/279 |
| 2006/0253919 | A1 | 11/2006 | Hauge et al. |
| 2009/0100537 | A1 | 4/2009 | Concibido et al. |
| 2012/0260368 | A1 | 10/2012 | Mitchum et al. |

FOREIGN PATENT DOCUMENTS

| | | |
|---|---|---|
| WO | WO 199931964 | 7/1999 |
| WO | WO 2014100229 | 6/2014 |

OTHER PUBLICATIONS

U.S. Appl. No. 12/961,684, filed Apr. 7, 2011, David M. Webb.
U.S. Appl. No. 13/544,470, filed Nov. 1, 2012, David M. Webb.
U.S. Appl. No. 13/779,957, filed Feb. 28, 2013, Daines et al.
U.S. Appl. No. 13/780,390, filed Feb. 28, 2013, Shendelman et al.
U.S. Appl. No. 13/786,948, filed Mar. 6, 2013, Allen et al.
Anand, S.C., "Identification of Additional Soybean Germplasm with Resistant to Race 3 of the Soybean Cyst Nematode," *Plant Disease*, 1984, vol. 68(7), pp. 593-595.
Anand, S.C., "Sources of resistance to the soybean cyst nematode," In Lamberti F., Taylor CE (eds) Cyst nematodes. NATO advanced study institute series. Plenum Press, New York, pp. 269-276.
Anand, S.C., "Genetic Diversity for Resistance to *Heterodera glycines* Race 5 in Soybean," *J. Nematol*, 1994, vol. 26(1), pp. 76-79.
Anand, S.C., et al., "Genetic Analyses of Soybean Genotypes Resistant to Soybean Cyst Nematode Race 5," *Crop. Sci.*, 1989, vol. 29, pp. 1181-1184.
Anand, S.C., et al., "Variation in Parasitic Potential of *Heterodera glycines* Populations," *Crop. Sci.*, 1994, vol. 34, pp. 1452-1454.
Arondel, V., et al., "Map-Based Cloning of a Gene Controlling Omega-3 Fatty Acid Desaturation in *Arabidopsis*," *Science*, 1992, vol. 258, pp. 1353-1355.
Baltazar, B.M., et al., "Identification of restriction fragment length polymorphisms (RFLPs) to map soybean cyst nematode resistance genes in soybean," *Soybean Genet. Newsletter*, 1992, vol. 19, pp. 120-122.
Bent, A., et al., "SCN Resistance Determinants at the Rhg1 Locus," *Molecular & Cellular Biology of the Soybean Conference*, Aug. 12-15, 2012, Abstract.
Box, G.E.P., and Draper, N.R., "Adequacy of Estimation and the Use of Transformation," *Response Surfaces, Mixtures, and Ridge Analyses*, 2007, pp. 271-302, John Wiley & Sons, Inc.
Caldwell, B.E., et al., "Inheritance of Resistance of Soybeans to the Cyst Nematode, *Heterodera glycines*," *Agronomy Journal*, 1960, vol. 52, pp. 635-636.
Concibido, V.C., et al., "A Decade of QTL Mapping for Cyst Nematode Resistance in Soybean," Crop Science, 2004, vol. 44, pp. 1121-1131.
Cook, D.E., et al., "Copy Number Variation of Multiple Genes at Rhg1 Mediates Nematode Resistance in Soybean," Science, Nov. 30, 2012; 1206-9, 338(6111); doi: 10.1126/science.1228746. Epub Oct. 11, 2012.
Gibson, S., et al., "Isolating plant genes," *Trends Biotech*, 1993, vol. 11(7), pp. 306-313.

(Continued)

*Primary Examiner* — Amjad Abraham
*Assistant Examiner* — Bratislav Stankovic

(57) ABSTRACT

Various methods and compositions are provided for identifying and/or selecting soybean plants or soybean germplasm with resistance or improved resistance to soybean cyst nematode. In certain embodiments, the method comprises detecting at least one marker locus that is associated with resistance to soybean cyst nematode. In other embodiments, the method further comprises detecting at least one marker profile or haplotype associated with resistance to soybean cyst nematode. In further embodiments, the method comprises crossing a selected soybean plant with a second soybean plant. Further provided are markers, primers, probes and kits useful for identifying and/or selecting soybean plants or soybean germplasm with resistance or improved resistance to soybean cyst nematode.

15 Claims, 4 Drawing Sheets

(56) References Cited

OTHER PUBLICATIONS

Golden, A.M., et al., "Terminology and Identity of Infraspecific Forms of the Soybean Cyst Nematode (*Heterodera glycines*)," *Plant Disease Reporter*, 1970, vol. 54(7), pp. 544-546.
Hartwig, E.E., et al., "Breeding Productive Soybeans with Resistance to the Soybean Cyst Nematode," In: Shibles R. (ed) Proceedings World Soy Res Conf. III, Westview Press, Boulder, Colo., pp. 394-399.
Keim, P., et al., "RFLP Analysis of Soybean Breeding Populations: I. Genetic Structure Differences due to Inbreeding Methods," *Crop Science*, 1994, vol. 34, pp. 55-61.
Keim, P, et al., "A rapid protocol for isolating soybean DNA," *Soybean Genet. Newsletter*, 1988, vol. 15, pp. 150-152.
Keim, P., et al., "Construction of a random recombinant DNA library that is primarily single copy sequences," *Soybean Genet. Newsletter*, 1988, vol. 15, pp. 147-148.
Keim, P, et al., "Restriction fragment length polymorphism diversity in soybean," *Theor. Appl. Genet.*, 1989, vol. 77 , pp. 786-792.
Kim, M., et al., "Fine Mapping of the SCN Resistance Locus rhg1-b from PI 88788," *The Plant Genome*, 2010, vol. 3(2), pp. 81-89.
Knapp, S.J., et al., "Mapping quantitative trait loci using nonsimultaneous and simultaneous estimators and hypothesis tests," *Plant Genomes: Methods for Genetic and Physical Mapping*, 1992, pp. 209-237, Kluwer Academic Publishers, The Netherlands.
Lande, R., et al., "Efficiency of Marker Assisted Selection in the Improvement of Quantitative Traits," *Genetics*, 1990, vol. 124, pp. 743-756.
Lander, E.S., et al., "Strategies for studying heterogeneous genetic traits in humans by using a linkage map of restriction fragment length polymorphisms," *Proc. Natl. Acad. Sci. USA*, 1986, vol. 83, pp. 7353-7357.
Lander, E.S., et al., "Mapping Mendelian Factors Underlying Quantitative Traits Using RFLP Linkage Maps," *Genetics*, 1989, vol. 121, pp. 185-199.
Landry, B.S., and Hubert, N., "A genetic map for *Brassica napus* based on restriction fragment length polymorphisms detected with expressed DNA sequences," *Genome*, 1991, vol. 34, pp. 543-552.
Lee, T.G., et al., "Copy Number Polymorphism in the SCN Resistance Lodus rgh1-b From PI 88788," *Molecular & Cellular Biology of the Soybean Conference*, Aug. 12-15, 2012, Abstract.
Lewers, K., et al., "A physical map of a gene-dense region in soybean linkage group A2 near the black seed coat and $Rhg_4$ loci," *Theor. Appl. Genet.*, 2002, vol. 104, pp. 254-260.
Lincoln, S.E., et al., "MAPMAKER/EXP," Whitehead Institute of Biomedical Research, Cambridge, Mass., (1993).
Lincoln, S.E., et al., "MAPMAKER/QTL," Whitehead Institute of Biomedical Research, Cambridge, Mass., (1990).
Liu, S., et al., "A soybean cyst nematode resistance gene points to a new mechanism of plant resistance to pathogens," *Nature*, 2012, vol. 492, pp. 256-263.
Mansur, L.M., et al., "Generation Mean Analysis of Resistance to Race 3 of Soybean Cyst Nemagode," *Crop Sci.*, 1993, vol. 33, pp. 1249-1253.
Marek, L.F., "Construction and Size Characterization of a Bacterial Artificial Chromosome (BAC) Library from Soybean," *Soybean Genet. Newsletter*, 1996, vol. 23, pp. 126-129.
Martin, G.B., et al., "Map-Based Cloning of a Protein Kinase Gene Conferring Disease Resistance in Tomato," *Science*, 1993, vol. 262, pp. 1432-1436.
McCann, J., et al., "Selection and Reproduction of Soybean Cyst Nematodes on Resistant Soybeans," *Crop Science*, 1982, vol. 22, pp. 78-80.
Mulrooney, R.P., "Soybean Disease Loss Estimate for Southern United States in 1987," *Plant Dis.*, 1988, vol. 72, p. 915.
Murray, M., and Thompson, W.F., "Rapid isolation of high molecular weight plant DNA," *Nucleic Acids Research*, 1980, vol. 8(19), pp. 4321-4325.
Myers, G.O., and Anand, S.C., "Inheritance of resistance and genetic relationships among soybean plant introductions to races of soybean cyst nematode," *Euphytica*, 1991, vol. 55, pp. 197-201.

Nelson, R.L., et al., "Evaluation of the USDA Soybean Germplasm Collection: Maturity Groups 000 to IV (PI 427.136 to PI 445.845)," *USDA-ARS Technical Bulletin*, 1988, No. 1726.
Niblack, T.L., et al., "Soybean Yield Losses Due to *Heterodera glycines* in Iowa," *Plant dis.*, 1992, vol. 76(9), pp. 943-948.
Parrish, J.E., and Nelson, D.L., "Methods for Finding Genes a Major Rate-Limiting Step in Positional Cloning," *GATA*, 1993, vol. 10(2), pp. 29-41.
Rao-Arelli, A.P., and Anand, S.C., "Genetic Relationships Among Soybean Plant Introductions for Resistance to Race 3 of Soybean Cyst Nematode," *Crop Sci.*, 1988, vol. 28, pp. 650-652.
Rao-Arelli, A.P., et al., "Additional dominant gene in PI 88.788 conferring resistance to soybean cyst nematode race 3," *Soybean Genet. Newsletter*, 1991, vol. 18, pp. 221-224.
Rao-Arelli, A.P., et al., "Soybean Resistance to Soybean Cyst Nematode Race 3 is Conditioned by an Additional Dominant Gene," *Crop Science*, 1992, vol. 32, pp. 862-864.
Rao-Arelli, A.P., and Clark, K.M., "Inhentance of Soybean Cyst Nematode Resistance Genes in Soybean Germplasm," *Agronomy Abstraces*, ASA, Madison, Wis., p. 100, Abstract.
Rao-Arelli, A.P., et al., "A Rapid Method for Inoculating Soybean Seedlings with *Heterodera glycines*," *Plant Disease*, 1991, vol. 75, pp. 594-595.
Rao-Arelli, A.P., et al., "Genetic Diversity Among Isolates of *Heterodera glycines* and Sources of Resistance in Soybeans," *Plant Disease*, 1992, vol. 76(9), pp. 894-896.
Riggs, R.D., and Schmitt, D.P., "Complete Characterization of the Race Scheme for *Heterodera glycines*," *Journal of Nematologists*, 1988, vol. 20(3), pp. 392-395.
Rommens, J.M., et al., "Identification of the Cystic Fibrosis Gene: Chromosome Walking and Jumping," *Science*, 1989, vol. 245, pp. 1059-1065.
Shoemaker, R.C., and Specht, J.E., "Integration of the Soybean Molecular and Classical Genetic Linkage Groups," *Crop Sci.*, 1995, vol. 35, pp. 436-446.
Tachibana, H., et al., "Registration of 'BSR101' Soybean," *Crop Science*, 1987, vol. 27, p. 612, Abstract.
Triantaphyllou, A., "Genetic Structure of Races of *Heterodera glycines* and Inheritance of Ability to Reproduce on Resistant Soybeans," *Journal of Nematology*, 1975, vol. 7(4), pp. 356-364.
Webb, D.M., et al., "Genetic mapping of soybean cyst nematode race-3 resistance loci in the soybean PI 437.654," *Theor. .Appl. Genet.*, 1995, vol. 91, pp. 574-581.
Weisemann, J.M., "Molecular markers located proximal to the soybean cyst nematode resistance gene, Rhg4," *Theor. Appl. Genet.*, 1992, vol. 85, pp. 136-138.
Weiss, M.G., "Genetic Linkage in Soybeans: Linkage Group VII," *Crop Science*, 1970, vol. 10, pp. 627-629.
Wicking, C., et al., "From linked marker to gene," *Trends Genet.*, 1991, vol. 7(9), pp. 288-289.
Winstead, N.N., et al., "Soybean Cyst Nematode in North Carolina," *Plant Dis. Rep.*, 1955, vol. 39(1), pp. 9-11.
Young, L.D., "Reproduction of Differentially Selected Soybean Cyst Nematode Populations on Soybeans," *Crop Science*, 1982, vol. 22, pp. 385-388.
Young, L.D., "Changes in the Reproduction of *Heterodera glycines* on Different Lines of *Glycine max*," *Journal of Nematology*, 1984, vol. 16(3), pp. 304-309.
Zhang, H-B., et al., "Map-based cloning in crop plants: tomato as a model system II. Isolation and characterization of a set of overlapping yeast artificial chromosomes encompassing the jointless locus," *Mol. Gen. Genet.*, 1994, vol. 244, pp. 613-621.
Zhu, et al., "Characterization and application of soybean YACs to molecular cytogenetics," *Mol. Gen. Genet.*, 1996, vol. 252, pp. 483-488.
Tuteja, J. H. and Vodkin, L. O. (2008) *Crop Sci.* 48(S1) S49-S68. doi:10.2135/cropsci2007.10.0542tpg; with Supplemental Data 1 and 2. (31 pages).
International Search Report and Written Opinion dated May 8, 2014 for PCT/US2013/076218 filed Dec. 18, 2013 and published as WO

(56) References Cited

OTHER PUBLICATIONS

2014/100229 on Jun. 26, 2014 (Applicants—Pioneer Hi-Bred International, Inc. // Inventors—Shendelman et al.) (17 pages).

* cited by examiner

Figure 1A

| Marker Name | LG | Physical | Genetic Consensus4.0 Positions | Approximate Centromere |
|---|---|---|---|---|
| BARCSOYSSR_08_0014 | A2_(8) | 182,295 | 0.00 | |
| Sat_383 | A2_(8) | 182,295 | 0.00 | |
| BARC-049051-10807 | A2_(8) | 448,232 | 6.33 | |
| BARCSOYSSR_08_0064 | A2_(8) | 1,306,504 | 7.43 | |
| Satt390 | A2_(8) | 1,306,504 | 7.43 | |
| BARC-021937-04237 | A2_(8) | 1,466,024 | 9.57 | |
| BARC-039839-07593 | A2_(8) | 2,035,742 | 11.55 | |
| BARC-014435-01365 | A2_(8) | 2,246,693 | 12.86 | |
| BARC-021463-04108 | A2_(8) | 2,986,176 | 14.66 | |
| BARC-031701-07215 | A2_(8) | 3,056,358 | 15.45 | |
| BARC-044051-08595 | A2_(8) | 3,174,985 | 16.44 | |
| BARC-032579-08998 | A2_(8) | 3,307,480 | 16.96 | |
| BARC-016965-02168 | A2_(8) | 3,341,884 | 20.27 | |
| BARC-065591-19578 | A2_(8) | 3,533,588 | 21.02 | |
| BARC-028679-05986 | A2_(8) | 3,800,144 | 22.79 | |
| BARCSOYSSR_08_0206 | A2_(8) | 4,000,361 | 23.82 | |
| Satt207 | A2_(8) | 4,000,361 | 23.82 | |
| BARC-013537-01155 | A2_(8) | 4,316,426 | 25.69 | |
| BARCSOYSSR_08_0262 | A2_(8) | 5,027,347 | 30.18 | |
| Satt493 | A2_(8) | 5,027,347 | 30.18 | |
| BARCSOYSSR_08_0273 | A2_(8) | 5,176,019 | 30.52 | |
| Satt589 | A2_(8) | 5,176,019 | 30.52 | |
| BARC-025925-05158 | A2_(8) | 5,278,616 | 31.20 | |
| BARCSOYSSR_08_0305 | A2_(8) | 5,715,429 | 32.94 | |
| Sat_409 | A2_(8) | 5,715,429 | 32.94 | |
| BARC-039593-07509 | A2_(8) | 5,765,344 | 33.26 | |
| BARCSOYSSR_08_0371 | A2_(8) | 6,751,708 | 38.87 | |
| Satt315 | A2_(8) | 6,751,708 | 38.87 | |
| BARC-025811-05087 | A2_(8) | 7,464,186 | 40.48 | |
| BARC-028361-05840 | A2_(8) | 7,716,559 | 44.48 | |
| BARC-021329-04038 | A2_(8) | 7,824,774 | 45.22 | |
| BARC-062265-17733 | A2_(8) | 7,963,465 | 45.59 | |
| BARC-028309-05824 | A2_(8) | 8,082,742 | 45.61 | |
| BARC-045047-08867 | A2_(8) | 8,110,728 | 45.62 | |
| BARCSOYSSR_08_0454 | A2_(8) | 8,219,326 | 46.28 | |
| Satt632 | A2_(8) | 8,219,326 | 46.28 | |
| BARC-012525-00285 | A2_(8) | 8,279,099 | 46.44 | |
| BARCSOYSSR_08_0458 | A2_(8) | 8,279,445 | 46.56 | |

Figure 1B

| | | | |
|---|---|---|---|
| Sat_162 | A2_(8) | 8,279,445 | 46.56 |
| S07160-1-Q1 | A2_(8) | 8,300,131 | 46.68 |
| BARC-048453-10596 | A2_(8) | 8,368,060 | 47.08 |
| BARC-038291-07245 | A2_(8) | 8,380,220 | 47.08 |
| BARC-039247-07486 | A2_(8) | 8,469,553 | 47.11 |
| BARC-014511-01568 | A2_(8) | 8,887,107 | 47.38 |
| BARC-027690-06633 | A2_(8) | 8,943,498 | 47.56 |
| BARCSOYSSR_08_0506 | A2_(8) | 9,211,913 | 47.87 |
| Sat_215 | A2_(8) | 9,211,913 | 47.87 |
| BARC-059853-16139 | A2_(8) | 9,407,115 | 48.04 |
| BARC-027618-06622 | A2_(8) | 9,578,780 | 48.49 |
| BARC-026091-05255 | A2_(8) | 9,749,954 | 50.42 |
| BARC-043119-08535 | A2_(8) | 9,997,689 | 51.31 |
| BARC-039145-07456 | A2_(8) | 10,166,248 | 51.92 |
| BARC-038631-07266 | A2_(8) | 10,303,015 | 52.38 |
| BARCSOYSSR_08_0579 | A2_(8) | 10,721,802 | 53.55 |
| Satt424 | A2_(8) | 10,721,802 | 53.55 |
| BARC-030611-06911 | A2_(8) | 10,826,342 | 55.06 |
| BARC-020307-04548 | A2_(8) | 10,947,663 | 55.10 |
| BARC-045081-08872 | A2_(8) | 10,954,474 | 55.11 |
| BARC-029671-06303 | A2_(8) | 11,536,514 | 56.73 |
| BARC-027614-06619 | A2_(8) | 11,570,109 | 56.88 |
| BARC-040893-07862 | A2_(8) | 11,845,155 | 57.43 |
| BARC-044869-08827 | A2_(8) | 11,922,404 | 58.86 |
| BARC-018941-03041 | A2_(8) | 12,022,737 | 59.30 |
| BARC-014665-01618 | A2_(8) | 12,471,926 | 61.07 |
| BARC-040357-07716 | A2_(8) | 12,972,647 | 62.13 |
| BARC-029593-06225 | A2_(8) | 13,111,220 | 63.06 |
| BARC-044663-08756 | A2_(8) | 13,446,458 | 64.42 |
| BARC-041459-08002 | A2_(8) | 13,463,703 | 64.42 |
| BARC-029315-06150 | A2_(8) | 13,902,606 | 66.58 |
| BARC-055265-13154 | A2_(8) | 14,004,161 | 66.58 |
| BARC-032791-09038 | A2_(8) | 14,265,356 | 67.71 |
| BARC-038455-10089 | A2_(8) | 14,850,506 | 69.58 |
| BARCSOYSSR_08_0849 | A2_(8) | 15,140,599 | 70.95 |
| Sat_199 | A2_(8) | 15,140,599 | 70.95 |
| BARCSOYSSR_08_0879 | A2_(8) | 15,562,968 | 72.78 |
| Sat_233 | A2_(8) | 15,562,968 | 72.78 |
| BARC-031627-07124 | A2_(8) | 15,733,404 | 75.01 |
| BARC-039899-07603 | A2_(8) | 15,818,113 | 76.43 |
| BARC-029669-06297 | A2_(8) | 16,164,943 | 77.06 |

Figure 1C

| | | | | |
|---|---|---|---|---|
| BARC-049031-10792 | A2_(8) | 16,250,468 | 77.06 | |
| BARC-049045-10806 | A2_(8) | 16,250,599 | 77.06 | |
| BARCSOYSSR_08_0909 | A2_(8) | 16,427,750 | 77.51 | |
| Satt377 | A2_(8) | 16,427,750 | 77.51 | |
| BARC-042491-08277 | A2_(8) | 16,624,607 | 79.14 | |
| BARC-022387-04319 | A2_(8) | 16,839,499 | 81.25 | |
| BARCSOYSSR_08_0948 | A2_(8) | 17,076,816 | 83.61 | |
| Satt525 | A2_(8) | 17,076,816 | 83.61 | |
| BARC-031601-07118 | A2_(8) | 17,167,641 | 84.15 | |
| BARC-022445-04327 | A2_(8) | 17,410,233 | 85.38 | |
| BARC-063091-18238 | A2_(8) | 17,412,255 | 85.58 | |
| BARC-028207-05794 | A2_(8) | 17,695,309 | 87.11 | |
| BARC-013001-00417 | A2_(8) | 17,738,311 | 88.06 | |
| BARC-054097-12336 | A2_(8) | 17,940,930 | 88.16 | |
| BARC-038877-07374 | A2_(8) | 17,940,998 | 88.16 | |
| BARC-054143-12351 | A2_(8) | 17,945,325 | 88.16 | |
| BARC-059821-16111 | A2_(8) | 18,439,010 | 89.50 | |
| BARC-041231-07943 | A2_(8) | 18,856,442 | 90.76 | |
| BARC-027788-06671 | A2_(8) | 18,952,545 | 90.84 | |
| BARC-050061-09354 | A2_(8) | 20,229,386 | 92.31 | |
| BARC-020835-03959 | A2_(8) | 20,441,412 | 92.31 | |
| BARC-021629-04158 | A2_(8) | 20,530,558 | 92.53 | |
| BARC-010797-00750 | A2_(8) | 21,133,646 | 92.81 | |
| BARC-019299-03876 | A2_(8) | 21,896,189 | 94.21 | |
| BARC-011001-00815 | A2_(8) | 21,896,207 | 94.37 | |
| BARC-065451-19476 | A2_(8) | 22,590,975 | 94.72 | |
| BARCSOYSSR_08_1216 | A2_(8) | 22,995,965 | 97.59 | |
| Sat_232 | A2_(8) | 22,995,965 | 97.59 | |
| BARCSOYSSR_08_1226 | A2_(8) | 23,213,226 | 100.07 | |
| Satt158 | A2_(8) | 23,213,226 | 100.07 | |
| BARC-061573-17277 | A2_(8) | 23,456,372 | 101.45 | |
| BARC-055297-13184 | A2_(8) | 23,691,540 | 101.47 | x |
| BARC-051883-11286 | A2_(8) | 24,848,454 | 101.52 | x |
| BARC-049593-09076 | A2_(8) | 29,150,451 | 101.52 | x |
| BARC-049595-09077 | A2_(8) | 29,158,623 | 101.52 | x |
| BARC-059127-15620 | A2_(8) | 34,040,540 | 101.52 | x |
| BARC-050571-09743 | A2_(8) | 34,793,726 | 101.52 | x |
| BARC-010965-00797 | A2_(8) | 35,156,936 | 101.52 | x |
| BARC-019295-03875 | A2_(8) | 35,156,963 | 101.52 | x |
| BARC-058307-15218 | A2_(8) | 35,334,725 | 101.52 | x |
| BARC-060765-16857 | A2_(8) | 35,475,655 | 101.58 | x |

Figure 1D

| | | | | |
|---|---|---|---|---|
| BARC-061979-17603 | A2_(8) | 35,484,031 | 101.58 | x |
| BARC-049905-09236 | A2_(8) | 36,079,891 | 101.92 | x |
| BARC-049903-09231 | A2_(8) | 36,240,677 | 101.92 | x |
| BARC-061059-17022 | A2_(8) | 36,596,871 | 102.46 | x |
| BARC-059569-15920 | A2_(8) | 37,183,791 | 102.46 | x |
| BARC-053631-11924 | A2_(8) | 37,319,425 | 102.46 | x |
| BARC-053637-11925 | A2_(8) | 37,564,284 | 102.46 | x |
| BARC-049851-09173 | A2_(8) | 38,097,310 | 102.94 | |
| BARC-028775-06010 | A2_(8) | 38,238,572 | 103.30 | |
| BARC-020321-04554 | A2_(8) | 38,332,877 | 103.34 | |
| BARC-050125-09401 | A2_(8) | 38,344,641 | 103.34 | |
| BARC-030625-06913 | A2_(8) | 38,346,614 | 103.34 | |
| BARC-010341-00598 | A2_(8) | 38,999,975 | 103.57 | |
| BARC-062129-17664 | A2_(8) | 39,451,763 | 103.87 | |
| BARCSOYSSR_08_1502 | A2_(8) | 39,470,511 | 104.54 | |
| Sat_097 | A2_(8) | 39,470,511 | 104.54 | |
| BARC-017137-02222 | A2_(8) | 39,754,026 | 105.48 | |
| BARC-043095-08525 | A2_(8) | 39,960,478 | 105.79 | |
| BARC-059367-15768 | A2_(8) | 40,107,338 | 107.56 | |
| BARCSOYSSR_08_1557 | A2_(8) | 40,656,421 | 107.64 | |
| Sat_138 | A2_(8) | 40,656,421 | 107.64 | |
| BARC-031481-07100 | A2_(8) | 40,693,079 | 109.19 | |
| BARC-053807-12035 | A2_(8) | 41,392,667 | 110.33 | |
| BARC-028831-06025 | A2_(8) | 41,533,033 | 110.33 | |
| BARC-050527-09711 | A2_(8) | 42,050,754 | 111.87 | |
| BARC-061019-17012 | A2_(8) | 42,542,685 | 113.98 | |
| BARC-039797-07587 | A2_(8) | 42,635,472 | 113.98 | |
| BARCSOYSSR_08_1679 | A2_(8) | 42,672,509 | 116.84 | |
| Sat_294 | A2_(8) | 42,672,509 | 116.84 | |
| BARC-026019-05227 | A2_(8) | 43,854,570 | 124.76 | |
| BARC-041819-08107 | A2_(8) | 44,461,605 | 128.69 | |
| BARC-020591-04686 | A2_(8) | 44,622,477 | 128.80 | |
| BARCSOYSSR_08_1811 | A2_(8) | 45,272,538 | 133.77 | |
| Satt228 | A2_(8) | 45,272,538 | 133.77 | |
| BARC-056517-14441 | A2_(8) | 45,888,470 | 135.44 | |
| BARC-054887-12192 | A2_(8) | 46,236,665 | 136.31 | |
| BARCSOYSSR_08_1890 | A2_(8) | 46,545,843 | 137.26 | |
| Satt538 | A2_(8) | 46,545,843 | 137.26 | |
| BARC-021953-04238 | A2_(8) | 46,546,520 | 139.89 | |
| BARC-053255-11775 | A2_(8) | 46,874,135 | 142.96 | |

GENETIC LOCI ASSOCIATED WITH SOYBEAN CYST NEMATODE RESISTANCE AND METHODS OF USE

CROSS-REFERENCE TO RELATED APPLICATIONS

This application is a Continuation of U.S. application Ser. No. 13/781,963, filed Mar. 1, 2013, now pending which claims the benefit of U.S. Provisional Application No. 61/740,567, filed Dec. 21, 2012, which is hereby incorporated herein in its entirety by reference.

FIELD OF THE INVENTION

This invention relates to methods of identifying and/or selecting soybean plants or germplasm that display resistance or improved resistance to Soybean Cyst Nematode.

REFERENCE TO A SEQUENCE LISTING SUBMITTED AS A TEXT FILE VIA EFS-WEB

The official copy of the sequence listing is submitted concurrently with the specification as a text file via EFS-Web, in compliance with the American Standard Code for Information Interchange (ASCII), with a file name of 20160119_3206USCNT_SequenceListing.TXT, a creation date of Jan. 19, 2016 and a size of 229 KB. The sequence listing filed via EFS-Web is part of the specification and is hereby incorporated in its entirety by reference herein.

BACKGROUND

Soybeans (*Glycine max* L. Merr.) are a major cash crop and investment commodity in North America and elsewhere. Soybean oil is one of the most widely used edible oils, and soybeans are used worldwide both in animal feed and in human food production. Additionally, soybean utilization is expanding to industrial, manufacturing, and pharmaceutical applications.

Soybean Cyst Nematode (SCN) is a parasitic pest which has threatened soybean production in the U.S. for more than fifty years. Soybean cyst nematode resistance is an economically important trait as infection can substantially reduce yields. Molecular characterization of soybean cyst nematode resistance would have important implications for soybean cultivar improvement.

There remains a need for soybean plants with improved resistance to soybean cyst nematode and methods for identifying and selecting such plants.

SUMMARY

Various methods and compositions are provided for identifying and/or selecting soybean plants or soybean germplasm with resistance or improved resistance to soybean cyst nematode. In certain embodiments, the method comprises detecting at least one marker locus that is associated with resistance to soybean cyst nematode. In other embodiments, the method further comprises detecting at least one marker profile or haplotype associated with resistance to soybean cyst nematode. In further embodiments, the method comprises crossing a selected soybean plant with a second soybean plant. Further provided are markers, primers, probes and kits useful for identifying and/or selecting soybean plants or soybean germplasm with resistance or improved resistance to soybean cyst nematode.

BRIEF DESCRIPTION OF THE FIGURES

FIG. 1 A-D provides a genetic map for loci on linkage group A2.

DETAILED DESCRIPTION

Before describing the present invention in detail, it is to be understood that this invention is not limited to particular embodiments, which can, of course, vary. It is also to be understood that the terminology used herein is for the purpose of describing particular embodiments only, and is not intended to be limiting.

Certain definitions used in the specification and claims are provided below. In order to provide a clear and consistent understanding of the specification and claims, including the scope to be given such terms, the following definitions are provided:

As used in this specification and the appended claims, terms in the singular and the singular forms "a," "an," and "the," for example, include plural referents unless the content clearly dictates otherwise. Thus, for example, reference to "plant," "the plant," or "a plant" also includes a plurality of plants; also, depending on the context, use of the term "plant" can also include genetically similar or identical progeny of that plant; use of the term "a nucleic acid" optionally includes, as a practical matter, many copies of that nucleic acid molecule; similarly, the term "probe" optionally (and typically) encompasses many similar or identical probe molecules.

Additionally, as used herein, "comprising" is to be interpreted as specifying the presence of the stated features, integers, steps, or components as referred to, but does not preclude the presence or addition of one or more features, integers, steps, or components, or groups thereof. Thus, for example, a kit comprising one pair of oligonucleotide primers may have two or more pairs of oligonucleotide primers. Additionally, the term "comprising" is intended to include examples encompassed by the terms "consisting essentially of" and "consisting of." Similarly, the term "consisting essentially of" is intended to include examples encompassed by the term "consisting of."

"Agronomics," "agronomic traits," and "agronomic performance" refer to the traits (and underlying genetic elements) of a given plant variety that contribute to yield over the course of a growing season. Individual agronomic traits include emergence vigor, vegetative vigor, stress tolerance, disease resistance or tolerance, insect resistance or tolerance, herbicide resistance, branching, flowering, seed set, seed size, seed density, standability, threshability, and the like.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

An "ancestral line" is a parent line used as a source of genes, e.g., for the development of elite lines.

An "ancestral population" is a group of ancestors that have contributed the bulk of the genetic variation that was used to develop elite lines.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

A "genetic map" is a description of genetic association or linkage relationships among loci on one or more chromosomes (or linkage groups) within a given species, generally depicted in a diagrammatic or tabular form.

"Genotype" is a description of the allelic state at one or more loci.

"Germplasm" means the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Introgression" means the entry or introduction of a gene, QTL, haplotype, marker profile, trait, or trait locus from the genome of one plant into the genome of another plant.

The terms "label" or "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to the tendency for alleles to segregate together more often than expected by chance if their transmission was independent. Typically, linkage refers to alleles on the same chromosome. Genetic recombination occurs with an assumed random frequency over the entire genome. Genetic maps are constructed by measuring the frequency of recombination between pairs of traits or markers, the lower the frequency of recombination, and the greater the degree of linkage.

"Linkage disequilibrium" is a non-random association of alleles at two or more loci and can occur between unlinked markers. It is based on allele frequencies within a population and is influenced by but not dependent on linkage.

"Linkage group" (LG) refers to traits or markers that generally co-segregate. A linkage group generally corresponds to a chromosomal region containing genetic material that encodes the traits or markers.

"Locus" is a defined segment of DNA.

A "map location" or "map position" is an assigned location on a genetic map relative to linked genetic markers where a specified marker can be found within a given species. Map positions are generally provided in centimorgans (cM), unless otherwise indicated, genetic positions provided are based on the *Glycine max* consensus map v 4.0 as provided by Hyten et al. (2010) Crop Sci 50:960-968. A "physical position" or "physical location" or "physical map location" is the position, typically in nucleotides bases, of a particular nucleotide, such as a SNP nucleotide, on a chromosome. Unless otherwise indicated, the physical position within the soybean genome provided is based on the Glyma 1.0 genome sequence described in Schmutz et al. (2010) Nature 463:178-183, available from the Phytozome website (phytozome-dot-net/soybean).

"Mapping" is the process of defining the association and relationships of loci through the use of genetic markers, populations segregating for the markers, and standard genetic principles of recombination frequency.

"Marker" or "molecular marker" or "marker locus" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest.

"Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

"Haplotype" refers to a combination of particular alleles present within a particular plant's genome at two or more linked marker loci, for instance at two or more loci on a particular linkage group. For instance, in one example, two specific marker loci on LG-A2 are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

As used herein, a "marker profile" means a combination of particular alleles present within a particular plant's genome at two or more marker loci which are not linked, for instance two or more loci on two or more different linkage groups or two or more chromosomes. For instance, in one example, a particular combination of marker loci or a particular combination of haplotypes define the marker profile of a particular plant.

The term "plant" includes reference to an immature or mature whole plant, including a plant from which seed or grain or anthers have been removed. Seed or embryo that will produce the plant is also considered to be the plant.

"Plant parts" means any portion or piece of a plant, including leaves, stems, buds, roots, root tips, anthers, seed, grain, embryo, pollen, ovules, flowers, cotyledons, hypocotyls, pods, flowers, shoots, stalks, tissues, tissue cultures, cells and the like.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid," "nucleic acid molecule," "nucleic acid sequence," "nucleic acid fragment," and "oligonucleotide" are used interchangeably herein to indicate a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

"Primer" refers to an oligonucleotide which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

"Quantitative trait loci" or "QTL" refer to the genetic elements controlling a quantitative trait.

"Recombination frequency" is the frequency of a crossing over event (recombination) between two genetic loci. Recombination frequency can be observed by following the segregation of markers and/or traits during meiosis.

"Resistance" and "improved resistance" are used interchangeably herein and refer to any type of increase in resistance or tolerance to, or any type of decrease in susceptibility. A "resistant plant" or "resistant plant variety" need not possess absolute or complete resistance. Instead, a "resistant plant," "resistant plant variety," or a plant or plant variety with "improved resistance" will have a level of resistance or tolerance which is higher than that of a comparable susceptible plant or variety.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

The term "yield" refers to the productivity per unit area of a particular plant product of commercial value. For example, yield of soybean is commonly measured in bushels of seed per acre or metric tons of seed per hectare per season. Yield is affected by both genetic and environmental factors.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Typically, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein, culture media or other chemical components.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press: Cold Spring Harbor, 1989 (hereinafter "Sambrook").

Methods are provided for identifying and/or selecting a soybean plant or soybean germplasm that displays resistance or improved resistance to soybean cyst nematode. The method comprises detecting in the soybean plant or germplasm, or a part thereof, at least one marker locus associated with resistance to soybean cyst nematode. Also provided are isolated polynucleotides and kits for use in identifying and/or detecting a soybean plant or soybean germplasm that displays resistance or improved resistance to soybean cyst nematode, and soybean plants, cells, and/or seeds comprising at least one marker locus conferring improved resistance to soybean cyst nematode.

Provided herein, marker loci associated with soybean cyst nematode resistance have been identified and mapped to the rhg4 (resistance to *Heterodera glycines* 4) locus on linkage group A2 on chromosome 8. Examples of soybean lines known to comprise the rhg4 resistance locus include, for example, Peking and PI437654.

These findings have important implications for soybean production, as identifying markers that can be used for selection of soybean cyst nematode resistance will greatly expedite the development of soybean cyst nematode resistance into elite cultivars.

Marker loci, haplotypes and marker profiles associated with resistance to soybean cyst nematode, are provided. Further provided are genomic loci that are associated with soybean resistance to soybean cyst nematode.

In certain embodiments, soybean plants or germplasm are identified that have at least one favorable allele, marker locus, haplotype or marker profile that positively correlates with resistance or improved resistance to soybean cyst nematode. However, in other embodiments, it is useful for exclusionary purposes during breeding to identify alleles, marker loci, haplotypes, or marker profiles that negatively correlate with resistance, for example, to eliminate such plants or germplasm from subsequent rounds of breeding.

In one embodiment, marker loci useful for identifying a first soybean plant or first soybean germplasm that displays resistance or improved resistance to soybean cyst nematode are associated with the rhg4 locus on linkage group A2 on chromosome 8. In another embodiment, the marker locus comprises: (a) S07160-1 or a closely linked marker on linkage group A2; or (b) Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

In certain embodiments, multiple marker loci that collectively make up a soybean cyst nematode resistance haplotype of interest are investigated. For example, 2, 3, 4, 5, 6, 7, 8, 9, 10, or more of the various marker loci provided herein can comprise a soybean cyst nematode resistance haplotype. In some embodiments, the haplotype comprises: (a) two or more marker loci associated with the Rhg4 locus on linkage group A2; or (b) two or more marker loci comprising S07160-1, Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

In one embodiment, the method of identifying a first soybean plant or a first soybean germplasm that displays resistance or improved resistance to soybean cyst nematode comprises detecting in the genome of the first soybean plant or in the genome of the first soybean germplasm at least one haplotype that is associated with the resistance, wherein the at least one haplotype comprises at least two of the various marker loci provided herein.

In certain embodiments, two or more marker loci or haplotypes can collectively make up a marker profile. The marker profile can comprise any two or more marker loci comprising: (a) marker loci comprising S07160-1 on linkage group A2, or a closely linked marker; (b) marker loci comprising Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto; (c) any marker loci associated with the rhg4 locus on linkage group A2; (d) any marker loci associated with the rhg1 locus on linkage group G, or a closely linked marker; (e) any marker loci associated with the rhg2 locus on linkage group M; and/or (f) any marker loci associated with resistance to soybean cyst nematode.

Any of the marker loci in any of the genomic loci disclosed herein can be combined in the marker profile. For example, the marker profile can comprise 2, 3, 4, 5, 6, 7, 8, 9, 10, 11, 12, 13, 14, 15, 16, 17, 18, 19, 20, or more marker loci or haplotypes associated with resistance to soybean cyst nematode.

In one embodiment, a method of identifying a first soybean plant or a first soybean germplasm that displays resistance or improved resistance to soybean cyst nematode comprises detecting in the genome of the first soybean plant or in the genome of the first soybean germplasm at least one marker profile that is associated with the resistance, wherein the at least one marker profile comprises the marker locus provided herein.

Not only can one detect the various markers provided herein, it is recognized that one could detect any markers that are closely linked to the various markers discussed herein. Non-limiting examples of closely linked markers on linkage group A2 are provided in FIG. 1 A-D.

In addition to the markers discussed herein, information regarding useful soybean markers can be found, for example, on the USDA's Soybase website, available at soybase.org. One of skill in the art will recognize that the identification of favorable marker alleles may be germplasm-specific. The determination of which marker alleles correlate with resistance (or susceptibility) is determined for the particular germplasm under study. One of skill will also recognize that methods for identifying the favorable alleles are routine and well known in the art, and furthermore, that the identification and use of such favorable alleles is well within the scope of the invention.

Various methods are provided to identify soybean plants and/or germplasm with resistance or improved resistance to soybean cyst nematode. In one embodiment, the method of identifying comprises detecting at least one marker locus associated with resistance to soybean cyst nematode. The term "associated with" in connection with a relationship between a marker locus and a phenotype refers to a statistically significant dependence of marker frequency with respect to a quantitative scale or qualitative gradation of the phenotype. Thus, an allele of a marker is associated with a trait of interest when the allele of the marker locus and the trait phenotypes are found together in the progeny of an organism more often than if the marker genotypes and trait phenotypes segregated separately.

Any combination of the marker loci provided herein can be used in the methods to identify a soybean plant or soybean germplasm that displays resistance or improved resistance to soybean cyst nematode. Any one marker locus or any combination of the markers set forth herein, or any closely linked marker can be used to aid in identifying and selecting soybean plants or soybean germplasm with resistance or improved resistance to soybean cyst nematode.

In one embodiment, a method of identifying a first soybean plant or a first soybean germplasm that displays resistance or improved resistance to soybean cyst nematode is provided. The method comprises detecting in the genome of the first soybean plant or first soybean germplasm at least one marker locus that is associated with resistance. In such a method, the at least one marker locus: (a) can comprise the marker locus S07160-1 on linkage group A2, or a closely linked marker; (b) can comprise the marker loci Gm08: 8300131, Gm08:8257778, Gm08:8257785, Gm08:8258163, Gm08:8258688, Gm08:8258742, Gm08:8259928, Gm08: 8260451, Gm08:8260590, Gm08:8261480, Gm08:8261684, Gm08:8262165, Gm08:8263213, Gm08:8263250, Gm08: 8263611, Gm08:8264149, Gm08:8265227, Gm08:8265364, Gm08:8265614, Gm08:8266183, Gm08:8266185, Gm08: 8266263, Gm08:8266350, Gm08:8266386, Gm08:8266473, Gm08:8266888, Gm08:8267085, Gm08:8267166, Gm08: 8267721, Gm08:8267826, Gm08:8268336, Gm08:8268861, Gm08:8269148, Gm08:8269785, Gm08:8270037, Gm08: 8270562, Gm08:8270652, Gm08:8271540, Gm08:8271591, Gm08:8271649, Gm08:8271672, Gm08:8271955, Gm08: 8273257, Gm08:8273355, Gm08:8273979, Gm08:8275766, Gm08:8275780, Gm08:8275959, Gm08:8276701, Gm08: 8276849, Gm08:8276913, Gm08:8277162, Gm08:8277227, Gm08:8277248, Gm08:8277381, Gm08:8277383, Gm08: 8277542, Gm08:8277625, Gm08:8277643, Gm08:8277876, Gm08:8277880, Gm08:8277969, Gm08:8278001, Gm08: 8278167, Gm08:8278274, Gm08:8278434, Gm08:8279165, Gm08:8279230, Gm08:8279854, Gm08:8280901, Gm08: 8280937, Gm08:8281564, Gm08:8282902, Gm08:8284027, Gm08:8286864, Gm08:8287265, Gm08:8287278, Gm08: 8287453, Gm08:8287459, Gm08:8288039, Gm08:8288141, Gm08:8288200, Gm08:8288470, Gm08:8288831, Gm08: 8289392, Gm08:8290740, Gm08:8291682, Gm08:8292207, Gm08:8297064, Gm08:8299433, Gm08:8299672, Gm08: 8301839, Gm08:8302134, Gm08:8303450, Gm08:8305237, Gm08:8305348, Gm08:8305905, Gm08:8306090, Gm08: 8306141, Gm08:8306210, Gm08:8306492, Gm08:8306627, Gm08:8307172, Gm08:8307665, Gm08:8308019, Gm08: 8308891, Gm08:8308917, Gm08:8309316, Gm08:8309423, Gm08:8309837, Gm08:8310383, Gm08:8310464, Gm08: 8310503, Gm08:8310663, Gm08:8311631, Gm08:8311906, Gm08:8312536, Gm08:8312819, Gm08:8313273, Gm08: 8313923, Gm08:8314010, Gm08:8314025, Gm08:8314208, Gm08:8314292, Gm08:8314295, Gm08:8314513, Gm08: 8314736, Gm08:8314791, Gm08:8314860, Gm08:8315543, Gm08:8315644, Gm08:8316113, Gm08:8316689, Gm08: 8316899, Gm08:8317852, Gm08:8317861, Gm08:8318033, Gm08:8319087, Gm08:8319642, Gm08:8319647, Gm08: 8320068, Gm08:8321253, Gm08:8321649, Gm08:8323937, Gm08:8324341, Gm08:8325127, Gm08:8325214, Gm08: 8326696, Gm08:8326877, Gm08:8328633, Gm08:8330929, Gm08:8331132, Gm08:8331181, Gm08:8331408, Gm08: 8331827, Gm08:8332651, Gm08:8332685, Gm08:8332957, Gm08:8343167, Gm08:8345187, Gm08:8345720, Gm08: 8346030, Gm08:8346050, Gm08:8346352, Gm08:8346726, Gm08:8347799, Gm08:8348022, Gm08:8348028, Gm08: 8349925, Gm08:8350122, Gm08:8350277, Gm08:8351061, Gm08:8351503, Gm08:8352313, Gm08:8352743, Gm08: 8353341, Gm08:8355175, Gm08:8360133, Gm08:8363193, Gm08:8363888, Gm08:8364195 or a marker closely linked thereto; or (c) can be any marker associated with the rhg4 locus on linkage group A2.

In other embodiments, two or more marker loci are detected in the method. In a specific embodiment, the germplasm is a soybean variety.

In other embodiments, the method further comprises crossing the selected first soybean plant or first soybean germplasm with a second soybean plant or second soybean germplasm. In a further embodiment of the method, the second soybean plant or second soybean germplasm comprises an exotic soybean strain or an elite soybean strain.

In specific embodiments, the first soybean plant or first soybean germplasm comprises a soybean variety. Any soybean line known to the art or disclosed herein may be used. Non-limiting examples of soybean varieties and their associated soybean cyst nematode resistance alleles encompassed by the methods provided herein include, for example, Peking and PI437654.

In another embodiment, the detection method comprises amplifying at least one marker locus and detecting the resulting amplified marker amplicon. In such a method, amplifying comprises (a) admixing an amplification primer or amplification primer pair for each marker locus being amplified with a nucleic acid isolated from the first soybean plant or the first soybean germplasm such that the primer or primer pair is complementary or partially complementary to a variant or fragment of the genomic locus comprising the marker locus and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon. In such a method, the primer or primer pair can comprise a variant or fragment of one or more of the genomic loci provided herein.

In one embodiment, the method involves amplifying a variant or fragment of one or more polynucleotides comprising SEQ ID NOS: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 or variants or fragments thereof.

In one embodiment, the primer or primer pair can comprise a variant or fragment of one or more polynucleotides comprising SEQ ID NOS: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 or complements thereof.

In specific embodiments, the primer or primer pair comprises a nucleic acid sequence comprising SEQ ID NOS: 1, 2, 3, 4, 5, 6, 7, 8 or variants or fragments thereof.

In a specific embodiment, the primer pair comprises SEQ ID NO:1 and SEQ ID NO:2.

In another embodiment, the method further comprises providing one or more labeled nucleic acid probes suitable for detection of each marker locus being amplified. In such a method, the labeled nucleic acid probe can comprise a sequence comprising a variant or fragment of one or more of the genomic loci provided herein. In one embodiment, the labeled nucleic acid probe can comprise a sequence comprising a variant or fragment of one or more polynucleotides comprising SEQ ID NOS: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 or complements thereof.

In specific embodiments, the labeled nucleic acid probe comprises a nucleic acid sequence comprising SEQ ID NOS: 9, 10 or variants or fragments thereof.

Non-limiting examples of primers, probes, genomic loci and amplicons that can be used in the methods and compositions provided herein are summarized in Tables 1, 2, 3A, 3B and 4, respectively.

TABLE 1

Non-Limiting Examples of Primer Sequences.

| Marker position | Linkage Group (ch) | Marker Name | Primer Name | SEQ ID NO | Primer Sequence | Allele (R/S) |
|---|---|---|---|---|---|---|
| 8300131 | A2 (Gm08) | D07160-1 | 136868 | 1 | TGTGTTGTGTTTGACTGCCATA | C/A |
| 8300131 | A2 (Gm08) | S07160-1 | 136869 | 2 | CATTTCCCAAGCCTCTTGAT | C/A |
| 8300131 | A2 (Gm08) | S07160-1 | 100532 | 3 | TCTAGCTCTGACATATTGATGATTCTTTTGTGTTGT | C/A |
| 8300131 | A2 (Gm08) | S07160-1 | 80588 | 4 | AAGCCTCTTGATAAGACAGTGTCTTCCAAATC | C/A |
| 8300131 | A2 (Gm08) | S07160-1 | 136870 | 5 | TCTTTTGTGTTGTGTTTGACTGC | C/A |

TABLE 1-continued

Non-Limiting Examples of Primer Sequences.

| Marker position | Linkage Group (ch) | Marker Name | Primer Name | SEQ ID NO | Primer Sequence | Allele (R/S) |
|---|---|---|---|---|---|---|
| 8300131 | A2 (Gm08) | S07160-1 | 136871 | 6 | TGAGGCTTTCCAGCATCTAAC | C/A |
| 8300131 | A2 (Gm08) | S07160-1 | 136872 | 7 | GGACTGGATCATGAGAATTGG | C/A |
| 8300131 | A2 (Gm08) | S07160-1 | 136873 | 8 | AAGCAGAAGGAGCATTGAGG | C/A |

R = Resistant; S = Susceptible

TABLE 2

Non-Limiting Examples of Probe Sequences.

| Marker Position | Linkage Group (ch) | Marker Name | Probe 1* Name | Probe 1 Sequence | Probe 2** Name | Probe 2 Sequence |
|---|---|---|---|---|---|---|
| 8300131 | A2 (Gm08) | S07160-1 | 102389 | ACTAACTGCATAaGATAT (SEQ ID NO: 9) | 102390 | CTAACTGCATAcGATATT (SEQ ID NO: 10) |

*Probe 1 detects the susceptible allele.
**Probe 2 detects the resistant allele.

TABLE 3A

Non-Limiting Examples of Genomic Loci Comprising the Various Marker Loci Provided Herein.

| Marker Position | Marker Name | SEQ ID NO | Resistant (R) or Susceptible (S) Allele | Reference Sequence |
|---|---|---|---|---|
| 8300131 | S07160-1 | 13 | R | TGGAATCTGAGAAGAGACTTGAGAAATGGTACTCTTTGAATCCATGTAAGGTAATCATTGCCACTGGATTCATTGCAAGCACACCTCAAAACATTCCTACCACACTGAAGAGAGATGGAAGTGACTTCTCGGCAGCAATTATGGGTGCTCTATTTAAGGCTCGTCAGGTCACAATTTGGACAGATGTTGATGGTGTGTATAGTGCAGATCCTAGAAAAGGTTTGTTATGCTTCGTACTCTGTCTCTGAGTTAAACAATGAGTGGACTGGATCATGAGAATTGGTTTTTAGTAACCAGAGGGAGTTCTAGCTCTGACATATTGATGATTCTTTTGTGTTGTGTTTGACTGCCATAACATGATGTTTGGATTAAATATAAACAATAATATCCTATGCAGTTAGTGAGGCTGTGATTTGGAAGACACTGTCTTATCAAGAGGCTTGGGAAATGGTGAGTTAGATGCTGGAAAGCCTCAATGCTCCTTCTGCTTGTAAAATTAAGGAGATTAACTTGCAAATTGTCTGTTGTACAGTCTTATTTGGGTGCCAATGTCTTGCATCCCCGCACAATTATTCCTGTGATGCGATATGGCATACCCATTATGATAAGGAACATTCCCA |
| 8300131 | S07160-1 | 14 | S | TGGAATCTGAGAAGAGACTTGAGAAATGGTACTCTTTGAATCCATGTAAGGTAATCATTGCCACTGGATTCATTGCAAGCACACCTCAAAACATTCCTACCACACTGAAGAGAGATGGAAGTGACTTCTCGGCAGCAATTATGGGTGCTCTATTTAAGGCTCGTCAGGTCACAATTTGGACAGATGTTGATGGTGTGTATAGTGCAGATCCTAGAAAAGGTTTGTTATGCTTCGTACTCTGTCTCTGAGTTAAACAATGAGTGGACTGGATCATGAGAATTGGTTTTTAGTAACCAGAGGGAGTTCTAGCTCTGACATATTGATGATTCTTTTGTGTTGTGTTTGACTGCCATAACATGATGTTTGGATTAAATATAAACAATAATATCATATGCAGTTAGTGAGGCTGTGATTTGGAAGACACTGTCTTATCAAGAGGCTTGGGAAATGGTGAGTTAGATGCTGGAAAGCCTCAATGCTCCTTCTGCTTGTAAAATTAAGGAGATTAACTTGCAAATTGTCTGTTGTACAGTCTTATTTGGGTGCCAATGTCTTGCATCCCCGCACAATTATTCCTGTGATGCGATATGGCATACCCATTATGATAAGGAACATTCCCA |

TABLE 3B

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:8356824 (Rhg4 mutation from Liu et al. Nature 2012*) | 8356824 | [C/G] | 15 | 198 | 0.857 | | GCCGGGCAACCGCTACTACGGCGGCAATGAATA CATCGACCAGATCGAAAACCTCTGCCGCTCACGC GCCCTCCAAGCCTTCCACCTCGACGCCCAATCCT GGGGCGTCAACGTCCAGCCCTACTCCGGCTCCCC GGCCAACTTCGCCGCCTACACCGCCGTCCTCAAC CCCCACGACCGCATCATGGGGCTAGATCTCC[C/ G]CTCCGGCGGCCACCTCACCCACGGCTACTACAC CTCCGGCGAAAGAAGATCTCCGCCACCTCCATT TACTTCGAGAGTCTCCCTTACAAGGTAAACTCCA CCACCGGCTACATCGACTAYGACCGCTTGGAAGA AAAAGCCCTAGACTTCAGGCCAAAACTCATAATC TGCGGTGGCAGCGCGTACCCTCGCGATTGGG |
| Gm08:8357600 (Rhg4 mutation from Liu et al. Nature 2012) | 8357600 | [A/T] | 16 | 199 | | 0.857 | CCGTTGCGCTTGGAAAATACTTGATGGGGAAAGG GTACAGCCTTGTCACTGGCGGAACGGAGAACCAT CTTGTTTTGTGGGATCTGAGACCTCTTGGATTGAC TGGTAATATATATAGGATTGGATCTCTACCTTCT GGTTTTGATTTGTTACAAATGTCTATAAATCTGAC TTGTTCGTTGTGTGATTGTTTTGCAGGG[A/T]ATA AGGTGGAGAAACTCTGTGATCTCTGTAACATTAC TGTTAACAAGAACGCTGTTTTTGGTGATAGCAGT GCCTTGGCCCCTGGTGGAGTGCGAATTGGTAACG ATCTTACTTCTCTTTTATATGCTACAATACAAATC TTGCTTTACTAACTCAATTGGAAACAAGATCTCA TTTATAAGATTATAAAAATGATTTCC |
| Gm08:8300131 (S07160-1) | 8300131 | [A/C] | 17 | 200 | 0.818 | 0.738 | CATATCGCATCACAGGAATAATTGTGCGGGGATG CAAGACATTGGCACCAAAATAAGACTGTACAAC AGACAATTTGCAAGTTAATCTCCTTAATTTTACA AGCAGAAGGAGCATTGAGGCTTTCCAGCATCTAA CTCACCATTTCCCAAGCCTCTTGATAAGACAGTG TCTTCAAAATCACAGCCTCACTAACTGCATA[A/C] GATATTATTGTTTATATTTAATCAAAACATCATGT TATGGCAGTCAAACACAACACAAAAGAATCATC AATATGTCAGAGCTAGAACTCCCTCTGGTTACTA AAAACCAATTCTCATGATCCAGTCCACTCATTGT TTAACTCAGAGACAGAGTACGAAGCATAACAAA CCTTTTCTAGGATCTGCACTATACACACCAT |
| Gm08:8257778 | 8257778 | [A/T] | 18 | 201 | 0.857 | 0.679 | TAGGATGTTTTTCAAATACACTCTTTTCTCGCTGT TTAAAAAAAAAATACACTCTCTTCTAATAATTA AAAGTTATTAAAAATCATAAATTTGAATGGATCT CATTTTTCATTGAGTAACTCTCTCTCGTGATTTTA TATTATCTCTGTGCTTTTTATTTTTTATTTTTAAAA AATATGTAAAAACCAAGAAACATAAT[A/T]AATG TGSTTCATCTTAATAAAACACTTCTTTCATCCTTA AATATAAGACTTTTATAATTAATTCACACTTATTA ATAAAATTACAAAGACTTTTATAATTAATTCACA CTTATTAATAAAATTGCTCGATTTAGTTAGTAATT AACATTATATTTGTTTGTAATTTTAATATTTTTA AGATTATCTTTAAAATTATTCA |
| Gm08:8257785 | 8257785 | [C/G] | 19 | 202 | 0.848 | 0.68 | TTTTTCAAATACACTCTTTTCTCGCTGTTTAAAAA AAAAAATACACTCTCTTCTAATAATTAAAAGTTA TTAAAAATCATAAATTTGAATGGATCTCATTTTTC ATTGAGTAACTCTCTCTCGTGATTTTATATTATCT CTGTGCTTTTTATTTTTTATTTTTAAAAATATGT AAAAACCAAGAAACATAATWAATGTG[C/G]TTCA TCTTAATAAAACACTTCTTTCATCCTTAAATATAA GACTTTTATAATTAATTCACACTTATTAATAAAAT TACAAAGACTTTTATAATTAATTCACACTTATTA ATAAAATTGCTCGATTTAGTTAGTAATTAACATT ATATTTGTTTGTAATTTTAATATTTTTTAAGATTA TCTTTAAAATTATTCAGACTAAA |
| Gm08:8258163 | 8258163 | [C/A] | 20 | 203 | 0.843 | 0.681 | TCTTTAAAATTATTCAGACTAAATATATATTTTTT TCATTTAATTATTTTCTACCCAACAATTAACATA TGAAAAGAGAATAATAGTAGTCGAGTTTTAATTT TAAAATTAAATCCTTCAATTCTCCAATCCTCCCAC GAAAGAGAAAATGACAATTCATAGCAATTRTTAT TTATAGACTACAACAACTAGGGGTATT[A/C]TAGT AAAAAGAAAACAAGTAATGCAAGAAAGAAGTC |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | TTATACAAAAGAACAAAGAATTTTTTAAATAATG TCTTATATTCATAGACGAAAGAAACAATTGATCC TTTATCATTTTTATTAAACAATAAATGCATAGAT GTAAATAAATTAAAGATTAGAAAAAAGTAAGAA CATAATTGGCAAAAAAATAATTAATGTC |
| Gm08:825 8688 | 8258688 | [C/G] | 21 | 204 | 0.895 | 0.688 | TAAAAAAGAAAACGTGGGAGAGTGCAATTAGG ATAAAGGGATTGGATTACTTGAAGAAAAAAARA ATAAAGGGGTTAGAAAAAGACCCTCTAGAAGTA TACGACAGCCTAAATTGAAATTGGGATACATAGT TTGGACTGTAATAGAATTGTGGATCTGTTTGCTC GTTTTATTTCAAAATAAAACAAAATAAAGAACT [C/G]CTAGCATRACAACAAAAAGTACTAATTTTTA ATCTCAAKGATCRGAACTTTGCRTTTCTTTCCCGT ATCTTGTCGAATTTTYATTGTAAGAAATATTCTTT GTGGGTTCAGTTATTCACCATTATTATTTCAGAG GGAGCGATGGGWGGAATTATAATACTTCTTCATC AGATTCAATTTTGATAAAGAAAATCATTCAA |
| Gm08:825 8742 | 8258742 | [G/A] | 22 | 205 | 1 | 0.587 | AAGAAAAAAARAATAAAGGGGTTAGAAAAAGAC CCTCTAGAAGTATACGACAGCCTAAATTGAAATT GGGATACATAGTTTGGACTGTAATAGAATTGTGG ATCTGTTTGCTCGTTTTATTTCAAAATAAAACAA AATAAAGAACTSCTAGCATRACAACAAAAAGTA CTAATTTTTAATCTCAAKGATCRGAACTTTGC[A/ G]TTTCTTTCCCGTATCTTGTCGAATTTTYATTGTA AGAAATATTCTTTGTGGGTTCAGTTATTCACCATT ATTATTTCAGAGGGAGCGATGGGWGGAATTATA ATACTTCTTCATCAGATTCAATTTTGATAAAGAA AATCATTCAAATAAGAGACTTTATTATCTTCAAA AAGCTAAGTACGGAAGATGCCAAAAAGAAA |
| Gm08:825 9928 | 8259928 | [C/T] | 23 | 206 | 0.896 | 0.688 | TTGGATCATTTAATTTATGAGGTGTGTGATTTTGT TTCCTAGTTTTTAATTTTGCAAATTGGATCATTTA AGTATTACAGGAATCCAATTTACTCAATTGAATT CTGAAAGATCAAAATTAAATAAATGCAATACCTA AGAGACAAAAATAATTAATCTATTTTTTTAAAG AAAATACTACTATCAGATATGGAAGCAC[C/T]AA CAAAACCAGTCCAGGAGAGACATCAGCACCTAC CTACGCACCCCAAAATCAGATACAACTTTAAGCT TACAACATCACCTATAGTAACCTAATATTGCTCA AAATGGAAGCAACCATTCCACAACCAATACAAC AAACAAAATCAATAAATTTACTACAAACTAGTCG AACCGTACCTCGTTAATGCCATAAACCTAG |
| Gm08:826 0451 | 8260451 | [C/T] | 24 | 207 | 0.818 | 0.622 | ACTAAGCTACACAAACTGAATCACGTCTAAGACG CTCTAAAAACAAAATCAGGAGGCAGGTTCCGCA AAATAGGACTGGATAATGATGTTGAAGCAGTAA TTTCTATCAAAATTAACAGGAAAAACTCTAAAAA AATCAGCCCCRGGAGAGAAATTTATATATATTTTTT GTAGATAAAAATTTAAATTAGGGGAAGACACG[C/ T]CTTCTTGTAAAACTACAAGAAAAATTAACAAC ATCAGCATTATAAAATTTATACATCGCATAACAA TATGCAAAATCCAAAAATCAATAAAACCTAAATTA TTGCTGGTATAACTATTTGACTAAATGTGCCATT GTTGSCCAGAGAATATTAAAATGTAATGAAATAA AGTATTTTAAATTAATTGACTAAGAATTGGCA |
| Gm08:826 0590 | 8260590 | [G/C] | 25 | 208 | 0.918 | 0.772 | GCCCCRGGAGAAATTTATATATATTTTTTGTAGA TAAAAATTTAAATTAGGGGAAGACACGYTTCTT GTAAAACTACAAGAAAAATTAACAACATCAGCA TTATAAAATTTATACATCGCATAACAATATGCAA AATCCAAAATCAATAAACCTAAATTATTGCTGG TATAACTATTTGACTAAATGTGCCATTGTTG[C/G] CCAGAGAATATTAAAATGTAATGAAATAAAGTA TTTTAAATTAATTGACTAAGAATTGGCATGGCTA TGAGAAATCATGCACTAATTGAGCAAAGATATG ATATATTTTTTATACTTGTCCTAACAATGTACTCC CACTAATTAAGTTACTAATTGAGCACTCCATAAT TTTTTTTGGAAGATGTTCTTTGGACACTGTG |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:826 1480 | 8261480 | [T/G] | 26 | 209 | 1 | 0.856 | TCATGTCTACCAAGTCCGACTAACTTWTCCGTCC ATCAACCATTTTTAACTGAGAATTGGTATGATA TCAAGAGTTAAGAGTTGTGACTGTATTTGGAAAA ATATTTCTTAAAATAAAATGATATTCAAAAAATA TATTTTAATAGTTTTTTCTGCTGATTTTCAGTCT ATAATTAAACGAATTTAGATACTCTATAT[G/T]AA AAAAGAGAAAATCATTTTTTCAATAACAGTCCCA AAACTTTTAAATTAAAAAAAATAAAGTAAAATTT ATCTTTTATTTTGAATTAAATCAAGACATACTACT ATACCTGATCAGTCCTGGATCGAATTCTCCCAAC CAAATCAACTCGCCATAAATACCCTCTTATATCC AGTTAATTAATGGTCCATCTCGTTTTG |
| Gm08:826 1684 | 8261684 | [A/T] | 27 | 210 | 1 | 0.791 | AAAGAGAAAATCATTTTTTCAATAACAGTCCCAA AACTTTTAAATTAAAAAAAATAAAGTAAAATTTA TCTTTTATTTTGAATTAAATCAAGACATACTACTA TACCTGATCAGTCCTGGATCGAATTCTCCCAACC AAATCAACTCGCCATAAATACCCTCTTATATCCA GTTAATTAATGGTCCATCTCGTTTTGAAA[A/T]TT TTTTAACCATGAAGTTTTTTTTAGTTACATGAGG AAAAGAAAGACAAGGGACAACCAAAAAAACTAC ACGTACTACTAAATTAAGGCAGATCACACTGCCA CTCCCTCTGCACAAAAACTGGTGGCCTCTGCCAG ACCACAGCATCAGAACTCAGAAGCATTGGTTGCA TCAGAGTTTTGTTATGGTGTATTTAGAA |
| Gm08:826 2165 | 8262165 | [T/A] | 28 | 211 | 0.919 | 0.918 | CCAATCCCGACACAACCAGCTCGAAATTTTCCGC ACCGCAGAATGTCGTGATTCTTGTGGCAACCAGA GTTGTTGTTCTTGCTAGCTCTATATTCTTCTCCTG TGTGGCAGTATTGCATCAATGCTACCATGCAGTG TCTAACAAGACTATATCATATATTTATGATAGTC TCTAATCAATTTTTGAAAAAATTAGAGTC[A/T]TA ATATTTATACATCTCATTTTCTTATAATTCACTTG CATCTTATTTCATTTTTTCCCCTATCATATAACAT ATCATATTTATTACATTCTCTCTATTTTTATTTTTA TTTCTCTCTCCATCTCTCTTCTCTTTTCACCCTAAA ATGGGGGTGAACACTCAACATGTTTTGAAAAATT ATTATTAGATTAATATGTATTG |
| Gm08:826 3213 | 8263213 | [G/C] | 29 | 212 | 0.913 | 0.699 | GGGTCATCCTTTCACTTGTTTGGTCTACACCACAC TCTTGTCTTGGGTCGCTGAGGTGGCGCGTGAGTT TCACCTCCCAACAGCGATGCTGTGGACTCAACCA GCTACGATACTCGACATCTTCTATTACTACTTTCA CGAACACGGTGAATACATCAAAGACAAAATCAA AGACCCCTCGTGTTTCATTGAATTACCAG[C/G]AT TGCCATTGTTGCTTGCACCACGGGACCTACCCTC YTTTTTATTGGGTTCAAACCCTACTATTGACTCTT TCATTGTCCCAATGTTTGAAAAGATGTTTTATGAT CTTGACGTGGAGACAAAGCCCAGAATACTTGTCA ACACCTTCGAAGCCTTGGAAGCGGAGGCTCTCAG AGCCGTTGATAAGTTCAACATGATCC |
| Gm08:826 3250 | 8263250 | [T/C] | 30 | 213 | 1 | 0.678 | TTGTCTTGGGTCGCTGAGGTGGCGCGTGAGTTTC ACCTCCCAACAGCGATGCTGTGGACTCAACCAGC TACGATACTCGACATCTTCTATTACTACTTTCACG AACACGGTGAATACATCAAAGACAAAATCAAAG ACCCCTCGTGTTTCATTGAATTACCAGSATTGCCA TTGTTGCTTGCACCACGGGACCTACCCTC[C/T]TT TTTATTGGGTTCAAACCCTACTATTGACTCTTTCA TTGTCCCAATGTTTGAAAAGATGTTTTATGATCTT GACGTGGAGACAAAGCCCAGAATACTTGTCAAC ACCTTCGAAGCCTTGGAAGCGGAGGCTCTCAGAG CCGTTGATAAGTTCAACATGATCCCAATCGGGCC GTTGATTCCCTCGGCTTTCTTGGATGG |
| Gm08:826 3611 | 8263611 | [C/T] | 31 | 214 | 0.924 | 0.682 | TCCCAATCGGGCCGTTGATTCCCTCGGCTTTCTTG GATGGGAAAGATMCTAATGATACTTCATTTGGCG GTGACATCTTCCGCCTCTCTAATGGTTGCAGCGA ATGGTTGGACTCGAAGCCAGAGATGTCGGTGGTT TATGTCTCGTTTGGTAGCCTTTGCGTGTTGCCTAA GACGCAAATGGAGGAACTTGCACGTGCG[C/T]TA TTAGATTGTGGAAGTCCTTTCCTGTGGGTCATTA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | AAGAAAAAGAAAATAAGTCACAAGTGGAAGGAA AAGAGGAGCTGAGCTGCATAGAGGAATTGGAAC AGAAGGGGAAGATAGTAAACTGGTGTTCTCAAG TGGAGGTTCTTTCACATGGTTCTGTGGGTTGTTTT GTTACACACTGTGGTTGGAATTCAACCATG |
| Gm08:826 4149 | 8264149 | [C/T] | 32 | 215 | 0.933 | 0.702 | AAATGAAGAAATTAGGCGGTGTTTGGAAGAGGT GATGGGGAGTGGAGAGAAAGGACAAGAATTGAG AAACAATGCAGAAAAGTGGAGGGGACTGGCCAG GGAAGCTGTCAAGGAAGGTGGCTCTTCGGATAA GAATCTAAGGGCTTTTTTAGATGATGTTGAAGTT TGACCATATGGCTGTCACATCAGCTTTTCCGTTT[C/T]TGAATTTTCCTGTCCGTTTCATTTTTCTTTTCT ATTATTGCATTTGCATGACTGAGAATCAAGTGAA ATTTCTTCTATATTAGTTTGAAATTTAAAAATATC TAAATGAGCCATGACTCCATGAGTAGTAATTTTG TGTTATAATTGATATATATATTTTCTCTTAAGTAG TGGCCAAAAATTTAATCTTTATGTAGATG |
| Gm08:826 5227 | 8265227 | [C/T] | 33 | 216 | 0.933 | 0.736 | ATGCATCTGGATCTGGTTTCCCTATTCATATTTCC AAAGCTTGCATGCTTTCTGGTTTCCTTGCCAATCA CTGCATGGAACAATCTTACCATCATAGGGCATGC TTCTTTTTTTAAGCTCGCTTGTGGTCTTCTTTTGGT ACATATGCTCCCCTCCCCCCTTTTTGTTTATTTTT GTTTTATGGTTCATAATAGAGTTTA[C/T]TGATGA AATAGCCAAATCATAGAATTAGTAAAATATCATG TACAAGGTCAAAATAGTATTTTTAGTAACCATCT TTTTTTTCTCGTACCTTACATAGAAGCTGACTCAA TGATAAAGGAAACCTAAAAATTAGTTTWAAAAA AACCTTTTGGCCTTTTTGACATMATATATGATATT TTTGTCAAAATATGAGACTTTTTT |
| Gm08:826 5364 | 8265364 | [A/T] | 34 | 217 | 1 | 0.824 | GGTACATATGCTCCCCTCCCCCCTTTTTGTTTATT TTTGTTTTATGGTTCATAATAGAGTTTAYTGATGA AATAGCCAAATCATAGAATTAGTAAAATATCATG TACAAGGTCAAAATAGTATTTTTAGTAACCATCT TTTTTTTCTCGTACCTTACATAGAAGCTGACTCAA TGATAAAGGAAACCTAAAAATTAGTTT[A/T]AAA AAAACCTTTTGGCCTTTTTGACATMATATATGAT ATTTTTGTCAAAATATGAGACTTTTTTTTTATAAA AACTAATAAAAAATATTTTTATTGGTAAACCT AGAACTTAAATTTTAGTTATTTTATTCTTAGASAA ACCTTACCTAACAAATAATTTAATTCAAATATTT GCCTTTCATTCTATTTTATTTCACC |
| Gm08:826 5614 | 8265614 | [G/A] | 35 | 218 | 0.838 | 0.8 | ATATGAGACTTTTTTTTTATAAAACTAATAAAA AAATATTTTTTATTGGTAAACCTAGAACTTAAAT TTTAGTTATTTTATTCTTAGASAAACCTTACCTAA CAAATAATTTAATTCAAATATTTGCCTTTCATTCT ATTTTATTTCACCTTAACAACTTCCCTGGCCACAA CATGTTGGATCTCAGTAAAAATTGATG[A/G]TGTA AGATCATTCCATTACGAAGAGATGCATGGCCTAT TATTCTTTCTCCATCCAAGAAAAAAATACATTTA TTCTTGCTTCCTGTTAAAACATAAAAAGACGTTTT ACCTTAGTATGATAACCTTCATAAATAGTTAAAT ATAGCATTGTCTTGAACTTTGAAATAAATTATGT TTAATTAGAACTTATAACTATAAGT |
| Gm08:826 6183 | 8266183 | [T/C] | 36 | 219 | 0.924 | 0.773 | ATATGTCAAGTATTATAATAAATATTTAATTATA TAAATAAATAATTTTATTCTTAAATATAAACATTT ACAAAGTTAAAGTAACAAAAAAGTAAGTTTTTA ATTCTCTTAATAATGTCATATCCTAATTTCGTACT AGGACTATCATTCGTCAACGTTTTGATTCTCCATT GTCAAATTGAATTGTTCGACACCAGTTG[C/T]TRT GTAAGACGGAAGATTATTCGACATTTCAGTAAAG AATGCAAAAAATGCCCAAATGGAAGGACAAAAG GATCATTTTTAGGCTTTTTCAGACCCCTGACTCGC TCAGGCTAGTCTCTGGCTCACCTAGGCCCCTAAA TAGTTTAGGGGTGAAGTAACTAGCTCGYCTGGAC GAGCAAGGTTACTTCAGGTTGAAGCAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:826 6185 | 8266185 | [G/A] | 37 | 220 | 0.924 | 0.773 | ATGTCAAGTATTATAATAAATATTTAATTATATA AATAAATAATTTTATTCTTAAATATAAACATTTA CAAAGTTAAAGTAACAAAAAAGTAAGTTTTTAAT TCTCTTAATAATGTCATATCCTAATTTCGTACTAG GACTATCATTCGTCAACGTTTTGATTCTCCATTGT CAAATTGAATTGTTCGACACCAGTTGYT[A/G]TGT AAGACGGAAGATTATTCGACATTTCAGTAAAGA ATGCAAAAAATGCCCAAATGGAAGGACAAAAGG ATCATTTTRAGGCTTTTTCAGACCCCTGACTCGCT CAGGCTAGTCTCTGGCTCACCTAGGCCCCTAAAT AGTTTAGGGGTGAAGTAACTAGCTCGYCTGGACG AGCAAGGTTACTTCAGGTTGAAGCAACA |
| Gm08:826 6263 | 8266263 | [A/G] | 38 | 221 | 0.904 | 0.816 | GTAACAAAAAAGTAAGTTTTTAATTCTCTTAATA ATGTCATATCCTAATTTCGTACTAGGACTATCATT CGTCAACGTTTTGATTCTCCATTGTCAAATTGAAT TGTTCGACACCAGTTGYTRTGTAAGACGGAAGAT TATTCGACATTTCAGTAAAGAATGCAAAAAATGC CCAAATGGAAGGACAAAAGGATCATTTT[A/G]AG GCTTTTTCAGACCCCTGACTCGCTCAGGCTAGTCT CTGGCTCACCTAGGCCCCTAAATAGTTTAGGGGT GAAGTAACTAGCTCGYCTGGACGAGCAAGGTTA CTTCAGGTTGAAGCAACARCTCGCTTGGGTGAGC TCCAGATCAACTAAGTCCCCTCATTTCCTATAAA TAGGCATGAGGGGCTGAAAGAAAGGGTT |
| Gm08:826 6350 | 8266350 | [T/C] | 39 | 222 | 1 | 0.895 | CCATTGTCAAATTGAATTGTTCGACACCAGTTGY TRTGTAAGACGGAAGATTATTCGACATTTCAGTA AAGAATGCAAAAAATGCCCAAATGGAAGGACAA AAGGATCATTTTRAGGCTTTTTCAGACCCCTGAC TCGCTCAGGCTAGTCTCTGGCTCACCTAGGCCCC TAAATAGTTTAGGGGTGAAGTAACTAGCTCG[C/T] CTGGACGAGCAAGGTTACTTCAGGTTGAAGCAA CARCTCGCTTGGGTGAGCTCCAGATCAACTAAGT CCCCTCATTTCCTATAAATAGGCATGAGGGGCTG AAAGAAAGGGTTCARCCTTCARATATTGAAAGG ATTTAGTGAAATTTGAAGAAAAGAAGAARAAAT AAAGGAAAAACAAGGTCGAGGTGCTACCGAATC |
| Gm08:826 6386 | 8266386 | [A/G] | 40 | 223 | 1 | 0.824 | TGTAAGACGGAAGATTATTCGACATTTCAGTAAA GAATGCAAAAAATGCCCAAATGGAAGGACAAAA GGATCATTTTRAGGCTTTTTCAGACCCCTGACTCG CTCAGGCTAGTCTCTGGCTCACCTAGGCCCCTAA ATAGTTTAGGGGTGAAGTAACTAGCTCGYCTGGA CGAGCAAGGTTACTTCAGGTTGAAGCAACA[A/G] CTCGCTTGGGTGAGCTCCAGATCAACTAAGTCCC CTCATTTCCTATAAATAGGCATGAGGGGCTGAAA GAAAGGGTTCARCCTTCARATATTGAAAGGATTT AGTGAAATTTGAAGAAAAGAAGAARAAATAAAG GAAAAACAAGGTCGAGGTGCTACCGAATCACGA TCGTAATCGATTTTCACATCGTTCTTCGTTCG |
| Gm08:826 6473 | 8266473 | [G/A] | 41 | 224 | 0.918 | 0.698 | CAGACCCCTGACTCGCTCAGGCTAGTCTCTGGCT CACCTAGGCCCCTAAATAGTTTAGGGGTGAAGTA ACTAGCTCGYCTGGACGAGCAAGGTTACTTCAGG TTGAAGCAACARCTCGCTTGGGTGAGCTCCAGAT CAACTAAGTCCCCTCATTTCCTATAATAGGCAT GAGGGGCTGAAAGAAAGGGTTCARCCTTCA[A/G] ATATTGAAAGGATTTAGTGAAATTTGAAGAAAA GAAGAARAAATAAAGGAAAAACAAGGTCGAGGT GCTACCGAATCACGATCGTAATCGATTTTCACAT CGTTCTTCGTTCGTCATCCGGTTAGTATTTATTTT AAGTATTTCAATTCAATCTATGCACCCATAAGGG TCTTCTTTGTCGATTCATGCATCTTCATCTC |
| Gm08:826 6888 | 8266888 | [T/C] | 42 | 225 | 0.924 | 0.698 | TGTAATCTATTTTCTTTTGGTAAAGTGAGTTTTGA CCGGTCATTTACGTCACCAAACATCTTTTAATTA GTTTGAAGTTTAATAAGTGAAATCAAGTTAAAAT CAACATGTAACCGAGCTTTTTATCCGCAAAATTC ACTTAAATCCGTTCAAGGTCCAAGGCCTTAATGG TCTCTTTTATTTTTGTTGGTTCGAATGAA[C/T]TTT TCAAAAGTTTAAAATCAACTCGACACGCAATTTT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | CTTGTTTTAAGAACTATGTAGGTCTGAGTTTCTCA TCGCAMTTGAGGATACGTAGGAGCAAGGGCAAC GCCTTTGTCGACCCGAAAAAATAAGAAGCATA AAAAGGGAAAATAAGTAATATTGAAGTCACGTT TTTGCACATTCGATTAAAGGTTGTCRTCC |
| Gm08:826 7085 | 8267085 | [A/G] | 43 | 226 | 0.912 | 0.808 | GAAYTTTTCAAAGTTTAAAATCAACTCGACACG CAATTTTCTTGTTTTAAGAACTATGTAGGTCTGAG TTTCTCATCGCAMTTGAGGATACGTAGGAGCAAG GGCAACGCCTTTGTCGACCCGAAAAAATAAGA AGCATAAAAAGGGAAAATAAGTAATATTGAAGT CACGTTTTTGCACATTCGATTAAAGGTTGTC[A/G] TCCCCTGTGACGAAYACGTGGGGTGTTAATACCT TTTTCGCTCGTAAATAACTCCCGTACCCTTATTTT CAAAATTCGCAKATCCCCCTTTTTGGTTTTTCTAA CGTTTTCCTCGAATAAACGTTGGTGGCGACTCCC GCGTGTTTTTCTTTTTGGAAGACGCATCCTTGAGT CTCGCCTCACCCCTCCCGTCGAAGGGT |
| Gm08:826 7166 | 8267166 | [T/G] | 44 | 227 | 1 | 0.836 | MTTGAGGATACGTAGGAGCAAGGGCAACGCCTT TGTCGACCCGAAAAAATAAGAAGCATAAAAAG GGAAAATAAGTAATATTGAAGTCACGTTTTTGCA CATTCGATTAAAGGTTGTCRTCCCCTGTGACGAA YACGTGGGGTGTTAATACCTTTTTCGCTCGTAAA TAACTCCCGTACCCTTATTTTCAAAATTCGCA[G/T] ATCCCCCTTTTTGGTTTTTCTAACGTTTTCCTCGA ATAAACGTTGGTGGCGACTCCCGCGTGTTTTTCTT TTTGGAAGACGCATCCTTGAGTCTCGCCTCACCC CTCCCGTCGAAGGGTAGGTTGCAACAGATAATAA TAAAAAAATTCAACCATGATATTCGCAACAATAA ATTAAATGCACACATACATATATATAGT |
| Gm08:826 7721 | 8267721 | [C/T] | 45 | 228 | 0.817 | 0.772 | GAATTAGTGTGAGTCTCAGATTCTTCAAATGGTC TATGAGTTCATATTCATGCAGTAAYGTCCTACTG CTTTTCTTATCATATATGAAAGTATTCAAAATCTC TTCTTCATCCTAGATGGAGGTATCTATAACTTCAT CTCCATCCCAAATGAAGGTGTCTCGTACATATTC AATTCTCAAAATAAAACATAAATTGTCA[C/T]TAC TTCCTAAAGGATGATAACCAATTCACACATATTT ATAAAATATCATTTCAAATAACTATCAAATAAAT ACTTTAATTCCATATACACTAATTAATAACTTGSA AGGTCATACCTTAGTTATAGCATCACGTAAGTCA ATTTATAATTAACTATGAAATAAAACATACACAC AAATTAAAATATATTTTAGTTGCTAT |
| Gm08:826 7826 | 8267826 | [G/C] | 46 | 229 | 0.831 | 0.824 | CTTCATCCTAGATGGAGGTATCTATAACTTCATCT CCATCCCAAATGAAGGTGTCTCGTACATATTCAA TTCTCAAAATAAAACATAAATTGTCAYTACTTCC TAAAGGATGATAACCAATTCACACATATTTATAA AATATCATTTCAAATAACTATCAAATAAATACTT TAATTCCATATACACTAATTAATAACTTG[C/G]AA GGTCATACCTTAGTTATAGCATCACGTAAGTCAA TTTATAATTAACTATGAAATAAAACATACACACA AATTAAAATATATTTTAGTTGCTATATATGATAG CTAAACACAAAATCCAAACAAGCTGATTGATGA ATTTTCAAATAAATTTTAAGATTGAATATGCAAC TAGTGAATATTTGTACATTGTAATACCTT |
| Gm08:826 8336 | 8268336 | [C/T] | 47 | 230 | 0.829 | 0.561 | ATCTAGTTTCTATCGTGCATATTTGTTGAAGTTAA ACACAAGATCCAAGYAAGCACATATGATGCATT ATAATTGCACTAAAATTTGAATATAGTTTCTATA TATCGTGCATGTTTGTTGGCTCTCCTTGACAAGCA TATCTATTTAATTTATACAAGTAGTAAATAAAT GATAAGACTAAATGATGAGTTCACATATA[C/T]TT TATTTGTACTCWTATATATATATATATATATAATT CTTGGATGGAAAGGACCCCGAAGATACTTCCTTG GGTGGTGACTTGTTACCGGTTTCAAATGGTTACG TTGAGTGGCTTGACTCAAAGGAAGACAAGTCCGT GGTTTACATTTCATTTGGGAGCTACTTTGTGTTGT CTAAGAGACAAACGGAGGAAATTGCA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:826 8861 | 8268861 | [A/C] | 48 | 231 | 1 | 0.722 | CAGGTGGAGGTTCAGTGGGTTGTTTTGTGACGCA CTGTGGTTGGAATTCGACCATGGAGAGCTAGGTT TCGGGGGTGCCCATGGTGGTGTTTCCTCAGTGGT CGTACCAAAAGACAAATGCTAAACTGATAGAAA ATGTGTGGAAGATAGGGGTGAGGGTGGATCATG AGGATGGGAAAGTAGAAGGAGAAAGAGATTAA [A/C]AAGTGTTCGGAAGAGGTGATGGGGAGTGGA GAGTTGAGAATGAATGTAAAGAAATGGAAGGGT TTGGCCAGGGAGGCAGCCAAGGAAGGTGGTCCT TCAGATTTCTTGATGCCATGACGTTGCAGAATCG ATAATCAATGCACGTGTTTGCCAAATAATTGACT TGGATTCCCGTGTTCTCAGTTCTTCCATGCTAAAT T |
| Gm08:826 9148 | 8269148 | [T/C] | 49 | 232 | 0.842 | 0.627 | AGGTGGTCCTTCAGATTTCTTGATGCCATGACGT TGCAGAATCGATAATCAATGCACGTGTTTGCCAA ATAATTGACTTGGATTCCCGTGTTCTCAGTTCTTC CATGCTAAATTATTCTTTTTCTGCTTCTWTTTCTT TTTCCAATCAATTGATTCTATGTTTAAGATTTTA TTATTTAGAACAATTAAATTATTATTG[C/T]TTTA AGAGATAGTATTATTTTAAGTTTAAATGTATATTT TTTATTCATAATTATATCTCTATTTAATCTGGTAT ACTCCTTAAAATTACTTTTATTTAATTATGTTTTT TTTTAAAATAATCAAATTATTCAATCTTATTGATA AGTGGTTTGTATCAAATGCTCACCTAAAAAGAT AAATAGACTCCCAAATATTAGA |
| Gm08:826 9785 | 8269785 | [T/C] | 50 | 233 | 0.912 | 0.808 | AGATAATTAATTTCTTTTAAATGGATGTAGGAAG AGACTAAATTATTACTAATCTTATTGCTTTATATT TTTTATAGTTATCTTTCCACTCCTACAGTACGAAA CACATGTAATAAATCAGTGCCATTAACATACAAC TCGACCTAATTGTAATTTGTAGTAACTTAGATAG TTTAGATTTTTTTTTGTTATGGTATTA[C/T]GTAT TTCATAAAAATTTATATTAATTTTCTTTTGAAAAA TATTATACWTCATATTGTCTTCTTGCCTTTGTAAA ATAAAAGTGTTAAAATATCAATACTYATGTTTAT TTGAACAAGTGAGATGCATGTAATCRCTATCATT ATTTAGGAATGYTAATGAACCTACTTGTTGCACT AATTAAGCYTGTTTCAACCTGTAA |
| Gm08:827 0037 | 8270037 | [G/T] | 51 | 234 | 0.924 | 0.823 | TATTGTCTTCTTGCCTTTGTAAAATAAAAGTGTTA AAATATCAATACTYATGTTTATTTGAACAAGTGA GATGCATGTAATCRCTATCATTATTTAGGAATGY TAATGAACCTACTTGTTGCACTAATTAAGCYTGT TTCAACCTGTAAAAAAAGTCTGTTTCAAAATTA TTTTTTATGCATTTTACTTAAAAAAATTA[G/T]AC CTAATGAATTTTGAATATTGATTTGATTTTTTAA GAGAATATATTTTTGAGTTATATATATATATATTA GTAGTCCTACCTCGTTCTAATATTTTATATTTTTT TAATAAAATATACAAATTTTTAAACAATTTTGTA TTAAGGAAAAATTAATCATTTTATTMTTATAATT ATACAAAATTTAGCTTTGAATGACC |
| Gm08:827 0562 | 8270562 | [C/A] | 52 | 235 | 1 | 0.704 | AATGAAAGTTTGAATATAAAAGGTTACTTTGTTT AAACTTAAAAAAAAATTCTAAAAAATATTTTTTA AGAAGTAAATATGATTTATTTATTAACAAGACAT TTTTCTATTTTAAGAAAAAAATACATAAAAAAT AATTATTTTATTAAAAAATGATCCAAACCCTTCA TCATTAATGTTAATGATTAATCTATTAATT[A/C]A TGTTTAATTTATTATATTATAATTATAATAGATTA TACAAAAGCAATTATACGATTTAATGTTTTATA TATTTAATTTTATATTTAARATGTGGAAGATGCGT TAGCAAGTATTAAGATATTGACTAAAAAAGAAA ATTAAAAAATATATAATTAAAACTAAAGCATTTT CTATAAATAAAAAATATAAGACTTTTTT |
| Gm08:827 0652 | 8270652 | [A/G] | 53 | 236 | 1 | 1 | TTAACAAGACATTTTTCTATTTTAAGAAAAAAA TACATAAAAAATAATTATTTTATTAAAAAATGAT CCAAACCCTTCATCATTAATGTTAATGATTAATCT ATTAATTMATGTTTAATTTATTATATTATAATTAT AATAGATTATACAAAAGCAATTATACGATTTAA TGTTTTATATATTTAATTTTATATTTAA[A/G]ATGT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | GGAAGATGCGTTAGCAAGTATTAAGATATTGACT AAAAAAGAAAATTAAAAAATATATAATTAAAAC TAAAGCATTTTCTATAAATAAAAAATATAAGACT TTTTTTTTACATGACATATAAAACTTACTCTATTC AATATTAAAATTGTTAAAGATTTAACTGGTATAT ACTAATAGTGTAAATATATTTTACAC |
| Gm08:827 1540 | 8271540 | [T/G] | 54 | 237 | 1 | 0.419 | TCAMATATTGATTCATCATGTAGTGAAAAACTAA TCWCTTTTACTCAACCTAASCTGTATCGATGYTA ATCATTGCTCTTAGTACATTGATTATAAAAAAAA TACTAGAAAGATAAAGTTTTTGTTAGAAATCATT TGCGAGTATATTTTAAAATAATTGAAGAATACAT TTTTATGCATTATATAGTTAAAGTGTTTTT[G/T]TT TTCCTTTTTTCACTTCCTCTATTTTAACCACTATTT TCTTTCTACACAMAAAAAAAAAATCCATCATTTTT CTTTTATCCTTTTAACAAATTTTGGTTTTGGACAG TRAACACACACAAAATATATATTTYTCTTCTAAT ATGATTTGTTTTATTTTTGATGCCAATATGTTATG ATTGTTTGATAATGTAAAAAATAT |
| Gm08:827 1591 | 8271591 | [C/A] | 55 | 238 | 0.919 | 0.625 | AASCTGTATCGATGYTAATCATTGCTCTTAGTAC ATTGATTATAAAAAAAATACTAGAAAGATAAAG TTTTTGTTAGAAATCATTTGCGAGTATATTTTAAA ATAATTGAAGAATACATTTTTATGCATTATATAG TTAAAGTGTTTTKTTTTCCTTTTTTCACTTCCTCT ATTTTAACCACTATTTTCTTTCTACACA[A/C]AAA AAAAAAATCCATCATTTTTCTTTTATCCTTTTAACA AATTTTGGTTTTGGACAGTRAACACACACAAAT ATATATTTYTCTTCTAATATGATTTGTTTTATTTTT GATGCCAATATGTTATGATTGTTTGATAATGTAA AAAAATATTASACTAATAATGCGTAGTACTAGYAA TTAACCTCATTTTTWAAATAGTTA |
| Gm08:827 1649 | 8271649 | [A/G] | 56 | 239 | 1 | 0.895 | AAGATAAAGTTTTTGTTAGAAATCATTTGCGAGT ATATTTTAAAATAATTGAAGAATACATTTTTATG CATTATATAGTTAAAGTGTTTTTKTTTTCCTTTTTT CACTTCCTCTATTTTAACCACTATTTTCTTTCTAC ACAMAAAAAAAAAATCCATCATTTTTCTTTTATCC TTTTAACAAATTTTGGTTTTGGACAGT[A/G]AACA CACACAAAATATATATTTYTCTTCTAATATGATTT GTTTTATTTTTGATGCCAATATGTTATGATTGTTT GATAATGTAAAAAATATTASACTAATAATGCGTA GTACTAGYAATTAACCTCATTTTTWAAATAGTTA AAAGAACTTGCTCATTCATTATTAATTTTTCATTA AAAATATTGTACCGGCCACTTTA |
| Gm08:827 1672 | 8271672 | [T/C] | 57 | 240 | 1 | 0.824 | CATTTGCGAGTATATTTTAAAATAATTGAAGAAT ACATTTTTATGCATTATATAGTTAAAGTGTTTTTK TTTTCCTTTTTTCACTTCCTCTATTTTAACCACTAT TTTCTTTCTACACAMAAAAAAAAAATCCATCATTT TTCTTTTATCCTTTTAACAAATTTTGGTTTTGGAC AGTRAACACACACAAAATATATATTT[C/T]TCTTC TAATATGATTTGTTTTATTTTTGATGCCAATATGT TATGATTGTTTGATAATGTAAAAAATATTASACT AATAATGCGTAGTACTAGYAATTAACCTCATTTT TWAAATAGTTAAAAGAACTTGCTCATTCATTATT AATTTTTCATTAAAAATATTGTACCGGCCACTTTA ATTTATTTTCAAATGCTATTAAA |
| Gm08:827 1955 | 8271955 | [T/C] | 58 | 241 | 0.699 | 0.847 | GTAGTACTAGYAATTAACCTCATTTTTWAAATAG TTAAAAGAACTTGCTCATTCATTATTAATTTTTCA TTAAAAATATTGTACCGGCCACTTTAATTTATTTT CAAATGCTATTAAAATAAAGCAATGAGTTAATGA CATTAATTAAGAAATGCATTTAAAATTTTATTAA TATTAAGGATCTTGTTAATTAATGTTTT[C/T]CCCC CACAAGTCTTCTCTTTCAAAGGCCTAATGTACAT TAGGACACTAAATGTCACCCCTTTAAATGAATAT TCAAACATTGATTCATCACTTAGTGAAAARTTAA TCTCTTCCACTTGACTCAACCGGTGCTGATGTTAA CCATTGCTCTTAATATTGGTTATAAAAAATAATA AAAAGATAAAGTTTTTGTTAGAAAT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:8273257 | 8273257 | [G/A] | 59 | 242 | 0.933 | 0.721 | ACCCAACGGTGCTTGTGAACACCTTTGAAGCTTT GGAAGAAGAAGCGTTGAGGGCCATTGATAAGAT CAACATGATCCCCATCGGGCCGTTGATTCCTTCT GCGTTCTTGGACGGGAATGACCCAACTGATACTT CGTTTGGTGGGGACATTTTTCAAGTCTCAAATGA TTACGTTGAATGGCTTGACTCAAAGGAAGAG[A/G] ATTCGGTGGTTTACGTTTCATTTGGTAGCTACTT TGAGCTTTCTAAGAGACAAATGGAGGAAATTGC ACGTGGGTTATTAGATTGTGGACGTCCATTYTTG TGGGTCGTTAGAGAAAAGGTAATTAATGGAAAA AAAGAAGAGGAGGAGGAGCTTTGTTGTTTCAGA GAGGAATTGGAGAAGTGGGGGAAGATAGTGACA |
| Gm08:8273355 | 8273355 | [T/C] | 60 | 243 | 0.854 | 0.825 | TCTGCGTTCTTGGACGGGAATGACCCAACTGATA CTTCGTTTGGTGGGGACATTTTTCAAGTCTCAAAT GATTACGTTGAATGGCTTGACTCAAAGGAAGAGR ATTCGGTGGTTTACGTTTCATTTGGTAGCTACTTT GAGCTTTCTAAGAGACAAATGGAGGAAATTGCA CGTGGGTTATTAGATTGTGGACGTCCATT[C/T]TT GTGGGTCGTTAGAGAAAAGGTAATTAATGGAAA AAAGAAGAGGAGGAGGAGCTTTGTTGTTTCAG AGAGGAATTGGAGAAGTGGGGGAAGATAGTGAC ATGGTGTTCTCAGGTGGAGGTTCTTTCGCATTCTT CTGTGGGTTGTTTTTAACACACTGTGGGTGGAA TTCGACCATGGAAAGCCTTGTTTCTGGGGT |
| Gm08:8273979 | 8273979 | [A/C] | 61 | 244 | 0.87 | 0.734 | GCGAAAGAAGGTGGCTCTTCAGAAGAATCTG AGGGCATTTGTGGATGATGTTAGACAAAAATTTA TGCATACACATGTGGGTGAATATTAATTAAGTTC GTCTCTAACTAGCTAGTAGTAAGCTGTAATGTGT TATTGTATGCTTATGATGCATGGCTTCAAACATT GAAAGATGAACTGAAAAAATTAAGAAATTAT[A/ C]AGTCAGTTAATAAAAATGTGCGAAAATGGAAT ATCTTCAATAATAACATGTGCGTRTTGCTAAAAA ATGAGTTGTTGTCACGTTAGATGGTGGATGCCAT ATAACTGTCCAATATGTTGCCCAATTCGTCAGGA AAAGATAAATATTTTGATAAAGATTATTATTACA TTGTTGCTTTATACTCCCTTCCTTTCTTTTTA |
| Gm08:8275766 | 8275766 | [T/G] | 62 | 245 | 0.928 | 0.903 | TGAAATGTCAATCAAAATATACAACAGTATGTGC ATGGATTCTTGATGACAATAATTCCAAAACCACA AATATGTATTTATAATCATCTTAAAAGCTCAGT GAGACACTTAGCKGTACAAATTAAATTTTTTAAA TCGTTGGGCAAAGAATCATCAGCAAATGTAGTTT TTTTTTTTTTTGAGAAATCACCCAATGTA[G/T]TC AATTGCGGAAGSAGGAGCTTGTCATTCCAGTAGT CCAATTTTTCAGTTATACTTTTGATTTTTATAGGG TAAGTACTAAGTAACCTAGCTAGTTTCTTAATCT CATGATCTCTTGGCTTATYTTTTTTTTTTTWAAT TGTGCTTGAGTCACTATACATATTTACTTGGTTG TCGAACAAAATTAAAATYTCTTCGT |
| Gm08:8275780 | 8275780 | [C/G] | 63 | 246 | 0.924 | 0.823 | AAATATACAACAGTATGTGCATGGATTCTTGATG ACAATAATTCCAAAACCACAAATATGTATTTATA ATCATCTTAAAAGCTCTAGTGAGACACTTAGCKG TACAAATTAAATTTTTTAAATCGTTGGGCAAAGA ATCATCAGCAAATGTAGTTTTTTTTTTTTTTTGAG AAATCACCCAATGTAKTCAATTGCGGAAG[C/G]A GGAGCTTGTCATTCCAGTAGTCCAATTTTTCAGTT ATACTTTTGATTTTTATAGGGTAAGTACTAAGTA ACCTAGCTAGTTTCTTAATCTCATGATCTCTTGGC TTATYTTTTTTTTTTWAATTTGTGCTTGAGTCA CTATACATATTTACTTGGTTGTCGAACAAAATTA AAATYTCTTCGTACCTAAACAAAACC |
| Gm08:8275959 | 8275959 | [T/C] | 64 | 247 | 0.929 | 0.837 | CAATGTAKTCAATTGCGGAAGSAGGAGCTTGTCA TTCCAGTAGTCCAATTTTTCAGTTATACTTTTGAT TTTTATAGGGTAAGTACTAAGTAACCTAGCTAGT TTCTTAATCTCATGATCTCTTGGCTTATYTTTTTTT TTTTTWAATTTGTGCTTGAGTCACTATACATATTT ACTTGGTTGTCGAACAAAATTAAAAT[C/T]TCTTC GTACCTAAACAAAACCTAACTTAAAGTCCCAGAC |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| | | | | | | | TAATTCAACAATAATCAACTCAATTTTTTTTTTT<br>TGCATGTTACATTTCATACATTAACTGTTGAGCTA<br>CTTTATGGGTTCCCTCCCGTGTAGGGTTTGTTTAA<br>TGATATTAGCTTGAAGTTTTCACTCTTTTGATCTT<br>CAAGAAGAGTTAAAGGTGGAC |
| Gm08:827<br>6701 | 8276701 | [T/C] | 65 | 248 | 0.874 | 0.923 | GCAACTTGAGGCTGAACTCGGTCGTGCGGTCAAG<br>CAAGACATTTCTGTGTACGTAGCTGTACAATAAT<br>ATACAATGAATTAGAATAATAACAGATTATGTGG<br>CATTAATTATTACAGCAGCAACTCATTCCTTGATT<br>CTGGGAATTAGCAATTTCTTCCAGCTTATATATAT<br>ACCAGCATCTCAATCCTTGATTGTACGA[C/T]ATA<br>ATTTTGCAATTTGATCCAAATTTATTACAGCTAGT<br>TAGGATACTACTCGTCTTACAATTTTTGACAAGG<br>TTTTGTCAGCAATGTTGAGGATGTTTAAGCTGAA<br>CACCGTCCGAGAAGTAAAATACTATTAAAGGAG<br>GCTAAAGGRATATATTGGATTAGAATTTTAAAAG<br>ATTATTTTAATATAAAAGGTTATATGA |
| Gm08:827<br>6849 | 8276849 | [A/G] | 66 | 249 | 0.904 | 0.79 | CAATTTCTTCCAGCTTATATATATACCAGCATCTC<br>AATCCTTGATTGTACGAYATAATTTTGCAATTTG<br>ATCCAAATTTATTACAGCTAGTTAGGATACTACT<br>CGTCTTACAATTTTTGACAAGGTTTTGTCAGCAAT<br>GTTGAGGATGTTTAAGCTGAACACCGTCCGAGAA<br>GTAAAATACTATTAAAGGAGGCTAAAGG[A/G]AT<br>ATATTGGATTAGAATTTTAAAAGATTATTTTAAT<br>ATAAAAGGTTATATGAATTTTAAAAATKATGTAG<br>AAGTATTATGACTTATTATATTTTTTACAARATT<br>TTTATAATAGTTTTAATTTTAATAAATTTATATGA<br>TAAGAATTTAAAAGACTTAAATTTTTTTAAAAAA<br>ATTTATAARATTTAAAAGAATTATAT |
| Gm08:827<br>6913 | 8276913 | [T/G] | 67 | 250 | 0.684 | 0.827 | ATTTGATCCAAATTTATTACAGCTAGTTAGGATA<br>CTACTCGTCTTACAATTTTTGACAAGGTTTTGTCA<br>GCAATGTTGAGGATGTTTAAGCTGAACACCGTCC<br>GAGAAGTAAAATACTATTAAAGGAGGCTAAAGG<br>RATATATTGGATTAGAATTTTAAAAGATTATTTT<br>AATATAAAAGGTTATATGAATTTTAAAAAT[G/T]<br>ATGTAGAAGTATTATGACTTATTATATTTTTTAC<br>AARATTTTTATAATAGTTTTAATTTTAATAAATTT<br>ATATGATAAGAATTTAAAAGACTTAAATTTTTTT<br>AAAAAAATTTATAARATTTAAAAGAATTATATGA<br>ATTTTTAAAATCACATTCAAAATTACAATAATTA<br>ATGAAGAAAATAACAAAAATAATGAGA |
| Gm08:827<br>7162 | 8277162 | [A/G] | 68 | 251 | 0.904 | 0.655 | TAGTTTTAATTTTAATAAATTTATATGATAAGAAT<br>TTAAAAGACTTAAATTTTTTTAAAAAAATTTATA<br>ARATTTAAAAGAATTATATGAATTTTTAAAATCA<br>CATTCAAAATTACAATAATTAATGAAGAAAATAA<br>CAAAAATAATGAGATTTGGATAAAAAAAGTAA<br>AATCAAAACAATTTTTTTAATCTTTCAATA[A/G]C<br>ATATTGATTCTAACTTTATATTCTCCTATATTAAC<br>CTTTCATGCAATAATATCTTCTCATTCTYACTTTT<br>GAATTTGAACAATARATTTAAAATTATACATTGA<br>TTTTCTGATTTTTTTAATTAGTCTAATTATTTCATA<br>ATAAATATAATGACATGTTATGGAATGCAATAAT<br>AAATATATACTAAAAAGAGTAATA |
| Gm08:827<br>7227 | 8277227 | [T/C] | 69 | 252 | 0.918 | 0.743 | TATAARATTTAAAAGAATTATATGAATTTTTAAA<br>ATCACATTCAAAATTACAATAATTAATGAAGAAA<br>ATAACAAAAATAATGAGATTTGGATAAAAAAA<br>GTAAAATCAAAACAATTTTTTTAATCTTTCAATA<br>RCATATTGATTCTAACTTTATATTCTCCTATATTA<br>ACCTTTCATGCAATAATATCTTCTCATTCT[C/T]AC<br>TTTTGAATTTGAACAATARATTTAAAATTATACA<br>TTGATTTTCTGATTTTTTTAATTAGTCTAATTATTT<br>CATAATAAATATAATGACATGTTATGGAATGCAA<br>TAATAAATATATACTAAAAAGAGTAATAAGAG<br>TGTGAAATTGGTAYRASAGTTATTAAGTCATGTG<br>GATAATGAAATTAAGAGTAACATTTAT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:827 7248 | 8277248 | [A/G] | 70 | 253 | 1 | 0.824 | ATGAATTTTTAAAATCACATTCAAAATTACAATA ATTAATGAAGAAAATAACAAAAAATAATGAGAT TTGGATAAAAAAAGTAAAATCAAAACAATTTTTT TAATCTTTCAATARCATATTGATTCTAACTTTATA TTCTCCTATATTAACCTTTCATGCAATAATATCTT CTCATTCTYACTTTTGAATTTGAACAATA[A/G]AT TTAAAATTATACATTGATTTTCTGATTTTTTTAAT TAGTCTAATTATTTCATAATAAATATAATGACAT GTTATGGAATGCAATAATAAATATATACTAAAAA AGAGTAATAAGAGTGTGAAATTGGTAYRASAGTT ATTAAGTCATGTGGATAATGAAATTAAGAGTAAC ATTTATGAAAATATTATATTGAGCAAG |
| Gm08:827 7381 | 8277381 | [G/A] | 71 | 254 | 1 | 0.756 | ATATTCTCCTATATTAACCTTTCATGCAATAATAT CTTCTCATTCTYACTTTTGAATTTGAACAATARAT TTAAAATTATACATTGATTTTCTGATTTTTTTAAT TAGTCTAATTATTTCATAATAAATATAATGACAT GTTATGGAATGCAATAATAAATATATACTAAAAA AGAGTAATAAGAGTGTGAAATTGGTAY[A/G]ASA GTTATTAAGTCATGTGGATAATGAAATTAAGAGT AACATTTATGAAAATATTATATTGAGCAAGTTAT AAACATAATCAMTAAAACTCATCATAAGAAAAA AAACATGATTAGTCTTGACACATAAGATAAACAT TAATTTAATTTAAAAAACAAAGRAAAAAGTGTA GAGGGGAGACATATATTTGACATTTTTTA |
| Gm08:827 7383 | 8277383 | [C/G] | 72 | 255 | 1 | 0.755 | ATTCTCCTATATTAACCTTTCATGCAATAATATCT TCTCATTCTYACTTTTGAATTTGAACAATARATTT AAAATTATACATTGATTTTCTGATTTTTTTAATTA GTCTAATTATTTCATAATAAATATAATGACATGT TATGGAATGCAATAATAAATATATACTAAAAAA GAGTAATAAGAGTGTGAAATTGGTAYRA[C/G]AG TTATTAAGTCATGTGGATAATGAAATTAAGAGTA ACATTTATGAAAATATTATATTGAGCAAGTTATA AACATAATCAMTAAAACTCATCATAAGAAAAAA AACATGATTAGTCTTGACACATAAGATAAACATT AATTTAATTTAAAAAACAAAGRAAAAGTGTAG AGGGGAGACATATATTTGACATTTTTTATT |
| Gm08:827 7542 | 8277542 | [A/G] | 73 | 256 | 0.862 | 0.648 | ATATACTAAAAAAGAGTAATAAGAGTGTGAAAT TGGTAYRASAGTTATTAAGTCATGTGGATAATGA AATTAAGAGTAACATTTATGAAAATATTATATTG AGCAAGTTATAAACATAATCAMTAAAACTCATC ATAAGAAAAAAACATGATTAGTCTTGACACAT AAGATAAACATTAATTTAATTTAAAAAACAAAG [A/G]AAAAGTGTAGAGGGGAGACATATATTTGA CATTTTTTATTTCAAAAGAATAAGAGAAATATAT ATGGTGCTTGCATCTTGAWGAACATTAAATAGAT AARAAGATATGTGTGATAAAAGAAAAAAAAAG TGTGGTAATCAATAGAAAAAAAAAAAGAGWAAA ATCATTCAAATCATTCAATAGAAAAGTGTGGGGT TGT |
| Gm08:827 7625 | 8277625 | [T/A] | 74 | 257 | 0.895 | 0.622 | TATGAAAATATTATATTGAGCAAGTTATAAACAT AATCAMTAAAACTCATCATAAGAAAAAAAACAT GATTAGTCTTGACACATAAGATAAACATTAATTT AATTTAAAAAACAAAGRAAAAAGTGTAGAGGGG AGACATATATTTGACATTTTTTATTTCAAAAGAA TAAGAGAAATATATATGGTGCTTGCATCTTGA[A/ T]GAACATTAAATAGATAARAAGATATGTGTGAT AAAAGAAAAAAAAAGTGTGGTAATCAATAGAA AAAAAAAGAGWAAAATCATTCAAATCATTCAA TAGAAAAGTGTGGGGTTGTTTAATTGATGTTTTA TATTAAAAATTAGATGAAATTCATCCAAATCAT TCTTAAAAAATAATGCATCAAAATTTGTATATTT |
| Gm08:827 7643 | 8277643 | [A/G] | 75 | 258 | 0.87 | 0.53 | AGCAAGTTATAAACATAATCAMTAAAACTCATC ATAAGAAAAAAACATGATTAGTCTTGACACAT AAGATAAACATTAATTTAATTTAAAAAACAAAGR AAAAGTGTAGAGGGGAGACATATATTTGACAT TTTTATTTCAAAAGAATAAGAGAAATATATATG GTGCTTGCATCTTGAWGAACATTAAATAGATAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | [A/G]AAGATATGTGTGATAAAAGAAAAAAAAAAG<br>TGTGGTAATCAATAGAAAAAAAAAAGAGWAAAA<br>ATCATTCAAATCATTCAATAGAAAAGTGTGGGGT<br>TGTTTAATTGATGTTTTATATTAAAAAATTAGATG<br>AAATTCATCCAAATCATTCTTAAAAAATAATGCA<br>TCAAAATTTGTATATTTTTAAATATTAAAAGACTT |
| Gm08:827<br>7876 | 8277876 | [C/T] | 76 | 259 | 0.836 | 0.713 | TGGTAATCAATAGAAAAAAAAAAGAGWAAAATC<br>ATTCAAATCATTCAATAGAAAAGTGTGGGGTTGT<br>TTAATTGATGTTTTATATTAAAAAATTAGATGAA<br>ATTCATCCAAATCATTCTTAAAAAATAATGCATC<br>AAAATTTGTATATTTTTAAATATTAAAAGACTTTT<br>TTATAAGTTATAAAAAATTATAATTGAATA[C/T]C<br>ACMAAATTTTATTATTTTTCTTAAAAAATCTTAW<br>ATGTTTTAATTGAATACCATAAGACTTTTTTATAT<br>AAAAAHTATTTTAAAATCTTTTMAAATCTTAATC<br>YAATATATCCACTAAGTTATYAAAGGCTAGGAG<br>GAAACAAGTGGASCATGAGACAATACATATATA<br>GGGGGGGAATATATGGAAATTGAAAAAAAAA |
| Gm08:827<br>7880 | 8277880 | [C/A] | 77 | 260 | 0.809 | 0.673 | AATCAATAGAAAAAAAAAAGAGWAAAATCATTC<br>AAATCATTCAATAGAAAAGTGTGGGGTTGTTTAA<br>TTGATGTTTTATATTAAAAAATTAGATGAAATTC<br>ATCCAAATCATTCTTAAAAAATAATGCATCAAAA<br>TTTGTATATTTTTAAATATTAAAAGACTTTTTTAT<br>AAGTTATAAAAAATTATAATTGAATAYCAC[A/C]<br>AAATTTTATTATTTTTCTTAAAAAATCTTAWATGT<br>TTTAATTGAATACCATAAGACTTTTTTATATAAA<br>AAHTATTTTAAAATCTTTTMAAATCTTAATCYAA<br>TATATCCACTAAGTTATYAAAGGCTAGGAGGAA<br>ACAAGTGGASCATGAGACAATACATATATAGGG<br>GGGAATATATGGAAATTGAAAAAAAAAAGAT |
| Gm08:827<br>7969 | 8277969 | [C/A] | 78 | 261 | 0.87 | 0.658 | TAGATGAAATTCATCCAAATCATTCTTAAAAAAT<br>AATGCATCAAAATTTGTATATTTTTAAATATTAA<br>AAGACTTTTTTATAAGTTATAAAAAATTATAATT<br>GAATAYCACMAAATTTTATTATTTTTCTTAAAAA<br>ATCTTAWATGTTTTAATTGAATACCATAAGACTT<br>TTTTATATAAAAAHTATTTTAAAATCTTTT[A/C]A<br>AATCTTAATCYAATATATCCACTAAGTTATYAAA<br>GGCTAGGAGGAAACAAGTGGASCATGAGACAAT<br>ACATATATAGGGGGGAATATATGGAAATTGAAA<br>AAAAAAGATGTGAAAAATAATAAATCTCAATA<br>GAAAATGAAGGAAGCATAAATGAAATAAAAGTG<br>AAATCAGGTGATGAGATAAAAAACAATTGTSTA |
| Gm08:827<br>8001 | 8278001 | [T/C] | 79 | 262 | 0.884 | 0.741 | ATAATGCATCAAAATTTGTATATTTTTAAATATTA<br>AAAGACTTTTTTATAAGTTATAAAAAATTATAAT<br>TGAATAYCACMAAATTTTATTATTTTTCTTAAAA<br>AATCTTAWATGTTTTAATTGAATACCATAAGACT<br>TTTTTATATAAAAAHTATTTTAAAATCTTTTMAA<br>ATCTTAATCYAATATATCCACTAAGTTAT[C/T]AA<br>AGGCTAGGAGGAAACAAGTGGASCATGAGACAA<br>TACATATATAGGGGGGAATATATGGAAATTGAA<br>AAAAAAAGATGTGAAAAATAATAAATCTCAAT<br>AGAAAATGAAGGAAGCATAAATGAAATAAAAGT<br>GAAATCAGGTGATGAGATAAAAAACAATTGTSTA<br>AAAAAATTGACGATAAGTCTATAATAAATAAA |
| Gm08:827<br>8167 | 8278167 | [C/G] | 80 | 263 | 0.861 | 0.847 | TTMAAATCTTAATCYAATATATCCACTAAGTTAT<br>YAAAGGCTAGGAGGAAACAAGTGGASCATGAGA<br>CAATACATATATAGGGGGGAATATATGGAAATT<br>GAAAAAAAAAGATGTGAAAAATAATAAATCTC<br>AATAGAAAATGAAGGAAGCATAAATGAAATAAA<br>AGTGAAATCAGGTGATGAGATAAAAAACAATTG<br>T[C/G]TAAAAAAATTGACGATAAGTCTATAATAA<br>ATAAAAAGTGAGGTCATATACATATTCCCGATTT<br>CTATAAAAAAAATGAATATTTGAAAATCAATTC<br>ATTTTCAATYTTTAAAAAATAAATAAAAAGAAT<br>TGAAGTTGTATATCAATCTATGGAGAATTAATTC<br>AAAAAATGATTTATAGAAGTTAGCAATAGAAAA<br>AT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:8278274 | 8278274 | [C/T] | 81 | 264 | 0.831 | 0.628 | AAAAGATGTGAAAAATAATAAATCTCAATAGAA AATGAAGGAAGCATAAATGAAATAAAAGTGAAA TCAGGTGATGAGATAAAAAACAATTGTSTAAAAA AATTGACGATAAGTCTATAATAAATAAAAAGTG AGGTCATATACATATTCCCGATTTCTATAAAAAA AAATGAATATTTGAAAATCAATTCATTTTCAAT[C/ T]TTTAAAAAATAAATAAAAAAGAATTGAAGTTG TATATCAATCTATGGAGAATTAATTCAAAAAATG ATTTATAGAAGTTAGCAATAGAAAAATACGTACT AACATTATAAGAAAGAGAAAATATTTTAAGAGA TAAATAGCAAAATAATATTTTATTTAASTGAATGA GTATCTTAAACCATATATCAAAATTTACAACAC |
| Gm08:8278434 | 8278434 | [C/G] | 82 | 265 | 0.858 | 0.647 | TAAAAAAAATGAATATTTGAAAATCAATTCATT TTCAATYTTTAAAAAATAAATAAAAAAGAATTGA AGTTGTATATCAATCTATGGAGAATTAATTCAAA AAATGATTTATAGAAGTTAGCAATAGAAAAATA CGTACTAACATTATAAGAAAGAGAAAATATTTTA AGAGATAAATAGCAAAATAATATTTATTTAA[C/G] TGAATGAGTATCTTAAACCATATATCAAAATTTA CAACACATTAAAATGAAAATCTTAAAAAGAAG GAACAACAAAACTTTTTATGAAAATTATAACCAA AAAAAAATAAAAATTAATATAAAGCTTAACATTT CTTTTGTTGAAGTACTAATATAAAGCTTAACATG ATAGCTAGGATAAGCACTATCCTATGGCCAC |
| Gm08:8279165 | 8279165 | [T/G] | 83 | 266 | 0.83 | 0.759 | TTTTGGTAAACAGATTTAATTTGATGTAAATCAT ATTAACATAATTAATATTAGGTATTTTAATAATTT TTTATTATTTTATTTGTATTGTTCATTAWTTGTTR AATAATATATAAGATAAAAAACATTTGTCATTT ATCTTTATCCTATCTTATTTTTTATCTTGTCTAATA TCATATTTTTAACAAATCAAATWGGG[G/T]GTAA GTGTTTGATAAATTTTTTCAAACAAATTACAAAT GTTAATATATTTTATTTTTTCAACAAKTAATATGT TAATCTTAATAAACAAATTCACATTTTATTTTTCA TTTACCAAAATAGATATATTATTTTTAAATATTGT TTGAAATAAATAATTTATAATTAATTWAAAAAA ATAAWAATTTCATTTCGTAACATA |
| Gm08:8279230 | 8279230 | [T/G] | 84 | 267 | 0.903 | 0.797 | ATTTTTTATTATTTTATTTGTATTGTTCATTAWTT GTTRAATAATATATAAGATAAAAAACATTTGTC ATTTATCTTTATCCTATCTTATTTTTTATCTTGTCT AATATCATATTTTTAACAAATCAAATWGGGKGTA AGTGTTTGATAAATTTTTTCAAACAAATTACAAA TGTTAATATATTTTATTTTTTCAACAA[G/T]TAATA TGTTAATCTTAATAAACAAATTCACATTTTATTTT TCATTTACCAAAATAGATATATTATTTTTAAATAT TGTTTGAAATAAATAATTTATAATTAATTWAAAA AAATAAWAATTTCATTTCGTAACATATTTTTCAC ATTGAAATAAACATGTACGACACACATATATACA TACATATATATATATATATAT |
| Gm08:8279854 | 8279854 | [A/C] | 85 | 268 | 0.842 | 0.759 | AAAAATAATTCATATTAATATACCAACTTAAGAA AGCTGTTAAATATATTAAAAAAAGGAAATATGTT ATTATTAAATCAAATTTTCATCAGTTAACAACCA ACATTTAATCTAATTTAGTTGTTTAAACAAAATT TGTATGTATTATAAATTTTTAATATTATTTTTATT TTTAAAAATAAAAACAGTGAAACAAT[A/C]AA CCTTGCATTATCATATATAGTCAATTAAAAAAAA GGAATGAGTGAAGGGGAAAAAGTGGAGGAAAA GGTAATGGATTCAATTCCTTCCATTAATATTTTAA ACAAAAATTAATAAATTAACATATTGGTAAAAA ATATAATATATTAATTTCTTGAAAATTTGTATCCAGT AGTACAACATTATAAATTATTTTTTAGGT |
| Gm08:8280901 | 8280901 | [A/C] | 86 | 269 | 0.929 | 0.848 | TTCTGCCAATGGAAGGGTATCCAATGCGATTCAT CCAGCCACGTGACCAGCATAAGCCTCGCTTCGCA KTCCCTCACCGGAACACTCCCCTCGGATCTCAAT TCCCTCTCTCAACTCCGCACTCTCTCCCTCCAAGA CAATTCCCTCACCGGCACCCTCCCTTCTCTCTCCA ACCTTTCTTTCCTCCAAACCGTCTACTT[A/C]AAC |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | CGCAACAACTTCTCCTCCGTGTCCCCCACCGCYT TCGCCTCCCTAACCTCCCTCCAAACCCTCAGCCTC GGCTCCAACCCTGCTCTCCAACCCTGGTCCTTCCC CACCGACCTCACTTCCTCCTCTAACCTAATCGAC CTCGACCTCGCCACCGTATCCCTCACCGGTCCCTT GCCGGACATTTTCGACAAATTCCC |
| Gm08:828 0937 | 8280937 | [T/C] | 87 | 270 | 1 | 0.848 | AGCCACGTGACCAGCATAAGCCTCGCTTCGCAKT CCCTCACCGGAACACTCCCCTCGGATCTCAATTC CCTCTCTCAACTCCGCACTCTCTCCCTCCAAGACA ATTCCCTCACCGGCACCCTCCCTTCTCTCTCCAAC CTTTCTTTCCTCCAAACCGTCTACTTMAACCGCA ACAACTTCTCCTCCGTGTCCCCCACCGC[C/T]TTC GCCTCCCTAACCTCCCTCCAAACCCTCAGCCTCG GCTCCAACCCTGCTCTCCAACCCTGGTCCTTCCCC ACCGACCTCACTTCCTCCTCTAACCTAATCGACCT CGACCTCGCCACCGTATCCCTCACCGGTCCCTTG CCGGACATTTTCGACAAATTCCCTTCCCTTCAAC ACCTTCGCCTCTCTTACAACAACCT |
| Gm08:828 1564 | 8281564 | [A/G] | 88 | 271 | 0.924 | 0.824 | GTTCCCGCTTCATTGACAAGTCTTCCTAGTTTGAA GAAAGTTTCTCTGGATAATAATGAGCTTCAGGGG CCTGTGCCCGTGTTTGGGAAAGGTGTGAATGTTA CTCTCGATGGGATTAATAGTTTTTGTCTTGATACT CCTGGGAATTGTGATCCCAGGGTGATGGTTTTGC TGCAGATTGCCGAGGCATTCGGGTATCC[A/G]ATT CGGTYGGCAGAGTCGTGGAAGGGGAATGATCCG TGTGATGGTTGGAACTATGTTGTGTGTGCTGCCG GAAAGATTATTACTGTCAATTTCGAGAAACAGGG TTTGCAGGGTACCATCTCCCCTGCATTTGCCAATT TGACTGACTTGAGGACTTTGTTTCTCAATGGCAA TAATTTGATCGGTTCTATACCTGATAG |
| Gm08:828 2902 | 8282902 | [T/G] | 89 | 272 | 1 | 0.848 | AAGGTTGCTGATTTTGGGTTGGTTAAAAATGCAC CAGATGGGAAGTATTCTGTTGAGACACGGTTGGC TGGAACATTTGGATATCTTGCACCTGAGTATGCA GGTACAGAAAGCCTTTGATTTTAGTTTTGTACAA TTGTGCCTTAATTTTGAAGTTCATATTTTATATGC TCGTATTTGGTGGTTATAGCTGTTGGTTA[G/T]TA CTTCAATATCATGCTTCGGTGTTCAGCAAATTTA AGTAGTTCACCAGAGTAATCGCTCACATACAAAA AAAAAGTAGAAAGAGTTGAAGGGAAAATAATTG ATACTCAATTCCTAGATACATGGCTACTTCAAAA TTCTTTGTGGCTATTTCTTTGCAATGTTATATTTT GCTCTTTTCACGTGTTTTGTTGAGTTGG |
| Gm08:828 4027 | 8284027 | [T/C] | 90 | 273 | 0.863 | 0.744 | GGAGCAATGGAAACCTACTAGCCATGATGAAGA AGAGGAAGACGGCTCTGGCGGTGACCTTCATATG AGCCTTCCTCAAGCTCTACGAAGGTGGCAAGCCA ACGAAGGCACTTCCTCAATATTTAATGACATTTC CATCTCACAAACCCAATCAAGCATCTCCTCTAAA CCTGCAGGGTTTGCAGACTCCTTTGATTCAA[C/T] GGATTGCCGTTAACCGAATTGATAAACGAGACA ACTATCCAAGGGCATCTTAGTCCATATGATAGTG GAAGGTTTAGTTGAGAATACCCAAGAAAACCAG AGGTTGTAAAGCTGTTTTGATCTATTAGCATCGC CAATTTCTTTGTAATTATTATTATTGTTCAAAAT GTCATTTTATGGTGTTCTTAAAATCTCCTC |
| Gm08:828 6864 | 8286864 | [A/T] | 91 | 274 | 1 | 0.687 | CAAGATTTGTAAGAGAAAACTTCTTGGCTCTATA TTTAASAACAAAAAATCTAAGAKRAAATGGGATT KAATGGAAATGATCGGTCGCAAGCATATCTAAAT TTGACAGGAAATCCATAAATGACTTGACCACCAT TAACAAGATAAATATTGTGTGAGATCTTTAAAAR TGAAGATTTTACGGGTTTAACAGATTAAAA[A/T]C TTTTACAATTTAATATCACATTCTTTTGAACACAT GAACACTTATTGATGATAGTTACATTCCATGCTT GCTTTCCTTGCACTTTATTTTTTGTTGGAAATTGA TCTAYGGAGAGATCTTTCAAGGAACATTGGCTAT AGCTGACATGATGATWGRAGGAAAAATTACAAA CAATAATTTATACAAATTTTATGTTTCA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:828 7265 | 8287265 | [T/C] | 92 | 275 | 0.776 | 0.917 | TAMAATAGAAGAAACCAGTATCTTGACTTCTTGA GAAATGAGGACAAGGAGCAAAACTATGCTAAGA ATCTTGATGGCTGAACCASCCATTTCAGAAAATG TAAATACAAGCTTCGATTCTCGAATTGCATAGCT CTTATATGTCGCGTTATTTATAAATGAATTGTTGT AATTTGTAAAACAATATGTTTTACGTTTCG[C/T]G TGAAGAATATCRCATTTATGAATGACTGAATTTT TAAGACAATGAAACTGAAGTTAAAGAAACATAA ATTACTCTAAAAAAAATTAAATACAGTGAAATTG TATAGATTTGATAAATATTTTTTTAATAGTTGATA TGATTTTGTTTTGTTAGGAGAAAGCTATCATTTTG TTCTCCTATAGTTATSTTTAGYAAGTTA |
| Gm08:828 7278 | 8287278 | [A/G] | 93 | 276 | 0.76 | 0.91 | ACCAGTATCTTGACTTCTTGAGAAATGAGGACAA GGAGCAAAACTATGCTAAGATCTTGATGGCTGA ACCASCCATTTCAGAAAATGTAAATACAAGCTTC GATTCTCGAATTGCATAGCTCTTATATGTCGCGTT ATTTATAAATGAATTGTTGTAATTTGTAAAACAA TATGTTTTACGTTTCGYGTGAAGAATATC[A/G]CA TTTATGAATGACTGAATTTTTAAGACAATGAAAC TGAAGTTAAAGAAACATAAATTACTCTAAAAAA AATTAAATACAGTGAAATTGTATAGATTTGATAA ATATTTTTTAATAGTTGATATGATTTTGTTTTGT TAGGAGAAAGCTATCATTTTGTTCTCCTATAGTT ATSTTTAGYAAGTTATTTTAATTAAATT |
| Gm08:828 7453 | 8287453 | [G/C] | 94 | 277 | 1 | 0.738 | TTTTACGTTTCGYGTGAAGAATATCRCATTTATG AATGACTGAATTTTTAAGACAATGAAACTGAAGT TAAAGAAACATAAATTACTCTAAAAAAAATTAA ATACAGTGAAATTGTATAGATTTGATAAATATTT TTTTAATAGTTGATATGATTTTGTTTTGTTAGGAG AAAGCTATCATTTTGTTCTCCTATAGTTAT[C/G]TT TAGYAAGTTATTTTAATTAAATTTTTTTATTAATT AAAAGATTTATTTGACTATTTGATAAATAATTTTT TTAAGTAATTTTTAATGTTTCTCTAGTATYTTTTA GTATTTTTTAAAATATTATTTAAAATAACATTTT TTAAACACTAATTTTTAATTTTTAACCTTTTTAATT TTATTCTCTTTATATCTTAAAAT |
| Gm08:828 7459 | 8287459 | [T/C] | 95 | 278 | 1 | 0.591 | GTTTCGYGTGAAGAATATCRCATTTATGAATGAC TGAATTTTTAAGACAATGAAACTGAAGTTAAAGA AACATAAATTACTCTAAAAAAAATTAAATACAGT GAAATTGTATAGATTTGATAAATATTTTTTTAATA GTTGATATGATTTGTTTTGTTAGGAGAAAGCTA TCATTTTGTTCTCCTATAGTTATSTTTAG[C/T]AAG TTATTTTAATTAAATTTTTTATTAATTAAAAGAT TTATTTGACTATTTGATAAATAATTTTTTTAAGTA ATTTTTAATGTTTCTCTAGTATYTTTTAGTATTTTT TTAAAATATTATTTAAAATAACATTTTTTAAACA CTAATTTTTAATTTTTAACCTTTTAATTTTATTCTC TTTATATCTTAAAATATTTAT |
| Gm08:828 8039 | 8288039 | [G/C] | 96 | 279 | 0.884 | 0.584 | TAACTTTTCAGTTTACTTTTGCAAATAAYATATTT CTTTCCTGGMATATKACAAAGCTAAACAATATTT CTTGAGTGTTTAATTGTTTTAAATTGAAATAGGA AGTGAGCATTTMCTAATATCTTAGCTCGAAACAT CTCTTTCATCTTTGTTGAAGTAAACCTCTGTATGG TAAAATTAAGAGGAGAAAGAAAAATGAA[C/G]T GGAGTAAGGTCTTGTTTGAAATTATTTTTTAATTT CAAAACTTGTTTTCAATATAATTTTTAGCTTTGTT ATATTTTAAAAATAAAATAAAAGAAAAAYAT TTGTTAAAATTCAAAAATAGATTTTTTTAAAAA AATGTTCATAAAATATCAGCATYTGTCAATTGCA TGTTTATGAGGTAAAAAATTGCTTTATT |
| Gm08:828 8141 | 8288141 | [T/C] | 97 | 280 | 0.823 | 0.713 | AAGTGAGCATTTMCTAATATCTTAGCTCGAAACA TCTCTTTCATCTTTGTTGAAGTAAACCTCTGTATG GTAAAATTAAGAGGAGAAAGAAAAATGAASTGG AGTAAGGTCTTGTTTGAATTATTTTTTAATTTCA AAACTTGTTTTCAATATAATTTTTAGCTTTGTTAT ATTTTAAAAATAAAATAAAAGAAAAAA[C/T]AT TTGTTAAAATTCAAAAATAGATTTTTTTAAAAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | AATGTTCATAAAATATCAGCATYTGTCAATTGCA TGTTTATGAGGTAAAAAATTGCTTTATTTATGAA AATATTTAGGATCCAAAACAAGAGTAGGAAAGT AATTTTTAAAAGACATTTTTTTCCAGCACTGCAAT TGTAGGAACAAGTTTTAAAATACAAATG |
| Gm08:828 8200 | 8288200 | [C/T] | 98 | 281 | 0.883 | 0.851 | CCTCTGTATGGTAAAATTAAGAGGAGAAAGAAA AATGAASTGGAGTAAGGTCTTGTTTGAAATTATT TTTTAATTTCAAAACTTGTTTTCAATATAATTTTT AGCTTTGTTATATTTTAAAAATAAAATAAAAAGA AAAAYATTTGTTAAAATTCAAAATAGATTTTT TTTAAAAAAATGTTCATAAAATATCAGCAT[C/T]T GTCAATTGCATGTTTATGAGGTAAAAAATTGCTT TATTTATGAAAATATTTAGGATCCAAAACAAGAG TAGGAAAGTAATTTTTAAAAGACATTTTTTTCCA GCACTGCAATTGTAGGAACAAGTTTTAAAATACA AATGYCTTGAAAATCTTTCTAATACTTAATGGAA AATATTAAATAAAAATAAAAATAAAAATA |
| Gm08:828 8470 | 8288470 | [A/T] | 99 | 282 | 0.852 | 0.652 | TAGGAAAGTAATTTTTAAAAGACATTTTTTTCCA GCACTGCAATTGTAGGAACAAGTTTTAAAATACA AATGYCTTGAAAATCTTTCTAATACTTAATGGAA AATATTAAATAAAAATAAAAATAAAAATAAAAA TATTTAATGTTTTAAAAACTTTAAAAACATTCAA ATACTTTCTTTATTTAATAAGAGGAGGATGA[A/T] GGGATTAGAATTATTCAATTTTTTTATATTAAAAT ATAACGAATCCATAACAAATTTACAGTAGTACTT TGTTTCATAAAAAAATACTGATTGGATGAAGCAG AKAGGAGAGAGGAAGATGTCAGTAAGTCATAAA TGTGCCATTAATACATTTAATAACTTTTTTTTTTT ACAAAAGGGAGAAAGGCTTACATTTAAAT |
| Gm08:828 8831 | 8288831 | [T/C] | 100 | 283 | 0.852 | 0.612 | TTTTTTTTTTTACAAAAGGGAGAAAGGCTTACAT TTAAATTGCTATTACTTTTTTTAAACGAAAAAGG GGTGAAACGCCCAAAATAAATCATCATAAATAA GATAATAAGATAAGGAAGGAGAAAATAAATTTA AATATTGATCACAAATAAATTTTGYATAAATACA AATAAAATATAAGATAATAAATATCGATCAAT[C/ T]CGTGAAACAATTTGCGGAAGAGCAAAATTTGA GAAAAAAAATCGAAGAARCAAAATTCGCGATAT TATAAAACTTTAGAGATAAAAAAAAATTCATGAT AAATAATACAGTATATTATAATTTTAATCTTTAGT TTTTAATACAACTGTAAAAAAAATTCATGATAAA TAATATATTATAATTATAATCTTTAGTTTTAA |
| Gm08:828 9392 | 8289392 | [G/A] | 101 | 284 | 0.929 | 0.785 | AACTTTTTGTTAGTAACAGAAAGTGTAAACTGGT TTGGAGAAAATGTGAGAGATGGCAGGATACTAT GAGTAACTAGTTGGATTGGAAAATGTTGTATCCA GCTGTAAATTACCCATTCCATTATTGGAAGGAAA TATTCCGCATGAGCCAAACTATGCGAAAATGACA TGGTGAAAATTGATAAAGGTAAAGAAAAAGT[A/ G]GAGCTCAGAAAGGTGTTATTCTTCATCAAGAA GAGCTATTTCCAAAGCAACTATRTTACTTGTGCA ACTCTTTATTTTTTGTACATATACTACTATTATTA TTACTTGTGCTACTCTGATAAATAGAAAGTAGAA AACAAAGAAGTGGTATTGATTGATGTTACGTAAG TTACATAAAAGTTTGATGCGTATTGATTGAT |
| Gm08:8298290740 | 8290740 | [A/T] | 102 | 285 | 1 | 0.912 | ACAAAGCAATGGATCCAGGACTCATATATGATAT CACCACTGAGGATTATGTCCAATTCCTATGTTCC ATGGATCACAGTAGTGCATCCATTAGCAAAGTGA CTAAGACCACCACAAGTTGTAAGAAAGGAAATC ACCAAGCACTGAACCTCAACCTTCCTTCCATATC AGTGCCAAACCTGAAGAGGGCTGCAACAGTA[A/ T]TGAGAACAGTGACAAACGTGGGAAATATTACT GCAGTCTRCAAAGCTCTAGTGAAAGTTCCACATG GCATAAAAGTTAGAGTTGAACCTCAAACTTTGAG TTTCAATTCAGRTGTACGAATCCTTAACTTTAKTG TCAGTTTTCTGTCAACTMAAAAATTTCATGGAGA TTACAAATTTGGGAGCCTAACATGGACAGAT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| Gm08:829 1682 | 8291682 | [G/A] | 103 | 286 | 0.866 | 0.715 | TAATATTTTTCTTTTTAAAATACAGAWGGAAGT ACAAGAATAAAAAGTGGTTCAACTTCCATGAATA AAAATGGTCTTTACATGATTTGCACTTAATCTAA ATAACCAAGCACAAAATATATCAAAYWTGTGTA TATTTTCAGTTTAGTATTAATTATTAATGACTAGC AATAGAATTTAGATTTATAGAGACAATACA[A/G] TTAGTAAATTTTATTTTAGAATTATTTTAAAATA TTCTAATAATTAAATTACTCTTTTGTTTTTACATT GCAAGTGCAAGCATCTAYGTGCAAAAGGAGGGT ACGATACTCAACAATAGATAAATTTGCACAACAT CATCAGTCTTTGTTYTTCTTTTTCTTTTTTACTTTA GATACGTAAGGCAGTAACAACATACGA |
| Gm08:829 2207 | 8292207 | [G/A] | 104 | 287 | 0.912 | 0.904 | GACAAAAGATAAGAGAAACAAGCTTACATTACT ACAACGTTATAAGAAGCAAATAACCTACGAAGA AAATCAAGATAAATAAATAGATGGTACAAATTT GCATGTGTTCGGATATCCATCGACATCATTCATTT CGATCAAAATTCACGTTTTGGACATAAAAGCAAT TCTTCGTCGCTTCAGATAATGCGTGTCGTGGA[A/ G]CAGAGGATGCAAAACCATACATGCAGAAAATT ATGCTTGCAGAATGACACWTACGATGGAGCACC AAGATATGAGGCAAGTCGTAAAATATCACTAAA TATTCCACCAGCGGTGACTTGAGCACCAGCTCCT GGCCCACGAACTATCAGAGGCTGATCCTTATACC TTCGTGTTGTAAATGCAATAATGTTATCTGACCC |
| Gm08:829 7064 | 8297064 | [C/T] | 105 | 288 | 0.929 | 0.857 | CTGTTATTGATTGATSAATCACTTATTACTATCTG ATGGAAGATGAGTTTTATATAATAGAGTTACCTT GTCCTGCAAGCTTACAATAGAAAMTTCAGCTGYC TACAGCTATTAAGACTAACTAAACTTCAGTTAAG CCAATATTAATTGTGTTTTACTATTTAAGTCCTAG TTTACAATTTCTCCTATATTTTTATTTC[C/T]ATTA CTTGTTTCGAAAGCAATCATCTGAATTTTCTCTAT CTTCTTGTATAATGATAAGAACCTTGGGAGATCT ACACCACAAAAACTAGTCATTGTAGTTTGGAGAG CCAAGGACCTTATACATCCTAAACTTCAAATGTG AGACTCAAGTCTCATACCTTGCAATTGGATCCTA ACATTCCATCTTGCTTTGCAGCCAC |
| Gm08:829 9433 | 8299433 | [A/T] | 106 | 289 | 0.929 | 0.787 | AAATGTAGAATGATAAATCTTCAGTCTGATATCA CTAAAGAGAGTCAAGTCTTAACAATTGAACAGA AACATGCATTTGGTTTTAGAAGAATTGGATTTAG CACCTGAGAAAGACGCCCATTATCCAAAGCTTGA CGAAATCTAGATTGCAATGCCTCAGCAACAGCTT TTACTTCTTTCTCGGGCACAGCAAAGCATAC[A/T] GAATGCTCACTACTAGCCTACATAAATACTGTTA ATGATTAATGCCATTTCTTATATATCARCGTGGA CAACTAGAAAAATTGAAAAAAGTTATAAGTGCA CCTGAGATATCATGATAACATTAGCTCCAACATC TTTTACTGCACCAAAAATAGCACTGGCAGTACCT GGAACACCAGCCATTCCAGTTCTGCAAAAAA |
| Gm08:829 9672 | 8299672 | [A/T] | 107 | 290 | 0.919 | 0.702 | TTAATGCCATTTCTTATATATCARCGTGGACAACT AGAAAAATTGAAAAAAGTTATAAGTGCACCTGA GATATCATGATAACATTAGCTCCAACATCTTTTA CTGCACCAAAAATAGCACTGGCAGTACCTGGAA CACCAGCCATTCCAGTTCTGCAAAAAAGCATCAA AGAAAAATTTATTGGAATCTACAACTTGGAC[A/T] ATTAATATTGGTTAAAGAAAACCTTAAATTAAA TAGAAATCCTCGTGCAGCAAAAAATGCCAACTAT TCATCATGTAACAACTGCAATTCATGACTCAC CCCTCGACGTTTACAAGTGCCAAGTTGTCTATGG TTGCAAATCCTTTGACAAAATTTTGCAGGTTCTG GCTATCTTCATGATCATTAACAGAAGGATGG |
| Gm08:830 1839 | 8301839 | [G/A] | 108 | 291 | 0.937 | 0.721 | CTTGTGGATAAGGTCATACATCATATCTGTCACC TTTGACATTGCAGAAACAACCACCAATTTCCTCT CCGAATCATCCTTAAGAATTATGTCYGCAACATT TTTTATTCTCTGAGAGGTTCCACACAGGTTCCAC CAAATTTGTGAACAGACCAAGTTTCTCCTTTGGG TAGTTGTTTTTCCTCCAAGGACACATTCG[A/G]TG AAACATCTGCTAGCAAATATAGAAAGGACAAAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | AAACATAAGTTACTGTATTTGTCTATTAGAGTTCT AAGGTTGACTTGATGGTAAAAGGAGAAGGGAGA GAGGGAAAGGTCGTGGGTGGGTTCAATTTTCTCC GCTAACAAAAAACTAACAATTAACAACTAATATT TGCTGATAATAAAAAAAACTRTATTCGTC |
| Gm08:830 2134 | 8302134 | [C/A] | 109 | 292 | 0.924 | 0.758 | GAAGGGAGAGAGGGAAAGGTCGTGGGTGGGTTC AATTTTCTCCGCTAACAAAAAACTAACAATTAAC AACTAATATTTGCTGATAATAAAAAAAACTRTAT TCGTCTATTTCAAAACATAACCATAAGAGTAAGT CGTAACCTGTAAATGAAGCACGTACAGATGTACT CGGTGCCTCTCTTCCCCGTGGTAAAGTAAGA[A/C] CCTTCCTGAGACAGAAACCATTGTATCGTCGTGA ATCAGTATATAGCAAAACACAAAAATCCAATTA ATCTCATGGGGAGAATATCATTTAAACTGCCAAA ATTCCGAAAACACTCTAATCTCTGCAAAGGATAA ATATACAAAAAGGAAAAAAAAAAGTACAGAATA TACTGCTTGTAGAACAACCAATCATCTAAGAG |
| Gm08:830 3450 | 8303450 | [T/C] | 110 | 293 | 0.843 | 0.582 | TTGAGTTGAAATAATGAAATGAAATGGATCATAA TCCATCATCATCTTCCATTATGTTTCATTTCAACT TTTACAAATCAAACAATCCAACACCTTTTCCTTCC ACTCCATCCTTCTTCATTCCATACTCTACAACCAA TCAAAACATATTCGAAGGTTTCCATGTATGTAGA ATTATAAATAGGTTGAACAAAATTTTA[C/T]TGRG TAGGTTGAAMAGAATTATTTGGTAYTATTATTCG TACGCCCCTAACCATGTGTTTGGATGAAGAATTT AAAAATTTCTAAGAAATTTAAATTCATAACATTT TAATTGCCTTGATTTTAATTCCTTTCCTTTTGTAA ATATTTTGTTTGGATGAGGTAATTCAAATTCTTGT ATTTTAATTTTCTTSTTTGGACAA |
| Gm08:830 5237 | 8305237 | [A/G] | 111 | 294 | 0.817 | 0.722 | AATGATAACAAATTGTACATATTATAGACTAAAA TGACAATAATTTTAATCTAAACAATTTATTTATAT TTTTTTAATTTTATGATGTGTTAAATTGTGACAGT GCCCTACAATTTTAAAGAACGTACAAAATAATTA TTTATTCAAAATTTTAAACATAACATTACCTTTCC CTACAACGTCCCCCCGATAGTGTCATC[A/G]GTAG GACTCTTGCTTCAGAACAAAACGCGAGTCCATAT AAGGCAACTGCAATTTTTTTAATTAGTCTTCCGTT TGTTTCGGGGGCTAATGGGGAATTATAGCAAGTG TGAKAATTTTCTATGCTTTTAAACTAAAATCTAC ATATTTATAAAAATATAAAAGTAAAAAAAAAAT GCCACGGATAGTTCAGTCAAAGATAAA |
| Gm08:830 5348 | 8305348 | [G/T] | 112 | 295 | 0.919 | 0.737 | AATTTTAAAGAACGTACAAAATAATTATTTATTC AAAATTTTAAACATAACATTACCTTTCCCTACAA CGTCCCCCCGATAGTGTCATCRGTAGGACTCTTG CTTCAGAACAAAACGCGAGTCCATATAAGGCAA CTGCAATTTTTTTAATTAGTCTTCCGTTTGTTTCG GGGGCTAATGGGGAATTATAGCAAGTGTGA[G/T] AATTTTCTATGCTTTTAAACTAAAATCTACATATT TATAAAAATATAAAAGTAAAAAAAAAAATGCCAC GGATAGTTCAGTCAAAGATAATTCGAAATCATAG TAAATATTAAATGATTGGATTTTACAACATSTATT TGAAAGAGTCATCATAAAACTTAATACCACAYTT TAACCMAAAACTTTAAAAGTCAACTTTAT |
| Gm08:830 5905 | 8305905 | [T/C] | 113 | 296 | 1 | 0.491 | CCAATCCTATTATGTTACCCAAGATGYCGTWAGT TCTCTAGGTGGTTTTTTCRAAACAAAAAAAAWTT ATTTGTAATAAAATAAATAATATTACTTCATTCTC ATGTCTTTTTATATTTAAGGTTATTATTAAGAAAT ATTTGATGAAAATAAACATTGTTCACCCTCGTAG CCTCCGTTATGGCGAGAGTGCCTCTCAT[C/T]TGC GTTCCRAACAGCCCTAGCTTRCACCATAATGGGT TGTGTCACCCTCGTAGCCTTCCYTGCATTCTCATT ATCATAAACGAYGCCGCTTTGGGAGACGCCTTCC ATGTCTATRCCACCCTTCAGAGCATAGGCCCCAC CATCTTGAGCTTGTGGGYTGTCGGACTAGGGYCG CTCTCTAAAGYCACCACCGCTGTAGC |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| Gm08:830 6090 | 8306090 | [T/C] | 114 | 297 | 1 | 0.494 | GAGAGTGCCTCTCATYTGCGTTCCRAACAGCCCT AGCTTRCACCATAATGGGTTGTGTCACCCTCGTA GCCTTCCYTGCATTCTCATTATCATAAACGAYGC CGCTTTGGGAGACGCCTTCCATGTCTATRCCACC CTTCAGAGCATAGGCCCCACCATCTTGAGCTTGT GGGYTGTCGGACTAGGGYCGCTCTCTAAAG[C/T] CACCACCGCTGTAGCGGTGGCGCTCGCCGCGTTT GTGGTGGTTCTTTCCTRGCCTCAGAGCACAAATT TGATAGCTAAACGCATATCATTGGGTCAGATAGT ACCACCATGTTGAAATTRAGAGGAAAGAAGTTTT AAAAACCCTAATTTGAGGAAGAAGAAGCAAGTG AAGAAGAAAATATTTGACAACTTTTTAAAAT |
| Gm08:830 6141 | 8306141 | [G/A] | 115 | 298 | 0.848 | 0.737 | GTTGTGTCACCCTCGTAGCCTTCCYTGCATTCTCA TTATCATAAACGAYGCCGCTTTGGGAGACGCCTT CCATGTCTATRCCACCCTTCAGAGCATAGGCCCC ACCATCTTGAGCTTGTGGGYTGTCGGACTAGGGY CGCTCTCTAAAGYCACCACCGCTGTAGCGGTGGC GCTCGCCGCGTTTGTGGTGGTTCTTTCCT[A/G]GC CTCAGAGCACAAATTTGATAGCTAAACGCATATC ATTGGGTCAGATAGTACCACCATGTTGAAATTRA GAGGAAAGAAGTTTTAAAAACCCTAATTTGAGG AAGAAGAAGCAAGTGAAGAAGAAAATATTTGAC AACTTTTTAAAATTTGCATCAAAGTCCAGCTTAC ATGTCATAATCTAGGACAATTTGWCACGTT |
| Gm08:830 6210 | 8306210 | [A/G] | 116 | 299 | 0.929 | 0.772 | CCATGTCTATRCCACCCTTCAGAGCATAGGCCCC ACCATCTTGAGCTTGTGGGYTGTCGGACTAGGGY CGCTCTCTAAAGYCACCACCGCTGTAGCGGTGGC GCTCGCCGCGTTTGTGGTGGTTCTTTCCTRGCCTC AGAGCACAAATTTGATAGCTAAACGCATATCATT GGGTCAGATAGTACCACCATGTTGAAATT[A/G]A GAGGAAAGAAGTTTTAAAAACCCTAATTTGAGG AAGAAGAAGCAAGTGAAGAAGAAAATATTTGAC AACTTTTTAAAATTTGCATCAAAGTCCAGCTTAC ATGTCATAATCTAGGACAATTTGWCACGTTAGAT AATCTATGTGACAYTAAAATTATTAAAAATATAT CTCATTAATGGYGTTAYTTTTAAATTTAACG |
| Gm08:830 6492 | 8306492 | [A/G] | 117 | 300 | 0.853 | 0.614 | TGCATCAAAGTCCAGCTTACATGTCATAATCTAG GACAATTTGWCACGTTAGATAATCTATGTGACAY TAAAATTATTAAAAATATATCTCATTAATGGYGT TAYTTTTAAATTTAACGGCAAAKACTATTTTRTA AAATTTATGCAAAAATAGAGACTATTTTTTACAT TTAAAAAAAGATAAAGACTAATTTGCAAAA[A/G] GAATCAAAAGTTAGAAATCAAAATACCTATTTAY TTAAWAAAAAAAACATCATGCGTTAGTTATAAC CTTAACTTCTAATTTTTTGCTAACGCCCAAAAAA ACTAAGAATTCGAATCAGAAGTAGGYAGAATAG KCAATTTGGTTCTTAAAAGTGTATGGAAGGAAAA AWTTTCCTTTGACTTTTTAAATTGGAACACGT |
| Gm08:830 6627 | 8306627 | [G/T] | 118 | 301 | 0.811 | 0.689 | AAAATTTATGCAAAAATAGAGACTATTTTTTACA TTTAAAAAAAGATAAAGACTAATTTGCAAAARG AATCAAAAGTTAGAAATCAAAATACCTATTTAYT TAAWAAAAAAAACATCATGCGTTAGTTATAACC TTAACTTCTAATTTTTTGCTAACGCCCAAAAAAA CTAAGAATTCGAATCAGAAGTAGGYAGAATAG[G/ T]CAATTTGGTTCTTAAAAGTGTATGGAAGGAAA AAWTTTCCTTTGACTTTTTAAATTGGAACACGTC TTGATTTTTTCCCTTGTTGCCCAAAAGCAGTCTT ATTATTCATCCGTTGGGAATTTTGTTTTAATTTC GCTGATMAAAAAATTGAGAATTTTATGTCTGCTT TGTGAATTACCATTTTWTCGGAACCTGCAT |
| Gm08:830 7172 | 8307172 | [T/C] | 119 | 302 | 0.854 | 0.63 | TAGAAGKAATAATTTTGTTTTGGCTTGTTGAATT GGAAAATGTTACAGTCCCGGTCATTCTTTTATTT TTATATGTTTATTTATTTTTGTCCAAATAGCAGGG TCATATTTCAAAACTTGGGTTTTACTTTCAAGCTTT GGAACAATGTTAGTGTAATTTGTGACTTTTGATA AGCCAAAGAAGTAACTTTCGTTCTTA[C/T]TTTC ATGTGACTTGTAACAAGTTACAAGTCAGTAATAT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | AACCTATAACTTWYTCTTCATCRTCTGCTTCTTCT TTTGATCATAATATCTGTTAAGTGATCTTTCATAG AGAGAGAGAGAGAGAGATGGAGAGGTGTGACA AGGTGATGAACCAACGCAACATGCATGATTGTCC TAAAACAGGTCCTGGCTATCCTTCAC |
| Gm08:830 7665 | 8307665 | [G/T] | 120 | 303 | 0.924 | 0.772 | TCTGAAAAGGCCAATTCAGCTTCATTGGAGGAAT AGATAGGCATTAGGCAGAGAGATCAAGATAGGT TTCTCAAGTTGTTGTTACAAACATTTTATATGACA TGATACTGGGAACAAGTGACATGTAGAAATATCT ATCTCTTTCTAGTGCTATGCATGAAGACTTGGTG CAGCTTAAACAATTTCTGTCAAAACGTGTA[G/T]T TTGGTGATTTTATATATATATATTGGTGATGAATA TTCAATTCAATGCAGGAACAGGAAGGGATAAGC CTGACTTTCTGGCCACAGTGGATGTGGATCCAAG CTCTCCAACGTATTCAAAAGTTATCCATAGGTTA CCTGTACCTTATTTAGGTGATGAACTGCACCATTT TGGGTGGAATTCATGCAGCTCTTGCTAT |
| Gm08:830 8019 | 8308019 | [A/G] | 121 | 304 | 1 | 0.837 | GTGATGAACTGCACCATTTTGGGTGGAATTCATG CAGCTCTTGCTATGGAGATCCATCAGCAGTTCGG CGATATCTGATTCTACCTTCACTGGTGTAAGATA CTAAACAGCCACTTTGGATTTTACTTGCACGCAT ATGCGCATGCAYACACACACATAACAAACACTG ACAAGGTTCAAGAACTTCACTGGTGTAAGAC[A/G] TCGGTTTTCTTGAAACGAAATCCTTATTAAGTCA GATTTACCATATTTCAGATCAGGCCGCATTTATG TGGTTGACACAAGATCAAATCCAAGGTCTCCATC TTTGCACAAAGTTGTTGAGCCAGAAGACATCATA AGTAAGACTGGATTAGCTTATGCACACACATCTC ATTGTCTTGCTTCTGGTGACGTCATGATCT |
| Gm08:830 8891 | 8308891 | [T/C] | 122 | 305 | 0.936 | 0.801 | CTGGTACCAACCACAGCATAAGACTATGATTAGC TCATCATGGGGTGCTCCTGCTGCTTTCACCAAAG GTTTTAACTTACAGCATGTCTCTGATGGTCTTTAT GGGAGGCATCTACATGTATACAGCTGGCCTGGGG GTGAACTGAGACAAACATTGGACCTTGGTGAGTC AGGGGTTCTACCCTTGGAGGTACATTGCT[C/T]AA TAAATAATTCTGGAGTTATTTCCWCCAATTATAA GCACTTTATGTTAATGTACTTGTGATTTAATCATA AATATGTTTGTCCTTTGCTACATTTTTTCTCTCTA GCCTGTACTTGTGAAGTAATATGTTAAAGGTGGC ATAATTTGTAAGCAACTTGTCCTAAATGCAGGTA AGGTTTCTGCATGATCCTTCTAAAGA |
| Gm08:830 8917 | 8308917 | [A/T] | 123 | 306 | 0.87 | 0.865 | TGATTAGCTCATCATGGGGTGCTCCTGCTGCTTTC ACCAAAGGTTTTAACTTACAGCATGTCTCTGATG GTCTTTATGGGAGGCATCTACATGTATACAGCTG GCCTGGGGGTGAACTGAGACAAACATTGGACCTT GGTGAGTCAGGGGTTCTACCCTTGGAGGTACATT GCTYAATAAATAATTCTGGAGTTATTTCC[A/T]CC AATTATAAGCACTTTATGTTAATGTACTTGTGATT TAATCATAAATATGTTTGTCCTTTGCTACATTTTT TCTCTCTAGCCTGTACTTGTGAAGTAATATGTTAA AGGTGGCATAATTTGTAAGCAACTTGTCCTAAAT GCAGGTAAGGTTTCTGCATGATCCTTCTAAAGAT ACAGGTTTCGTKGGGTGTGCATTGT |
| Gm08:830 9316 | 8309316 | [T/A] | 124 | 307 | 0.924 | 0.912 | GTCAAGTAACATGGTACGGTTTTCAAGACCGAG GATGAATCATGGAGTCATGAGGTACACAAAAG GATATAGTAAAAAATCAATGCCTAAATTTTAGGA GAATCATGACATCTCATTAATCAGAAGGTTTACA TTCAGCTATTCTATTTTTATTTCATTCCTATAATTT TGGGATTCCTGGTTCTTGGAATTTCCTTT[A/T]TA ATTTTCTTCACCTTTTCTATATATTGTATCTGTGCT CATATGAAATAATAGAGATGATATAATTTTCATA CTCTACTCTACTCATAGATATCCATACTCATTTTR TATTGTCATCTGGTATGCGTTTGTGCAGCTTCAAC CAAGGTATAATGATCAATAATACTTACACACTAG ACTGACTTTGCAGGTTGCAATATC |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| Gm08:830 9423 | 8309423 | [G/A] | 125 | 308 | 0.854 | 0.824 | TGACATCTCATTAATCAGAAGGTTTACATTCAGC TATTCTATTTTTATTTCATTCCTATAATTTTGGGA TTCCTGGTTCTTGGAATTTCCTTTWTAATTTTCTT CACCTTTTCTATATATTGTATCTGTGCTCATATGA AATAATAGAGATGATATAATTTTCATACTCTACT CTACTCATAGATATCCATACTCATTTT[A/G]TATT GTCATCTGGTATGCGTTTGTGCAGCTTCAACCAA GGTATAATGATCAATAATACTTACACACTAGACT GACTTTGCAGGTTGCAATATCAGTGAAACCATTG AAAGTGCAAAACTGGATTCTTCCAGAAATGCCTG GGCTTATAACTGATTTTCTGATATCTCTTGATGAT CGGTTTCTGTACTTTGTGAATTGGC |
| Gm08:830 9837 | 8309837 | [A/C] | 126 | 309 | 0.924 | 0.824 | TAGACAATATAACATTGAGGACCCTAAAAATCCT GTACTGACTGGCCAAGTATGGGTTGGGGGACTAC TTCAGAAAGGAAGCCCTATAGTAGCAATAACCG AAGATGGTAATACTTGGCAATCTGATGTTCCAGA CATCCAGGTTTGTGCAGTTTAACTTTTGAAATTA GTGATTCTAGTGTCATGCTTGTTGATTTCTC[A/C] CATGTTTGGAGTTGATTGGTTCTTAGATGTACTA GATATAATAGACTTGTGCATTACATTGGTGCCTT CAAACTTTTTGTCACTTTTGTATTTTATCTTGTGTT ATGCTTAAACGTGGTAAATAATTGCACTTTAAAT TTTGACCCTTTAGTGGTTGAAGGTGAAGAGATCA AAATTTTTAATTTCAGGGAAATAAGTTG |
| Gm08:831 0383 | 8310383 | [A/T] | 127 | 310 | 0.918 | 0.677 | AAAATGGTGGTCTGAAAATTAACCCTAATTTCTT TGTTGACTTTGGAGCTGAGCCTGGGGGTCCCTGC CTTGCCCATGAGATGAGATATCCTGGTGGTGACT GCACTTCAGATATATGGATTTAATAGCTATGCTA CTTGAGGCCAGGCTACAAGCAATATCCATGTGAA TAAAATCCTTAGTCCTAGAATGAATCGAGG[A/T] GGGCTAATGTTATAAATAAATAATAGTTGCATAT GTATGATGGTTGCATTGTAATAAAGTTATATTGT CATGTAGTTTTCMGTACTTTCTCATTTACATCATC CTAAACAGTGTTCTCTRTGAAATAAATCTTGCTC ACCTACAAAATTTGGGTCTTCTGATTGAGTAAAT CTCTATTGGAGTAACATTCTAGATTAATG |
| Gm08:831 0464 | 8310464 | [A/C] | 128 | 311 | 0.924 | 0.787 | TGAGATATCCTGGTGGTGACTGCACTTCAGATAT ATGGATTTAATAGCTATGCTACTTGAGGCCAGGC TACAAGCAATATCCATGTGAATAAAATCCTTAGT CCTAGAATGAATCGAGGWGGGCTAATGTTATAA ATAAATAATAGTTGCATATGTATGATGGTTGCAT TGTAATAAAGTTATATTGTCATGTAGTTTTC[A/C] GTACTTTCTCATTTACATCATCCTAAACAGTGTTC TCTRTGAAATAAATCTTGCTCACCTACAAAATTT GGGTCTTCTGATTGAGTAAATCTCTATTGGAGTA ACATTCTAGATTAATGGCCTTACTTGGGATTCTAT GATTTTCATTCACATCATGAATGTGCTGCACCTTC TACGTTGCTTGTTCCCATTTGAATGYA |
| Gm08:831 0503 | 8310503 | [A/G] | 129 | 312 | 0.933 | 0.734 | TTTAATAGCTATGCTACTTGAGGCCAGGCTACAA GCAATATCCATGTGAATAAAATCCTTAGTCCTAG AATGAATCGAGGWGGGCTAATGTTATAAATAAA TAATAGTTGCATATGTATGATGGTTGCATTGTAA TAAAGTTATATTGTCATGTAGTTTTCMGTACTTTC TCATTTACATCATCCTAAACAGTGTTCTCT[A/G]T GAAATAAATCTTGCTCACCTACAAAATTTGGGTC TTCTGATTGAGTAAATCTCTATTGGAGTAACATT CTAGATTAATGGCCTTACTTGGGATTCTATGATTT TCATTCACATCATGAATGTGCTGCACCTTCTACGT TGCTTGTTCCCATTTGAATGYATTTGAAATCACA ACCCAACCAAATCATTTCAATATGATG |
| Gm08:831 0663 | 8310663 | [T/C] | 130 | 313 | 1 | 0.847 | CMGTACTTTCTCATTTACATCATCCTAAACAGTG TTCTCTRTGAAATAAATCTTGCTCACCTACAAAA TTTGGGTCTTCTGATTGAGTAAATCTCTATTGGAG TAACATTCTAGATTAATGGCCTTACTTGGGATTCT ATGATTTTCATTCACATCATGAATGTGCTGCACCT TCTACGTTGCTTGTTCCCATTTGAATG[C/T]ATTTG AAATCACAACCCAACCAAATCATTTCAATATGAT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | GTACTTCTTAACAAATCAATGCACAAATAATTTT AATCATAAATTCAGAACTTATGCAGTGAATATTC TCGTTGTTAAGTTATAAGGGGCGGGGGGAATCTT ATATATGTGATTTTTGGTATATGAACGTTTGGTTT GTGAATTGTGATTGTCAGATGGTA |
| Gm08:831 1631 | 8311631 | [A/C] | 131 | 314 | 0.843 | 0.772 | ACAACAGAGGATGCTCCAGGATATGCAAATGCA GAAAATGAAGTCTTCAGTTCGTTCAATGGGAAGA ATAAGGAAATCATATACCTATTTTTCATCTTTTAT ATTTATGCAGTCGTCTATGATGAATTGATGAGTG TTTTCCTGGCCATGTGTGTTGTTTTGGCTTCTGCT TTGTAAACACAAGATAATAATACAGGCAC[A/C]A TAATAAACTGTATAATGACATGAAGATCAATATC TTTCTTTGAAGCTAAGAAAAATTGTTATAGCATG TAGCTACTTTTGTTGTCCCACAAATGTGTGGCAT GGAGCAATTTTTTAATATATTCAAAATATTTATTT TGTGGACTCGACAGTCTACATCTATTTTATGAAG TGTAGTGAATCCAACATCAAACCCCTTT |
| Gm08:831 1906 | 8311906 | [A/G] | 132 | 315 | 0.824 | 0.62 | ACTTTTGTTGTCCCACAAATGTGTGGCATGGAGC AATTTTTTAATATATTCAAAATATTTATTTTGTGG ACTCGACAGTCTACATCTATTTTATGAAGTGTAG TGAATCCAACATCAAACCCCTTTGTCCCACTTTA CAAAAACCCTCTGATCATTTGAACCTCCTAAATG AATACAAACTGTGTCCATAAAAAAAAATT[A/G]T TGTGTCCTACGTGCAAAAAAAAAAAAAAAMTT CACTACCCTATTTTGTTTTTATCATGTTAAATATA TGAAAATAAATTATTGCCAAGTCCAAATTGTTTG CTACTATTGAAGCCTGCATTTGTCTCGATGTAAA ATAGTAGTACTTATCCAAACACAGTATCAGGTTG AAGCAAACTAGTTCATATTATTGATGAGA |
| Gm08:831 2536 | 8312536 | [T/A] | 133 | 316 | 0.924 | 0.824 | CCACCACAACTGTATGTTGAGGTCCATTGTCTGA TAGAAGACTGAGAGTTTAGGTGGGGCAACTTCG AGGAATATGTACCAAATATTTTAGATGTATGATT ATATCAACACACACACCTTTGCCTCTGTTCTCTCC TTTTTCTTTTGCCATGATAATACCCTTCCTATAAT CCTATTCACCCAACGCCACATTTGTTTTC[A/T]TG TATACTTAAATGTGTGTTAAGGGTAAGGGCTTCA AATAAGAAACTTAGCTAAAACAGTTAAGTAACT ATTTACTCCCATCATTTTGCACAAATTTTTATGAA CTTAGATTTTACCAAAGGAGGGACAAAACTAAG AACCAAAAAAWTATCATCATATTCAGAWGCCAC AACCAACCACATGTTTTCTATACATATTTT |
| Gm08:831 2819 | 8312819 | [G/A] | 134 | 317 | 0.87 | 0.836 | ATTTTGCACAAATTTTTATGAACTTAGATTTTACC AAAGGAGGGACAAAACTAAGAACCAAAAAAWT ATCATCATATTCAGAWGCCACAACCAACCACAT GTTTTCTATACATATTTTTCAATATGGGGTACTA ACAAAAAAGTCTTATTTGGTATGGAATTTTTAAT TACTCTATATTTATAGTATACAATATACTTG[A/G] GACATATTAGAATTTTATCTTCCAAGAGCAACCT AATCTCAGTTATCTCATACATATGCAATCGCTTAT TAGCAGAGTAAATCAGWAGTCTTCACAGAAAAG AGAAAAAAAATCATCTGTAGCACATGGAAAATA ACATAATTTCCTTGTTGTCCAAAAGGTTTGGTGA AGTGCGCTCTATCAGCTTATCACTAATGCAA |
| Gm08:831 3273 | 8313273 | [A/G] | 135 | 318 | 0.854 | 0.699 | GCTTCTTAGTGGAGAGTGGAAGRWAGGGTACAT CCAATCCAAGACACAGAACAGAAGAATGCCTC AAAATCATCCACCATYARACTTGTTTGTTTCTGCT ACTTCATGCTCTTCAGCTCTATGCATTTCACCAGC TGCACCGTGCTCTCATTGAAAAGTCATGCAAGCA CATGCAATGGTTCCATAGCTGAATGCAATC[A/G] AGAAGATGAGCTGTTGATGGAGTCTGAAATAAG CCGAAGGTTTCTGGAGCAGAAGAGATCATACATT TCCAATGGAGCTTTACAGAGAGACAAACCAGTTT GTAATGGTGGTGGCTCTGGTGAAGCTTATAGTAA AACTGGAGGGTGTCTTCCTCCCCCCTCAAATCCT CAAAGTAGAGGCTGCTCTAAGTATTATCGTT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:831 3923 | 8313923 | [A/G] | 136 | 319 | 0.655 | 0.806 | AGGAAAGATCTATGATTGTATTAATTATCCGTTT CTTGTCATCTCCAATCTTTCTTTGTTCCATTATGC TRGATGGAATTTGATTTTTTCTTCTTTTTTTTTGG GTGAAATGTTTTKGTAATGCACATAATGCAACCA TAAGGTATAAATCCTCTTACACATTCTACCTCGA TATACATATTTAAATAATAAAATATAT[A/G]AAA ATATAGAATTATATAAATGAGATTTTATTTTAA ACATATAAGAGTTCACRTGGGTAAAGTATTCACA TTCACTTTACTATTAYCAAATAAAATTTGTSAGA AACATTTTCGGCTCAACATCATGCAATTAAACCA GAAACTTATGTCTCAATGTCAYATTCTATYAGAT CATTTTATTCYGACATCCTCCAACATA |
| Gm08:831 4010 | 8314010 | [T/C] | 137 | 320 | 0.842 | 0.823 | TTCTTCTTTTTTTTTGGGTGAAATGTTTTKGTAA TGCACATAATGCAACCATAAGGTATAAATCCTCT TACACATTCTACCTCGATATACATATTTAAATAA TAAAATATATRAAAATATAGAATTATATAAAATG AGATTTTATTTTAAACATATAAGAGTTCACRTGG GTAAAGTATTCACATTCACTTTACTATTA[C/T]CA AATAAAATTTGTSAGAAACATTTTCGGCTCAACA TCATGCAATTAAACCAGAAACTTATGTCTCAATG TCAYATTCTATYAGATCATTTTATTCYGACATCCT CCAACATAAGATTTCTTAAAGCAATCCATCTAGT CATTTGCTTCCACAAACACAAGGTTCGAGATCAT CACAAGATCCAAACACAAACAGCAYAC |
| Gm08:831 4025 | 8314025 | [C/G] | 138 | 321 | 0.817 | 0.808 | TGGGTGAAATGTTTTKGTAATGCACATAATGCAA CCATAAGGTATAAATCCTCTTACACATTCTACCT CGATATACATATTTAAATAATAAAATATATRAAA ATATAGAATTATATAAAATGAGATTTTATTTTAA ACATATAAGAGTTCACRTGGGTAAAGTATTCACA TTCACTTTACTATTAYCAAATAAAATTTGT[C/G]A GAAACATTTTCGGCTCAACATCATGCAATTAAAC CAGAAACTTATGTCTCAATGTCAYATTCTATYAG ATCATTTTATTCYGACATCCTCCAACATAAGATTT CTTAAAGCAATCCATCTAGTCATTTGCTTCCACA AACACAAGGTTCGAGATCATCACAAGATCCAAA CACAAACAGCAYACARGGAATGAGTTATC |
| Gm08:831 4208 | 8314208 | [T/C] | 139 | 322 | 0.757 | 0.829 | TAYCAAATAAAATTTGTSAGAAACATTTTCGGCT CAACATCATGCAATTAAACCAGAAACTTATGTCT CAATGTCAYATTCTATYAGATCATTTTATTCYGA CATCCTCCAACATAAGATTTCTTAAAGCAATCCA TCTAGTCATTTGCTTCCACAAACACAAGGTTCGA GATCATCACAAGATCCAAACACAAACAGCA[C/T] ACARGGAATGAGTTATCACATTCCCAACTAATAG AGAGAAACGAGACAATATGTAGATATACATATT ATATAAATGAAATATARCTYACTYAAACATAGCT CACATCATTCCATCACTTATCGTGTAACATCACA TCTCAACACTACACATCTCACACATTTTCACATTA TTTACGTRCTCAAGGATCGAAACACAATAT |
| Gm08:831 4292 | 8314292 | [A/G] | 140 | 323 | 1 | 0.715 | YAGATCATTTTATTCYGACATCCTCCAACATAAG ATTTCTTAAAGCAATCCATCTAGTCATTTGCTTCC ACAAACACAAGGTTCGAGATCATCACAAGATCC AAACACAAACAGCAYACARGGAATGAGTTATCA CATTCCCAACTAATAGAGAGAAACGAGACAATA TGTAGATATACATATTATATAAATGAAATATA[A/ G]CTYACTYAAACATAGCTCACATCATTCCATCAC TTATCGTGTAACATCACATCTCAACACTACACAT CTCACACATTTTCACATTATTTACGTRCTCAAGGA TCGAAACACAATATCACTCAACCAATCAATATCG AYCAATRCACAAGCGTTATGCAACAAATATACTA AGACTTAATCCTATATGTAATGTGGTATCA |
| Gm08:831 4295 | 8314295 | [C/T] | 141 | 324 | 1 | 0.715 | ATCATTTTATTCYGACATCCTCCAACATAAGATTT CTTAAAGCAATCCATCTAGTCATTTGCTTCCACA AACACAAGGTTCGAGATCATCACAAGATCCAAA CACAAACAGCAYACARGGAATGAGTTATCACAT TCCCAACTAATAGAGAGAAACGAGACAATATGT AGATATACATATTATATAAATGAAATATARCT[C/ T]ACTYAAACATAGCTCACATCATTCCATCACTTA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| | | | | | | | TCGTGTAACATCACATCTCAACACTACACATCTC ACACATTTTCACATTATTTACGTRCTCAAGGATC GAAACACAATATCACTCAACCAATCAATATCGAY CAATRCACAAGCGTTATGCAACAAATATACTAAG ACTTAATCCTATATGTAATGTGGTATCATGT |
| Gm08:831 4513 | 8314513 | [A/G] | 142 | 325 | 1 | 0.895 | ATCATTCCATCACTTATCGTGTAACATCACATCTC AACACTACACATCTCACACATTTTCACATTATTTA CGTRCTCAAGGATCGAAACACAATATCACTCAAC CAATCAATATCGAYCAATRCACAAGCGTTATGCA ACAAATATACTAAGACTTAATCCTATATGTAATG TGGTATCATGTYAGTGAAAAATCTCATC[A/G]GG CGCCTAGAAGTATATGACAAGATAAACCACACA CTGGTAAGTCAGGTCACTCTCAYTAGATAAAATC ATAAGGAGATTAGTTAGGGTCACTCTRTTTTGCG AGAACACTTCAATCATACGAAATCAACATAGGTT TCAAGGAACATTCAAACCGAGTATATTTACCCCT AAGGCCTACACTCTAAAGAGTCCGTTAGG |
| Gm08:831 4736 | 8314736 | [T/C] | 143 | 326 | 0.871 | 0.614 | GATAAACCACACACTGGTAAGTCAGGTCACTCTC AYTAGATAAAATCATAAGGAGATTAGTTAGGGT CACTCTRTTTTGCGAGAACACTTCAATCATACGA AATCAACATAGGTTTCAAGGAACATTCAAACCGA GTATATTTACCCCTAAGGCCTACACTCTAAAGAG TCCGTTAGGACCTCTCCCTCTTGATTCAGGT[C/T] CAACCTAGAAAATATTTTAGCACCYAGACTCTAT TTATGAACTGTACAAAACACYCGACTCCTCAATT GTTCTCAAAATAATTTTATCTCATCGCGCCTCAA AGTGATTAAACTCGTCGAGTTYCCACAATGGTTC TCATCACAATACTCGTCGCACATTAACTCATCGT TCTGAAAGGGTCTTATAGTCGTGTGGTGGT |
| Gm08:831 4791 | 8314791 | [T/C] | 144 | 327 | 0.884 | 0.688 | ATTAGTTAGGGTCACTCTRTTTTGCGAGAACACT TCAATCATACGAAATCAACATAGGTTTCAAGGAA CATTCAAACCGAGTATATTTACCCCTAAGGCCTA CACTCTAAAGAGTCCGTTAGGACCTCTCCCTCTT GATTCAGGTYCAACCTAGAAAATATTTTAGCACC YAGACTCTATTTATGAACTGTACAAAACAC[C/T]C GACTCCTCAATTGTTCTCAAAATAATTTTATCTCA TCGCGCCTCAAAGTGATTAAACTCGTCGAGTTYC CACAATGGTTCTCATCACAATACTCGTCGCACAT TAACTCATCGTTCTGAAAGGGTCTTATAGTCGTG TGGTGGTAYGGTACATAACTCAAAACTCCATGCA CACAATATTTCAATACACATGTATTTTA |
| Gm08:831 4860 | 8314860 | [T/C] | 145 | 328 | 0.912 | 0.715 | ATTCAAACCGAGTATATTTACCCCTAAGGCCTAC ACTCTAAAGAGTCCGTTAGGACCTCTCCCTCTTG ATTCAGGTYCAACCTAGAAAATATTTTAGCACCY AGACTCTATTTATGAACTGTACAAAACACYCGAC TCCTCAATTGTTCTCAAAATAATTTTATCTCATCG CGCCTCAAAGTGATTAAACTCGTCGAGTT[C/T]CC ACAATGGTTCTCATCACAATACTCGTCGCACATT AACTCATCGTTCTGAAAGGGTCTTATAGTCGTGT GGTGGTAYGGTACATAACTCAAAACTCCATGCAC ACAATATTTCAATACACATGTATTTTAYAATTCA ACAYGCACTCAATTTATCACATACGCTCAATCTC GTTATAATCTCAATATAACAATTTATCA |
| Gm08:831 5543 | 8315543 | [A/T] | 146 | 329 | 0.825 | 0.756 | GTTTATTCTAACCTCAATTGCGATAAACTCATCTC TTACCTCTAAGYAGGCTCACATGTGTAGTCYGAC AACGATAGTGACGTTTCTAGCGATTTCCTAAGAT TCTTCAAAATTTTCCTAAGATTTTCTAACRTYAGA GAAAAGAGAAAGGATTATAACCTATATTTCACT GTCTCCGTCTCCRTGCGAGGGACATTTC[A/T]CTA ACTGAAGACATTGTTTCACAAATCCTAAYAGTGG GATTGTGAGAAAATGAGTTTYAAACCTGATTTTT AAATTTCACAATGATTCAATGGTTAATGARTCCG AGATCATAGTTTTAATGGRACAAGTTTGGATGTA TGCAGGAAGAGCATCTTGTGAGGGACATTGTTCT CACCACAGACATTATTTAAAAATTCCA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
| --- | --- | --- | --- | --- | --- | --- | --- |
| Gm08:831 5644 | 8315644 | [G/A] | 147 | 330 | 0.929 | 0.786 | ATTCTTCAAAATTTTCCTAAGATTTTCTAACRTYA GAGAAAAAGAGAAAGGATTATAACCTATATTTC ACTGTCTCCGTCTCCRTGCGAGGGACATTTCWCT AACTGAAGACATTGTTTCACAAATCCTAAYAGTG GGATTGTGAGAAAATGAGTTTYAAACCTGATTTT TAAATTTCACAATGATTCAATGGTTAATGA[A/G]T CCGAGATCATAGTTTTAATGGRACAAGTTTGGAT GTATGCAGGAAGAGCATCTTGTGAGGGACATTGT TCTCACCACAGACATTATTTAAAAATTCCAACGA TGGGAATGTGAGAAAATGAGTTTGGAACTTGGTG TTCAAATTTCATGATAATTCAATGATTAACGAGT ATAGGATCGTAGTTTTACCTGATAGGTTT |
| Gm08:831 6113 | 8316113 | [T/C] | 148 | 331 | 1 | 0.85 | TAGAAATATATTATGTGTAAAATCTGATCTAATA TRTCTATTTATAGATATSGTACTCTYAATTTATTA TTTACTCTAKCTTTTCTTTATTTTATTTTTATW AAAAAAATTCTATTTTTACTCCCTATCAAATGAA TAAATAAAATATTCTTTTTTATTTTCCTTCAAAYT ATTATTTTAATTATAAAATTATTTTT[C/T]CTAAT TTATTTAATTATAAAAATCTTATTATTTTTCAAAA ACTCTATTTATTTTTAAATAAAATGCTTTTWAATT TATTTAAAAAAAGACGAGATGTTACAAATGTTTG AAGCACACTTTGCAATGTTATAAATGTTGACCTC AGACATCAATTGCAATATACACACCATAAAACA ACATATGAAGTACACGTATGAGAT |
| Gm08:831 6689 | 8316689 | [G/A] | 149 | 332 | 0.896 | 0.63 | GCTCGAATATAATGAATCTAAACATATATGAAAA ATCAGTAACTGACCTTTTCGACACAGTCACATGA ACAAACTCGCAGCAACAACGCATACACTAGTAA CAGCAGTCARCGCACTCTCTTGAGAAAATTTGAT GTAAATGTATTTATAACTTTGTGACAAATATTTT TTTCCCTCATTCCACACAGGAATAAAAAGT[A/G]T CCAAGTGAGTGAAAGAGATGAGGAATAGATAGA CWTCTTTCTCCTTATTTTAAAATCCCAAGAAACT AATTACCTAGAACATTTGTAACAAAAACTAGTGT TAATTTATTTCCATTTATCCCTTTTCTCTCTGCTTT ATTTRTGGGAWGCTATAAAGAACGCTCTTCTCTC CTGAAAATTGCTMATTTAAGAAATTATT |
| Gm08:831 6899 | 8316899 | [C/A] | 150 | 333 | 0.895 | 0.737 | GTGAAAGAGATGAGGAATAGATAGACWTCTTTC TCCTTATTTTAAAATCCCAAGAAACTAATTACCT AGAACATTTGTAACAAAAACTAGTGTTAATTTAT TTCCATTTATCCCTTTTCTCTCTGCTTTATTTRTGG GAWGCTATAAAGAACGCTCTTCTCTCCTGAAAAT TGCTMATTTAAGAAATTATTTTCGAAGGA[A/C]C ACATTTTAATCTGTTAGAAATAGCCMAAAAAAA ATAGACAGAAAAATTACTCTAATTTTTTTTTTTT TKGAATGATTGACTAGTCAAATTAACTCCAGTAA ACAAACAAGCAGCGGCGGGTTGAACATGAATAA CTTTCAATATGCCCCTTTGTTAAGCTAAAAGATT ACCCTAACATGGAAGTTTATGCTACATATA |
| Gm08:831 7852 | 8317852 | [A/G] | 151 | 334 | 0.924 | 0.776 | CATTTTGTCATTATACTTTGCACGAAGTGGGTCAT TGTAAGTCCACCTGTATTACAATTCAACAATAAC AAGAATGTCGAATAATTTTAGTATTTTACAGCAG TTAATATGTAAGTATAAAATGCTACTTGCAGTAG AAGAAACCCTTTTTTCAGGGGAAGGGGAGGTCTG GACTCTGGAGGTTAGTTGCACGTTAAGCA[A/G]A ATGAATCSCTATCATCAATGTGTTAACAATCCA AAATTCTTGGTAAGGGAGAAATATCGGACAGAA AAAAAATTAAGATGTCAGAAAGCCAATGCAGAA TTTTCTCAGCAAATACATTGAATGCTGCCTTAAC ATACTAAAACCCCATTATTCGAAAGATGATTATC AATATTTAATARCATGACTGCAAGCCTATCA |
| Gm08:831 7861 | 8317861 | [C/G] | 152 | 335 | 0.924 | 0.923 | ATTATACTTTGCACGAAGTGGGTCATTGTAAGTC CACCTGTATTACAATTCAACAATAACAAGAATGT CGAATAATTTTAGTATTTTACAGCAGTTAATATG TAAGTATAAAATGCTACTTGCAGTAGAAGAAACC CTTTTTTCAGGGGAAGGGGAGGTCTGGACTCTGG AGGTTAGTTGCACGTTAAGCARAATGAATC[C/G] CTATCATCAATGTGTTAACAAATCCAAAATTCTT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | GGTAAGGGAGAAATATCGGACAGAAAAAAAATT AAGATGTCAGAAAGCCAATGCAGAATTTTCTCAG CAAATACATTGAATGCTGCCTTAACATACTAAAA CCCCATTATTCGAAAGATGATTATCAATATTTAA TARCATGACTGCAAGCCTATCAACCAACAAT |
| Gm08:831 8033 | 8318033 | [A/G] | 153 | 336 | 0.912 | 0.809 | GTTAGTTGCACGTTAAGCARAATGAATCSCTATC ATCAATGTGTTAACAAATCCAAAATTCTTGGTAA GGGAGAAATATCGGACAGAAAAAAAATTAAGAT GTCAGAAAGCCAATGCAGAATTTTCTCAGCAAAT ACATTGAATGCTGCCTTAACATACTAAAACCCCA TTATTCGAAAGATGATTATCAATATTTAATA[A/G] CATGACTGCAAGCCTATCAACCAACAATACATGA AAAAATTCTGGTGTGATAAAAAAAATTGTGTAGA CTCCTTTTAATGTCATAAAATCAGAAGTGTGGCA GAATCAGTCTAACATGTTACATCAACATTGAAAA CATAAACAGATTCAGGACTCTGTAGATAATAAAT GTAGCATTTCAGATATTCTCAGAACAGAGA |
| Gm08:831 9087 | 8319087 | [C/T] | 154 | 337 | 1 | 0.857 | AACCCAAAAGTACTATGAAAACAGATGAGCATA ACTCATGAGCATGCACTTTTGTCAAGATCTCAAA CCATATCAAGGGCTGCTAATAAACAACTCATTTA AATTGTGAGTTGTGACATGCAATATGATCCCTTC TTACTGTCCAGCTAAATTCACATAGAAGTCAAGG GAGTCAGGGTAAAGTTGACAAACTAAGAACG[C/ T]TGTAAACAATAAACTTCAAGCCAAGTACATAT TTCTACAAAATGAATGCCAAAAAAATAAAATAA GATTTGTGAGATGGCATAATTATGCTTACTCTAA ATGAAATATGTCTTTTAACTATATTCCTTCCAATC AACTCTCCCTCTTGAACCTCAATCTCACCCACAA TCAAATTCCTAAATAAGCAAAATGATAGGTAC |
| Gm08:831 9642 | 8319642 | [C/T] | 155 | 338 | 0.853 | 0.531 | TTCTCCCAGCCCAAGCCTAATTCCACCCTACCTTG TACACACCCTTCTCGGGCTAATGTTCTCTGTCTTC TTACAACAAGCCCACATGCACTCCTCCCATGCTC TGCTACAGGGTTGACAGTTGGTTATATCTCTCTCC TAAAATTGATCAAGTGAACCTTTTGCCTATCCTT ACATACACCTTATTTTGTGATCTTGGG[C/T]CTTG RGGCCTCCATCASAAAACCATTCTTCATAAAAAC TCTCATTTCACTCTTCTGATGACTAATAGCAGAA AATTTTTTAGATAACAAGAGAAAAAGAAATCTTA AATGAACATTTCACTATTGRCATGAGCATCTCAA TATCATCACATGAATCCGAGATCATTTTGGACCA GTGCCATAGCAGATGAACTTCATAAG |
| Gm08:831 9647 | 8319647 | [G/A] | 156 | 339 | 0.853 | 0.587 | CCAGCCCAAGCCTAATTCCACCCTACCTTGTACA CACCCTTCTCGGGCTAATGTTCTCTGTCTTCTTAC AACAAGCCCACATGCACTCCTCCCATGCTCTGCT ACAGGGTTGACAGTTGGTTATATCTCTCTCCTAA AATTGATCAAGTGAACCTTTTGCCTATCCTTACAT ACACCTTATTTTGTGATCTTGGGYCTTG[A/G]GGC CTCCATCASAAAACCATTCTTCATAAAAACTCTC ATTTCACTCTTCTGATGACTAATAGCAGAAAATT TTTTAGATAACAAGAGAAAAGAAATCTTAAAT GAACATTTCACTATTGRCATGAGCATCTCAATAT CATCACATGAATCCGAGATCATTTTGGACCAGTG CCATAGCAGATGAACTTCATAAGTAAAT |
| Gm08:832 0068 | 8320068 | [C/T] | 157 | 340 | 1 | 0.837 | TTTTTCTCAGGATAAAACAACAAAAAACTAATAC CAAAGAATAGAATAAACAATCTACCACTATTCTT GAAACCGAAAGATATAGAACATAGGAGAAATTG AACTTACGGGTTATTCCAATCAGTAGTATCCTCA TTGACAAGATGGGTCCACTTGGTTCTTCCACTAC GACCAAAGTGCTTAACTTGCATAACCTTTGG[C/T] AATATTGTCTTGTCCATTTTATCCTCCCCAGTTGG GGCAGAGAAATCACGAGCGAAAATACCATCAGA TCCAACGGTGGCAGCTCGGTCATCAGATTCATTC TGGAAGAAAGCACCTTTGTGATAGTATTTCTGCA TAAATCTCCATTTCTGCTTTGGTGGTGGAGCAGG TTTGGGATTCCTCCTTTCCCACTCCCTCCT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:832 1253 | 8321253 | [C/A] | 158 | 341 | 0.919 | 0.773 | TCATCAGCCCATTCAGGAACTTTACCGGGCCAAT AACGCTTAACTTTAGTTTGGCCAATTTTACCTCTG AGCTTATCCCTAATGGCTATTACAGTATCACTAA CACCCGCTGTCACCGACATTGTTCTTCCTCAATTG AACGCCAAACCCTATATTGCACAGATGCATAGTA AATCGGTAAAATGTTTGTTTACACAGCA[A/C]AG AAACAGAAGATTCCAGATTAAATAGCAAGAAAA TAAATAAATGAATCAAGAAACACAGAAAGATCA ATAGTGAATGATAAATTTTGATATGCGAAACATT GGAAGGGTTTGTGTTCSAAACACTAACACTTGAA TTGTTAGAGAGAATAGAAGAAAGTTWGAAGGA CTTACAATTACAGCGACCGGAAGGAACCCTC |
| Gm08:832 1649 | 8321649 | [C/A] | 159 | 342 | 1 | 1 | CCCTCTCTGTCTCTGTCCCGTTCCAGGCAGCGCGT CGCCCCACCCCAGCTTGTTCTGTGAACTTTTATTT GATTTACTTTCTATAGTATTTATTTTTGTTTTTATG AGTATGTAAATGACATCTTTATACGAATATTATG TTTTCATTAAATAATAATAATAATAAATTTCTTAA AATTAAATATATATACACTAATGCT[A/C]ATAAA AAAATTGAACGAATATCATATTTATTAAAACTAA TTTTTTTATACTAAACTAAAAATAATTTAAAATTT ATTATTATTATTATTATAAAGATATTTAAATTTTA TATTTTGGAATTGTATATATAAGATAAAATACAT TTAAGTTTCCTAAGTTACAACTTTCGCATCGGTTA CATTTTAMAGGWTATATATATA |
| Gm08:832 3937 | 8323937 | [G/A] | 160 | 343 | 1 | 0.918 | ATGTCTTTGTCCAAGGCTTGCTAACAAAAAAGGA GATTGCAAGATCAATAAAATACCTTACAATAATG AGAGACAAAGGGTTTTCAGTAGATGCTGCTACCA CAGAAATTACTATCAACTACTTATCTACTAATGA AGGAGACACCAGAATTCGAGAATTTTTTTTTCCA AAAAGATAGCAAATGCCAAGAGTTTCACTT[A/G] GACATTTATTCAAATCCTGACTCTCAATTCATCCA TGTTCCACAATCCTATAGGACCCCATAGAGAGAA CTGGCATAGGCTTCAGAACTTACMATTTGTTAAA TATATAAAATCATTACCATTCAAGTGCWTCCACC TGACAATTTATGTGATTAGGAGAGTTGGTCCTTA ACAGGTATCACAACCTTTAAGAAATTATG |
| Gm08:832 4341 | 8324341 | [C/A] | 161 | 344 | 0.929 | 0.787 | TTGATCCTTGTTGCTTCTCTTCTTCATAATTAACT TATATTTGAGCCCAAGGTAAAGTGGGTTTGTGCA TTGTCCRCACTTCAAGCTCAAAAAGCTCTGTTTTA AGGGGGTCTTAGATATAAATCTTTCTTAGCTCCA CCAATCAGCTTAAGCTGTGAATAGAATTGTTCCT TGACATTTTTAGTGGTAAGTATTTTCAC[A/C]TCT GCTTGCACATTTATTTTGATATAACCTCAAGTTAT TAAAATAGCTTAAAAAAATAGACCTATATACAAT TTAGAAATTGTGCTGTATCCTTGCATTTTTATGGA ACTGAGTAATTTTTACTTATGTATATTTGCCTTC AAGTAAGTTTAATAATGAAGCAAGTTGCATTAGG GATAAGCCAATCAATATTGCTAGT |
| Gm08:832 5127 | 8325127 | [T/A] | 162 | 345 | 0.829 | 0.706 | TGTTATTTTATATTTTGTTTCCTTTCTTGTGTATTT TACTTTTCTGTTTTAGGAGGATTCCTGATCCTTCT GCACTGTACTCCTTTTCTCTCCTAGTTCATTGTTT GTGATGGGAAWTTTTTTTCCATATTTATTACCTGT TAGGAGACGAAAATCTAAGATCTAATTTATGGAT GCTTGCTGTCCTTTCTGCAAACGTN[A/T]TTTTTT TTTTTACTTTTGACAGTTTTCCCCCCATTTAAAAT AACAGTTTGACTTCATGGTTCTTGGTTTGCAGATT GAAATCACTYTATGCACTCATTTTGTTATAACTTA TGTGCGAGGAAGACCGCAAATAGTTCAGCGATG GATCATAGAAGGTTAGTCAAACATTTTTTCTTTG CAATATCTGCTCAGCTTGTTT |
| Gm08:832 5214 | 8325214 | [T/C] | 163 | 346 | 0.929 | 0.837 | CTCTCCTAGTTCATTGTTTGTGATGGGAAWTTTTT TTCCATATTTATTACCTGTTAGGAGACGAAAATC TAAGATCTAATTTATGGATGCTTGCTGTCCTTTCT GCAAACGTNWTTTTTTTTTTTTACTTTTGACAGTT TTCCCCCCATTTAAAATAACAGTTTGACTTCATG GTTCTTGGTTTGCAGATTGAAATCACT[C/T]TATG CACTCATTTTGTTATAACTTATGTGCGAGGAAGA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| | | | | | | | CCGCAAATAGTTCAGCGATGGATCATAGAAGGTT<br>AGTCAAACATTTTTTCTTTGCAATATCTGCTCAGC<br>TTGTTTTTTGTAATTCAAATTTTTTAGCATCATAA<br>GTTGTTCGTTTGAAATTTTGAATGAATATTTATCT<br>GTTAAGTTATATTTCACTTTTCT |
| Gm08:8326696 | 8326696 | [C/T] | 164 | 347 | 1 | 0.768 | AATATATTTATCTCAGAATAATGCTTTGACTTTTA<br>CAATGTTCCCCTCACAAAATTGATCTCTTTAAAA<br>AATAAAAAATAAAAACTTTGGAGTTTGTCCAGCT<br>TGGCTCCAATCTTAACCAAAGCAGCATTAAAGCT<br>TTGAAGTATAGAGCAAAAGTACACCATATTAGGC<br>TAATCAATGAAAAGGTACAAAGCTCCCGT[C/T]A<br>GATTTTGAACTAGRCAGATAACTAAGNGAGTGTT<br>TAGTTTGGTTGTTTTTGATTTTATTTTCACTGAA<br>AATARAAAACGGTGATGAAAATGTGTTTGGTTTG<br>ATTTCTGAAAACATTTTCRGTAAAAATGAAAACA<br>GTAAACAACTAGAAAATGAAAACAAAAAATTTT<br>CGTTTTCAGWATTTTCAGTTGAGAACAGA |
| Gm08:8326877 | 8326877 | [T/A] | 165 | 348 | 0.884 | 0.808 | AAAGGTACAAAGCTCCCGTYAGATTTTGAACTAG<br>RCAGATAACTAAGNGAGTGTTTAGTTTGGTTGTT<br>TTTTGATTTTATTTTCACTGAAAATARAAAACGGT<br>GATGAAAATGTGTTTGGTTTGATTTCTGAAAACA<br>TTTTCRGTAAAAATGAAAACAGTAAACAACTAGA<br>AAATGAAAACAAAAAATTTTCGTTTTCAG[A/T]AT<br>TTTCAGTTGAGAACAGAAACCTCATTTTGGTTAA<br>AATGAAATTGYGGTGACAATAAATGTAGTTTTAA<br>RCAAATCTAAAAATACAAAAGACAATAAGTCA<br>ATATATCATAAATTTTCAGTATTTTTATTTCATRA<br>AAACAGAAAACAAGAAATCAAACCAAACATRTT<br>TTCAGAATTTAAATCTTTTGAAAATAAAA |
| Gm08:8328633 | 8328633 | [T/A] | 166 | 349 | 0.919 | 0.651 | TCTCTTCAAAAGCCAAGTCCTTGGTTAGGACAGT<br>GGTACTTAACATGGTTAATGCAAATGGTTTGTWG<br>CAAATTCATAATAGACCTTTCAACCAGCTTTTGG<br>CTCATTTTATTGCATTAGTCTTATTTGTTTTGGAG<br>AATTTCTTTTATTTTTTGGTAACTAGCAGATTTC<br>TTATCCTCCTCCTAGTTGTGCTTCTCTT[A/T]TCTC<br>TTTAATGAATTTCCTCCTATGTAAAAAGCAATAG<br>AAAAAGAAAACCAGTTTTAAAAAAATAAATAA<br>AAGAACTAATTTCAGGTACCTTCTTCCATTTTGCA<br>ATTAGATTGCGGTCAGCATATCCTTGATCTAAAC<br>AGAATTCATACAGTTCTTTAGAAATTTCCTTCCTC<br>CGATGGTATAGATCAAATATGTAGC |
| Gm08:8330929 | 8330929 | [G/A] | 167 | 350 | 1 | 0.789 | TAAGTAAATCTAGAAAATATATAACTTTTGACAA<br>AAAATTATATCACTATTTAAATATATCTTTTTTC<br>CTTTGTTTCTTATTTCCTAAATAAATTTTTTTATTA<br>AATTTATTAACAAAAATTTCTCATAATTAACGAA<br>TGAGGTTAAAAATAATAAAAAAATGAYAAATAT<br>AATAAAAACAAATTAAATTTAAAGACTT[A/G]AA<br>ACATAATTTTTKTGTCWCATGAAAATATTTTTTTT<br>ATTCTAAACAAATTGTTTAAAGATAATRAAAATA<br>TCATTTTTTTAAATCCTAWAAATATACCARATAA<br>CTATAATTATTTAAATTAAATCACTCTAGCATAT<br>ATTTTTAATAAATCAAATTAATATATACAAATAT<br>TTTAATTTACTTTAAATTTAAAGATAA |
| Gm08:8331132 | 8331132 | [C/T] | 168 | 351 | 1 | 0.657 | ACATAATTTTTKTGTCWCATGAAAATATTTTTTTT<br>ATTCTAAACAAATTGTTTAAAGATAATRAAAATA<br>TCATTTTTTTAAATCCTAWAAATATACCARATAA<br>CTATAATTATTTAAATTAAATCACTCTAGCATAT<br>ATTTTTAATAAATCAAATTAATATATACAAATAT<br>TTTAATTTACTTTAAATTTAAAGATAATA[C/T]GA<br>TAATATAAATATAGTAAAATTTTATAGAATTTTT<br>AAACAATATTTTYCATTTATCTTTTTTTTTCTTTT<br>ATCTCTCTAGTTGCATGGAGCATGAGCCAACTTC<br>CTAGTTTATTGTATATTTCGTGATAATGTTGTGG<br>CATTTGTTAGACATTTAAAATATTTAAATCTTATT<br>AATTATTTTWAAATCATATTTATA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:833 1181 | 8331181 | [C/T] | 169 | 352 | 0.87 | 0.612 | GTTTAAAGATAATRAAAATATCATTTTTTTAAAT CCTAWAAATATACCARATAACTATAATTATTTAA ATTAAATCACTCTAGCATATATTTTAATAAATC AAATTAATATATACAAATATTTTAATTTACTTTAA ATTTAAAGATAATAYGATAATATAAATATAGTAA AATTTTATAGAATTTTTAAACAATATTTT[C/T]CA TTTATCTTTTTTTTTCTTTTATCTCTCAGTTGCA TGGAGCATGAGCCAACTTCCTAGTTTATTGTATA TTTTCGTGATAATGTTGTGGCATTTGTTAGACATT TTAAAATATTAAATCTTATTAATTATTTTWAAAT CATATTTATATGAAAAATATGATTTTTTATTTAAT CTTTCTAGAAAAATCTTAATGTAT |
| Gm08:833 1408 | 8331408 | [C/T] | 170 | 353 | 0.842 | 0.771 | TCTCTAGTTGCATGGAGCATGAGCCAACTTCCTA GTTTATTGTATATTTTCGTGATAATGTTGTGGCAT TTGTTAGACATTTTAAAATATTAAATCTTATTAAT TATTTTWAAATCATATTTATATGAAAAATATGAT TTTTTATTTAATCTTTCTAGAAAAATCTTAATGTA TCCACTTCCAACTTTTACATTTAAAAT[C/T]CCATT ATATATTTTTTTCTAATTAACCTTCTCTAACAAT TGTTCAACACTTTCTTCCTAAACCTCTATTTCAGT TTCTCTCCCTCTTCGGTCTTCCCATTGAATTCCAG GATTTTACATACAAAAAATTTGWTAGTTTTGTTG TCTTGACAAGTTTTCGGAGGATTTGTTAAATTCTA AAGGACTTATGCACTACGTTG |
| Gm08:833 1827 | 8331827 | [C/A] | 171 | 354 | 0.838 | 0.772 | CGTGATGTCACTCATCTCATATTATCTATTTTGTG ACTAACTCATGAATTTATGATAGATTGATGATCG GTGATTTTGGCCTACTACAATAACAATTTTAACTT TTAAGGAATAATCCCGACCACTTTAAGGTATATT AATATATTAATTATTTTTTCTCCAATCTTAATTT AATTTGTTTGATGGTAATGAATCAGAT[A/C]AACG ATTTTGGGACTGTTGTTGTTGTTCCATTTTCAGTT TTTTATTTTGTTTATGACTAGTTGAGTTTGYAATC GGTTCTTGCTCGGTGATTTTAGAGGTTTTGGACAT GATTTTAGAGTATGTTGTATTGTGTAAAACTTTGT TGCAATCTCGTGTGGTTAAATGGGTGTTAGGATG TGAAAATTTTATGTCTAAAATT |
| Gm08:833 2651 | 8332651 | [A/G] | 172 | 355 | 1 | 0.836 | AATACACTTGTGCATTCAAATATCCATAATAGTT AATAACAACAACTTATTCAATATACTATATTATC TAGGGTCACTAGATTAAACCCACTTCTAAAAAAA TCTTAAAACATCCAAATTTTATTAATACGTTATCT TGAACATACTTTCTTCTATAAATGTTAAAATTTAT TTGAAAATTTGAAATCTTAGAAGGTCTC[A/G]TAC TTTAATTAATAAATATCTTTTATAATTTTTMATGA ATAGTACAATCAAGTGTGTTAAAAAATATTTTCT TGAAACTCCTCTAAATTTAATGCTACAAAAATTA CTTTTTCTTGCTTTCTCTTCAAACTTAGTGAGCAT TTTTGCACTCTTAAATTATGTTTGTCAAAATATTT GAATTGATTTTAGTTTTTTTATT |
| Gm08:833 2685 | 8332685 | [C/A] | 173 | 356 | 0.857 | 0.772 | AATAACAACAACTTATTCAATATACTATATTATC TAGGGTCACTAGATTAAACCCACTTCTAAAAAAA TCTTAAAACATCCAAATTTTATTAATACGTTATCT TGAACATACTTTCTTCTATAAATGTTAAAATTTAT TTGAAAATTTGAAATCTTAGAAGGTCTCRTACTT TAATTAATAAATATCTTTTATAATTTTT[A/C]ATG AATAGTACAATCAAGTGTGTTAAAAAATATTTTC TTGAAACTCCTCTAAATTTAATGCTACAAAAATT ACTTTTTCTTGCTTTCTCTTCAAACTTAGTGAGCA TTTTTGCACTCTTAAATTATGTTTGTCAAAATATT TGAATTGATTTTAGTTTTTTTTATTAACAGAAAAG TTTATTTAGTTGTTTGATAAAGAA |
| Gm08:833 2957 | 8332957 | [T/C] | 174 | 357 | 0.902 | 0.787 | ACTTTTTCTTGCTTTCTCTTCAAACTTAGTGAGCA TTTTTGCACTCTTAAATTATGTTTGTCAAAATATT TGAATTGATTTTAGTTTTTTTATTAACAGAAAAG TTTATTTAGTTGTTTGATAAAGAAGTTTTTTAAAT AATTTTTAACATTTTTTTAAACACTACTTCAAGTA ATATTTTTWAAAATATTATTTATTT[C/T]TTCATAT ATTCTYTTTTTATTTATTTTTAATATATTTATCAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| | | | | | | | ATTTATTATTTATCCTTTTTAAGCAAATCATTATT TTATTATTTTWAAGTTATTTTATATTTTTAACTA TTTCAAAAACTAATTTTATCACACACTTAATTTTA ATAAATTAATTTTTTAACTTCCAACTAATTTATTA GTTTTCAGCTAATTTTAT |
| Gm08:834 3167 | 8343167 | [C/T] | 175 | 358 | 0.904 | 0.883 | TGATTTTTCTGCATCTGAAACAATTTGAAATTTCA AAATTTCTCTTTTCTTTACGAGGTCATCAAAGCAC AAAGCTAACAAATTCCCTAGAAGAGGGTGCATA AAACTCCAACCTGTTTCCTCTGTTTTTTCCCTTGC AATTATTACTCTTTTTTATTGRTAGAAATTGAATT RTTGAARTATAAATGTGAAATAAAGTC[C/T]CAC ATCCAATAAAAATAAAAAAATTTAACATCATATA AGTAAAAATAACTAAATCTTAAAGTTTTTAAATT GCTATTCTCTTTCATGTAAAGATAAAACACATAA ATCTAACTCTTAAAGTCTCTTGATTACTATTTTTC ATCTTTCATGATATAAGTGATGATTAGCCTCTA GATTTCATGGTGATTATAGAAGTGTA |
| Gm08:834 5187 | 8345187 | [A/G] | 176 | 359 | 0.933 | 0.799 | CAAGATAGGACCTTTTTACTTTGTTGGTCTATTAA TATCCAAGTTGTTCATGCTTATTTTCACACCTAAC ATTAGCTTATTCAAGATTCTTAATAAAATATTAG GGAAAAATATCATGAAACTTTTATCAAAATTGTTT ATTTGTCGTTGACGTTTTTGGAAACATCTCAATA GTGACTTGTTACTCAATCAATCTTTACT[A/G]GCA CTCTCATACTTGGTTTTCGTTATTCCTGTTTTCAA ACCACATACTTTGACTAATGGACTATGAATGAGG CTGCGTATAAAAATACAATTGGCGTATTCGAGAT GCAAATTGTGTTATTGGCCTCTTGTCCTTTTCCAG ATCAGTATTGAGAAGTTCAGGCAAGGCTTGTATT GAATCTGACTCTGACAGATACATAA |
| Gm08:834 5720 | 8345720 | [A/G] | 177 | 360 | 0.871 | 0.587 | ATACGACTTTTWCTTGTTGCCACTCTTTACCAAC AGCATTCAAGACGTACGTTAGGATATTCAAATCC AATGCGTCACTGAGGAACTTTTGCACTCATTTTT CACGCAAAAACAGAGAATCATCCAGCACAGAGT CTTGCAAAAATTGATGTGAAACAAGAATGCTCTG AGCCTAAATTGGATCAATGTGCATGCTAAA[A/G] TTTAGACCCATATMKTATKGGGAAGTTTTTATCC CTTAGTCGCTTTTGTCTTTTTCCTTTCCTTTTTCTA AGCAACAAACCATATTGTTTTATAATTTGGGCGA GGTCTAAATTCGTTTTATCATTGTAACAAAAACT AAAGAAATTAAAGCAAACGATTTCATAGGCTATT TGGGAGCTATGTTTTATGAGGTTAATAA |
| Gm08:834 6030 | 8346030 | [C/G] | 178 | 361 | 0.87 | 0.721 | AAATTCGTTTTATCATTGTAACAAAAACTAAAGA AATTAAAGCAAACGATTTCATAGGCTATTTGGGA GCTATGTTTTATGAGGTTAATAACAAATAGGAA TCTCTTGATTTTAAGAATGAACAATTTTTTTTTCA CTATGAAAGGAGTCCTGAACATTATAATTGGATT GGGTGTTAAGGAGAGAAATAGAAAGGAGA[C/G] ATTTCACTCGATTGGTCARAAAGAAATAAGAAC GAAATTGACAAATTCTGTGGGTTCATTTGGGAAA TTCTTCTCCATTGTTCATGATTGGAAATGATTTTG TGTATCTTCTTTTTTTTTCTTAATTTCTTTTTAAAA AATCAAATAATTTTTTWAAAATAATTTCTTTATT AAAATACTTTTACTTTAYGATAAATA |
| Gm08:834 6050 | 8346050 | [A/G] | 179 | 362 | 0.929 | 0.718 | ACAAAAACTAAAGAAATTAAAGCAAACGATTTC ATAGGCTATTGGGAGCTATGTTTTATGAGGTTAA ATAACAAATAGGAATCTCTTGATTTTAAGAATG AACAATTTTTTTTCACTATGAAAGGAGTCCTGA ACATTATAATTGGATTGGGTGTTAAGGAGAGAAA TAGAAAGGAGASATTTCACTCGATTGGTTCA[A/G] AAAGAAATAAGAACGAAATTGACAAATTCTGTG GGTTCATTTGGGAAATTCTTCTCCATTGTTCATGA TTGGAAATGATTTTGTGTATCTTCTTTTTTTTTCTT AATTTCTTTTTAAAAAATCAAATAATTTTTTTWA AAATAATTTCTTTATTAAAATACTTTTACTTTAYG ATAAATACTATGAATTAAAAAGATAAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | r² with 8357600 | r² with 8356824 | Consensus Reference Sequence (200 bp flanking SNP) [S/R] |
|---|---|---|---|---|---|---|---|
| Gm08:834 6352 | 8346352 | [T/G] | 180 | 363 | 0.936 | 0.841 | CTTAATTTCTTTTTAAAAAATCAAATAATTTTTTT WAAAATAATTTCTTTATTAAAATACTTTTACTTT AYGATAAATACTATGAATTAAAAAGATAAATAT ATTCTCTTATTTTCTTATTTCTCTTCCAAGGATTGT CGAGATGGGAGAAGATTAACGTAAAGAATTTTT ATTTTTTTATTAAAACAGCGAAAATATAG[G/T]GT ATATATATAAAAGGCACAATGGGTGCCCCCAAT CAATTACAAAGTGGATAAAAGTCCAACAAAGAT AGTATACCTCGGTTACACCATATTAACAAAGGAG AGTAAATATAGTTTAACCAAGGCCAAAAACATC ACTCCTAGCCACACTCCAGTAAATATAGTTTAAC GTGAAGAATTTGATTCAACTTGTGAGAGCT |
| Gm08:834 6726 | 8346726 | [G/A] | 181 | 364 | 0.87 | 0.8 | AAGAATTTGATTCAACTTGTGAGAGCTTCACCCC TTAAGTTAATTCACCATATAGCTCAAATCGGATT AGTTGGAGAACTTAATTACCCTGATTGCCCTTTCT TAAAAATATTGCAGAAGCACCAAATAATACCAC AATGTGTCGATGTGTTTCCGAAACTAGATGATAG ATGGGTAGGAATTTTTTTATTTTCTTTGAT[A/G]T ATTGAAAAGGCAGAAAGAAACACAAATTTTAGT ATTTAATAAAGCAAAATGCACACATCCCCCAAAC AAAACAAGCCTTATTCAACCCAAATTGGTTTCAT ATCACAGAAACCAACAGGATGCCGCCTTCCTCCT TACTGGTCCCACCCACTCGAACAAAAGTTSTACA GAAATAAAAATGGCTACAATTCTTCTACCA |
| Gm08:834 7799 | 8347799 | [C/A] | 182 | 365 | 0.919 | 0.757 | AGAGCCTGAAGGGCACAGATGGGATCAATCTCG GTCACGATGACACGAGCACCAGCCTGCTTCATTG CAGCAGCACAACCCTTGCCAACATCACCATATCC AGCCACAACAGCCACCTTTCCAGCAATCATAACA TCGGTAGCCCTCATGAGACCATCAGGGAGAGAG TGACGGCACCCATACAAGTTGTCAAACTGTTA[A/ C]AAAACCACAGATTAAAAGGTTAAACAAACAAA ACACAAGCAACAAAGCAAAATCCAATTATAATC AACTAGATCCATGACCAGCTAGTATAATGTCCTC AAAATCCAATCACCCACTTCTTACTTTCAATACC CTAATCAATAAACAACCCGTCACAAAAGACTCG GTTTGGATCAATGTTTGCAAAACCAATTTTGAAT |
| Gm08:834 8022 | 8348022 | [T/A] | 183 | 366 | 0.854 | 0.848 | AACAAACAAAACACAAGCAACAAAGCAAAATCC AATTATAATCAACTAGATCCATGACCAGCTAGTA TAATGTCCTCAAAATCCAATCACCCACTTCTTACT TTCAATACCCTAATCAATAAACAACCCGTCACAA AAGACTCGGTTTGGATCAATGTTTGCAAAACCAA TTTTGAATGAAAACGATTTCGAGTTAAAAT[A/T]G ATTTYGAAACAACATGATTTATGTTTGAACATTT TTTTATTTTAAAACCAAAAACAGTAGTAAAATTC AGTATAATTTATTTTATCCTATCCAAAGTAGCTT CAAATCAAAATGTGCACTCAGAATCAATTCCTTA TTTGTGTAATAAAACATGTGACCATTTACCTAAA GTCACGTTAGCAAGCAACTTACTAATGT |
| Gm08:834 8028 | 8348028 | [T/C] | 184 | 367 | 0.844 | 0.787 | CAAAACACAAGCAACAAAGCAAAATCCAATTAT AATCAACTAGATCCATGACCAGCTAGTATAATGT CCTCAAAATCCAATCACCCACTTCTTACTTTCAAT ACCCTAATCAATAAACAACCCGTCACAAAAGACT CGGTTTGGATCAATGTTTGCAAAACCAATTTTGA ATGAAAACGATTTCGAGTTAAAATWGATTT[C/T] GAAACAACATGATTTATGTTTGAACATTTTTTTAT TTTAAAACCAAAAACAGTAGTAAAATTCAGTATA ATTTATTTTATCCTATCCAAAGTAGCTTCAAATC AAAATGTGCACTCAGAATCAATTCCTTATTTGTG TAATAAAACATGTGACCATTTACCTAAAGTCACG TTAGCAAGCAACTTACTAATGTTCTGAC |
| Gm08:834 9925 | 8349925 | [G/T] | 185 | 368 | 0.929 | 0.717 | AMTATGAAAAATTATACTTCAAACAAGTCTCTCA TAAGAATGTTTATGGTCTCATACAGATGAATATT TTCACTTCGAATACACGTAAAACTAATATGAATT CACACAAGTGATTAAAGATCTAAAACTAACTTTT GTCTTCTTTTTTTATAGATGTGGGTTTCATTCTCT ATCATGCCACTAAAACTATCATCTAATA[G/T]ATT CTTTGACATCTAAGGACTAATTGAATAAATACAA |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| | | | | | | | TTAAGTAAAATTGTCTATGATTTAGGCCTGTGGA ATAATCCTTGAGTAAGCCTTTATTGACATCGCTA ACAAGTAGCATGTCATTAAGGTTTCATTCGATGG TATTGATCAGGCCTCTATAAAATTTTGTACATTTT AATATGCATCAAATGAGCATACKGGT |
| Gm08:835 0122 | 8350122 | [T/G] | 186 | 369 | 0.929 | 0.649 | ATAKATTCTTTGACATCTAAGGACTAATTGAATA AATACAATTAAGTAAAATTGTCTATGATTTAGGC CTGTGGAATAATCCTTGAGTAAGCCTTTATTGAC ATCGCTAACAAGTAGCATGTCATTAAGGTTTCAT TCGATGGTATTGATCAGGCCTCTATAAAATTTTG TACATTTTAATATGCATCAAATGAGCATAC[G/T]G GTAAAGATTTCGGTGCTCAAGTTAATAGTTGGTA AAGTAAAAGCATTATATGTAAGATTTTCATGTAC TTGKTAAAGCTAAGGGACTATCGGAGATTGTTGA TAAGCATTTAAAAAACTCTCAACAATCTTCTATC TGCCTATAAAGTTTTCTYAAAAAGCATTTAAAAA ATTTATAGGTTAATTAGAGATTTGTTAGG |
| Gm08:835 0277 | 8350277 | [C/T] | 187 | 370 | 0.929 | 0.699 | CTCTATAAAATTTTGTACATTTTAATATGCATCAA ATGAGCATACKGGTAAAGATTTCGGTGCTCAAGT TAATAGTTGGTAAAGTAAAAGCATTATATGTAAG ATTTTCATGTACTTGKTAAAGCTAAGGGACTATC GGAGATTGTTGATAAGCATTTAAAAAACTCTCAA CAATCTTCTATCTGCCTATAAAGTTTTCT[C/T]AA AAAGCATTTAAAAAATTTATAGGTTAATTAGAGA TTTGTTAGGTAGGTTAACATACATGTAAAGATTT TTCTTTTTTTGGAAAATACATGTAAAGAGTTTTGT AAAAGTAGAACTTGTGAATACGTGATTTATAAGA CAATTCATATTCCTCCCAATCAGGTAATTTTGTGC AAAAAGTCTTATTAAGTTGGTGTGTA |
| Gm08:835 1061 | 8351061 | [G/A] | 188 | 371 | 1 | 0.823 | ATATTGTAAAACACAAAATATTTATATTCCAATC TTMAATGTTTTTATTTGACATTATAAATATTTAAA GGATAGAATCAATGTTAATCAAGTTAACATAAAA AATAAAAAATTACATAGCATTCAACATGTAGGTA TCAAATCTATGTTATAAAATGTTTATTAGATAGA GAAAAATATTTGCTAAAATTTWGATAATT[A/G]T GCTATGTTTATATGTTGAATGATGGGTAAAATAA AATGACGCATAATTAAGTAACATAAGTAAAATA AAAATTAAGTTTAATTTTTATGAATTATCAATAT AAAAAAATAAAATATATTCCTAACATTTCTCTTT CCTCTATTTTACATTCATTTTATTTTCTTAATTTTT TTCATTTTGATATCCTTTAATATAATAA |
| Gm08:835 1503 | 8351503 | [A/G] | 189 | 372 | 0.869 | 0.718 | CCCGGTCAAAATATAGGTTTAACAATTAGTCAAT TACTATATAAATAGGTTTGTATTTGAATATGTTA GTAAAAGTAGTTTTAATATATCTTATTCCAGTA AAATTATCAATTACTTTTAATAATAAAGTCTACAC AAATTTGTATAAAACTATTTTCCCCCTACGATAA AGTTGTTTCGAAAAAAAAGTAAGTTGGA[A/G]A AATTTATTGAAGTGATGAAAACTATTTTTATGGT TATTTTTTATCACACAAATTAATTTTGGAATCTTA TAATTAGAAATGGTTGAATTTATATATTGGTTAA CTTTATTTTCTTATTTCGTCCACAGTAATGAATTG TTTCAAACAAAAAAAAATCAATTAATATATATT TTATAATTTTACTATTGAAAAATACCT |
| Gm08:835 2313 | 8352313 | [C/T] | 190 | 373 | 1 | 0.743 | AGCATAATCACAATTATTGAGAAGATATTTTTAT TTTATTTTTACCGAATCGTCGCACGACTCGGCGT GTTGCAACCGCATTAAATCTTTGTGTTGGTCTCAC CCTGTCTTTTTGTGGATGATCGATCCTCTTGGATT GGTTTTTATAAAACTCAACTTCCCATCGGTGTTCT TTAGTAATTGGAGTATCTTTGGATGTT[C/T]GTTA CATTTTATGATAAATTTAAATGATCCACAATCAC TAACTCAATTTTGCAAAGCAGGATTCTGAATGTT TTTGTAAATCTCGTTTTGTCCTAAAAGTTCGTCTA TAACAATAAACAAACATGCACTTGGTTGTTTTT AAAATTGTCTCAAAACTCTGTTATAAAGAAATAA GACCTAAAGATATTTTTTACAAATT |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:835 2743 | 8352743 | [C/T] | 191 | 374 | 0.843 | 0.72 | ATATCCTTAGATTAATTTATTTTSTTGATAAAAAA AAWKGATAAAAATTTCCATGCTTTAAATTTGTCA TTGGTCCATCTGATCGACTCTATACATCAAACTT GAGTGTTATTTGCATACAAAAGGAAAACATCAG AGACATGACAGAGTAGGTTGCATTGGTGTTTAGT TGACCTGATTAAGAAGTTACACACAAAGTG[C/T] TCCTCTATCTCCTCTTCAAGGTCCTCCTACCTATA GTCTTCTTGTACCTCTTATTATATGGATTAATTAG TGTAGAATTATTTCAACTTAATTAATAATTTTGAA TTTAAGTCATGAGAATGAGTATCAAAAYTTTTTC ACCTATAAAATCGAATRTGCTTCAAATAAGATT GTCTCTAATAAATAATATGTGTTTAAT |
| Gm08:835 3341 | 8353341 | [A/T] | 192 | 375 | 0.812 | 0.774 | AAACCTATGTCGGTTGGTTCCTCTTTAAAGAAAA GAGAATAAAAATAACAAAGAAAAAAAAGTCGCC TTCCATTTCATTCGCATTCATAGTAAAAGAGTGA GCGATCCCGGGAAATGAATTAATATACGACTAA AAAGATTTGAGAATTATAATAATTAATAATTAAT AATTCTTTTTCAAAAGTAAAGTACAGTACTGC[A/ T]GGAAACATGAGCATGTTCATAGATTAAAATTT AAAAGAATATTATCAGTAACAAAAAAATAAAAA TTAACCCATGCATCCAAGAAAGAAATACYCATGT GCTTCAGTTGTCCGCTGTCTGAGATGTGGTGACC TTTTTTCAAATGATCATAATAGTTACTTCATAATG ACGACATGCATCAAACTATTTTTTCTTCAAAA |
| Gm08:835 5175 | 8355175 | [C/T] | 193 | 376 | 0.867 | 0.787 | TATCCCCCATGTTAATGAAGCAAGGTGTGGGGGA AGGAAAGAGTCAGCATCAGTGAAGTAGAGAGGG GGGTTGGTGATTTTGGTGGGAATAAATTGGCTAT ATTGCCCCCACCAACCTCGTTGCTACCAAATACC AACAACACTGACTCACTGAGAATTGGGAAAGAA ACTTAAAACCAAGTCTTGCAGTGACGTACATG[C/ T]AGTGTGTGCATCACACATTCAGGTTTCCAGTCA AATTGTAGAACAAATGAATTTCTTGCTTTAACTT AAGTTGAAGTTTAAGAAGTGAAGCTGATGCTTGT TTTTGAATGAAAAGCCTTTGATAGTTTGATGTAA GCATTTTCCAAATTTAACTCTTCCCATGCTTGACA GAGCCAATTAAGCTAACTGGTTTGATAACA |
| Gm08:836 0133 | 8360133 | [A/G] | 194 | 377 | 1 | 0.773 | CACCCCTCATTAGAGGCTTAGGATTTTTTTGAGTC CTAGAACACACATCTTATCTCAATAATGATTTCT ATCATTGCCAGAATTACAATTAAAAACTAAAATA TAATCAATTAGATTGAATTGAACTTCTACAGACC CCAAAGGCACTCGATGCATTTTCACTGTATGTGG TTTGTCTTTCTGTACTATACTGCACGCTT[A/G]GC AAAATAATCAGTAACACATGTTAAGAGAGCTTGC ACTTTATTTTTATCTTGTTGACGGGTTTGTTGTCA TTGAAAACACATTATATTCAGAGGAATTTGACTC AACATGTTCAACCCACCAATTATCACATTTAAAC AAATYTAAATCAATCGCAAATCATATATATTCAG AATTTTACATATTAAATATTTCATATC |
| Gm08:836 3193 | 8363193 | [T/A] | 195 | 378 | 1 | 0.703 | AATAACATGGTTATGTTGAAAACAAAAGAAAAA AATATCAAATTTAATTCATGAATCTTTCAACTAA TTAAAAAATGACCAATCCTAACTAGTTGCAGAAG CTATTAATTAAATTTTTAAAAAAGTATATCTTTCT CTCTTATGACTCACATAATTTATAKTCCCTATACT CAAAGTCTCACATAATTTATACTACAAAA[A/T]CT TAGGTTTAATTTCGTACCTATTGTTAATGTTTCCT AATCGAAATTAGAATTTCACCCCGATAATTAAAA GTTTACATTAAAAAATTAYATAAATTACCGAAAT AAAACTCAAATTTAGTCAAACAATAATGTAAGC ACTAAGCAGCAACTAAGAAGCTATAAACAAAGT TTTGATAAATAGTTAAATTTATCCTCCA |
| Gm08:836 3888 | 8363888 | [A/G] | 196 | 379 | 0.825 | 0.809 | AAGTGGGGAACTGTCGATCCATGGTGCTGGCAGC AACCGTAACATGCCAGGGTGCGAGATTTTCCGCA GTGGCTTCCGCGGGCCCACTGTTGCCAGCAGAGC AAACCACCACAACGCCACGCTTGGCCGCATGGA AGGATCCGATGGCAACACTATCCTTGAAAAACGT GGAGGAAGAGCCACCGAGCGAGACGGAGAGG[A/ G]CATCGACGCCGTCGTGGATGGCGAGGTCGAAG |

TABLE 3B-continued

Non-Limiting Examples of Genomic Loci Comprising the Various Marker Loci Provided Herein.

| SNP Marker Name | SNP Position | SNP [S/R] | SEQ ID NO [S] | SEQ ID NO [R] | $r^2$ with 8357600 | $r^2$ with 8356824 | Consensus Reference Sequence (200 bp flanking SNP) [S/R] |
|---|---|---|---|---|---|---|---|
| Gm08:8364195 | 8364195 | [A/G] | 197 | 380 | 0.919 | 0.788 | GCCGCCAAGATATCAGCGTCGAAGCACTCCTCGC CTCCGACGGGGGGCCAGCAGACCTTGTAGGCTGC CACACGTGCCATTGGTGAGCCACCCTTGGCTGTT CCCTGGCCCTGGCCGAAGACGCTGACACGTGCGA CCATGTTCCCGCCAGCTGTGGATAGGGTGTGG TGCCATTGGTGAGCCACCCTTGGCTGTTCCCTGG CCCTGGCCGAAGACGCTGACACGTGCGACCATGT TCCCGCCAGCTGTGGATAGGGTGTGGGTCCCGTG GCCCTCGTTGTCACGTGGCGAGTCAAAGGAGGA GTTCAGTGGGCCCGCCACTGAGGCGTAG[CCCTTG TTGAAGTACCTTGCCCCTATTAGCTTCCTGCA/G] TTCAACATCTCCACTTAACGTTTCTTTAATTTWTC AAAACAAAATCATTGAAAGATTGGTCTGGTTGGT GTGAAAACACTAGTACTATAAAAGAATAAGATA ACGAAAGAAACATGTCTGCGTTCAAAGGAGTGC TTAACCCTTTCATTGTAGTATTCACCTAATAAAG AGTGCCAATTTAAAGGCATATGACTACAGAA |

R = Resistant; S = Susceptible
*Liu et al. (2012). A soybean cyst nematode resistance gene points to a new mechanism of plant resistance to pathogens. Nature 492: 256-260.

TABLE 4

Non-limiting Examples of Amplicons Comprising the Various Marker Loci Provided Herein.

| Marker Name | Linkage Group (ch) | Primer 1 | Primer 2 | Resistant (R) or Susceptible (S) Allele | SEQ ID NO | Amplicon Sequence | Amplicon Size (bp) |
|---|---|---|---|---|---|---|---|
| S07160-1 | A2 (Gm08) | 136868 | 136869 | R | 11 | TGTGTTGTGTTTGACTG CCATAACATGATGTTTG GATTAAATATAAACAA TAATATCCTATGCAGTT AGTGAGGCTGTGATTT GGAAGACACTGTCTTA TCAAGAGGCTTGGGAA ATG | 118 |
| S07160-1 | A2 (Gm08) | 136868 | 136869 | S | 12 | TGTGTTGTGTTTGACTG CCATAACATGATGTTTG GATTAAATATAAACAA TAATATCATATGCAGTT AGTGAGGCTGTGATTT GGAAGACACTGTCTTA TCAAGAGGCTTGGGAA ATG | 118 |

In another embodiment, the method of detecting comprises DNA sequencing of at least one of the marker loci provided herein. As used herein, "sequencing" refers to sequencing methods for determining the order of nucleotides in a molecule of DNA. Any DNA sequencing method known in the art can be used in the methods provided herein. Non-limiting examples of DNA sequencing methods useful in the methods provided herein include Next Generation Sequencing (NGS) technologies, for example, as described in Egan, A. N, et al. (2012) *American Journal of Botany* 99(2):175-185; genotyping by sequencing (GBS) methods, for example, as described in Elshire, R. J., et al. (2011) *PLoS ONE* 6(5):e19379; Molecular Inversion Probe (MIP) genotyping, as described, for example, in Hardenbol, P., et al. (2003) *Nature Biotechnology* 21(6):673-678; or high throughput genotyping by whole-genome resequencing, as described, for example in Huang, X et al., (2009) *Genome Research* 19:1068-1076. Each of the above references is incorporated by reference in their entirety herein.

An active variant of any one of SEQ ID NOS: 1-380 can comprise a polynucleotide having at least 75%, 80% 85%, 90%, 91%, 92%, 93%, 94%, 95%, 96%, 97%, 98% or 99% sequence identity to SEQ ID NOS: 1-380 as long as it is capable of amplifying and/or detecting the marker locus of interest. By "fragment" is intended a portion of the polynucleotide. A fragment or portion can comprise at least 5, 6, 7, 8, 9, 10, 11, 12, 13, 14, 15, 16, 17, 18, 19, 20, 25, 30, 40, 50, 75, 100, 150, 200, 250, 300, 350, 400 contiguous nucleotides of SEQ ID NOS: 1-380 as long as it is capable of amplifying and/or detecting the marker locus of interest.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; or any equivalent program thereof. By "equivalent program" is intended any sequence comparison program that, for any two sequences in question, generates an alignment having identical nucleotide residue matches and an identical percent sequence identity when compared to the corresponding alignment generated by GAP Version 10.

Traits or markers are considered to be linked if they co-segregate. A 1/100 probability of recombination per generation is defined as a map distance of 1.0 centiMorgan (1.0 cM). Genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. Genetic elements located within a chromosome segment are also genetically linked, typically within a genetic recombination distance of less than or equal to 50 centimorgans (cM), e.g., about 49, 40, 30, 20, 10, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). In specific embodiments, a closely linked marker is within 10 cM, 9 cM, 8 cM, 7 cM, 6 cM, 5 cM, 4 cM, 3 cM, 2 cM or 1 cM of any given marker disclosed herein. In further embodiments, a marker associated with one of the markers disclosed herein can be within 75 Kb, 60 Kb, 50 Kb, 40 Kb, 30 Kb, 20K, 10 Kb, 5 Kb or less of the disclosed marker.

Put another way, closely linked loci co-segregate at least about 90% of the time. Genetic linkage as evaluated by recombination frequency is impacted by the chromatin structure of the region comprising the loci. Typically, the region is assumed to have a euchromatin structure during initial evaluations. However, some regions, such are regions closer to centrosomes, have a heterochromatin structure. Without further information, the predicted physical distance between genetic map positions is based on the assumption that the region is euchromatic, however if the region comprises heterochromatin the markers may be physically closer together. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 2 Kb, about 1 Kb, about 500 nucleotides, about 250 nucleotides, or less.

When referring to the relationship between two genetic elements, such as a genetic element contributing to resistance and a proximal marker, "coupling" phase linkage indicates the state where the "favorable" allele at the resistance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for resistance) is physically linked with an "unfavorable" allele at the proximal marker locus, and the two "favorable" alleles are not inherited together (i.e., the two loci are "out of phase" with each other).

Markers are used to define a specific locus on the soybean genome. Each marker is therefore an indicator of a specific segment of DNA, having a unique nucleotide sequence. Map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans.

Favorable genotypes associated with at least trait of interest may be identified by one or more methodologies. In some examples one or more markers are used, including but not limited to AFLPs, RFLPs, ASH, SSRs, SNPs, indels, padlock probes, molecular inversion probes, microarrays, sequencing, and the like. In some methods, a target nucleic acid is amplified prior to hybridization with a probe. In other cases, the target nucleic acid is not amplified prior to hybridization, such as methods using molecular inversion probes (see, for example Hardenbol et al. (2003) Nat Biotech 21:673-678). In some examples, the genotype related to a specific trait is monitored, while in other examples, a genome-wide evaluation including but not limited to one or more of marker panels, library screens, association studies, microarrays, gene chips, expression studies, or sequencing such as whole-genome resequencing and genotyping-by-sequencing (GBS) may be used. In some examples, no target-specific probe is needed, for example by using sequencing technologies, including but not limited to next-generation sequencing methods (see, for example, Metzker (2010) Nat Rev Genet 11:31-46; and, Egan et al. (2012) Am J Bot 99:175-185) such as sequencing by synthesis (e.g., Roche 454 pyrosequencing, Illumina Genome Analyzer, and Ion Torrent PGM or Proton systems), sequencing by ligation (e.g., SOLiD from Applied Biosystems, and Polnator system from Azco Biotech), and single molecule sequencing (SMS or third-generation sequencing) which eliminate template amplification (e.g., Helicos system, and PacBio RS system from Pacific BioSciences). Further technologies include optical sequencing systems (e.g., Starlight from Life Technologies), and nanopore sequencing (e.g., GridION from Oxford Nanopore Technologies). Each of these may be coupled with one or more enrichment strategies for organellar or nuclear genomes in order to reduce the complexity of the genome under investigation via PCR, hybridization, restriction enzyme (see, e.g., Elshire et al. (2011) PLoS ONE 6:e19379), and expression methods. In some examples, no reference genome sequence is needed in order to complete the analysis.

The use of marker assisted selection (MAS) to select a soybean plant or germplasm which has a certain marker locus, haplotype or marker profile is provided. For instance, in certain examples a soybean plant or germplasm possessing a certain predetermined favorable marker locus or haplotype will be selected via MAS. In certain other examples, a soybean plant or germplasm possessing a certain predetermined favorable marker profile will be selected via MAS.

Using MAS, soybean plants or germplasm can be selected for markers or marker alleles that positively correlate with soybean cyst nematode resistance, without actually raising soybean and measuring for resistance (or, contrawise, soybean plants can be selected against if they possess markers that negatively correlate with resistance). MAS is a powerful tool to select for desired phenotypes and for introgressing desired traits into cultivars of soybean (e.g., introgressing desired traits into elite lines). MAS is easily adapted to high throughput molecular analysis methods that can quickly screen large numbers of plant or germplasm genetic material for the markers of interest and is much more cost effective than raising and observing plants for visible traits.

In some embodiments, the molecular markers or marker loci are detected using a suitable amplification-based detection method. In these types of methods, nucleic acid primers are typically hybridized to the conserved regions flanking the polymorphic marker region. In certain methods, nucleic acid probes that bind to the amplified region are also employed. In general, synthetic methods for making oligonucleotides, including primers and probes, are well known in the art. For example, oligonucleotides can be synthesized chemically according to the solid phase phosphoramidite triester method described by Beaucage and Caruthers (1981) Tetrahedron Letts 22:1859-1862, e.g., using a commercially available automated synthesizer, e.g., as described in Needham-VanDevanter, et al. (1984) Nucleic Acids Res. 12:6159-6168. Oligonucleotides, including modified oligonucleotides, can also be ordered from a variety of commercial sources known to persons of skill in the art.

It will be appreciated that suitable primers and probes to be used can be designed using any suitable method. It is not intended that the invention be limited to any particular primer, primer pair or probe. For example, primers can be designed using any suitable software program, such as LASERGENE® or Primer3.

It is not intended that the primers be limited to generating an amplicon of any particular size. For example, the primers used to amplify the marker loci and alleles herein are not limited to amplifying the entire region of the relevant locus. In some embodiments, marker amplification produces an amplicon at least 20 nucleotides in length, or alternatively, at least 50 nucleotides in length, or alternatively, at least 100 nucleotides in length, or alternatively, at least 200 nucleotides in length.

Non-limiting examples of polynucleotide primers useful for detecting the marker loci provided herein are provided in Table 1 and include, for example, SEQ ID NOS: 1, 2, 3, 4, 5, 6, 7, 8 or variants or fragments thereof.

PCR, RT-PCR, and LCR are in particularly broad use as amplification and amplification-detection methods for amplifying nucleic acids of interest (e.g., those comprising marker loci), facilitating detection of the markers. Details regarding the use of these and other amplification methods are well known in the art and can be found in any of a variety of standard texts. Details for these techniques can also be found in numerous journal and patent references, such as Mullis, et al. (1987) U.S. Pat. No. 4,683,202; Arnheim & Levinson (Oct. 1, 1990) C&EN 36-47; Kwoh, et al. (1989) Proc. Natl. Acad. Sci. USA 86:1173; Guatelli, et al., (1990) Proc. Natl. Acad. Sci. USA87:1874; Lomell, et al., (1989) J. Clin. Chem. 35:1826; Landegren, et al., (1988) Science 241:1077-1080; Van Brunt, (1990) Biotechnology 8:291-294; Wu and Wallace, (1989) Gene 4:560; Barringer, et al., (1990) Gene 89:117, and Sooknanan and Malek, (1995) Biotechnology 13:563-564.

Such nucleic acid amplification techniques can be applied to amplify and/or detect nucleic acids of interest, such as nucleic acids comprising marker loci. Amplification primers for amplifying useful marker loci and suitable probes to detect useful marker loci or to genotype SNP alleles are provided. For example, exemplary primers and probes are provided in SEQ ID NOS: 1, 2, 3, 4, 5, 6, 7, 8, 9, 10 and in Tables 1 and 2, and the genomic loci comprising the various marker loci provided herein are provided in SEQ ID NOS: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 and in Tables 3A and 3B. Non-limiting examples of amplicon sequences comprising the marker loci provided herein are provided SEQ ID NOS: 11, 12 and in Table 4.

However, one of skill will immediately recognize that other primer and probe sequences could also be used. For instance primers to either side of the given primers can be used in place of the given primers, so long as the primers can amplify a region that includes the allele to be detected, as can primers and probes directed to other SNP marker loci. Further, it will be appreciated that the precise probe to be used for detection can vary, e.g., any probe that can identify the region of a marker amplicon to be detected can be substituted for those examples provided herein. Further, the configuration of the amplification primers and detection probes can, of course, vary. Thus, the compositions and methods are not limited to the primers and probes specifically recited herein.

In certain examples, probes will possess a detectable label. Any suitable label can be used with a probe. Detectable labels suitable for use with nucleic acid probes include, for example, any composition detectable by spectroscopic, radioisotopic, photochemical, biochemical, immunochemical, electrical, optical, or chemical means. Useful labels include biotin for staining with labeled streptavidin conjugate, magnetic beads, fluorescent dyes, radiolabels, enzymes, and colorimetric labels. Other labels include ligands, which bind to antibodies labeled with fluorophores, chemiluminescent agents, and enzymes. A probe can also constitute radiolabelled PCR primers that are used to generate a radiolabelled amplicon. Labeling strategies for labeling nucleic acids and corresponding detection strategies can be found, e.g., in Haugland (1996) *Handbook of Fluorescent Probes and Research Chemicals Sixth Edition* by Molecular Probes, Inc. (Eugene Oreg.); or Haugland (2001) *Handbook of Fluorescent Probes and Research Chemicals Eighth Edition* by Molecular Probes, Inc. (Eugene Oreg.).

Detectable labels may also include reporter-quencher pairs, such as are employed in Molecular Beacon and TaqMan™ probes. The reporter may be a fluorescent organic dye modified with a suitable linking group for attachment to the oligonucleotide, such as to the terminal 3' carbon or terminal 5' carbon. The quencher may also be an organic dye, which may or may not be fluorescent, depending on the embodiment. Generally, whether the quencher is fluorescent or simply releases the transferred energy from the reporter by non-radiative decay, the absorption band of the quencher should at least substantially overlap the fluorescent emission band of the reporter to optimize the quenching. Non-fluorescent quenchers or dark quenchers typically function by absorbing energy from excited reporters, but do not release the energy radiatively.

Selection of appropriate reporter-quencher pairs for particular probes may be undertaken in accordance with known techniques. Fluorescent and dark quenchers and their relevant optical properties from which exemplary reporter-quencher pairs may be selected are listed and described, for example, in Berlman, *Handbook of Fluorescence Spectra of Aromatic Molecules,* 2nd ed., Academic Press, New York, 1971, the content of which is incorporated herein by reference. Examples of modifying reporters and quenchers for covalent attachment via common reactive groups that can be added to an oligonucleotide in the present invention may be found, for example, in Haugland, *Handbook of Fluorescent Probes and Research Chemicals,* Molecular Probes of Eugene, Oreg., 1992, the content of which is incorporated herein by reference.

In certain examples, reporter-quencher pairs are selected from xanthene dyes including fluoresceins and rhodamine dyes. Many suitable forms of these compounds are available commercially with substituents on the phenyl groups, which can be used as the site for bonding or as the bonding functionality for attachment to an oligonucleotide. Another useful group of fluorescent compounds for use as reporters are the naphthylamines, having an amino group in the alpha or beta position. Included among such naphthylamino compounds are 1-dimethylaminonaphthyl-5 sulfonate, 1-anilino-8-naphthalene sulfonate and 2-p-touidinyl-6-naphthalene sulfonate. Other dyes include 3-phenyl-7-isocyanatocoumarin; acridines such as 9-isothiocyanatoacridine; N-(p-(2-benzoxazolyl)phenyl)maleimide; benzoxadiazoles; stilbenes; pyrenes and the like. In certain other examples, the reporters and quenchers are selected from fluorescein and rhodamine dyes. These dyes and appropriate linking methodologies for attachment to oligonucleotides are well known in the art.

Suitable examples of reporters may be selected from dyes such as SYBR green, 5-carboxyfluorescein (5-FAM™ available from Applied Biosystems of Foster City, Calif.), 6-carboxyfluorescein (6-FAM), tetrachloro-6-carboxyfluorescein (TET), 2,7-dimethoxy-4,5-dichloro-6-carboxyfluorescein, hexachloro-6-carboxyfluorescein (HEX), 6-carboxy-2',4,7, 7'-tetrachlorofluorescein (6-TET™ available from Applied Biosystems), carboxy-X-rhodamine (ROX), 6-carboxy-4', 5'-dichloro-2',7'-dimethoxyfluorescein (6-JOE™ available from Applied Biosystems), VIC™ dye products available from Molecular Probes, Inc., NED™ dye products available from Applied Biosystems, and the like. Suitable examples of quenchers may be selected from 6-carboxy-tetramethyl-rhodamine, 4-(4-dimethylaminophenylazo) benzoic acid (DABYL), tetramethylrhodamine (TAMRA), BHQ-0™, BHQ-1™, BHQ-2™, and BHQ-3™, each of which are available from Biosearch Technologies, Inc. of Novato, Calif., QSY-7™, QSY-9™, QSY-21™ and QSY-35™, each of which are available from Molecular Probes, Inc., and the like.

In one aspect, real time PCR or LCR is performed on the amplification mixtures described herein, e.g., using molecular beacons or TaqMan™ probes. A molecular beacon (MB) is an oligonucleotide which, under appropriate hybridization conditions, self-hybridizes to form a stem and loop structure. The MB has a label and a quencher at the termini of the oligonucleotide; thus, under conditions that permit intra-molecular hybridization, the label is typically quenched (or at least altered in its fluorescence) by the quencher. Under conditions where the MB does not display intra-molecular hybridization (e.g., when bound to a target nucleic acid, such as to a region of an amplicon during amplification), the MB label is unquenched. Details regarding standard methods of making and using MBs are well established in the literature and MBs are available from a number of commercial reagent sources. See also, e.g., Leone, et al., (1995) Molecular beacon probes combined with amplification by NASBA enable homogenous real-time detection of RNA, Nucleic Acids Res. 26:2150-2155; Tyagi and Kramer, (1996) Molecular beacons: probes that fluoresce upon hybridization, Nature Biotechnology 14:303-308; Blok and Kramer, (1997) Amplifiable hybridization probes containing a molecular switch, Mol Cell Probes 11:187-194; Hsuih. et al., (1997) Novel, ligation-dependent PCR assay for detection of hepatitis C in serum, J Clin Microbiol 34:501-507; Kostrikis, et al., (1998) Molecular beacons: spectral genotyping of human alleles, Science 279:1228-1229; Sokol, et al., (1998) Real time detection of DNA:RNA hybridization in living cells, Proc. Natl. Acad. Sci. U.S.A. 95:11538-11543; Tyagi, et al., (1998) Multicolor molecular beacons for allele discrimination, Nature Biotechnology 16:49-53; Bonnet, et al., (1999) Thermodynamic basis of the chemical specificity of structured DNA probes, Proc. Natl. Acad. Sci. U.S.A. 96:6171-6176; Fang, et al. (1999) Designing a novel molecular beacon for surface-immobilized DNA hybridization studies, J. Am. Chem. Soc. 121:2921-2922; Marras, et al., (1999) Multiplex detection of single-nucleotide variation using molecular beacons, Genet. Anal. Biomol. Eng. 14:151-156; and Vet, et al., (1999) Multiplex detection of four pathogenic retroviruses using molecular beacons, Proc. Natl. Acad. Sci. U.S.A. 96:6394-6399. Additional details regarding MB construction and use is found in the patent literature, e.g., U.S. Pat. Nos. 5,925,517; 6,150,097; and 6,037,130.

Another real-time detection method is the 5'-exonuclease detection method, also called the TaqMan™ assay, as set forth in U.S. Pat. Nos. 5,804,375; 5,538,848; 5,487,972; and 5,210,015, each of which is hereby incorporated by reference in its entirety. In the TaqMan™ assay, a modified probe, typically 10-25 nucleic acids in length, is employed during PCR which binds intermediate to or between the two members of the amplification primer pair. The modified probe possesses a reporter and a quencher and is designed to generate a detectable signal to indicate that it has hybridized with the target nucleic acid sequence during PCR. As long as both the reporter and the quencher are on the probe, the quencher stops the reporter from emitting a detectable signal. However, as the polymerase extends the primer during amplification, the intrinsic 5' to 3' nuclease activity of the polymerase degrades the probe, separating the reporter from the quencher, and enabling the detectable signal to be emitted. Generally, the amount of detectable signal generated during the amplification cycle is proportional to the amount of product generated in each cycle.

It is well known that the efficiency of quenching is a strong function of the proximity of the reporter and the quencher, i.e., as the two molecules get closer, the quenching efficiency increases. As quenching is strongly dependent on the physical proximity of the reporter and quencher, the reporter and the quencher are preferably attached to the probe within a few nucleotides of one another, usually within 30 nucleotides of one another, more preferably with a separation of from about 6 to 16 nucleotides. Typically, this separation is achieved by attaching one member of a reporter-quencher pair to the 5' end of the probe and the other member to a nucleotide about 6 to 16 nucleotides away, in some cases at the 3' end of the probe.

Separate detection probes can also be omitted in amplification/detection methods, e.g., by performing a real time amplification reaction that detects product formation by modification of the relevant amplification primer upon incorporation into a product, incorporation of labeled nucleotides into an amplicon, or by monitoring changes in molecular rotation properties of amplicons as compared to unamplified precursors (e.g., by fluorescence polarization).

Further, it will be appreciated that amplification is not a requirement for marker detection—for example, one can directly detect unamplified genomic DNA simply by performing a Southern blot on a sample of genomic DNA. Procedures for performing Southern blotting, amplification e.g., (PCR, LCR, or the like), and many other nucleic acid detection methods are well established and are taught, e.g., in Sambrook, et al., *Molecular Cloning—A Laboratory Manual* (3d ed.), Vol. 1-3, Cold Spring Harbor Laboratory, Cold Spring Harbor, N.Y., 2000 ("Sambrook"); *Current Protocols in Molecular Biology*, F. M. Ausubel, et al., eds., Current Protocols, a joint venture between Greene Publishing Associates, Inc. and John Wiley & Sons, Inc., (supplemented through 2002) ("Ausubel")) and *PCR Protocols A Guide to Methods and Applications* (Innis, et al., eds) Academic Press Inc. San Diego, Calif. (1990) (Innis). Additional details regarding detection of nucleic acids in plants can also be found, e.g., in *Plant Molecular Biology* (1993) Croy (ed.) BIOS Scientific Publishers, Inc.

Other techniques for detecting SNPs can also be employed, such as allele specific hybridization (ASH). ASH technology is based on the stable annealing of a short, single-stranded, oligonucleotide probe to a completely complementary single-stranded target nucleic acid. Detection is via an isotopic or non-isotopic label attached to the probe. For each polymorphism, two or more different ASH probes are designed to have identical DNA sequences except at the polymorphic nucleotides. Each probe will have exact homology with one allele sequence so that the range of probes can distinguish all the known alternative allele sequences. Each probe is hybridized to the target DNA. With appropriate probe design and hybridization conditions, a single-base mismatch between the probe and target DNA will prevent hybridization.

Real-time amplification assays, including MB or Taq-Man™ based assays, are especially useful for detecting SNP alleles. In such cases, probes are typically designed to bind to the amplicon region that includes the SNP locus, with one allele-specific probe being designed for each possible SNP allele. For instance, if there are two known SNP alleles for a particular SNP locus, "A" or "C," then one probe is designed with an "A" at the SNP position, while a separate probe is designed with a "C" at the SNP position. While the probes are typically identical to one another other than at the SNP position, they need not be. For instance, the two allele-specific probes could be shifted upstream or downstream relative to one another by one or more bases. However, if the probes are not otherwise identical, they should be designed such that they bind with approximately equal efficiencies, which can be accomplished by designing under a strict set of parameters that restrict the chemical properties of the probes. Further, a different detectable label, for instance a different reporter-quencher pair, is typically employed on each different allele-specific probe to permit differential detection of each probe. In certain examples, each allele-specific probe for a certain SNP locus is 11-20 nucleotides in length, dual-labeled with a florescence quencher at the 3' end and either the 6-FAM (6-carboxyfluorescein) or VIC (4,7,2'-trichloro-7'-phenyl-6-carboxyfluorescein) fluorophore at the 5' end.

To effectuate SNP allele detection, a real-time PCR reaction can be performed using primers that amplify the region including the SNP locus, for instance the sequences listed in Tables 3A and 3B, the reaction being performed in the presence of all allele-specific probes for the given SNP locus. By then detecting signal for each detectable label employed and determining which detectable label(s) demonstrated an increased signal, a determination can be made of which allele-specific probe(s) bound to the amplicon and, thus, which SNP allele(s) the amplicon possessed. For instance, when 6-FAM- and VIC-labeled probes are employed, the distinct emission wavelengths of 6-FAM (518 nm) and VIC (554 nm) can be captured. A sample that is homozygous for one allele will have fluorescence from only the respective 6-FAM or VIC fluorophore, while a sample that is heterozygous at the analyzed locus will have both 6-FAM and VIC fluorescence.

The KASPar® and Illumina® Detection Systems are additional examples of commercially-available marker detection systems. KASPar® is a homogeneous fluorescent genotyping system which utilizes allele specific hybridization and a unique form of allele specific PCR (primer extension) in order to identify genetic markers (e.g. a particular SNP locus associated with soybean cyst nematode resistance). Illumina® detection systems utilize similar technology in a fixed platform format. The fixed platform utilizes a physical plate that can be created with up to 384 markers. The Illumina® system is created with a single set of markers that cannot be changed and utilizes dyes to indicate marker detection.

These systems and methods represent a wide variety of available detection methods which can be utilized to detect markers associated with resistance or improved resistance to soybean cyst nematode, but any other suitable method could also be used.

Introgression of soybean cyst nematode resistance into non-resistant or less-resistant soybean germplasm is provided. Any method for introgressing one or more marker loci into soybean plants known to one of skill in the art can be used. Typically, a first soybean germplasm that contains soybean cyst nematode resistance derived from a particular marker locus, haplotype or marker profile and a second soybean germplasm that lacks such resistance derived from the marker locus, haplotype or marker profile are provided.

The first soybean germplasm may be crossed with the second soybean germplasm to provide progeny soybean germplasm. These progeny germplasm are screened to determine the presence of soybean cyst nematode resistance derived from the marker locus, haplotype or marker profile, and progeny that tests positive for the presence of resistance derived from the marker locus, haplotype or marker profile are selected as being soybean germplasm into which the marker locus, haplotype or marker profile has been introgressed. Methods for performing such screening are well known in the art and any suitable method can be used.

One application of MAS is to use the resistance markers, haplotypes or marker profiles to increase the efficiency of an introgression or backcrossing effort aimed at introducing a resistance trait into a desired (typically high yielding) background. In marker assisted backcrossing of specific markers from a donor source, e.g., to an elite genetic background, one selects among backcross progeny for the donor trait and then uses repeated backcrossing to the elite line to reconstitute as much of the elite background's genome as possible.

Thus, the markers and methods can be utilized to guide marker assisted selection or breeding of soybean varieties with the desired complement (set) of allelic forms of chromosome segments associated with superior agronomic performance (resistance, along with any other available markers for yield, disease tolerance, etc.). Any of the disclosed marker loci, marker alleles, haplotypes, or marker profiles can be introduced into a soybean line via introgression, by traditional breeding (or introduced via transformation, or both) to yield a soybean plant with superior agronomic performance. The number of alleles associated with resistance that can be introduced or be present in a soybean plant ranges from 1 to the number of alleles disclosed herein, each integer of which is incorporated herein as if explicitly recited.

The markers and methods provided herein can also be utilized to guide marker assisted selection or breeding of soybean varieties comprising other soybean cyst nematode resistance markers or alleles to create a molecular stack for soybean cyst nematode resistance. For example, any of the marker loci provided herein can be introduced into a soybean line having one or more of the soybean cyst nematode resistance loci rhg1, rhg2, rhg3 or rhg5. In one embodiment, any one or more of the marker loci provided herein can be stacked with the rhg1 locus. In another embodiment, any one or more of the marker loci provided herein can be stacked with the rhg2 locus. In a further embodiment, any one or more of the marker loci provided herein can be stacked with the rhg1 and rhg2 loci.

This also provides a method of making a progeny soybean plant and these progeny soybean plants, per se. The method comprises crossing a first parent soybean plant with a second soybean plant and growing the female soybean plant under plant growth conditions to yield soybean plant progeny. Methods of crossing and growing soybean plants are well within the ability of those of ordinary skill in the art. Such soybean plant progeny can be assayed for alleles associated with resistance and, thereby, the desired progeny selected. Such progeny plants or seed can be sold commercially for soybean production, used for food, processed to obtain a desired constituent of the soybean, or further utilized in subsequent rounds of breeding. At least one of the first or second soybean plants is a soybean plant in that it comprises at least one of the marker loci or marker profiles, such that the progeny are capable of inheriting the marker locus or marker profile.

Often, a method is applied to at least one related soybean plant such as from progenitor or descendant lines in the subject soybean plants pedigree such that inheritance of the desired resistance can be traced. The number of generations separating the soybean plants being subject to the methods provided herein will generally be from 1 to 20, commonly 1 to 5, and typically 1, 2, or 3 generations of separation, and quite often a direct descendant or parent of the soybean plant will be subject to the method (i.e., 1 generation of separation).

Genetic diversity is important for long term genetic gain in any breeding program. With limited diversity, genetic gain will eventually plateau when all of the favorable alleles have been fixed within the elite population. One objective is to incorporate diversity into an elite pool without losing the genetic gain that has already been made and with the minimum possible investment. MAS provides an indication of which genomic regions and which favorable alleles from the original ancestors have been selected for and conserved over time, facilitating efforts to incorporate favorable variation from exotic germplasm sources (parents that are unrelated to the elite gene pool) in the hopes of finding favorable alleles that do not currently exist in the elite gene pool.

For example, the markers, haplotypes, primers, probes, and marker profiles can be used for MAS in crosses involving elite×exotic soybean lines by subjecting the segregating progeny to MAS to maintain major yield alleles, along with the resistance marker alleles herein.

As an alternative to standard breeding methods of introducing traits of interest into soybean (e.g., introgression), transgenic approaches can also be used to create transgenic plants with the desired traits. In these methods, exogenous nucleic acids that encode a desired marker loci, marker profile or haplotype are introduced into target plants or germplasm. For example, a nucleic acid that codes for a resistance trait is cloned, e.g., via positional cloning, and introduced into a target plant or germplasm.

Experienced plant breeders can recognize resistant soybean plants in the field, and can select the resistant individuals or populations for breeding purposes or for propagation. In this context, the plant breeder recognizes "resistant" and "non-resistant" or "susceptible" soybean plants. However, plant resistance is a phenotypic spectrum consisting of extremes in resistance and susceptibility, as well as a continuum of intermediate resistance phenotypes. Evaluation of these intermediate phenotypes using reproducible assays are of value to scientists who seek to identify genetic loci that impart resistance, to conduct marker assisted selection for resistant populations, and to use introgression techniques to breed a resistance trait into an elite soybean line, for example.

By "improved resistance" is intended that the plants show a decrease in the disease symptoms that are the outcome of plant exposure to soybean cyst nematode. That is, the damage caused by soybean cyst nematode is prevented, or alternatively, the disease symptoms caused by soybean cyst nematode is minimized or lessened. Thus, improved resistance to soybean cyst nematode can result in reduction of the disease symptoms by at least about 2% to at least about 6%, at least about 5% to about 50%, at least about 10% to about 60%, at least about 30% to about 70%, at least about 40% to about 80%, or at least about 50% to about 90% or greater. Hence, the methods provided herein can be utilized to protect plants from soybean cyst nematode.

Screening and selection of soybean cyst nematode resistant soybean plants may be performed, for example, by exposing plants to soybean cyst nematode and selecting those plants showing resistance to soybean cyst nematode. Various assays can be used to measure resistance or improved resistance to soybean cyst nematode. For example, soybean cyst nematode resistance can be determined by visual observations after plant exposure to a particular race of soybean cyst nematode, such as race 1, 2, 3, 5 or 14. Scores range from 1 to 9 and indicate visual observations of resistance as compared to other genotypes in the test. A score of 1 indicates soybean cyst nematode are able to infect the plant and cause yield loss, while a score of 9 indicates soybean cyst nematode resistance. Preliminary scores are reported as double digits, for example, '55' indicates a preliminary score of 5 on the scale of 1 to 9.

Non-limiting examples of soybean cyst nematode resistance phenotypic screening are described in detail below.

Multiple populations of *Heterodera glycines* are maintained and increased on host plants. These populations are used to identify, purify, and characterize elite soybean varieties for resistance to soybean cyst nematode. The following races of soybean cyst nematode are maintained: Race 1 (Type HG 2.5), Race 2 (Type HG 1.2.5.7), Race 3 (Type HG 0 or Type HG 7), Race 5 (Type HG 2.5.7), and Race 14 (Type HG 1.3.6.7).

Eggs or second stage juveniles (J2) are used to inoculate host plants to increase their population. Soybean cyst nematode infestation requires a minimum 35 days before the cysts reach maturity and can be used to inoculate soybean experiments. Cyst eggs/J2 inoculant is harvested through a series of washings, grindings, and screenings. Screens are used progressing from larger to smaller sizes, ending with a #500 (25 μm) screen.

Soybean plants are grown in cones. Cones are long containers approximately 12 inches long and 1.5 inches in diameter at the top (e.g., Ray Leach Cone-tainers™). The cone is designed to easily remove the root mass. Three to seven days after planting, an inoculum channel is made in the cone containing the experimental line by poking a 4 inch hole with a 10 ml pipette tip. One ml of inoculum is dispensed into the channel. The plants are watered manually for the duration of the test, with watering being moderately light during the first 3-5 days until J2 infects the roots.

Plants are scored approximately 28-35 days following inoculation when cyst reproduction on susceptible checks is sufficiently high. Plants are removed from their cones and the soil is removed from the roots by gently dipping the roots into a bucket of water. The plants are screened to identify native resistance to one or more of the five races of soybean cyst nematode inoculated using a combination of three methods (1) visual 9-6-1 score; (2) visual full count; and/or (3) microscope count score depending on the stage of the line when screened. In general, lines earlier in the development cycle (R1-R2) are screened by the visual 9-6-1 method, and lines that have progressed to later development phases (R3-R5) are screened by the visual full count and/or microscope count method(s).

One typical phenotyping method is a visual evaluation of the roots. Susceptible checks are first evaluated for the development of cysts on the root system. These counts are recorded and averaged across the experiment to determine the susceptible (SUS) check average. Roots from the test plants are then scored based on a comparison with the average of the susceptible checks as follows:
9=0-15% of the susceptible checks average
6=16-40% of the susceptible checks average
1=≥41% of the susceptible checks average Visual Counts:
In this method, known checks are counted and reported in full. Observed cysts on the test plants are counted for comparison to the susceptible check plant scores. Cyst counts are converted to 1-9 scores based on the female index (FI). The female index (FI) is the percentage of the number of females cysts produced on each experimental line divided by the number produced on a standard susceptible soybean check, then the result is multiplied by 100. A low FI (<10) means that the soybean cyst nematode population is not able to reproduce well on the test line, a high FI means that the soybean cyst nematode population is able to reproduce well on the test line.

Microscope Counts:
Cysts counts for soybean cyst nematode assays for checks and experimental line are determined by washing cysts from roots and counting the number of cysts under the microscope.

At about 28-35 days after inoculation, roots from the susceptible check controls are examined for yellow cysts to assess whether to begin the process of evaluating the test. Experimental lines are compared with known standard checks. Once adequate levels of cysts are detected on the check varieties, plants from the test lines are removed from cones one at a time. Soil is removed from roots by gently dipping the roots into a bucket of water. The root tissue is placed on a 850 micron (#20) pore sieve stacked over a 250 micron (#60) pore sieve and sprayed with a jet of water to dislodge cysts from the roots. Collected cysts are rinsed from the #60 sieve into a clean labeled cup using no more than 30 mls of additional water.

Once all the samples are collected, each sample is counted using a gridded counting dish under a stereo microscope. The number of cysts counted are recorded for each sample. Cyst counts on the test plants are converted to the 1-9 scoring scale based on the female index (FI) described above.

The following exemplary soybean cyst nematode checks, provided in Table 5, can be planted and used to monitor cyst development:

TABLE 5

Exemplary soybean cyst nematode checks.

| Race 1 | Race 2 | Race 3 | Race 5 | Race 14 |
|---|---|---|---|---|
| 92B12 RES | 95M60 RES | 9182 RES | 92B12 RES | 9182 RES |
| 9281 SUS | 9281 SUS | 9281 SUS | 9281 SUS | 9281 SUS |
| 9234 RES | PI437654 RES | 9234 RES | 9234 RES | 9234 SUS |
| 9392 SUS | 9392 SUS | 9392 SUS | 9392 SUS | 9392 SUS |
| 91M12 MR | 9234 MR | 93B15 MR | 91M12 SUS | 93B15 MR |

RES = Resistant;
SUS = Susceptible; and,
MR = Moderately Resistant

In some examples, a kit or an automated system for detecting marker loci, haplotypes, and marker profiles, and/or correlating the marker loci, haplotypes, and marker profiles with a desired phenotype (e.g., soybean cyst nematode resistance) are provided. As used herein, "kit" refers to a set of reagents for the purpose of performing the various methods of detecting or identifying herein, more particularly, the identification and/or the detection of a soybean plant or germplasm having improved resistance to soybean cyst nematode.

In one embodiment, a kit for detecting or selecting at least one soybean plant or soybean germplasm with resistance or improved resistance to soybean cyst nematode is provided. Such a kit comprises (a) primers or probes for detecting one or more marker loci associated with resistance to soybean cyst nematode, wherein at least one of the primers and probes in the kit are capable of detecting a marker locus, wherein the marker locus is associated with the rhg4 locus on linkage group A2; and (b) instructions for using the primers or probes for detecting the one or more marker loci and correlating the detected marker loci with predicted resistance to soybean cyst nematode.

In a specific embodiment, the primers and probes of the kit are capable of detecting a marker locus comprising: (a) S07160-1 or a marker closely linked thereto on linkage group A2; or (ii) a marker locus comprising Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

Thus, a typical kit or system can include a set of marker probes or primers configured to detect at least one favorable allele of one or more marker loci associated with resistance to soybean cyst nematode, for instance a favorable marker locus, haplotype or marker profile. These probes or primers can be configured, for example, to detect the marker loci noted in the tables and examples herein, e.g., using any available allele detection format, such as solid or liquid phase array based detection, microfluidic-based sample detection, etc. The systems and kits can further include packaging materials for packaging the probes, primers, or instructions, controls such as control amplification reactions that include probes, primers or template nucleic acids for amplifications, molecular size markers, or the like.

A typical system can also include a detector that is configured to detect one or more signal outputs from the set of marker probes or primers, or amplicon thereof, thereby identifying the presence or absence of the allele. A wide variety of signal detection apparatus are available, including photo multiplier tubes, spectrophotometers, CCD arrays, scanning detectors, phototubes and photodiodes, microscope stations, galvo-scans, microfluidic nucleic acid amplification detection appliances and the like. The precise configuration of the detector will depend, in part, on the type of label used to detect the marker allele, as well as the instrumentation that is most conveniently obtained for the user. Detectors that detect fluorescence, phosphorescence, radioactivity, pH, charge, absorbance, luminescence, temperature, magnetism or the like can be used. Typical detector examples include light (e.g., fluorescence) detectors or radioactivity detectors. For example, detection of a light emission (e.g., a fluorescence emission) or other probe label is indicative of the presence or absence of a marker allele. Fluorescent detection is generally used for detection of amplified nucleic acids (however, upstream and/or downstream operations can also be performed on amplicons, which can involve other detection methods). In general, the detector detects one or more label (e.g., light) emission from a probe label, which is indicative of the presence or absence of a marker allele. The detector(s) optionally monitors one or a plurality of signals from an amplification reaction. For example, the detector can monitor optical signals which correspond to "real time" amplification assay results.

System or kit instructions that describe how to use the system or kit or that correlate the presence or absence of the favorable allele with the predicted resistance are also provided. For example, the instructions can include at least one look-up table that includes a correlation between the presence or absence of the favorable alleles, haplotypes, or marker profiles and the predicted resistance. The precise form of the instructions can vary depending on the components of the system, e.g., they can be present as system software in one or more integrated unit of the system (e.g., a microprocessor, computer or computer readable medium), or can be present in one or more units (e.g., computers or computer readable media) operably coupled to the detector. As noted, in one typical example, the system instructions include at least one look-up table that includes a correlation between the presence or absence of the favorable alleles and predicted resistance. The instructions also typically include instructions providing a user interface with the system, e.g., to permit a user to view results of a sample analysis and to input parameters into the system.

Isolated polynucleotides comprising the nucleic acid sequences of the primers and probes provided herein are also encompassed herein. In one embodiment, the isolated polynucleotide comprises a polynucleotide capable of detecting a marker locus of the soybean genome comprising: (a) S07160-1, or a marker closely linked thereto on linkage group A2; or (b) Gm08:8300131, Gm08:8257778, Gm08:

8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

In specific embodiments, the isolated polynucleotide comprises: (a) a polynucleotide comprising SEQ ID NOS: 1, 2, 3, 4, 5, 6, 7, 8, 9 or 10; (c) a polynucleotide having at least 90% sequence identity to SEQ ID NOs: 1, 2, 3, 4, 5, 6, 7, 8, 9 or 10; or (d) a polynucleotide comprising at least 10 contiguous nucleotides of SEQ ID NOs: 1, 2, 3, 4, 5, 6, 7, 8, 9 or 10.

In certain embodiments, the isolated nucleic acids are capable of hybridizing under stringent conditions to nucleic acids of a soybean cultivar resistant to soybean cyst nematode, for instance to particular SNPs that comprise a marker locus, haplotype or marker profile.

As used herein, a substantially identical or complementary sequence is a polynucleotide that will specifically hybridize to the complement of the nucleic acid molecule to which it is being compared under high stringency conditions. A polynucleotide is said to be the "complement" of another polynucleotide if they exhibit complementarity. As used herein, molecules are said to exhibit "complete complementarity" when every nucleotide of one of the polynucleotide molecules is complementary to a nucleotide of the other. Two molecules are said to be "minimally complementary" if they can hybridize to one another with sufficient stability to permit them to remain annealed to one another under at least conventional "low-stringency" conditions. Similarly, the molecules are said to be "complementary" if they can hybridize to one another with sufficient stability to permit them to remain annealed to one another under conventional "high-stringency" conditions.

Appropriate stringency conditions which promote DNA hybridization, for example, 6× sodium chloride/sodium citrate (SSC) at about 45° C., followed by a wash of 2×SSC at 50° C., are known to those skilled in the art or can be found in *Current Protocols in Molecular Biology*, John Wiley & Sons, N.Y. (1989), 6.3.1-6.3.6. Typically, stringent conditions for hybridization and detection will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Non-limiting examples of methods and compositions disclosed herein are as follows:
1. A method of identifying a first soybean plant or a first soybean germplasm that displays resistance or improved resistance to soybean cyst nematode, the method comprising detecting in the genome of said first soybean plant or in the genome of said first soybean germplasm at least one marker locus that is associated with the resistance, wherein the at least one marker locus comprises (a) S07160-1 or a marker closely linked thereto on linkage group A2; or (b) Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

2. The method of embodiment 1, wherein at least two marker loci are detected.

3. The method of embodiment 2, wherein the at least two marker loci comprise a haplotype that is associated with said resistance.

4. The method of embodiment 1, wherein the germplasm is a soybean variety.

5. The method of embodiment 1, wherein the method further comprises selecting the first soybean plant or first soybean germplasm or a progeny thereof having the at least one marker locus.

6. The method of embodiment 5, further comprising crossing the selected first soybean plant or first soybean germplasm with a second soybean plant or second soybean germplasm.

7. The method of embodiment 6, wherein the second soybean plant or second soybean germplasm comprises an exotic soybean strain or an elite soybean strain.

8. The method of embodiment 1, wherein the detecting comprises DNA sequencing of at least one of said marker loci.

9. The method of embodiment 1, wherein the detecting comprises amplifying at least one of said marker loci and detecting the resulting amplified marker amplicon.

10. The method of embodiment 9, wherein the amplifying comprises:
(a) admixing an amplification primer or amplification primer pair for each marker locus being amplified with a nucleic acid isolated from the first soybean plant or the first soybean germplasm, wherein the primer or primer pair is complementary or partially complementary to a variant or fragment of the genomic locus comprising the marker locus, and is capable of initiating DNA polymerization by a DNA polymerase using the soybean nucleic acid as a template; and (b) extending the primer or primer pair in a DNA polymerization reaction comprising a DNA polymerase and a template nucleic acid to generate at least one amplicon.

11. The method of embodiment 10, wherein said method comprises amplifying a variant or fragment of one or more polynucleotides comprising SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379 or 380.

12. The method of embodiment 10, wherein said primer or primer pair comprises a variant or fragment of one or more polynucleotides comprising SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 or complements thereof.

13. The method of embodiment 12, wherein said primer or primer pair comprises a nucleic acid sequence comprising SEQ ID NOs: 1, 2, 3, 4, 5, 6, 7, 8 or variants or fragments thereof.

14. The method of embodiment 13, wherein said primer pair comprises SEQ ID NO: 1 and SEQ ID NO: 2.

15. The method of embodiment 10, wherein the method further comprises providing one or more labeled nucleic acid probes suitable for detection of each marker locus being amplified.

16. The method of embodiment 15, wherein said labeled nucleic acid probe comprises a nucleic acid sequence comprising a variant or fragment of one or more polynucleotides comprising SEQ ID NOs: 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380 or complements thereof.

17. The method of embodiment 16, wherein the labeled nucleic acid probe comprises a nucleic acid sequence comprising SEQ ID NOs: 9 or 10.

18. An isolated polynucleotide capable of detecting a marker locus of the soybean genome comprising (a) S07160-1 or a marker closely linked thereto on linkage group A2; or (b) Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto.

19. The isolated polynucleotide of embodiment 18, wherein the polynucleotide comprises:
(a) a polynucleotide comprising SEQ ID NOs: 1, 2, 3, 4, 5, 6, 7, or 8; (b) a polynucleotide comprising SEQ ID NOs: 9 or 10; (c) a polynucleotide having at least 90% sequence identity to the polynucleotides set forth in parts (a) or (b); or (d) a polynucleotide comprising at least 10 contiguous nucleotides of the polynucleotides set forth in parts (a) or (b).

20. A kit for detecting or selecting at least one soybean plant or soybean germplasm with resistance or improved resistance to soybean cyst nematode, the kit comprising:
a) primers or probes for detecting one or more marker loci associated with resistance to soybean cyst nematode, wherein the primers or probes are capable of detecting a marker locus comprising (i) S07160-1 or a marker closely linked thereto; or (ii) Gm08:8300131, Gm08:8257778, Gm08:8257785, Gm08:8258163, Gm08:8258688, Gm08:8258742, Gm08:8259928, Gm08:8260451, Gm08:8260590, Gm08:8261480, Gm08:8261684, Gm08:8262165, Gm08:8263213, Gm08:8263250, Gm08:8263611, Gm08:8264149, Gm08:8265227, Gm08:8265364, Gm08:8265614, Gm08:8266183, Gm08:8266185, Gm08:8266263, Gm08:8266350, Gm08:8266386, Gm08:8266473, Gm08:8266888, Gm08:8267085, Gm08:8267166, Gm08:8267721, Gm08:8267826, Gm08:8268336, Gm08:8268861, Gm08:8269148, Gm08:8269785, Gm08:8270037, Gm08:8270562, Gm08:8270652, Gm08:8271540, Gm08:8271591, Gm08:8271649, Gm08:8271672, Gm08:8271955, Gm08:8273257, Gm08:8273355, Gm08:8273979, Gm08:8275766, Gm08:8275780, Gm08:8275959, Gm08:8276701, Gm08:8276849, Gm08:8276913, Gm08:8277162, Gm08:8277227, Gm08:8277248, Gm08:8277381, Gm08:8277383, Gm08:8277542, Gm08:8277625, Gm08:8277643, Gm08:8277876, Gm08:8277880, Gm08:8277969, Gm08:8278001, Gm08:8278167, Gm08:8278274, Gm08:8278434, Gm08:8279165, Gm08:8279230, Gm08:8279854, Gm08:8280901, Gm08:8280937, Gm08:8281564, Gm08:8282902, Gm08:8284027, Gm08:8286864, Gm08:8287265, Gm08:8287278, Gm08:8287453, Gm08:8287459, Gm08:8288039, Gm08:8288141, Gm08:8288200, Gm08:8288470, Gm08:8288831, Gm08:8289392, Gm08:8290740, Gm08:8291682, Gm08:8292207, Gm08:8297064, Gm08:8299433, Gm08:8299672, Gm08:8301839, Gm08:8302134, Gm08:8303450, Gm08:8305237, Gm08:8305348, Gm08:8305905, Gm08:8306090, Gm08:8306141, Gm08:8306210, Gm08:8306492, Gm08:8306627, Gm08:8307172, Gm08:8307665, Gm08:8308019, Gm08:8308891, Gm08:8308917, Gm08:8309316, Gm08:8309423, Gm08:8309837, Gm08:8310383, Gm08:8310464, Gm08:8310503, Gm08:8310663, Gm08:8311631, Gm08:8311906, Gm08:8312536, Gm08:8312819, Gm08:8313273, Gm08:8313923, Gm08:8314010, Gm08:8314025, Gm08:8314208, Gm08:8314292, Gm08:8314295, Gm08:8314513, Gm08:8314736, Gm08:8314791, Gm08:8314860, Gm08:8315543, Gm08:8315644, Gm08:8316113, Gm08:8316689, Gm08:8316899, Gm08:8317852, Gm08:8317861, Gm08:8318033, Gm08:8319087, Gm08:8319642, Gm08:8319647, Gm08:8320068, Gm08:8321253, Gm08:8321649, Gm08:8323937, Gm08:8324341, Gm08:8325127, Gm08:8325214, Gm08:8326696, Gm08:8326877, Gm08:8328633, Gm08:8330929, Gm08:8331132, Gm08:8331181, Gm08:8331408, Gm08:8331827, Gm08:8332651, Gm08:8332685, Gm08:8332957, Gm08:8343167, Gm08:8345187, Gm08:8345720, Gm08:8346030, Gm08:8346050, Gm08:8346352, Gm08:8346726, Gm08:8347799, Gm08:8348022, Gm08:8348028, Gm08:8349925, Gm08:8350122, Gm08:8350277, Gm08:8351061, Gm08:8351503, Gm08:8352313, Gm08:8352743, Gm08:8353341, Gm08:8355175, Gm08:8360133, Gm08:8363193, Gm08:8363888, Gm08:8364195 or a marker closely linked thereto; and b) instructions for using the primers or probes for detecting the one or more marker loci and correlating the detected marker loci with predicted resistance to soybean cyst nematode.

EXPERIMENTAL

The following examples are offered to illustrate, but not to limit the claimed invention. It is understood that the examples and embodiments described herein are for illustrative purposes only, and persons skilled in the art will recognize various reagents or parameters that can be altered without departing from the spirit of the invention or the scope of the appended claims.

Example 1: Marker Loci Associated with Soybean Cyst Nematode Resistance on Linkage Group A2

A SNP marker for the Rhg4 locus (Soybean Cyst Nematode Resistance) on Linkage Group A2 was developed for use in high throughput genotype screening, this marker, as well as markers genetically associated to this marker, are provided. Markers from this region are relevant to elite breeding populations and facilitate selection of soybean plants with resistance to SCN at the Rhg4 locus tracing back to PI437654 and Peking as well as stacks with other marker assisted traits, including yield genes.

S07160-1-Q1 was developed and optimized for high throughput PCR-based methods, such as Taqman™ assays. Optimization involved evaluation of amplification, Res, Sus, and heterozygous clustering, primer length, primer composition and the like. The marker distinguishes between the resistant allele from PI437654 or Peking (C) and a susceptible allele from BSR101 (A). Primers and probes useful for detecting the polymorphism are summarized below in Tables 6 and 7, respectively.

TABLE 6

Primers

| Primers: | Oligo ID | Sequence | Product Size |
|---|---|---|---|
| Primer 1 | 136868 | TGTGTTGTGTTTGACTGCCATA (SEQ ID NO: 1) | |
| Primer 2 | 136869 | CATTTCCCAAGCCTCTTGAT (SEQ ID NO: 2) | 117 bp |

TABLE 7

Probes

| Probes: | Sequence |
|---|---|
| 102389 | 6FAM- ACTAACTGCATAaGATAT (SEQ ID NO: 9) |
| 102390 | VIC- CTAACTGCATAcGATATT (SEQ ID NO: 10) |

The marker was validated against a panel of 31 public or proprietary soybean lines comprising 2 resistant check lines, 27 susceptible lines, and 2 other lines. A summary of the rhg4 marker is provided below in Table 8.

Exemplary Amplification Mix

| | |
|---|---|
| H20 | 4.28 ul |
| Hot Tub buffer | 0.5 ul |
| Rox Dye (50X) | 0.075 ul |
| DNTPs (24 mM) | 0.039 ul |
| Primer (100 um) | 0.0375 ul |
| Primer (100 um) | 0.0375 ul |
| FAM Probe (100 um | 0.005 ul |
| VIC Probe(100 um | 0.005 ul |
| Hot Tub enzyme | 0.025 ul |
| Total volume | 5.005 ul |

TABLE 8

Summary of rhg4 marker.

| Gene/locus | Markers | LG | Position (genetic map); GmConsensus 4.0 | Physical Map Position | Allele (R/S) | Source | Public Name | Genetic Pos_PHI Consensus Map v1.1 |
|---|---|---|---|---|---|---|---|---|
| rhg4 | S07160-1 | A2 | 46.68 | 8300131 | C/A | Peking, PI437654 | pBLT65 | 51.42 |

R = Resistant;
S = Susceptible

Example 2: Identification of SNPs in Linkage Disequilibrium with Known Mutations at the Rhg4 Locus

Summary

The Rhg4 locus, which conditions resistance to soybean cyst nematode, has been cloned and found to encode a serine hydroxymethyltransferase (Liu et al. (2012). A soybean cyst nematode resistance gene points to a new mechanism of plant resistance to pathogens. Nature 492, 256-260). Two non-synonymous base substitutions that tightly correlate with SCN resistance were identified in the Rhg4 allele from the resistant source Forrest (Liu et al. Nature, 2012). Using SNP genotype data obtained from re-sequencing 385 Pioneer proprietary elite lines, 181 SNPs were identified that are in high linkage disequilibrium with the described mutations. These SNPs can be used for a variety of plant breeding efforts, including marker assisted selection of the Rhg4 locus.

Methods:

Linkage Disequilibrium was calculated using Haploview 4.2. 7810 SNP loci were evaluated across 385 elite lines. An interval of ~1.2 mb or 6.5 cM (Gm08:7800225-8999989 bp; 48.26-54.80 cM) spanning the Rhg4 mutations was interrogated for SNP selection. An $r^2$ above or equal to 0.8 is considered high for this analysis.

Haploview settings were set as follows: Ignore Pairwise comparisons: >100 kb; HW p-value cutoff: 0.000; Min genotype %: 50; Max # mendel errors: 1; Min Minor Allele Frequency=0.01.

Results

The 181 Rhg4 SNPs in Linkage Disequilibrium with the described mutations (Liu et al. Nature, 2012) are summarized in Table 3B.

TABLE 9

Summary of SEQ ID NOs.

| SEQ ID NO | Description |
|---|---|
| 1 | Primer 136868 |
| 2 | Primer 136869 |
| 3 | Primer 100532 |
| 4 | Primer 80588 |
| 5 | Primer 136870 |
| 6 | Primer 136871 |
| 7 | Primer 136872 |
| 8 | Primer 136873 |
| 9 | Probe 102389 |
| 10 | Probe 102390 |
| 11 | Amplicon comprising resistance allele |
| 12 | Amplicon comprising susceptible allele |
| 13 | Reference Sequence comprising S07160-1 resistance allele |
| 14 | Reference Sequence comprising S07160-1 susceptible allele |
| 15-380 | Consensus Reference Sequences comprising the various marker loci provided herein (see Table 3B) |

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. A method of producing a soybean plant or soybean germplasm that displays resistance or improved resistance to soybean cyst nematode, the method comprising:
   (a) isolating nucleic acids from a genome of a first soybean plant or soybean germplasm;
   (b) detecting in the first soybean plant or soybean germplasm at least one marker locus that is associated with the resistance, wherein the at least one marker locus comprises S07160-1 (Gm08:8300131) or a marker locus within 2 cM of S07160-1 on linkage group A2, wherein the S07160-1 marker locus comprises an allele C at Gm08:8300131;
   (c) selecting said first soybean plant or soybean germplasm, wherein the soybean plant or soybean germplasm comprise said allele C at Gm08:8300131 associated with resistance or improved resistance to soybean cyst nematode; and,
   (d) crossing said selected first soybean plant or soybean germplasm with a second soybean plant or soybean germplasm, thus producing a soybean plant or soybean germplasm with resistance or improved resistance to soybean cyst nematode, wherein said produced soybean plant or soybean germplasm comprises at least marker locus S07160-1 comprising said allele C at Gm08:8300131.

2. The method of claim 1, wherein at least two marker loci are detected.

3. The method of claim 2, wherein the at least two marker loci comprise a haplotype that is associated with said resistance.

4. The method of claim 1, wherein the germplasm is a soybean variety.

5. The method of claim 1, wherein the second soybean plant or second soybean germplasm comprises an elite soybean strain.

6. The method of claim 1, wherein the detecting comprises DNA sequencing of at least one of said marker loci.

7. The method of claim 1, wherein the detecting comprises amplifying at least one of said marker loci and detecting the resulting amplified marker amplicon.

8. The method of claim 7, wherein the amplifying comprises:
   a) admixing an amplification primer or amplification primer pair for each marker locus being amplified with a nucleic acid isolated from the first soybean plant or the first soybean germplasm, wherein the primer or primer pair is complementary to the genomic locus comprising the marker locus, and is capable of initiating DNA polymerization by a DNA polymerase using the soybean nucleic acid as a template; and
   b) extending the primer or primer pair in a DNA polymerization reaction comprising a DNA polymerase and a template nucleic acid to generate at least one amplicon.

9. The method of claim 8, wherein said method comprises amplifying SEQ ID NO: 200.

10. The method of claim 8, wherein said primer or primer pair comprises SEQ ID NO: 200.

11. The method of claim 10, wherein said primer or primer pair comprises a nucleic acid sequence comprising SEQ ID NOs: 1 or 2.

12. The method of claim 11, wherein said primer pair comprises SEQ ID NO: 1 and SEQ ID NO: 2.

13. The method of claim 8, wherein the method further comprises providing one or more labeled nucleic acid probes suitable for detection of each marker locus being amplified.

14. The method of claim 13, wherein said labeled nucleic acid probe comprises a nucleic acid sequence comprising SEQ ID NO: 200.

15. The method of claim 14, wherein the labeled nucleic acid probe comprises a nucleic acid sequence comprising SEQ ID NO: 10.

* * * * *

SEQUENCE LISTING

```
<160> NUMBER OF SEQ ID NOS: 380

<210> SEQ ID NO 1
<211> LENGTH: 22
<212> TYPE: DNA
<213> ORGANISM: Artificial Sequence
<220> FEATURE:
<223> OTHER INFORMATION: Primer 136868

<400> SEQUENCE: 1
tgtgttgtgt ttgactgcca ta                                              22
```

```
<210> SEQ ID NO 2
<211> LENGTH: 20
<212> TYPE: DNA
<213> ORGANISM: Artificial Sequence
<220> FEATURE:
<223> OTHER INFORMATION: Primer 136869

<400> SEQUENCE: 2
catttcccaa gcctcttgat                                             20

<210> SEQ ID NO 3
<211> LENGTH: 36
<212> TYPE: DNA
<213> ORGANISM: Artificial Sequence
<220> FEATURE:
<223> OTHER INFORMATION: Primer 100532

<400> SEQUENCE: 3
tctagctctg acatattgat gattcttttg tgttgt                           36

<210> SEQ ID NO 4
<211> LENGTH: 32
<212> TYPE: DNA
<213> ORGANISM: Artificial Sequence
<220> FEATURE:
<223> OTHER INFORMATION: Primer 80588

<400> SEQUENCE: 4
aagcctcttg ataagacagt gtcttccaaa tc                               32

<210> SEQ ID NO 5
<211> LENGTH: 23
<212> TYPE: DNA
<213> ORGANISM: Artificial Sequence
<220> FEATURE:
<223> OTHER INFORMATION: Primer 136870

<400> SEQUENCE: 5
tcttttgtgt tgtgtttgac tgc                                         23

<210> SEQ ID NO 6
<211> LENGTH: 21
<212> TYPE: DNA
<213> ORGANISM: Artificial Sequence
<220> FEATURE:
<223> OTHER INFORMATION: Primer 136871

<400> SEQUENCE: 6
tgaggctttc cagcatctaa c                                           21

<210> SEQ ID NO 7
<211> LENGTH: 21
<212> TYPE: DNA
<213> ORGANISM: Artificial Sequence
<220> FEATURE:
<223> OTHER INFORMATION: Primer 136872

<400> SEQUENCE: 7
ggactggatc atgagaattg g                                           21

<210> SEQ ID NO 8
<211> LENGTH: 20
<212> TYPE: DNA
<213> ORGANISM: Artificial Sequence
<220> FEATURE:
<223> OTHER INFORMATION: Primer 136873
```

-continued

```
<400> SEQUENCE: 8
aagcagaagg agcattgagg                                                   20

<210> SEQ ID NO 9
<211> LENGTH: 18
<212> TYPE: DNA
<213> ORGANISM: Artificial Sequence
<220> FEATURE:
<223> OTHER INFORMATION: Probe 102389

<400> SEQUENCE: 9
actaactgca taagatat                                                     18

<210> SEQ ID NO 10
<211> LENGTH: 18
<212> TYPE: DNA
<213> ORGANISM: Artificial Sequence
<220> FEATURE:
<223> OTHER INFORMATION: Probe 102390

<400> SEQUENCE: 10
ctaactgcat acgatatt                                                     18

<210> SEQ ID NO 11
<211> LENGTH: 118
<212> TYPE: DNA
<213> ORGANISM: Artificial Sequence
<220> FEATURE:
<223> OTHER INFORMATION: Amplicon comprising S07160-1 resistance allele

<400> SEQUENCE: 11
tgtgttgtgt ttgactgcca taacatgatg tttggattaa atataaacaa taatatccta       60
tgcagttagt gaggctgtga tttggaagac actgtcttat caagaggctt gggaaatg       118

<210> SEQ ID NO 12
<211> LENGTH: 118
<212> TYPE: DNA
<213> ORGANISM: Artificial Sequence
<220> FEATURE:
<223> OTHER INFORMATION: Amplicon comprising S07160-1 susceptible allele

<400> SEQUENCE: 12
tgtgttgtgt ttgactgcca taacatgatg tttggattaa atataaacaa taatatcata       60
tgcagttagt gaggctgtga tttggaagac actgtcttat caagaggctt gggaaatg       118

<210> SEQ ID NO 13
<211> LENGTH: 620
<212> TYPE: DNA
<213> ORGANISM: Artificial Sequence
<220> FEATURE:
<223> OTHER INFORMATION: Reference Sequence comprising S07160-1
      resistance
      allele

<400> SEQUENCE: 13
tggaatctga gaagagactt gagaaatggt actctttgaa tccatgtaag gtaatcattg       60
ccactggatt cattgcaagc acacctcaaa acattcctac cacactgaag agagatggaa      120
gtgacttctc ggcagcaatt atgggtgctc tatttaaggc tcgtcaggtc acaatttgga      180
cagatgttga tggtgtgtat agtgcagatc ctagaaaagg tttgttatgc ttcgtactct      240
gtctctgagt taaacaatga gtggactgga tcatgagaat tggttttag taaccagagg       300 gagttctagc tctgacatat tgatgattct tttgtgttgt gtttgactgc ataacatga       360
```

```
tgtttggatt aaatataaac aataatatcc tatgcagtta gtgaggctgt gatttggaag    420
acactgtctt atcaagaggc ttgggaaatg gtgagttaga tgctggaaag cctcaatgct    480
ccttctgctt gtaaaattaa ggagattaac ttgcaaattg tctgttgtac agtcttattt    540
gggtgccaat gtcttgcatc cccgcacaat tattcctgtg atgcgatatg cataccccat    600
tatgataagg aacattccca                                                620
```

<210> SEQ ID NO 14
<211> LENGTH: 620
<212> TYPE: DNA
<213> ORGANISM: Artificial Sequence
<220> FEATURE:
<223> OTHER INFORMATION: Reference Sequence comprising S07160-1
      susceptible allele

<400> SEQUENCE: 14

```
tggaatctga gaagagactt gagaaatggt actctttgaa tccatgtaag gtaatcattg     60
ccactggatt cattgcaagc acacctcaaa acattcctac cacactgaag agagatggaa    120
gtgacttctc ggcagcaatt atgggtgctc tatttaaggc tcgtcaggtc acaatttgga    180
cagatgttga tggtgtgtat agtgcagatc ctagaaaagg tttgttatgc ttcgtactct    240
gtctctgagt taaacaatga gtggactgga tcatgagaat tggttttttag taaccagagg    300 gagttctagc tctgacatat tgatgattct tttgtgttgt gtttgactgc ataacatga    360 tgtttggatt aaatataaac aataatatca tatgcagtta gtgaggctgt gatttggaag    420
acactgtctt atcaagaggc ttgggaaatg gtgagttaga tgctggaaag cctcaatgct    480
ccttctgctt gtaaaattaa ggagattaac ttgcaaattg tctgttgtac agtcttattt    540
gggtgccaat gtcttgcatc cccgcacaat tattcctgtg atgcgatatg cataccccat    600
tatgataagg aacattccca                                                620
```

<210> SEQ ID NO 15
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 15

```
gccgggcaac cgctactacg gcggcaatga atacatcgac cagatcgaaa acctctgccg     60
ctcacgcgcc ctccaagcct tccacctcga cgcccaatcc tggggcgtca acgtccagcc    120
ctactccggc tccccggcca acttcgccgc ctacaccgcc gtcctcaacc cccacgaccg    180
catcatgggg ctagatctcc cctccggcgg ccacctcacc cacggctact acacctccgg    240
cggaaagaag atctccgcca cctccattta cttcgagagt ctcccttaca aggtaaactc    300
caccaccggc tacatcgact aygaccgctt ggaagaaaaa gccctagact tcaggccaaa    360
actcataatc tgcggtggca gcgcgtaccc tcgcgattgg g                        401
```

<210> SEQ ID NO 16
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 16

```
ccgttgcgct tggaaaatac ttgatgggga aagggtacag ccttgtcact ggcggaacgg     60
```

```
agaaccatct tgttttgtgg gatctgagac ctcttggatt gactggtaat atatatagga        120
ttggatctct accttctggt tttgatttgt tacaaatgtc tataaatctg acttgttcgt        180
tgtgtgattg ttttgcaggg aataaggtgg agaaactctg tgatctctgt aacattactg        240
ttaacaagaa cgctgttttt ggtgatagca gtgccttggc ccctggtgga gtgcgaattg        300
gtaacgatct tacttctctt ttatatgcta caatacaaat cttgctttac taactcaatt        360
ggaaacaaga tctcatttat aagattataa aaatgatttc c                            401
```

<210> SEQ ID NO 17
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 17

```
catatcgcat cacaggaata attgtgcggg gatgcaagac attggcacca aaataagact         60
gtacaacaga caatttgcaa gttaatctcc ttaattttac aagcagaagg agcattgagg        120 cttttccagca tctaactcac catttcccaa gcctcttgat aagacagtgt cttcaaaatc       180
acagcctcac taactgcata agatattatt gtttatattt aatcaaaaca tcatgttatg       240
gcagtcaaac acaacacaaa agaatcatca atatgtcaga gctagaactc cctctggtta       300
ctaaaaacca attctcatga tccagtccac tcattgttta actcagagac agagtacgaa       360
gcataacaaa ccttttctag gatctgcact atacacacca t                           401
```

<210> SEQ ID NO 18
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 18

```
taggatgttt ttcaaataca ctcttttctc gctgtttaaa aaaaaaaata cactctcttc         60
taataattaa aagttattaa aaatcataaa tttgaatgga tctcattttt cattgagtaa        120
ctctctctcg tgattttata ttatctctgt gcttttttatt ttttattttt aaaaaatatg       180
taaaaaccaa gaaacataat aaatgtgstt catcttaata aaacacttct ttcatcctta       240
aatataagac ttttataatt aattcacact tattaataaa attacaaaga cttttataat       300 taattccacac ttattaataa aattgctcga tttagttagt aattaacatt atatttgttt      360
gtaattttaa tattttttaa gattatcttt aaaattattc a                           401
```

<210> SEQ ID NO 19
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 19

```
tttttcaaat acactctttt ctcgctgttt aaaaaaaaaa atacactctc ttctaataat         60
taaaagttat taaaaatcat aaatttgaat ggatctcatt tttcattgag taactctctc        120
tcgtgatttt atattatctc tgtgcttttt attttttatt tttaaaaaat atgtaaaaac        180
caagaaacat aatwaatgtg cttcatctta ataaaacact tctttcatcc ttaaatataa       240
```

```
gactttata   attaattcac   acttattaat   aaaattacaa   agactttat    aattaattca      300 cacttattaa  taaaattgct   cgatttagtt   agtaattaac   attatatttg   tttgtaattt      360
taatattttt  taagattatc   tttaaaatta   ttcagactaa   a                            401
```

<210> SEQ ID NO 20
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 20

```
tctttaaaat  tattcagact   aaatatatat   ttttttcatt   taattatttt   ctacccaaac      60
aattaacata  tgaaaagaga   ataatagtag   tcgagtttta   attttaaaat   taaatccttc     120
aattctccaa  tcctcccacg   aaagagaaaa   tgacaattca   tagcaattrt   tatttataga    180
ctacaacaac  tagggtatt    atagtaaaaa   gaaaaacaag   taatgcaaga   aagaagtctt    240
atacaaaaga  acaagaatt    ttttaaataa   tgtcttatat   tcatagacga   aagaaacaat    300
tgatccttta  tcatttttat   taaacaataa   atgcatagat   gtaaataaat   taaagattag    360
aaaaaagtaa  gaacataatt   ggcaaaaaaa   taattaatgt   c                          401
```

<210> SEQ ID NO 21
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 21

```
taaaaaaaga  aaacgtggga   gagtgcaatt   aggataaagg   gattggatta   cttgaagaaa     60
aaaaraataa  aggggttaga   aaaagaccct   ctagaagtat   acgacagcct   aaattgaaat   120
tgggatacat  agtttggact   gtaatagaat   tgtggatctg   tttgctcgtt   ttatttcaaa   180
ataaaacaaa  ataaagaact   cctagcatra   caacaaaaag   tactaatttt   taatctcaak   240
gatcrgaact  ttgcrttct    ttcccgtatc   tgtcgaatt    ttyattgtaa   gaaatattct   300
ttgtgggttc  agttattcac   cattattatt   tcagagggag   cgatgggwgg   aattataata   360
cttcttcatc  agattcaatt   ttgataaaga   aaatcattca   a                          401
```

<210> SEQ ID NO 22
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 22

```
aagaaaaaaa  raataaaggg   gttagaaaaa   gaccctctag   aagtatacga   cagcctaaat     60
tgaaattggg  atacatagtt   tggactgtaa   tagaattgtg   gatctgtttg   ctcgtttat    120 ttcaaaataa  aacaaaataa   agaactscta   gcatracaac   aaaaagtact   aattttaat    180 ctcaakgatc  rgaactttgc   atttcttcc    cgtatcttgt   cgaattttya   ttgtaagaaa    240
tattctttgt  gggttcagtt   attcaccatt   attatttcag   agggagcgat   gggwggaatt    300
ataatacttc  ttcatcagat   tcaattttga   taaagaaaat   cattcaaata   agagacttta    360
ttatcttcaa  aaagctaagt   acggaagatg   ccaaaaagaa   a                          401
```

<210> SEQ ID NO 23
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 23

| | | | | | | |
|---|---|---|---|---|---|---|
| ttggatcatt | taatttatga | ggtgtgtgat | tttgtttcct | agtttttaat | tttgcaaatt | 60 |
| ggatcattta | agtattacag | gaatccaatt | tactcaattg | aattctgaaa | gatcaaaatt | 120 |
| aaataaatgc | aatacctaag | agacaaaaaa | taattaatct | atttttttaa | agaaaatact | 180 |
| actatcagat | atggaagcac | caacaaaacc | agtccaggag | agacatcagc | acctacctac | 240 |
| gcaccccaaa | atcagataca | actttaagct | tacaacatca | cctatagtaa | cctaatattg | 300 |
| ctcaaaatgg | aagcaaccat | tccacaacca | atacaacaaa | caaaatcaat | aaatttacta | 360 |
| caaactagtc | gaaccgtacc | tcgttaatgc | cataaaccta | g | | 401 |

<210> SEQ ID NO 24
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 24

| | | | | | | |
|---|---|---|---|---|---|---|
| actaagctac | acaaactgaa | tcacgtctaa | gacgctctaa | aaacaaaatc | aggaggcagg | 60 |
| ttccgcaaaa | taggactgga | taatgatgtt | gaagcagtaa | tttctatcaa | aattaacagg | 120 |
| aaaaactcta | aaaaaatcag | ccccrggaga | aatttatata | tattttttgt | agataaaaat | 180 |
| ttaaattagg | ggaagacacg | ccttcttgta | aaactacaag | aaaaattaac | aacatcagca | 240 |
| ttataaaatt | tatacatcgc | ataacaatat | gcaaaatcca | aaaatcaata | aacctaaatt | 300 |
| attgctggta | taactatttg | actaaatgtg | ccattgttgs | ccagagaata | ttaaaatgta | 360 |
| atgaaataaa | gtattttaaa | ttaattgact | aagaattggc | a | | 401 |

<210> SEQ ID NO 25
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 25

| | | | | | | |
|---|---|---|---|---|---|---|
| gccccrggag | aaatttatat | atatttttg | tagataaaaa | tttaaattag | gggaagacac | 60 |
| gycttcttgt | aaaactacaa | gaaaaattaa | caacatcagc | attataaaat | ttatacatcg | 120 |
| cataacaata | tgcaaaatcc | aaaaatcaat | aaacctaaat | tattgctggt | ataactattt | 180 |
| gactaaatgt | gccattgttg | cccagagaat | attaaaatgt | aatgaaataa | agtattttaa | 240 |
| attaattgac | taagaattgg | catggctatg | agaaatcatg | cactaattga | gcaaagatat | 300 |
| gatatatttt | ttatacttgt | cctaacaatg | tactcccact | aattaagtta | ctaattgagc | 360 |
| actccataat | ttttttttgga | agatgttctt | tggacactgt | g | | 401 |

<210> SEQ ID NO 26
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 26

```
tcatgtctac caagtccgac taacttwtcc gtccatcaac cattttttaa ctgagaattg    60
gtatgatatc aagagttaag agttgtgact gtatttggaa aaatatttct taaaataaaa   120
tgatattcaa aaaatatatt tttaatagtt ttttctgctg attttcagtc tataattaaa   180
cgaatttaga tactctatat gaaaaagag aaaatcattt tttcaataac agtcccaaaa    240
cttttaaatt aaaaaaaata aagtaaaatt tatcttttat tttgaattaa atcaagacat   300
actactatac ctgatcagtc ctggatcgaa ttctcccaac caaatcaact cgccataaat   360
accctcttat atccagttaa ttaatggtcc atctcgtttt g                       401
```

<210> SEQ ID NO 27
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 27

```
aaagagaaaa tcattttttc aataacagtc ccaaaacttt taaattaaaa aaaataaagt    60
aaaatttatc ttttattttg aattaaatca agacatacta ctatacctga tcagtcctgg   120
atcgaattct cccaaccaaa tcaactcgcc ataaataccc tcttatatcc agttaattaa   180
tggtccatct cgttttgaaa attttttaac catgaagttt ttttttagtt acatgaggaa   240
aagaaagaca agggacaacc aaaaaaacta cacgtactac taaattaagg cagatcacac   300
tgccactccc tctgcacaaa aactggtggc ctctgccaga ccacagcatc agaactcaga   360
agcattggtt gcatcagagt tttgttatgg tgtatttaga a                       401
```

<210> SEQ ID NO 28
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 28

```
ccaatcccga cacaaccagc tcgaaatttt ccgcaccgca gaatgtcgtg attcttgtgg    60
caaccagagt tgttgttctt gctagctcta tattcttctc ctgtgtggca gtattgcatc   120
aatgctacca tgcagtgtct aacaagacta tatcatatat ttatgatagt ctctaatcaa   180
tttttgaaaa aattagagtc ataatattta tacatctcat tttcttataa ttcacttgca   240
tcttatttca tttttttcccc tatcatataa catatcatat ttattacatt ctctctattt   300
ttatttttat ttctctctcc atctctcttc tcttttcacc ctaaaatggg ggtgaacact   360
caacatgttt tgaaaaatta ttattagatt aatatgtatt g                       401
```

<210> SEQ ID NO 29
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 29

```
gggtcatcct ttcacttgtt tggtctacac cacactcttg tcttgggtcg ctgaggtggc    60
gcgtgagttt cacctcccaa cagcgatgct gtggactcaa ccagctacga tactcgacat   120
cttctattac tactttcacg aacacggtga atacatcaaa gacaaaatca agacccctc    180
```

```
gtgtttcatt gaattaccag cattgccatt gttgcttgca ccacgggacc taccctcytt    240
tttattgggt tcaaaccota ctattgactc tttcattgtc ccaatgtttg aaaagatgtt    300
ttatgatctt gacgtggaga caaagcccag aatacttgtc aacaccttcg aagccttgga    360
agcggaggct ctcagagccg ttgataagtt caacatgatc c                        401
```

<210> SEQ ID NO 30
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 30

```
ttgtcttggg tcgctgaggt ggcgcgtgag tttcacctcc caacagcgat gctgtggact     60
caaccagcta cgatactcga catcttctat tactactttc acgaacacgg tgaatacatc    120
aaagacaaaa tcaagaccc ctcgtgtttc attgaattac cagsattgcc attgttgctt    180
gcaccacggg acctaccctc cttttattg ggttcaaacc ctactattga ctctttcatt    240
gtcccaatgt ttgaaaagat gttttatgat cttgacgtgg agacaaagcc cagaatactt    300
gtcaacacct tcgaagcctt ggaagcggag gctctcagag ccgttgataa gttcaacatg    360
atcccaatcg ggccgttgat ccctcggct tcttggatg g                          401
```

<210> SEQ ID NO 31
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 31

```
tcccaatcgg gccgttgatt ccctcggctt tcttggatgg gaaagatmct aatgatactt     60
catttggcgg tgacatcttc cgcctctcta atggttgcag cgaatggttg gactcgaagc    120
cagagatgtc ggtggtttat gtctcgtttg gtagcctttg cgtgttgcct aagacgcaaa    180
tggaggaact tgcacgtgcg ctattagatt gtggaagtcc tttcctgtgg gtcattaaag    240
aaaaagaaaa taagtcacaa gtggaaggaa aagaggagct gagctgcata gaggaattgg    300
aacagaaggg gaagatagta aactggtgtt ctcaagtgga ggttctttca catggttctg    360
tgggttgttt tgttacacac tgtggttgga attcaaccat g                        401
```

<210> SEQ ID NO 32
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 32

```
aaatgaagaa attaggcggt gtttggaaga ggtgatgggg agtggagaga aaggacaaga     60
attgagaaac aatgcagaaa agtggagggg actggccagg gaagctgtca aggaaggtgg    120
ctcttcggat aagaatctaa gggcttttt agatgatgtt gaagtttgac catatggctg    180
tcacatcagc ttttccgttt ctgaattttc ctgtccgttt catttttctt ttctattatt    240
gcatttgcat gactgagaat caagtgaaat ttccttctata ttagtttgaa atttaaaaat    300
atctaaatga gccatgactc catgagtagt aattttgtgt tataattgat atatatattt    360
```

```
tctcttaagt agtggccaaa aatttaatct ttatgtagat g                401
```

<210> SEQ ID NO 33
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 33

```
atgcatctgg atctggtttc cctattcata tttccaaagc ttgcatgctt tctggtttcc    60
ttgccaatca ctgcatggaa caatcttacc atcatagggc atgcttcttt ttttaagctc   120
gcttgtggtc ttcttttggt acatatgctc ccctcccccc ttttgttta tttttgtttt    180
atggttcata atagagttta ctgatgaaat agccaaatca tagaattagt aaaatatcat   240
gtacaaggtc aaaatagtat ttttagtaac catctttttt ttctcgtacc ttacatagaa   300
gctgactcaa tgataaagga aacctaaaaa ttagtttwaa aaaacccttt tggccttttt   360
gacatmatat atgatatttt tgtcaaaata tgagactttt t                       401
```

<210> SEQ ID NO 34
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 34

```
ggtacatatg ctcccctccc ccctttttgt ttatttttgt tttatggttc ataatagagt    60
ttaytgatga aatagccaaa tcatagaatt agtaaaatat catgtacaag gtcaaaatag   120
tattttagt aaccatcttt tttttctcgt accttacata gaagctgact caatgataaa    180
ggaaacctaa aaattagttt aaaaaaaacc ttttggcctt tttgacatma tatatgatat   240
ttttgtcaaa atatgagact tttttttat aaaaactaat aaaaaaatat ttttattgg    300
taaacctaga acttaaattt tagttatttt attcttagas aaaccttacc taacaaataa   360
tttaattcaa atatttgcct ttcattctat tttatttcac c                       401
```

<210> SEQ ID NO 35
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 35

```
atatgagact tttttttat aaaaactaat aaaaaaatat ttttattgg taaacctaga     60
acttaaattt tagttatttt attcttagas aaaccttacc taacaaataa tttaattcaa   120
atatttgcct ttcattctat tttatttcac cttaacaact tccctggcca caacatgttg   180
gatctcagta aaaattgatg atgtaagatc attccattac gaagagatgc atggcctatt   240
attctttctc catccaagaa aaaatacat ttattcttgc ttcctgttaa aacataaaaa    300
gacgttttac cttagtatga taaccttcat aaatagttaa atatagcatt gtcttgaact   360
ttgaaataaa ttatgtttaa ttagaactta taactataag t                       401
```

<210> SEQ ID NO 36
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 36

```
atatgtcaag tattataata aatatttaat tatataaata aataatttta ttcttaaata      60
taaacattta caaagttaaa gtaacaaaaa agtaagtttt taattctctt aataatgtca     120
tatcctaatt tcgtactagg actatcattc gtcaacgttt tgattctcca ttgtcaaatt     180
gaattgttcg acaccagttg ctrtgtaaga cggaagatta ttcgacattt cagtaaagaa     240
tgcaaaaaat gcccaaatgg aaggacaaaa ggatcatttt raggcttttt cagacccctg     300
actcgctcag gctagtctct ggctcaccta ggccccctaaa tagtttaggg gtgaagtaac    360
tagctcgyct ggacgagcaa ggttacttca ggttgaagca a                         401
```

<210> SEQ ID NO 37
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 37

```
atgtcaagta ttataataaa tatttaatta tataaataaa taatttttatt cttaaatata    60
aacatttaca aagttaaagt aacaaaaaag taagttttta attctcttaa taatgtcata   120
tcctaatttc gtactaggac tatcattcgt caacgttttg attctccatt gtcaaattga   180
attgttcgac accagttgyt atgtaagacg gaagattatt cgacatttca gtaaagaatg   240
caaaaaatgc ccaaatggaa ggacaaaagg atcattttra ggcttttttca gacccctgac  300
tcgctcaggc tagtctctgg ctcacctagg ccctaaata gtttagggt gaagtaacta     360
gctcgyctgg acgagcaagg ttacttcagg ttgaagcaac a                         401
```

<210> SEQ ID NO 38
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 38

```
gtaacaaaaa agtaagtttt taattctctt aataatgtca tatcctaatt tcgtactagg    60
actatcattc gtcaacgttt tgattctcca ttgtcaaatt gaattgttcg acaccagttg   120
ytrtgtaaga cggaagatta ttcgacattt cagtaaagaa tgcaaaaaat gcccaaatgg   180
aaggacaaaa ggatcatttt aaggcttttt cagacccctg actcgctcag gctagtctct   240
ggctcaccta ggccccctaaa tagtttaggg gtgaagtaac tagctcgyct ggacgagcaa   300
ggttacttca ggttgaagca acarctcgct tgggtgagct ccagatcaac taagtcccct    360
catttcctat aaataggcat gaggggctga agaaagggt t                          401
```

<210> SEQ ID NO 39
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 39

```
ccattgtcaa attgaattgt tcgacaccag ttgytrtgta agacggaaga ttattcgaca    60
```

```
tttcagtaaa gaatgcaaaa aatgcccaaa tggaaggaca aaaggatcat tttraggctt      120
tttcagaccc ctgactcgct caggctagtc tctggctcac ctaggccct aaatagttta      180 ggggtgaagt aactagctcg cctggacgag caaggttact tcaggttgaa gcaacarctc      240
gcttgggtga gctccagatc aactaagtcc cctcatttcc tataaatagg catgaggggc      300
tgaaagaaag ggttcarcct tcaratattg aaaggattta gtgaaatttg aagaaaagaa      360
gaaraaataa aggaaaaaca aggtcgaggt gctaccgaat c                          401
```

```
<210> SEQ ID NO 40
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 40
tgtaagacgg aagattattc gacatttcag taaagaatgc aaaaaatgcc caaatggaag       60
gacaaaagga tcattttrag gcttttttcag acccctgact cgctcaggct agtctctggc     120
tcacctaggc ccctaaatag tttaggggtg aagtaactag ctcgyctgga cgagcaaggt     180
tacttcaggt tgaagcaaca actcgcttgg gtgagctcca gatcaactaa gtcccctcat     240
ttcctataaa taggcatgag gggctgaaag aaagggttca rccttcarat attgaaagga     300
tttagtgaaa tttgaagaaa agaagaaraa ataaaggaaa aacaaggtcg aggtgctacc     360
gaatcacgat cgtaatcgat tttcacatcg ttcttcgttc g                         401
```

```
<210> SEQ ID NO 41
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 41 cagaccctg actcgctcag gctagtctct ggctcaccta ggcccctaaa tagtttaggg       60
gtgaagtaac tagctcgyct ggacgagcaa ggttacttca ggttgaagca acarctcgct     120
tgggtgagct ccagatcaac taagtcccct catttcctat aaataggcat gagggggctga    180 agaaagggt tcarccttca aatattgaaa ggatttagtg aaatttgaag aaaagaagaa      240
raaataaagg aaaaacaagg tcgaggtgct accgaatcac gatcgtaatc gattttcaca     300
tcgttcttcg ttcgtcatcc ggttagtatt tattttaagt atttcaattc aatctatgca     360
cccataaggg tcttctttgt cgattcatgc atcttcatct c                         401
```

```
<210> SEQ ID NO 42
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 42
tgtaatctat tttcttttgg taaagtgagt tttgaccggt catttacgtc accaaacatc       60
ttttaattag tttgaagttt aataagtgaa atcaagttaa atcaacatg taaccgagct      120 ttttatccgc aaaattcact taaatccgtt caaggtccaa ggccttaatg gtctctttta     180
tttttgttgg ttcgaatgaa cttttcaaaa gtttaaaatc aactcgacac gcaatttttct    240 tgttttaaga actatgtagg tctgagtttc tcatcgcamt tgaggatacg taggagcaag    300
```

```
ggcaacgcct ttgtcgaccc gaaaaaataa agaagcataa aaagggaaaa taagtaatat      360
tgaagtcacg tttttgcaca ttcgattaaa ggttgtcrtc c                          401
```

<210> SEQ ID NO 43
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 43

```
gaayttttca aaagtttaaa atcaactcga cacgcaattt tcttgtttta agaactatgt       60
aggtctgagt ttctcatcgc amttgaggat acgtaggagc aagggcaacg cctttgtcga      120
cccgaaaaaa taaagaagca taaaaaggga aaataagtaa tattgaagtc acgttttgc       180 acattcgatt aaaggttgtc atcccctgtg acgaayacgt ggggtgttaa tacctttttc     240
gctcgtaaat aactcccgta cccttatttt caaaattcgc akatccccct ttttggtttt     300
tctaacgttt tcctcgaata aacgttggtg gcgactcccg cgtgttttc tttttggaag      360 acgcatcctt gagtctcgcc tcaccectcc cgtcgaaggg t                          401
```

<210> SEQ ID NO 44
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 44

```
mttgaggata cgtaggagca agggcaacgc ctttgtcgac ccgaaaaaat aaagaagcat       60
aaaaagggaa aataagtaat attgaagtca cgttttgca cattcgatta aaggttgtcr      120 tccectgtga cgaayacgtg gggtgttaat acctttttcg ctcgtaaata actcccgtac     180 ccttatttc aaaattcgca gatccccctt tttggttttt ctaacgtttt cctcgaataa     240
acgttggtgg cgactcccgc gtgttttct ttttggaaga cgcatccttg agtctcgcct     300 caccectccc gtcgaagggt aggttgcaac agataataat aaaaaaattc aaccatgata     360
ttcgcaacaa taaattaaat gcacacatac atatatatag t                          401
```

<210> SEQ ID NO 45
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 45

```
gaattagtgt gagtctcaga ttcttcaaat ggtctatgag ttcatattca tgcagtaayg       60
tctcactgct tttcttatca tatatgaaag tattcaaaat ctcttcttca tcctagatgg      120
aggtatctat aacttcatct ccatcccaaa tgaaggtgtc tcgtacatat tcaattctca     180
aaataaaaca taaattgtca ctacttccta aaggatgata accaattcac acatatttat     240
aaaatatcat ttcaaataac tatcaaataa atactttaat tccatataca ctaattaata     300
acttgsaagg tcataccetta gttatagcat cacgtaagtc aatttataat taactatgaa     360
ataaaacata cacacaaatt aaaatatatt ttagttgcta t                          401
```

<210> SEQ ID NO 46

```
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 46
cttcatccta gatggaggta tctataactt catctccatc ccaaatgaag gtgtctcgta      60
catattcaat tctcaaaata aaacataaat tgtcaytact tcctaaagga tgataaccaa     120
ttcacacata tttataaaat atcatttcaa ataactatca aataaatact ttaattccat     180
atacactaat taataacttg caaggtcata ccttagttat agcatcacgt aagtcaattt     240
ataattaact atgaaataaa acatacacac aaattaaaat atattttagt tgctatatat     300
gatagctaaa cacaaaatcc aaacaagctg attgatgaat tttcaaataa attttaagat     360
tgaatatgca actagtgaat atttgtacat tgtaataacct t                         401

<210> SEQ ID NO 47
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 47
atctagtttc tatcgtgcat atttgttgaa gttaaacaca agatccaagy aagcacatat      60
gatgcattat aattgcacta aaatttgaat atagtttcta tatatcgtgc atgtttgttg     120
gctctccttg acaagcatat ctatttaatt tatacaagta gtaaataaaa tgataagact     180
aaatgatgag ttcacatata ctttatttgt actcwtatat atatatatat atataattct     240
tggatggaaa ggaccccgaa gatacttcct tgggtggtga cttgttaccg gtttcaaatg     300
gttacgttga gtggcttgac tcaaaggaag acaagtccgt ggtttacatt tcatttggga     360
gctactttgt gttgtctaag agacaaacgg aggaaattgc a                         401

<210> SEQ ID NO 48
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 48
caggtggagg ttcagtgggt tgttttgtga cgcactgtgg ttggaattcg accatggaga      60
gctaggtttc gggggtgccc atggtggtgt ttcctcagtg gtcgtaccaa aagacaaatg     120
ctaaactgat agaaaatgtg tggaagatag gggtgagggt ggatcatgag gatgggaaag     180
tagaaggaga aagagattaa aaagtgttcg gaagaggtga tggggagtgg agagttgaga     240
atgaatgtaa agaaatggaa gggtttggcc agggaggcag ccaaggaagg tggtccttca     300
gatttcttga tgccatgacg ttgcagaatc gataatcaat gcacgtgttt gccaaataat     360
tgacttggat tcccgtgttc tcagttcttc catgctaaat t                         401

<210> SEQ ID NO 49
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 49
```

```
aggtggtcct tcagatttct tgatgccatg acgttgcaga atcgataatc aatgcacgtg    60
tttgccaaat aattgacttg gattcccgtg ttctcagttc ttccatgcta aattattctt   120
tttctgcttc twtttctttt tccaatcaat tgattctatg tttaagattt ttattattta   180
gaacaattaa attattattg ctttaagaga tagtattatt ttaagtttaa atgtatattt   240
tttattcata attatatctc tatttaatct ggtatactcc ttaaaattac ttttatttaa   300
ttatgttttt tttaaaaata atcaaattat tcaatcttat tgataagtgg tttgtatcaa   360
atgctcacct aaaaaagata aatagactcc caaatattag a                      401

<210> SEQ ID NO 50
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 50
agataattaa tttcttttaa atggatgtag gaagagacta aattattact aatcttattg    60
ctttatattt tttatagtta tctttccact cctacagtac gaaacacatg taataaatca   120
gtgccattaa catacaactc gacctaattg taatttgtag taacttagat agtttagatt   180 tttttttgt tatggtatta cgtatttcat aaaaatttat attaattttc ttttgaaaaa   240
tattatacwt catattgtct tcttgccttt gtaaataaa agtgttaaaa tatcaatact   300
yatgtttatt tgaacaagtg agatgcatgt aatcrctatc attatttagg aatgytaatg   360
aacctacttg ttgcactaat taagcytgtt tcaacctgta a                      401

<210> SEQ ID NO 51
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 51
tattgtcttc ttgcctttgt aaaataaaag tgttaaaata tcaatactya tgtttatttg    60
aacaagtgag atgcatgtaa tcrctatcat tatttaggaa tgytaatgaa cctacttgtt   120
gcactaatta agcytgtttc aacctgtaaa aaaagtctg tttcaaaatt ttttttatg    180 cattttactt aaaaaaatta gacctaatga atttgaata ttgatttgat tttttaaga    240 gaatatattt ttgagttata tatatatata ttagtagtcc tacctcgttc taatattta   300 tattttttta ataaaatata caaattttta aacaattttg tattaaggaa aaattaatca   360
ttttattmtt ataattatac aaaatttagc tttgaatgac c                      401

<210> SEQ ID NO 52
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 52
aatgaaagtt tgaatataaa aggttacttt gtttaaactt aaaaaaaaat tctaaaaaat    60
attttttaag aagtaaatat gatttattta ttaacaagac atttttctat ttttaagaaa   120 aaatacata aaaaataatt attttattaa aaaatgatcc aaacccttca tcattaatgt   180
```

```
taatgattaa tctattaatt aatgtttaat ttattatatt ataattataa tagattatac      240
aaaaagcaat tatacgattt aatgttttat atatttaatt ttatatttaa ratgtggaag      300
atgcgttagc aagtattaag atattgacta aaaaagaaaa ttaaaaaata tataattaaa      360
actaaagcat tttctataaa taaaaaatat aagactttt t                           401

<210> SEQ ID NO 53
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 53
ttaacaagac attttctat ttttaagaaa aaaatacata aaaataatt attttattaa         60 aaaatgatcc aaaccttca tcattaatgt taatgattaa tctattaatt matgtttaat      120
ttattatatt ataattataa tagattatac aaaaagcaat tatacgattt aatgttttat      180
atatttaatt ttatatttaa aatgtggaag atgcgttagc aagtattaag atattgacta      240
aaaaagaaaa ttaaaaaata tataattaaa actaaagcat tttctataaa taaaaaatat      300 aagactttt ttttacatga catataaaac ttactctatt caatattaaa attgttaaag      360
atttaactgg tatatactaa tagtgtaaat atattttaca c                          401

<210> SEQ ID NO 54
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 54
tcamatattg attcatcatg tagtgaaaaa ctaatcwctt ttactcaacc taasctgtat       60
cgatgytaat cattgctctt agtacattga ttataaaaaa aatactagaa agataaagtt      120
tttgttagaa atcatttgcg agtatatttt aaaataattg aagaatacat ttttatgcat      180
tatatagtta aagtgttttt gttttccttt tttcacttcc tctatttaa ccactatttt       240 cttttctacac amaaaaaaaa atccatcatt tttctttat ccttttaaca aattttggtt      300
ttggacagtr aacacacaca aaatatatat ttytcttcta atatgatttg ttttatttt      360 gatgccaata tgttatgatt gtttgataat gtaaaaaata t                          401

<210> SEQ ID NO 55
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 55
aasctgtatc gatgytaatc attgctctta gtacattgat tataaaaaaa atactagaaa       60
gataaagttt ttgttagaaa tcatttgcga gtatatttta aaataattga agaatacatt      120
tttatgcatt atatagttaa agtgttttk ttttccttt ttcacttcct ctattttaac       180
cactattttc tttctacaca aaaaaaaaa tccatcattt ttcttttatc cttttaacaa      240
attttggttt tggacagtra acacacacaa aatatatatt tytcttctaa tatgatttgt      300
tttatttttg atgccaatat gttatgattg tttgataatg taaaaaatat tasactaata      360
atgcgtagta ctagyaatta acctcatttt twaaatagtt a                          401
```

<210> SEQ ID NO 56
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 56

```
aagataaagt ttttgttaga aatcatttgc gagtatattt taaaataatt gaagaataca      60
tttttatgca ttatatagtt aaagtgtttt tkttttcctt ttttcacttc ctctattta     120 accactattt tctttctaca camaaaaaaa aatccatcat ttttctttta tccttttaac    180
aaattttggt tttggacagt aaacacacac aaaatatata tttytcttct aatatgattt    240
gttttatttt tgatgccaat atgttatgat tgtttgataa tgtaaaaaat attasactaa    300
taatgcgtag tactagyaat taacctcatt tttwaaatag ttaaaagaac ttgctcattc    360
attattaatt tttcattaaa aatattgtac cggccacttt a                        401
```

<210> SEQ ID NO 57
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 57

```
catttgcgag tatattttaa aataattgaa gaatacattt ttatgcatta tatagttaaa      60 gtgttttkt tttccttttt tcacttcctc tattttaacc actatttct ttctacacam     120 aaaaaaaat ccatcatttt tcttttatcc ttttaacaaa ttttggtttt ggacagtraa    180
cacacacaaa atatatattt ctcttctaat atgatttgtt ttattttga tgccaatatg    240 ttatgattgt ttgataatgt aaaaaatatt asactaataa tgcgtagtac tagyaattaa    300
cctcattttt waaatagtta aaagaacttg ctcattcatt attaattttt cattaaaaat    360
attgtaccgg ccactttaat ttattttcaa atgctattaa a                        401
```

<210> SEQ ID NO 58
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 58

```
gtagtactag yaattaacct catttttwaa atagttaaaa gaacttgctc attcattatt      60 aattttcat taaaatatt gtaccggcca ctttaattta ttttcaaatg ctattaaaat     120
aaagcaatga gttaatgaca ttaattaaga aatgcattta aaatttatt aatattaagg    180 atcttgttaa ttaatgtttt ccccccacaa gtcttctctt tcaaaggcct aatgtacatt    240
aggacactaa atgtcacccc tttaaatgaa tattcaaaca ttgattcatc acttagtgaa    300
aarttaatct cttccacttg actcaaccgg tgctgatgtt aaccattgct cttaatattg    360
gttataaaaa ataataaaaa gataaagttt ttgttagaaa t                        401
```

<210> SEQ ID NO 59
<211> LENGTH: 401
<212> TYPE: DNA
<213> ORGANISM: Artificial Sequence
<220> FEATURE:

<223> OTHER INFORMATION: Consensus Reference Sequence

<400> SEQUENCE: 59

```
acccaacggt gcttgtgaac acctttgaag ctttggaaga agaagcgttg agggccattg      60
ataagatcaa catgatcccc atcgggccgt tgattccttc tgcgttcttg acgggaatg      120 acccaactga tacttcgttt ggtggggaca tttttcaagt ctcaaatgat tacgttgaat     180
ggcttgactc aaaggaagag aattcggtgg tttacgtttc atttggtagc tactttgagc     240
tttctaagag acaaatggag gaaattgcac gtgggttatt agattgtgga cgtccattyt     300
tgtgggtcgt tagagaaaag gtaattaatg gaaaaaaaga agaggaggag gagctttgtt     360
gtttcagaga ggaattggag aagtggggga agatagtgac a                         401
```

<210> SEQ ID NO 60
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 60

```
tctgcgttct tggacgggaa tgacccaact gatacttcgt ttggtgggga catttttcaa      60
gtctcaaatg attacgttga atggcttgac tcaaaggaag agrattcggt ggtttacgtt     120
tcatttggta gctactttga gctttctaag agacaaatgg aggaaattgc acgtgggtta     180
ttagattgtg gacgtccatt cttgtgggtc gttagagaaa aggtaattaa tggaaaaaaa     240
gaagaggagg aggagctttg ttgtttcaga gaggaattgg agaagtgggg gaagatagtg     300
acatggtgtt ctcaggtgga ggttctttcg cattcttctg tgggttgttt tttaacacac     360
tgtgggtgga attcgaccat ggaaagcctt gtttctgggg t                         401
```

<210> SEQ ID NO 61
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 61

```
gcgaaagaag gtggctcttc agagaagaat ctgagggcat ttgtggatga tgttagacaa      60
aaatttatgc atacacatgt gggtgaatat taattaagtt cgtctctaac tagctagtag     120
taagctgtaa tgtgttattg tatgcttatg atgcatggct tcaaacattg aaagatgaac     180
tgaaaaaatt aagaaattat aagtcagtta ataaaaatgt gcgaaaatgg aatatcttca     240
ataataacat gtgcgtrttg ctaaaaaatg agttgttgtc acgttagatg gtggatgcca     300
tataactgtc caatatgttg cccaattcgt caggaaaaga taaatatttt gataaagatt     360
attattacat tgttgcttta tactcccttc ctttcttttt a                         401
```

<210> SEQ ID NO 62
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 62

```
tgaaatgtca atcaaaatat acaacagtat gtgcatggat tcttgatgac aataattcca      60
aaaccacaaa tatgtatta taatcatctt aaaagctcta gtgagacact tagckgtaca     120
```

```
aattaaattt tttaaatcgt tgggcaaaga atcatcagca aatgtagttt tttttttttt    180
ttgagaaatc acccaatgta gtcaattgcg gaagsaggag cttgtcattc cagtagtcca    240 attttcagt  tatacttttg attttatag  ggtaagtact  aagtaaccta gctagtttct   300
taatctcatg atctcttggc ttatyttttt tttttttwaa  tttgtgcttg agtcactata   360
catatttact tggttgtcga acaaaattaa aatytcttcg t                        401

<210> SEQ ID NO 63
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 63
aaatatacaa cagtatgtgc atggattctt gatgacaata attccaaaac cacaaatatg     60
tatttataat catcttaaaa gctctagtga gacacttagc kgtacaaatt aaattttta    120 aatcgttggg caaagaatca tcagcaaatg tagttttttt tttttttga gaaatcaccc    180 aatgtaktca attgcggaag caggagcttg tcattccagt agtccaattt ttcagttata   240
cttttgattt ttatagggta agtactaagt aacctagcta gtttcttaat ctcatgatct   300
cttggcttat ytttttttt  tttwaatttg tgcttgagtc actatacata tttacttggt   360
tgtcgaacaa aattaaaaty tcttcgtacc taaacaaaac c                        401

<210> SEQ ID NO 64
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 64
caatgtaktc aattgcggaa gsaggagctt gtcattccag tagtccaatt tttcagttat     60
acttttgatt tttatagggt aagtactaag taacctagct agtttcttaa tctcatgatc    120
tcttggctta tyttttttt  ttttwaattt gtgcttgagt cactatacat atttacttgg    180
ttgtcgaaca aaattaaaat ctcttcgtac ctaaacaaaa cctaacttaa agtcccagac    240
taattcaaca ataatcaact caattttttt tttttgcat  gttacatttc atacattaac    300
tgttgagcta ctttatgggt tccctcccgt gtagggtttg tttaatgata ttagcttgaa    360
gttttcactc ttttgatctt caagaagagt taaaggtgga c                        401

<210> SEQ ID NO 65
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 65
gcaacttgag gctgaactcg gtcgtgcggt caagcaagac atttctgtgt acgtagctgt     60
acaataatat acaatgaatt agaataataa cagattatgt ggcattaatt attacagcag    120
caactcattc cttgattctg ggaattagca atttcttcca gcttatatat ataccagcat    180
ctcaatcctt gattgtacga cataatttg  caatttgatc caaatttatt acagctagtt    240
aggatactac tcgtcttaca attttgaca  aggttttgtc agcaatgttg aggatgttta    300
```

```
agctgaacac cgtccgagaa gtaaaatact attaaaggag gctaaaggra tatattggat    360
tagaatttta aaagattatt ttaatataaa aggttatatg a                        401
```

<210> SEQ ID NO 66
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 66

```
caatttcttc cagcttatat ataccagc atctcaatcc ttgattgtac gayataattt      60
tgcaatttga tccaaattta ttacagctag ttaggatact actcgtctta caattttga     120 caaggttttg tcagcaatgt tgaggatgtt taagctgaac accgtccgag aagtaaaata   180
ctattaaagg aggctaaagg aatatattgg attagaattt aaaagatta ttttaatata    240 aaaggttata tgaattttaa aaatkatgta gaagtattat gacttattat attttttac    300 aarattttta taatagtttt aatttaata aatttatatg ataagaattt aaaagactta    360 aatttttta aaaaaattta taaratttaa aagaattata t                        401
```

<210> SEQ ID NO 67
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 67

```
atttgatcca aatttattac agctagttag gatactactc gtcttacaat ttttgacaag    60
gttttgtcag caatgttgag gatgtttaag ctgaacaccg tccgagaagt aaaatactat   120
taaaggaggc taaaggrata tattggatta gaattttaaa agattatttt aatataaaag   180
gttatatgaa ttttaaaaat gatgtagaag tattatgact tattatattt ttttacaara   240 ttttttataat agttttaatt ttaataaatt tatatgataa gaatttaaaa gacttaaatt   300
tttttaaaaa aatttataar atttaaaaga attatatgaa ttttttaaaat cacattcaaa   360 attacaataa ttaatgaaga aaataacaaa aaataatgag a                       401
```

<210> SEQ ID NO 68
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 68

```
tagtttaat tttaataaat ttatatgata agaatttaaa agacttaaat ttttttaaaa     60
aaatttataa ratttaaaag aattatatga attttaaaa tcacattcaa aattacaata    120
attaatgaag aaaataacaa aaaataatga gatttggata aaaaaagtaa aatcaaaaca   180 attttttaa tctttcaata acatattgat tctaacttta tattctccta tattaacctt    240
tcatgcaata atatcttctc attctyactt ttgaatttga acaataratt taaaattata   300
cattgatttt ctgatttttt taattagtct aattatttca taataaatat aatgacatgt   360
tatggaatgc aataataaat atatactaaa aaagagtaat a                       401
```

<210> SEQ ID NO 69
<211> LENGTH: 401

<212> TYPE: DNA
<213> ORGANISM: Artificial Sequence
<220> FEATURE:
<223> OTHER INFORMATION: Consensus Reference Sequence

<400> SEQUENCE: 69

```
tataaratttt aaaagaatta tatgaatttt taaaatcaca ttcaaaatta caataattaa      60
tgaagaaaat aacaaaaaat aatgagattt ggataaaaaa agtaaaatca aaacaattttt    120
tttaatcttt caatarcata ttgattctaa ctttatattc tcctatatta accttttcatg    180
caataatatc ttctcattct cacttttgaa tttgaacaat aratttaaaa ttatacattg     240
attttctgat ttttttaatt agtctaatta tttcataata aatataatga catgttatgg     300
aatgcaataa taaatatata ctaaaaaaga gtaataagag tgtgaaattg gtayrasagt     360
tattaagtca tgtggataat gaaattaaga gtaacattta t                         401
```

<210> SEQ ID NO 70
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 70

```
atgaattttt aaaatcacat tcaaaattac aataattaat gaagaaaata acaaaaaata      60
atgagatttg gataaaaaaa gtaaaatcaa aacaattttt ttaatctttc aatarcatat    120
tgattctaac tttatattct cctatattaa ccttttcatgc aataatatct tctcattcty    180
acttttgaat ttgaacaata aatttaaaat tatacattga ttttctgatt tttttaatta    240
gtctaattat ttcataataa atataatgac atgttatgga atgcaataat aaatatatac    300
taaaaaagag taataagagt gtgaaattgg tayrasagtt attaagtcat gtggataatg    360
aaattaagag taacatttat gaaaatatta tattgagcaa g                         401
```

<210> SEQ ID NO 71
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 71

```
atattctcct atattaacct ttcatgcaat aatatcttct cattctyact tttgaatttg      60
aacaatarat ttaaaattat acattgattt tctgattttt ttaattagtc taattatttc    120
ataataaata taatgacatg ttatggaatg caataataaa tatatactaa aaagagtaa     180
taagagtgtg aaattggtay aasagttatt aagtcatgtg gataatgaaa ttaagagtaa    240
catttatgaa aatattatat tgagcaagtt ataaacataa tcamtaaaac tcatcataag    300
aaaaaaaaca tgattagtct tgacacataa gataaacatt aatttaattt aaaaaacaaa    360
graaaaagtg tagaggggag acatatattt gacattttt a                         401
```

<210> SEQ ID NO 72
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 72

```
attctcctat attaaccttt catgcaataa tatcttctca ttctyacttt tgaatttgaa      60
caatarattt aaaattatac attgattttc tgattttttt aattagtcta attatttcat     120
aataaatata atgacatgtt atggaatgca ataataaata tatactaaaa aagagtaata     180
agagtgtgaa attggtayra cagttattaa gtcatgtgga taatgaaatt aagagtaaca     240
tttatgaaaa tattatattg agcaagttat aaacataatc amtaaaactc atcataagaa     300
aaaaaacatg attagtcttg acacataaga taaacattaa tttaatttaa aaaacaaagr     360
aaaaagtgta gagggagac atatatttga catttttat t                           401
```

<210> SEQ ID NO 73
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 73

```
atatactaaa aagagtaat aagagtgtga aattggtayr asagttatta agtcatgtgg       60
ataatgaaat taagagtaac atttatgaaa atattatatt gagcaagtta taaacataat     120
camtaaaact catcataaga aaaaaaacat gattagtctt gacacataag ataaacatta     180
atttaattta aaaacaaag aaaaagtgt agagggaga catatatttg acattttta         240 tttcaaaaga ataagagaaa tatatatggt gcttgcatct tgawgaacat taaatagata     300
araagatatg tgtgataaaa gaaaaaaaa agtgtggtaa tcaatagaaa aaaaaaagag      360
waaaatcatt caaatcattc aatagaaaag tgtggggttg t                          401
```

<210> SEQ ID NO 74
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 74

```
tatgaaaata ttatattgag caagttataa acataatcam taaaactcat cataagaaaa      60
aaaacatgat tagtcttgac acataagata acattaatt taatttaaaa acaaagraa       120 aaagtgtaga ggggagacat atatttgaca tttttatttt caaagaata agagaaatat      180 atatggtgct tgcatcttga agaacattaa atagataara agatatgtgt gataaaagaa     240 aaaaaaagt gtggtaatca atagaaaaaa aaaagagwaa aatcattcaa atcattcaat      300 agaaagtgt ggggttgttt aattgatgtt ttatattaaa aaattagatg aaattcatcc      360
aaatcattct taaaaaataa tgcatcaaaa tttgtatatt t                          401
```

<210> SEQ ID NO 75
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 75

```
agcaagttat aaacataatc amtaaaactc atcataagaa aaaaacatg attagtcttg       60 acacataaga taaacattaa tttaatttaa aaaacaaagr aaaaagtgta gagggagac      120 atatatttga catttttat ttcaaaagaa taagagaaat atatatggtg cttgcatctt      180
gawgaacatt aaatagataa aaagatatgt gtgataaaag aaaaaaaaaa gtgtggtaat     240
```
caatagaaaa aaaaaagagw aaaatcattc aaatcattca atagaaaagt gtggggttgt    300
ttaattgatg ttttatatta aaaaattaga tgaaattcat ccaaatcatt cttaaaaaat    360
aatgcatcaa aatttgtata tttttaaata ttaaaagact t                        401

<210> SEQ ID NO 76
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 76
tggtaatcaa tagaaaaaaa aaagagwaaa atcattcaaa tcattcaata gaaaagtgtg     60
gggttgttta attgatgttt tatattaaaa aattagatga aattcatcca aatcattctt    120 aaaaataat gcatcaaaat ttgtatattt ttaaatatta aaagactttt ttataagtta     180
taaaaaatta taattgaata ccacmaaatt ttattatttt tcttaaaaaa tcttawatgt    240
tttaattgaa taccataaga ctttttttata aaaaahtat tttaaaatct tttmaaatct    300
taatcyaata tatccactaa gttatyaaag gctaggagga aacaagtgga scatgagaca    360
atacatatat agggggggaat atggaaat tgaaaaaaaa a                         401

<210> SEQ ID NO 77
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 77
aatcaataga aaaaaaaag agwaaaatca ttcaaatcat tcaatagaaa agtgtggggt     60
tgtttaattg atgttttata ttaaaaaatt agatgaaatt catccaaatc attcttaaaa    120
aataatgcat caaaatttgt atattttaa atattaaaag acttttttat aagttataaa    180
aaattataat tgaataycac aaaatttat tattttcttt aaaaaatctt awatgtttta    240
attgaatacc ataagacttt tttatataaa aahtatttta aaatctttm aaatcttaat    300 cyaatatatc cactaagtta tyaaaggcta ggaggaaaca agtggascat gagacaatac    360
atatataggg gggaatatat ggaaattgaa aaaaaaaga t                         401

<210> SEQ ID NO 78
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 78
tagatgaaat tcatccaaat cattcttaaa aaataatgca tcaaaatttg tatattttta     60
aatattaaaa gactttttta taagttataa aaaattataa ttgaatayca cmaaatttta    120
ttatttttct aaaaaatct tawatgtttt aattgaatac cataagactt ttttatataa    180 aaahtattt aaaatctttt aaaatcttaa tcyaatatat ccactaagtt atyaaaggct    240
aggaggaaac aagtggasca tgagacaata catatatagg gggaatata tggaaattga    300 aaaaaaaag atgtgaaaaa taataaatct caatagaaaa tgaaggaagc ataaatgaaa    360
taaaagtgaa atcaggtgat gagataaaaa acaattgtst a                        401

<210> SEQ ID NO 79
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 79
ataatgcatc aaaatttgta tattttttaaa tattaaaaga ctttttttata agttataaaa    60 aattataatt gaataycacm aaatttttatt attttttctta aaaaatcttta watgttttaa   120 ttgaatacca taagactttt ttatataaaa ahtatttttaa aatcttttma aatcttaatc    180
yaatatatcc actaagttat caaaggctag gaggaaacaa gtggascatg agacaataca    240
tatatagggg ggaatatatg gaaattgaaa aaaaaaagat gtgaaaaata ataaatctca    300
atagaaaatg aaggaagcat aaatgaaata aaagtgaaat caggtgatga gataaaaaac    360
aattgtstaa aaaaattgac gataagtcta taataaataa a                          401

<210> SEQ ID NO 80
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 80
ttmaaatctt aatcyaatat atccactaag ttatyaaagg ctaggaggaa acaagtggas    60
catgagacaa tacatatata gggggggaata tggaaattt gaaaaaaaaa agatgtgaaa    120
aataataaat ctcaatagaa aatgaaggaa gcataaatga aataaaagtg aaatcaggtg    180
atgagataaa aaacaattgt ctaaaaaaat tgacgataag tctataataa ataaaaagtg    240
aggtcatata catattcccg atttctataa aaaaaaatga atatttgaaa atcaattcat    300
tttcaatytt taaaaaataa ataaaaaaga attgaagttg tatatcaatc tatggagaat    360
taattcaaaa aatgatttat agaagttagc aatagaaaaa t                          401

<210> SEQ ID NO 81
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 81
aaaagatgtg aaaaataata aatctcaata gaaaatgaag gaagcataaa tgaaataaaa    60
gtgaaatcag gtgatgagat aaaaaacaat tgtstaaaaa aattgacgat aagtctataa   120
taaataaaaa gtgaggtcat atacatattc ccgatttcta taaaaaaaaa tgaatatttg   180
aaaatcaatt cattttcaat cttttaaaaaa taaataaaaa agaattgaag ttgtatatca   240
atctatggag aattaattca aaaaatgatt tatagaagtt agcaatagaa aaatacgtac   300
taacattata agaaagagaa aatatttttaa gagataaata gcaaaataat atttatttaa   360
stgaatgagt atcttaaacc atatatcaaa atttacaaca c                          401

<210> SEQ ID NO 82
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 82

```
taaaaaaaaa tgaatatttg aaaatcaatt cattttcaat ytttaaaaaa taaataaaaa    60
agaattgaag ttgtatatca atctatggag aattaattca aaaatgatt tatagaagtt    120
agcaatagaa aaatacgtac taacattata agaaagagaa aatattttaa gagataaata   180
gcaaataat atttatttaa ctgaatgagt atcttaaacc atatatcaaa atttacaaca    240
cattaaaatg aaaaatctta aaagaagga acaacaaaac tttttatgaa aattataacc    300
aaaaaaaaat aaaaattaat ataaagctta acatttcttt tgttgaagta ctaatataaa    360
gcttaacatg atagctagga taagcactat cctatggcca c                        401
```

<210> SEQ ID NO 83
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 83

```
ttttggtaaa cagatttaat ttgatgtaaa tcatattaac ataattaata ttaggtattt    60
taataatttt ttattatttt atttgtattg ttcattawtt gttraataat atataagata    120
aaaaacattt tgtcatttat ctttatccta tcttattttt tatcttgtct aatatcatat    180
ttttaacaaa tcaaatwggg ggtaagtgtt tgataaattt tttcaaacaa attacaaatg    240
ttaatatatt ttatttttc aacaaktaat atgttaatct taataaacaa attcacattt    300
tattttttcat ttaccaaaat agatatatta tttttaaata ttgtttgaaa taaataattt    360
ataattaatt waaaaaaata awaatttcat ttcgtaacat a                        401
```

<210> SEQ ID NO 84
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 84

```
atttttatt attttatttg tattgttcat tawttgttra ataatatata agataaaaaa    60
cattttgtca tttatcttta tcctatctta tttttatct tgtctaatat catatttta    120
acaaatcaaa twgggkgtaa gtgtttgata aattttttca acaaattac aaatgttaat    180
atattttatt ttttcaacaa gtaatatgtt aatcttaata aacaaattca cattttattt    240
ttcatttacc aaaatagata tattatttttt aaatattgtt tgaaataaat aatttataat    300
taattwaaaa aaataawaat ttcatttcgt aacatatttt tcacattgaa ataaacatgt    360
acgacacaca tatatacata catatatata tatatatata t                        401
```

<210> SEQ ID NO 85
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 85

```
aaaaataatt catattaata taccaactta agaaagctgt taaatatatt aaaaaaagga    60
aatatgttat tattaaatca aatttcatc agttaacaac caacattta atctaattta    120
```

```
gttgtttaaa caaaatttgt atgtattata aatttttaat attattttta ttttttaaaaa    180 taaaaaacag tgaaaacaat aaaccttgca ttatcatata tagtcaatta aaaaaaagga     240
atgagtgaag gggaaaaagt ggaggaaaag gtaatggatt caattccttc cattaatatt    300
ttaaacaaaa attaataaat taacatattg gtaaaaaata taatattaat ttcttgaaaa    360
tttgtatcca gtagtacaac attataaatt atttttttagg t                       401

<210> SEQ ID NO 86
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 86
ttctgccaat ggaagggtat ccaatgcgat tcatccagcc acgtgaccag cataagcctc    60
gcttcgcakt ccctcaccgg aacactcccc tcggatctca attccctctc tcaactccgc   120
actctctccc tccaagacaa ttccctcacc ggcaccctcc cttctctctc caacctttct   180
ttcctccaaa ccgtctactt aaaccgcaac aacttctcct ccgtgtcccc caccgcyttc   240
gcctccctaa cctccctcca aaccctcagc ctcggctcca accctgctct ccaaccctgg   300
tccttcccca ccgacctcac ttcctcctct aacctaatcg acctcgacct cgccaccgta   360
tccctcaccg gtcccttgcc ggacattttc gacaaattcc c                       401

<210> SEQ ID NO 87
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 87
agccacgtga ccagcataag cctcgcttcg caktccctca ccggaacact cccctcggat     60
ctcaattccc tctctcaact ccgcactctc tccctccaag acaattccct caccggcacc   120
ctcccttctc tctccaacct ttcttttcctc caaaccgtct acttmaaccg caacaacttc   180
tcctccgtgt cccccaccgc cttcgcctcc ctaacctccc tccaaaccct cagcctcggc   240
tccaaccctg ctctccaacc ctggtccttc cccaccgacc tcacttcctc ctctaaccta   300
atcgacctcg acctcgccac cgtatccctc accggtccct tgccggacat tttcgacaaa   360
ttcccttccc ttcaacacct tcgcctctct tacaacaacc t                        401

<210> SEQ ID NO 88
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 88
gttcccgctt cattgacaag tcttcctagt ttgaagaaag tttctctgga taataatgag    60
cttcaggggc ctgtgcccgt gtttgggaaa ggtgtgaatg ttactctcga tgggattaat   120
agtttttgtc ttgatactcc tgggaattgt gatcccaggg tgatggtttt gctgcagatt   180
gccgaggcat tcgggtatcc aattcggtyg gcagagtcgt ggaaggggaa tgatccgtgt   240
gatggttgga actatgttgt gtgtgctgcc ggaaagatta ttactgtcaa tttcgagaaa   300
cagggtttgc agggtaccat ctcccctgca tttgccaatt tgactgactt gaggactttg   360
```
tttctcaatg gcaataattt gatcggttct atacctgata g      401

```
<210> SEQ ID NO 89
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 89
```
aaggttgctg atttttgggtt ggttaaaaat gcaccagatg ggaagtattc tgttgagaca      60
cggttggctg gaacatttgg atatcttgca cctgagtatg caggtacaga aagcctttga      120
ttttagtttt gtacaattgt gccttaattt tgaagttcat attttatatg ctcgtatttg      180
gtggttatag ctgttggtta gtacttcaat atcatgcttc ggtgttcagc aaatttaagt      240
agttcaccag agtaatcgct cacatacaaa aaaaaagtag aaagagttga agggaaaata      300
attgatactc aattcctaga tacatggcta cttcaaaatt ctttgtggct atttctttgc      360
aatgttatat tttgctcttt tcacgtgttt tgttgagttg g      401

```
<210> SEQ ID NO 90
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 90
```
ggagcaatgg aaacctacta gccatgatga agaagaggaa gacggctctg gcggtgacct      60
tcatatgagc cttcctcaag ctctacgaag gtggcaagcc aacgaaggca cttcctcaat      120
atttaatgac atttccatct cacaaaccca atcaagcatc tcctctaaac ctgcagggtt      180
tgcagactcc tttgattcaa cggattgccg ttaaccgaat tgataaacga gacaactatc      240
caagggcatc ttagtccata tgatagtgga aggtttagtt gagaataccc aagaaaacca      300
gaggttgtaa agctgtttttg atctattagc atcgccaatt tctttgtaat tatttattat      360
tgttcaaaat gtcattttta tggtgttctt aaaatctcct c      401

```
<210> SEQ ID NO 91
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 91
```
caagatttgt aagagaaaac ttcttggctc tatatttaas aacaaaaaat ctaagakraa      60
atgggattka atggaaatga tcggtcgcaa gcatatctaa atttgacagg aaatccataa      120
atgacttgac caccattaac aagataaata ttgtgtgaga tctttaaaar tgaagatttt      180
acgggtttaa cagattaaaa acttttacaa tttaatatca cattcttttg aacacatgaa      240
cacttattga tgatagttac attccatgct tgctttcctt gcactttatt ttttgttgga      300
aattgatcta yggagagatc tttcaaggaa cattggctat agctgacatg atgatwgrag      360
gaaaaattac aaacaataat ttatacaaat tttatgtttc a      401

```
<210> SEQ ID NO 92
<211> LENGTH: 401
<212> TYPE: DNA
```

-continued

<213> ORGANISM: Artificial Sequence
<220> FEATURE:
<223> OTHER INFORMATION: Consensus Reference Sequence

<400> SEQUENCE: 92

| tamaatagaa gaaaccagta tcttgacttc ttgagaaatg aggacaagga gcaaaactat | 60 |
| gctaagaatc ttgatggctg aaccasccat ttcagaaaat gtaaatacaa gcttcgattc | 120 |
| tcgaattgca tagctcttat atgtcgcgtt atttataaat gaattgttgt aatttgtaaa | 180 |
| acaatatgtt ttacgtttcg cgtgaagaat atcrcattta tgaatgactg aattttttaag | 240 |
| acaatgaaac tgaagttaaa gaaacataaa ttactctaaa aaaaattaaa tacagtgaaa | 300 |
| ttgtatagat ttgataaata tttttttaat agttgatatg attttgtttt gttaggagaa | 360 |
| agctatcatt ttgttctcct atagttatst ttagyaagtt a | 401 |

<210> SEQ ID NO 93
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 93

| accagtatct tgacttcttg agaaatgagg acaaggagca aaactatgct aagaatcttg | 60 |
| atggctgaac casccatttc agaaaatgta atacaagct tcgattctcg aattgcatag | 120 |
| ctcttatatg tcgcgttatt tataaatgaa ttgttgtaat tgtaaaaca atatgtttta | 180 |
| cgtttcgygt gaagaatatc acatttatga atgactgaat tttaagaca atgaaactga | 240 |
| agttaaagaa acataaatta ctctaaaaaa aattaaatac agtgaaattg tatagatttg | 300 |
| ataaatattt ttttaatagt tgatatgatt tgttttgtt aggagaaagc tatcattttg | 360 |
| ttctcctata gttatsttta gyaagttatt taattaaat t | 401 |

<210> SEQ ID NO 94
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 94

| ttttacgttt cgygtgaaga atatcrcatt tatgaatgac tgaattttta agacaatgaa | 60 |
| actgaagtta aagaaacata aattactcta aaaaaaatta atacagtga aattgtatag | 120 |
| atttgataaa tatttttta atagttgata tgattttgtt ttgttaggag aaagctatca | 180 |
| ttttgttctc ctatagttat ctttagyaag ttattttaat taaatttttt tattaattaa | 240 |
| aagatttatt tgactatttg ataaataatt ttttaagta attttttaatg tttctctagt | 300 |
| atyttttagt atttttttaa aatattattt aaaataacat ttttaaaca ctaattttta | 360 |
| attttttaacc ttttaattt attctcttta tatcttaaaa t | 401 |

<210> SEQ ID NO 95
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 95

| gtttcgygtg aagaatatcr catttatgaa tgactgaatt tttaagacaa tgaaactgaa | 60 |

```
gttaaagaaa cataaattac tctaaaaaaa attaaataca gtgaaattgt atagatttga    120
taaatatttt tttaatagtt gatatgattt tgttttgtta ggagaaagct atcattttgt    180
tctcctatag ttatstttag caagttattt taattaaatt tttttattaa ttaaaagatt    240
tatttgacta tttgataaat aatttttta agtaattttt aatgtttctc tagtatyttt    300
tagtattttt ttaaaatatt atttaaaata acatttttta aacactaatt tttaattttt    360 aacctttttaa ttttattctc tttatatctt aaaatattta t                      401

<210> SEQ ID NO 96
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 96
taacttttca gtttactttt gcaaataaya tatttctttc ctggmatatk acaaagctaa     60
acaatatttc ttgagtgttt aattgtttta aattgaaata ggaagtgagc atttmctaat    120
atcttagctc gaaacatctc tttcatcttt gttgaagtaa acctctgtat ggtaaaatta    180
agaggagaaa gaaaaatgaa ctggagtaag gtcttgtttg aaattatttt ttaatttcaa    240
aacttgtttt caatataatt tttagctttg ttatatttta aaaataaaat aaaaagaaaa    300
aayatttgtt aaaattcaaa aatagatttt ttttaaaaaa atgttcataa aatatcagca    360
tytgtcaatt gcatgtttat gaggtaaaaa attgctttat t                       401

<210> SEQ ID NO 97
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 97
aagtgagcat ttmctaatat cttagctcga aacatctctt tcatctttgt tgaagtaaac     60
ctctgtatgg taaaattaag aggagaaaga aaaatgaast ggagtaaggt cttgtttgaa    120 attattttt aatttcaaaa cttgttttca atataatttt tagctttgtt atattttaaa    180
aataaaataa aaagaaaaa catttgttaa aattcaaaaa tagattttt ttaaaaaat     240 gttcataaaa tatcagcaty tgtcaattgc atgtttatga ggtaaaaaat tgctttattt    300
atgaaaatat ttaggatcca aaacaagagt aggaaagtaa ttttttaaaag acattttttt    360 ccagcactgc aattgtagga acaagtttta aaatacaaat g                       401

<210> SEQ ID NO 98
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 98
cctctgtatg gtaaaattaa gaggagaaag aaaaatgaas tggagtaagg tcttgtttga     60
aattattttt taatttcaaa acttgttttc aatataattt ttagctttgt tatattttaa    120
aaataaaata aaaagaaaaa ayatttgtta aaattcaaaa atagattttt tttaaaaaaa    180
tgttcataaa atatcagcat ctgtcaattg catgtttatg aggtaaaaaa ttgctttatt    240
```

```
tatgaaaata tttaggatcc aaaacaagag taggaaagta attttttaaaa gacatttttt    300 tccagcactg caattgtagg aacaagtttt aaaatacaaa tgycttgaaa atctttctaa    360
tacttaatgg aaaatattaa ataaaaataa aaataaaaat a                        401

<210> SEQ ID NO 99
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 99
taggaaagta attttttaaaa gacatttttt tccagcactg caattgtagg aacaagtttt    60
aaaatacaaa tgycttgaaa atctttctaa tacttaatgg aaaatattaa ataaaaataa   120
aaataaaaat aaaaatattt aatgttttaa aaactttaaa aacattcaaa tactttcttt   180
atttaataag aggaggatga agggattaga attattcaat ttttttatat taaaatataa   240
cgaatccata acaaatttac agtagtactt tgtttcataa aaaaatactg attggatgaa   300
gcagakagga gagaggaaga tgtcagtaag tcataaatgt gccattaata catttaataa   360
cttttttttt ttacaaaagg gagaaaggct tacatttaaa t                       401

<210> SEQ ID NO 100
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 100 ttttttttt tacaaaaggg agaaaggctt acatttaaat tgctattact tttttttaaac     60 gaaaaggggg tgaaacgccc aaaataaatc atcataaata agataataag ataaggaagg   120
agaaaataaa tttaaatatt gatcacaaat aaatttgya taaatacaaa taaaatataa   180
gataataaat atcgatcaat ccgtgaaaca atttgcggaa gagcaaaatt tgagaaaaaa   240
aatcgaagaa rcaaaattcg cgatattata aaactttaga gataaaaaaa aattcatgat   300
aaataataca gtatattata attttaatct ttagttttta atacaactgt aaaaaaaatt   360
catgataaat aatatattat aattataatc tttagttttta a                      401

<210> SEQ ID NO 101
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 101
aactttttgt tagtaacaga aagtgtaaac tggtttggag aaaatgtgag agatggcagg     60
atactatgag taactagttg gattggaaaa tgttgtatcc agctgtaaat tacccattcc   120
attattggaa ggaaatattc cgcatgagcc aaactatgcg aaaatgacat ggtgaaaatt   180
gataaaggta agaaaaagt agagctcaga aaggtgttat tcttcatcaa gaagagctat   240
ttccaaagca actatrttac ttgtgcaact ctttattttt tgtacatata ctactattat   300
tattacttgt gctactctga taaatagaaa gtagaaaaca aagaagtggt attgattgat   360
gttacgtaag ttacataaaa gtttgatgcg tattgattga t                       401
```

<210> SEQ ID NO 102
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 102

```
acaaagcaat ggatccagga ctcatatatg atatcaccac tgaggattat gtccaattcc      60
tatgttccat ggatcacagt agtgcatcca ttagcaaagt gactaagacc accacaagtt    120
gtaagaaagg aaatcaccaa gcactgaacc tcaaccttcc ttccatatca gtgccaaacc    180
tgaagagggc tgcaacagta atgagaacag tgacaaacgt gggaaatatt actgcagtct    240
rcaaagctct agtgaaagtt ccacatggca taaaagttag agttgaacct caaactttga    300
gtttcaattc agrtgtacga atccttaact ttaktgtcag ttttctgtca actmaaaaat    360
ttcatggaga ttacaaattt gggagcctaa catggacaga t                        401
```

<210> SEQ ID NO 103
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 103

```
taatattttt tcttttaaa atacagawgg aagtacaaga ataaaagtg gttcaacttc       60
catgaataaa aatggtcttt acatgatttg cacttaatct aaataaccaa gcacaaaata    120
tatcaaaywt gtgtatattt tcagtttagt attaattatt aatgactagc aatagaattt    180
agatttatag agacaataca attagtaaat tttattttag aaattatttt aaaatattct    240
aataattaaa ttactctttt gttttacat tgcaagtgca agcatctayg tgcaaaagga     300
gggtacgata ctcaacaata gataaatttg cacaacatca tcagtctttg ttyttctttt    360
tcttttttac tttagatacg taaggcagta acaacatacg a                        401
```

<210> SEQ ID NO 104
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 104

```
gacaaaagat aagagaaaca agcttacatt actacaacgt tataagaagc aaataaccta     60
cgaagaaaat caagataaat aaatagatgg tacaaatttg catgtgttcg gatatccatc    120
gacatcattc atttcgatca aaattcacgt tttggacata aaagcaattc ttcgtcgctt    180
cagataatgc gtgtcgtgga acagaggatg caaaaccata catgcagaaa attatgcttg    240
cagaatgaca cwtacgatgg agcaccaaga tatgaggcaa gtcgtaaaat atcactaaat    300
attccaccag cggtgacttg agcaccagct cctggcccac gaactatcag aggctgatcc    360
ttataccttc gtgttgtaaa tgcaataatg ttatctgacc c                        401
```

<210> SEQ ID NO 105
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 105

| | | | | | |
|---|---|---|---|---|---|
| ctgttattga | ttgatsaatc | acttattact | atctgatgga | agatgagttt | tatataatag | 60 |
| agttaccttg | tcctgcaagc | ttacaataga | aamttcagct | gyctacagct | attaagacta | 120 |
| actaaacttc | agttaagcca | atattaattg | tgttttacta | tttaagtcct | agtttacaat | 180 |
| ttctcctata | tttttatttc | cattacttgt | ttcgaaagca | atcatctgaa | ttttctctat | 240 |
| cttcttgtat | aatgataaga | accttgggag | atctacacca | caaaaactag | tcattgtagt | 300 |
| ttggagagcc | aaggacctta | tacatcctaa | acttcaaatg | tgagactcaa | gtctcatacc | 360 |
| ttgcaattgg | atcctaacat | tccatcttgc | tttgcagcca | c | | 401 |

<210> SEQ ID NO 106
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 106

| | | | | | |
|---|---|---|---|---|---|
| aaatgtagaa | tgataaatct | tcagtctgat | atcactaaag | agagtcaagt | cttaacaatt | 60 |
| gaacagaaac | atgcatttgg | ttttagaaga | attggattta | gcacctgaga | aagacgccca | 120 |
| ttatccaaag | cttgacgaaa | tctagattgc | aatgcctcag | caacagcttt | tacttctttc | 180 |
| tcgggcacag | caaagcatac | agaatgctca | ctactagcct | acataaatac | tgttaatgat | 240 |
| taatgccatt | tcttatatat | carcgtggac | aactagaaaa | attgaaaaaa | gttataagtg | 300 |
| cacctgagat | atcatgataa | cattagctcc | aacatctttt | actgcaccaa | aaatagcact | 360 |
| ggcagtacct | ggaacaccag | ccattccagt | tctgcaaaaa | a | | 401 |

<210> SEQ ID NO 107
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 107

| | | | | | |
|---|---|---|---|---|---|
| ttaatgccat | ttcttatata | tcarcgtgga | caactagaaa | aattgaaaaa | agttataagt | 60 |
| gcacctgaga | tatcatgata | acattagctc | caacatcttt | tactgcacca | aaaatagcac | 120 |
| tggcagtacc | tggaacacca | gccattccag | ttctgcaaaa | aagcatcaaa | gaaaaattta | 180 |
| ttggaatcta | caacttggac | aattaatatt | ggttaaagaa | aaccttaaat | taaatagaaa | 240 |
| tcctcgtgca | gcaaaaaatg | ccaactattc | atcatgtaac | acaactgcaa | ttcatgactc | 300 |
| accccctcgac | gtttacaagt | gccaagttgt | ctatggttgc | aaatcctttg | acaaaatttt | 360 |
| gcaggttctg | gctatcttca | tgatcattaa | cagaaggatg | g | | 401 |

<210> SEQ ID NO 108
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 108

| | | | | | |
|---|---|---|---|---|---|
| cttgtggata | aggtcataca | tcatatctgt | cacctttgac | attgcagaaa | caaccaccaa | 60 |
| tttcctctcc | gaatcatcct | taagaattat | gtcygcaaca | ttttttattc | tctgagaggt | 120 |
| tcccacacag | gttccaccaa | atttgtgaac | agaccaagtt | tctcctttgg | gtagttgttt | 180 |

-continued

| | |
|---|---|
| ttcctccaag gacacattcg atgaaacatc tgctagcaaa tatagaaagg acaaaaaaac | 240 |
| ataagttact gtatttgtct attagagttc taaggttgac ttgatggtaa aaggagaagg | 300 |
| gagagaggga aaggtcgtgg gtgggttcaa ttttctccgc taacaaaaaa ctaacaatta | 360 |
| acaactaata tttgctgata ataaaaaaaa ctrtattcgt c | 401 |

<210> SEQ ID NO 109
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 109

| | |
|---|---|
| gaagggagag agggaaaggt cgtgggtggg ttcaattttc tccgctaaca aaaactaac | 60 |
| aattaacaac taatatttgc tgataataaa aaaaactrta ttcgtctatt tcaaaacata | 120 |
| accataagag taagtcgtaa cctgtaaatg aagcacgtac agatgtactc ggtgcctctc | 180 |
| ttccccgtgg taaagtaaga accttcctga gacagaaacc attgtatcgt cgtgaatcag | 240 |
| tatatagcaa acacaaaaa tccaattaat ctcatgggga gaatatcatt taaactgcca | 300 |
| aaattccgaa aacactctaa tctctgcaaa ggataaatat acaaaaagga aaaaaaaag | 360 |
| tacagaatat actgcttgta gaacaaccaa tcatctaaga g | 401 |

<210> SEQ ID NO 110
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 110

| | |
|---|---|
| ttgagttgaa ataatgaaat gaaatggatc ataatccatc atcatcttcc attatgtttc | 60 |
| atttcaactt ttacaaatca aacaatccaa cacctttcc ttccactcca tccttcttca | 120 |
| ttccatactc tacaaccaat caaaacatat tcgaaggttt ccatgtatgt agaattataa | 180 |
| ataggttgaa caaaatttta ctgrgtaggt tgaamagaat tatttggtay tattattcgt | 240 |
| acgcccctaa ccatgtgttt ggatgaagaa tttaaaaatt tctaagaaat ttaaattcat | 300 |
| aacattttaa ttgccttgat tttaattcct ttccttttgt aaatattttg tttggatgag | 360 |
| gtaattcaaa ttcttgtatt ttaattttct tstttggaca a | 401 |

<210> SEQ ID NO 111
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 111

| | |
|---|---|
| aatgataaca aattgtacat attatagact aaaatgacaa taattttaat ctaaacaatt | 60 |
| tatttatatt tttttaattt tatgatgtgt taaattgtga cagtgcccta caattttaaa | 120 |
| gaacgtacaa aataattatt tattcaaaat tttaaacata acattacctt tccctacaac | 180 |
| gtcccccga tagtgtcatc agtaggactc ttgcttcaga acaaaacgcg agtccatata | 240 |
| aggcaactgc aatttttta attagtcttc cgtttgtttc gggggctaat ggggaattat | 300 |
| agcaagtgtg akaattttct atgctttaa actaaaatct acatatttat aaaaatataa | 360 | aagtaaaaaa aaaatgccac ggatagttca gtcaaagata a    401

<210> SEQ ID NO 112
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 112
aattttaaag aacgtacaaa ataattattt attcaaaatt ttaaacataa cattacctttt    60
ccctacaacg tcccccccgat agtgtcatcr gtaggactct tgcttcagaa caaaacgcga    120
gtccatataa ggcaactgca atttttttaa ttagtcttcc gtttgtttcg ggggctaatg    180
gggaattata gcaagtgtga gaattttcta tgcttttaaa ctaaaatcta catatttata    240
aaaatataaa agtaaaaaaa aaatgccacg gatagttcag tcaaagataa ttcgaaatca    300
tagtaaatat taaatgattg gatttttacaa catstatttg aaagagtcat cataaaactt    360
aataccacay tttaaccmaa aactttaaaa gtcaacttta t                        401

<210> SEQ ID NO 113
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 113
ccaatcctat tatgttaccc aagatgycgt wagttctcta ggtggttttt tcraaacaaa    60
aaaaawttat ttgtaataaa ataaataata ttacttcatt ctcatgtctt tttatattta    120
aggttattat taagaaatat ttgatgaaaa taaacattgt tcaccctcgt agcctccgtt    180
atggcgagag tgcctctcat ctgcgttccr aacagcccta gcttrcacca taatgggttg    240
tgtcaccctc gtagccttcc ytgcattctc attatcataa acgaygccgc tttgggagac    300
gccttccatg tctatrccac ccttcagagc ataggcccca ccatcttgag cttgtgggyt    360
gtcggactag ggycgctctc taaagycacc accgctgtag c                        401

<210> SEQ ID NO 114
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 114
gagagtgcct ctcatytgcg ttccraacag ccctagcttr caccataatg ggttgtgtca    60
ccctcgtagc cttccytgca ttctcattat cataaacgay gccgctttgg gagacgcctt    120
ccatgtctat rccacccttc agagcatagg ccccaccatc ttgagcttgt gggytgtcgg    180
actagggycg ctctctaaag ccaccaccgc tgtagcggtg gcgctcgccg cgtttgtggt    240
ggttctttcc trgcctcaga gcacaaattt gatagctaaa cgcatatcat tgggtcagat    300
agtaccacca tgttgaaatt ragaggaaag aagttttaaa aaccctaatt tgaggaagaa    360
gaagcaagtg aagaagaaaa tatttgacaa cttttttaaaa t                       401

<210> SEQ ID NO 115
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 115

| | | | | |
|---|---|---|---|---|
| gttgtgtcac | cctcgtagcc | ttccytgcat | tctcattatc | ataaacgayg | ccgctttggg | 60 |
| agacgccttc | catgtctatr | ccacccttca | gagcataggc | cccaccatct | tgagcttgtg | 120 |
| ggytgtcgga | ctagggycgc | tctctaaagy | caccaccgct | gtagcggtgg | cgctcgccgc | 180 |
| gtttgtggtg | gttctttcct | agcctcagag | cacaaatttg | atagctaaac | gcatatcatt | 240 |
| gggtcagata | gtaccaccat | gttgaaattr | agaggaaaga | agttttaaaa | accctaattt | 300 |
| gaggaagaag | aagcaagtga | agaagaaaat | atttgacaac | ttttttaaaat | ttgcatcaaa | 360 |
| gtccagctta | catgtcataa | tctaggacaa | tttgwcacgt | t | | 401 |

<210> SEQ ID NO 116
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 116

| | | | | |
|---|---|---|---|---|
| ccatgtctat | rccacccttc | agagcatagg | ccccaccatc | ttgagcttgt | gggytgtcgg | 60 |
| actagggycg | ctctctaaag | ycaccaccgc | tgtagcggtg | gcgctcgccg | cgtttgtggt | 120 |
| ggttctttcc | trgcctcaga | gcacaaattt | gatagctaaa | cgcatatcat | tgggtcagat | 180 |
| agtaccacca | tgttgaaatt | aagaggaaag | aagttttaaa | aaccctaatt | tgaggaagaa | 240 |
| gaagcaagtg | aagaagaaaa | tatttgacaa | cttttttaaaa | tttgcatcaa | agtccagctt | 300 |
| acatgtcata | atctaggaca | atttgwcacg | ttagataatc | tatgtgacay | taaaattatt | 360 |
| aaaaatatat | ctcattaatg | gygttayttt | taaatttaac | g | | 401 |

<210> SEQ ID NO 117
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 117

| | | | | |
|---|---|---|---|---|
| tgcatcaaag | tccagcttac | atgtcataat | ctaggacaat | ttgwcacgtt | agataatcta | 60 |
| tgtgacayta | aaattattaa | aaatatatct | cattaatggy | gttayttta | aatttaacgg | 120 |
| caaakactat | tttrtaaaat | ttatgcaaaa | atagagacta | ttttttacat | ttaaaaaaag | 180 |
| ataaagacta | atttgcaaaa | agaatcaaaa | gttagaaatc | aaaataccta | tttayttaaw | 240 |
| aaaaaaaaca | tcatgcgtta | gttataacct | taacttctaa | ttttttgcta | acgcccaaaa | 300 |
| aaactaagaa | ttcgaatcag | aagtaggyag | aatagkcaat | ttggttctta | aaagtgtatg | 360 |
| gaaggaaaaa | wtttcctttg | acttttaaa | ttggaacacg | t | | 401 |

<210> SEQ ID NO 118
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 118

| | | | | |
|---|---|---|---|---|
| aaaatttatg | caaaaataga | gactattttt | tacatttaaa | aaaagataaa | gactaatttg | 60 |

```
caaaargaat caaaagttag aaatcaaaat acctatttay ttaawaaaaa aaacatcatg    120
cgttagttat aaccttaact tctaattttt tgctaacgcc caaaaaaact aagaattcga    180
atcagaagta ggyagaatag gcaatttggt tcttaaaagt gtatggaagg aaaaawtttc    240
ctttgacttt ttaaattgga acacgtcttg attttttttcc cttgttgccc aaaagcagtc    300
ttattattca tccgttggga attttttgttt taatttcgct gatmaaaaaa ttgagaattt    360
tatgtctgct ttgtgaatta ccattttwtc ggaacctgca t                        401
```

<210> SEQ ID NO 119
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 119

```
tagaagkaat aattttgttt tggcttgttg aattggaaaa tgttacagtc ccggtcattc     60 ttttatttt tatatgttta tttattttg tccaaatagc agggtcatat tcaaaacttg    120
ggttttactt tcaagctttg gaacaatgtt agtgtaattt gtgacttttg ataaagccaa    180
agaagtaact ttcgttctta cttcatgtg acttgtaaca agttacaagt cagtaatata    240
acctataact twytcttcat crtctgcttc ttcttttgat cataatatct gttaagtgat    300
ctttcataga gagagagaga gagagatgga gaggtgtgac aaggtgatga accaacgcaa    360
catgcatgat tgtcctaaaa caggtcctgg ctatccttca c                        401
```

<210> SEQ ID NO 120
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 120

```
tctgaaaagg ccaattcagc ttcattggag gaatagatag gcattaggca gagagatcaa     60
gataggtttc tcaagttgtt gttacaaaca tttatatga catgtactg ggaacaagtg    120 acatgtagaa atatctatct cttttctagtg ctatgcatga agacttggtg cagcttaaac    180
aatttctgtc aaaacgtgta gtttggtgat tttatatata tatattggtg atgaatattc    240
aattcaatgc aggaacagga agggataagc ctgactttct ggccacagtg gatgtggatc    300
caagctctcc aacgtattca aaagttatcc ataggttacc tgtaccttat ttaggtgatg    360
aactgcacca ttttgggtgg aattcatgca gctcttgcta t                        401
```

<210> SEQ ID NO 121
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 121

```
gtgatgaact gcaccatttt gggtggaatt catgcagctc ttgctatgga gatccatcag     60
cagttcggcg atatctgatt ctaccttcac tggtgtaaga tactaaacag ccacttttgga    120 ttttacttgc acgcatatgc gcatgcayac acacacataa caaacactga caaggttcaa    180
gaacttcact ggtgtaagac atcggttttc ttgaaacgaa atccttatta agtcagattt    240
accatatttc agatcaggcc gcatttatgt ggttgacaca agatcaaatc caaggtctcc    300
```
atctttgcac aaagttgttg agccagaaga catcataagt aagactggat tagcttatgc    360
acacacatct cattgtcttg cttctggtga cgtcatgatc t                        401

<210> SEQ ID NO 122
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 122
ctggtaccaa ccacagcata agactatgat tagctcatca tggggtgctc ctgctgcttt    60
caccaaaggt tttaacttac agcatgtctc tgatggtctt tatgggaggc atctacatgt    120
atacagctgg cctggggggtg aactgagaca aacattggac cttggtgagt caggggttct   180
acccttggag gtacattgct caataaataa ttctggagtt atttccwcca attataagca    240
ctttatgtta atgtacttgt gatttaatca taaatatgtt tgtcctttgc tacatttttt    300
ctctctagcc tgtacttgtg aagtaatatg ttaaaggtgg cataatttgt aagcaacttg    360
tcctaaatgc aggtaaggtt tctgcatgat ccttctaaag a                        401

<210> SEQ ID NO 123
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 123
tgattagctc atcatggggt gctcctgctg cttcaccaa aggttttaac ttacagcatg     60
tctctgatgg tctttatggg aggcatctac atgtatacag ctggcctggg ggtgaactga   120
gacaaacatt ggaccttggt gagtcagggg ttctacccct tggaggtacat tgctyaataa   180 ataattctgg agttatttcc accaattata agcactttat gttaatgtac ttgtgattta   240
atcataaata tgtttgtcct ttgctacatt ttttctctct agcctgtact tgtgaagtaa   300
tatgttaaag gtggcataat ttgtaagcaa cttgtcctaa atgcaggtaa ggtttctgca   360
tgatccttct aaagatacag gtttcgtkgg gtgtgcattg t                        401

<210> SEQ ID NO 124
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 124
gtcaagtaac atggtacggt ttttcaagac cgaggatgaa tcatggagtc atgaggtaca    60
caaaaaggat atagtaaaaa atcaatgcct aaattttagg agaatcatga catctcatta   120
atcagaaggt ttacattcag ctattctatt tttatttcat tcctataatt tgggattcc    180 tggttcttgg aatttccttt ataattttct tcacctttc tatatattgt atctgtgctc    240
atatgaaata atagagatga tataattttc atactctact ctactcatag atatccatac   300 tcatttrta ttgtcatctg gtatgcgttt gtgcagcttc aaccaaggta taatgatcaa    360
taatacttac acactagact gactttgcag gttgcaatat c                       401

<210> SEQ ID NO 125

<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 125

```
tgacatctca ttaatcagaa ggtttacatt cagctattct attttatttt cattcctata      60
attttgggat tcctggttct tggaatttcc tttwtaattt tcttcacctt ttctatatat     120
tgtatctgtg ctcatatgaa ataatagaga tgatataatt ttcatactct actctactca     180
tagatatcca tactcatttt atattgtcat ctggtatgcg tttgtgcagc ttcaaccaag     240
gtataatgat caataatact tacacactag actgactttg caggttgcaa tatcagtgaa     300
accattgaaa gtgcaaaact ggattcttcc agaaatgcct gggcttataa ctgattttct     360
gatatctctt gatgatcggt ttctgtactt tgtgaattgg c                         401
```

<210> SEQ ID NO 126
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 126

```
tagacaatat aacattgagg accctaaaaa tcctgtactg actggccaag tatgggttgg      60
gggactactt cagaaaggaa gccctatagt agcaataacc gaagatggta atacttggca     120
atctgatgtt ccagacatcc aggtttgtgc agtttaactt tgaaattag tgattctagt      180
gtcatgcttg ttgatttctc acatgtttgg agttgattgg ttcttagatg tactagatat     240
aatagacttg tgcattacat tggtgccttc aaacttttg tcactttgt attttatctt      300
gtgttatgct taaacgtggt aaataattgc actttaaatt ttgacccttt agtggttgaa     360
ggtgaagaga tcaaaatttt taatttcagg gaaataagtt g                         401
```

<210> SEQ ID NO 127
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 127

```
aaaatggtgg tctgaaaatt aaccctaatt tctttgttga ctttggagct gagcctgggg      60
gtccctgcct tgcccatgag atgagatatc ctggtggtga ctgcacttca gatatatgga     120
tttaatagct atgctacttg aggccaggct acaagcaata tccatgtgaa taaaatcctt     180
agtcctagaa tgaatcgagg agggctaatg ttataaataa ataatagttg catatgtatg     240
atggttgcat tgtaataaag ttatattgtc atgtagtttt cmgtactttc tcatttacat     300
catcctaaac agtgttctct rtgaaataaa tcttgctcac ctacaaaatt tgggtcttct     360
gattgagtaa atctctattg gagtaacatt ctagattaat g                         401
```

<210> SEQ ID NO 128
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 128

```
tgagatatcc tggtggtgac tgcacttcag atatatggat ttaatagcta tgctacttga      60
ggccaggcta caagcaatat ccatgtgaat aaaatcctta gtcctagaat gaatcgaggw     120
gggctaatgt tataaataaa taatagttgc atatgtatga tggttgcatt gtaataaagt     180
tatattgtca tgtagttttc agtacttcct catttacatc atcctaaaca gtgttctctr     240
tgaaataaat cttgctcacc tacaaaattt gggtcttctg attgagtaaa tctctattgg     300
agtaacattc tagattaatg gccttacttg ggattctatg attttcattc acatcatgaa     360
tgtgctgcac cttctacgtt gcttgttccc atttgaatgy a                         401
```

<210> SEQ ID NO 129
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 129

```
tttaatagct atgctacttg aggccaggct acaagcaata tccatgtgaa taaaatcctt      60
agtcctagaa tgaatcgagg wgggctaatg ttataaataa ataatagttg catatgtatg     120
atggttgcat tgtaataaag ttatattgtc atgtagtttt cmgtactttc tcatttacat     180
catcctaaac agtgttctct atgaaataaa tcttgctcac ctacaaaatt tgggtcttct     240
gattgagtaa atctctattg gagtaacatt ctagattaat ggccttactt gggattctat     300
gattttcatt cacatcatga atgtgctgca ccttctacgt tgcttgttcc catttgaatg     360
yatttgaaat cacaacccaa ccaaatcatt tcaatatgat g                         401
```

<210> SEQ ID NO 130
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 130

```
cmgtactttc tcatttacat catcctaaac agtgttctct rtgaaataaa tcttgctcac      60
ctacaaaatt tgggtcttct gattgagtaa atctctattg gagtaacatt ctagattaat     120
ggccttactt gggattctat gattttcatt cacatcatga atgtgctgca ccttctacgt     180
tgcttgttcc catttgaatg catttgaaat cacaacccaa ccaaatcatt tcaatatgat     240
gtacttctta acaaatcaat gcacaaataa ttttaatcat aaattcagaa cttatgcagt     300
gaatattctc gttgttaagt tataaggggc gggggaatc ttatatatgt gattttttggt     360 atatgaacgt ttggtttgtg aattgtgatt gtcagatggt a                         401
```

<210> SEQ ID NO 131
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 131

```
acaacagagg atgctccagg atatgcaaat gcagaaaatg aagtcttcag ttcgttcaat      60
gggaagaata aggaaatcat atacctattt ttcatcttt atatttatgc agtcgtctat     120
gatgaattga tgagtgtttt cctggccatg tgtgttgttt tggcttctgc tttgtaaaca     180
```

```
caagataata atacaggcac aataataaac tgtataatga catgaagatc aatatctttc      240
tttgaagcta agaaaaattg ttatagcatg tagctacttt tgttgtccca caaatgtgtg      300
gcatggagca attttttaat atattcaaaa tatttatttt gtggactcga cagtctacat      360
ctattttatg aagtgtagtg aatccaacat caaacccctt t                         401
```

```
<210> SEQ ID NO 132
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 132
acttttgttg tcccacaaat gtgtggcatg gagcaatttt ttaatatatt caaaatattt       60
attttgtgga ctcgacagtc tacatctatt ttatgaagtg tagtgaatcc aacatcaaac      120 cccttgtcc cacttacaa aaaccctctg atcatttgaa cctcctaaat gaatacaaac        180
tgtgtccata aaaaaaaatt attgtgtcct acgtgcaaaa aaaaaaaaaa aamttcacta     240
ccctattttg tttttatcat gttaaatata tgaaaataaa ttattgccaa gtccaaattg     300
tttgctacta ttgaagcctg catttgtctc gatgtaaaat agtagtactt atccaaacac     360
agtatcaggt tgaagcaaac tagttcatat tattgatgag a                         401
```

```
<210> SEQ ID NO 133
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 133
ccaccacaac tgtatgttga ggtccattgt ctgatagaag actgagagtt taggtggggc       60
aacttcgagg aatatgtacc aaatatttta gatgtatgat tatatcaaca cacacacctt      120
tgcctctgtt ctctcctttt tcttttgcca tgataatacc cttcctataa tcctattcac      180
ccaacgccac atttgttttc atgtatactt aaatgtgtgt taagggtaag ggcttcaaat      240
aagaaactta gctaaaacag ttaagtaact atttactccc atcattttgc acaaattttt      300
atgaacttag attttaccaa aggagggaca aaactaagaa ccaaaaaawt atcatcatat      360
tcagawgcca caaccaacca catgttttct atacatattt t                         401
```

```
<210> SEQ ID NO 134
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 134
attttgcaca aatttttatg aacttagatt ttaccaaagg agggacaaaa ctaagaacca       60
aaaaawtatc atcatattca gawgccacaa ccaaccacat gttttctata catttttt       120 caatatgggg tactaacaaa aaagtcttat ttggtatgga attttttaatt actctatatt    180 tatagtatac aatatacttg agacatatta gaatttatc ttccaagagc aacctaatct      240
cagttatctc atacatatgc aatcgcttat tagcagagta atcagwagt cttcacagaa      300 aagagaaaaa aaatcatctg tagcacatgg aaaataacta aatttccttg ttgtccaaaa     360
ggtttggtga agtgcgctct atcagcttat cactaatgca a                         401
```

<210> SEQ ID NO 135
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 135

| | |
|---|---:|
| gcttcttagt ggagagtgga agrwagggta catccaatcc aagacacaga acagaagaat | 60 |
| ggcctcaaaa tcatccacca tyaracttgt ttgtttctgc tacttcatgc tcttcagctc | 120 |
| tatgcatttc accagctgca ccgtgctctc attgaaaagt catgcaagca catgcaatgg | 180 |
| ttccatagct gaatgcaatc aagaagatga gctgttgatg gagtctgaaa taagccgaag | 240 |
| gtttctggag cagaagagat catacatttc caatggagct ttacagagag acaaaccagt | 300 |
| ttgtaatggt ggtggctctg gtgaagctta tagtaaaact ggagggtgtc ttcctccccc | 360 |
| ctcaaatcct caaagtagag gctgctctaa gtattatcgt t | 401 |

<210> SEQ ID NO 136
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 136

| | |
|---|---:|
| aggaaagatc tatgattgta ttaattatcc gtttcttgtc atctccaatc tttctttgtt | 60 |
| ccattatgct rgatggaatt tgattttttc ttctttttt tttgggtgaa atgttttkgt | 120 |
| aatgcacata atgcaaccat aaggtataaa tcctcttaca cattctacct cgatatacat | 180 |
| atttaaataa taaaatatat aaaaatatag aattatataa aatgagattt tattttaaac | 240 |
| atataagagt tcacrtgggt aaagtattca cattcacttt actattayca aataaaattt | 300 |
| gtsagaaaca ttttcggctc aacatcatgc aattaaacca gaaacttatg tctcaatgtc | 360 |
| ayattctaty agatcatttt attcygacat cctccaacat a | 401 |

<210> SEQ ID NO 137
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 137

| | |
|---|---:|
| ttcttcttt tttttgggt gaaatgtttt kgtaatgcac ataatgcaac cataaggtat | 60 |
| aaatcctctt acacattcta cctcgatata catatttaaa taataaaata tatraaaata | 120 |
| tagaattata taaatgaga ttttatttta acatataag agttcacrtg ggtaaagtat | 180 |
| tcacattcac tttactatta ccaaataaaa tttgtsagaa acattttcgg ctcaacatca | 240 |
| tgcaattaaa ccagaaactt atgtctcaat gtcayattct atyagatcat tttattcyga | 300 |
| catcctccaa cataagattt cttaaagcaa tccatctagt catttgcttc cacaaacaca | 360 |
| aggttcgaga tcatcacaag atccaaacac aaacagcaya c | 401 |

<210> SEQ ID NO 138
<211> LENGTH: 401
<212> TYPE: DNA
<213> ORGANISM: Artificial Sequence
<220> FEATURE:

<223> OTHER INFORMATION: Consensus Reference Sequence

<400> SEQUENCE: 138

```
tgggtgaaat gttttkgtaa tgcacataat gcaaccataa ggtataaatc ctcttacaca      60
ttctacctcg atatacatat ttaaataata aaatatatra aaatatagaa ttatataaaa     120
tgagatttta ttttaaacat ataagagttc acrtgggtaa agtattcaca ttcactttac     180
tattaycaaa taaaatttgt cagaaacatt ttcggctcaa catcatgcaa ttaaaccaga     240
aacttatgtc tcaatgtcay attctatyag atcattttat tcygacatcc tccaacataa     300
gatttcttaa agcaatccat ctagtcattt gcttccacaa acacaaggtt cgagatcatc     360
acaagatcca aacacaaaca gcayacargg aatgagttat c                         401
```

<210> SEQ ID NO 139
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 139

```
taycaaataa aatttgtsag aaacattttc ggctcaacat catgcaatta aaccagaaac      60
ttatgtctca atgtcayatt ctatyagatc attttattcy gacatcctcc aacataagat     120
ttcttaaagc aatccatcta gtcatttgct tccacaaaca caaggttcga gatcatcaca     180
agatccaaac acaaacagca cacarggaat gagttatcac attcccaact aatagagaga     240
aacgagacaa tatgtagata tacatattat ataaatgaaa tatarctyac tyaaacatag     300
ctcacatcat tccatcactt atcgtgtaac atcacatctc aacactacac atctcacaca     360
ttttcacatt atttacgtrc tcaaggatcg aaacacaata t                         401
```

<210> SEQ ID NO 140
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 140

```
yagatcattt tattcygaca tcctccaaca taagatttct taaagcaatc catctagtca      60
tttgcttcca caaacacaag gttcgagatc atcacaagat ccaaacacaa acagcayaca     120
rggaatgagt tatcacattc ccaactaata gagagaaacg agacaatatg tagatataca     180
tattatataa atgaaatata actyactyaa acatagctca catcattcca tcacttatcg     240
tgtaacatca catctcaaca ctacacatct cacacatttt cacattattt acgtrctcaa     300
ggatcgaaac acaatatcac tcaaccaatc aatatcgayc aatrcacaag cgttatgcaa     360
caaatatact aagacttaat cctatatgta atgtggtatc a                         401
```

<210> SEQ ID NO 141
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 141

```
atcattttat tcygacatcc tccaacataa gatttcttaa agcaatccat ctagtcattt      60
gcttccacaa acacaaggtt cgagatcatc acaagatcca aacacaaaca gcayacargg     120
```

```
aatgagttat cacattccca actaatagag agaaacgaga caatatgtag atatacatat    180
tatataaatg aaatatarct cactyaaaca tagctcacat cattccatca cttatcgtgt    240
aacatcacat ctcaacacta cacatctcac acattttcac attatttacg trctcaagga    300
tcgaaacaca atatcactca accaatcaat atcgaycaat rcacaagcgt tatgcaacaa    360
atatactaag acttaatcct atatgtaatg tggtatcatg t                        401
```

<210> SEQ ID NO 142
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 142

```
atcattccat cacttatcgt gtaacatcac atctcaacac tacacatctc acacattttc    60
acattattta cgtrctcaag gatcgaaaca caatatcact caaccaatca atatcgayca    120
atrcacaagc gttatgcaac aaatatacta agacttaatc ctatatgtaa tgtggtatca    180
tgtyagtgaa aaatctcatc aggcgcctag aagtatatga caagataaac cacacactgg    240
taagtcaggt cactctcayt agataaaatc ataaggagat tagttagggt cactctrttt    300
tgcgagaaca cttcaatcat acgaaatcaa cataggtttc aaggaacatt caaaccgagt    360
atatttaccc ctaaggccta cactctaaag agtccgttag g                        401
```

<210> SEQ ID NO 143
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 143

```
gataaaccac acactggtaa gtcaggtcac tctcaytaga taaaatcata aggagattag    60
ttagggtcac tctrttttgc gagaacactt caatcatacg aaatcaacat aggtttcaag    120
gaacattcaa accgagtata tttaccccta aggcctacac tctaaagagt ccgttaggac    180
ctctccctct tgattcaggt ccaacctaga aaatatttta gcaccyagac tctatttatg    240
aactgtacaa aacacycgac tcctcaattg ttctcaaaat aatttttatct catcgcgcct    300 caaagtgatt aaactcgtcg agttyccaca atggttctca tcacaatact cgtcgcacat    360
taactcatcg ttctgaaagg gtcttatagt cgtgtggtgg t                        401
```

<210> SEQ ID NO 144
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 144

```
attagttagg gtcactctrt tttgcgagaa cacttcaatc atacgaaatc aacataggtt    60
tcaaggaaca ttcaaaccga gtatatttac ccctaaggcc tacactctaa agagtccgtt    120
aggacctctc cctcttgatt caggtycaac ctagaaaata ttttagcacc yagactctat    180
ttatgaactg tacaaaacac ccgactcctc aattgttctc aaaataattt tatctcatcg    240
cgcctcaaag tgattaaact cgtcgagtty ccacaatggt tctcatcaca atactcgtcg    300
```

```
cacattaact catcgttctg aaagggtctt atagtcgtgt ggtggtaygg tacataactc    360
aaaactccat gcacacaata tttcaataca catgtatttt a                        401
```

<210> SEQ ID NO 145
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 145

```
attcaaaccg agtatattta cccctaaggc ctacactcta aagagtccgt taggacctct     60
ccctcttgat tcaggtycaa cctagaaaat attttagcac cyagactcta tttatgaact   120
gtacaaaaca cycgactcct caattgttct caaaataatt ttatctcatc gcgcctcaaa   180
gtgattaaac tcgtcgagtt cccacaatgg ttctcatcac aatactcgtc gcacattaac   240
tcatcgttct gaaagggtct tatagtcgtg tggtggtayg gtacataact caaaactcca   300
tgcacacaat atttcaatac acatgtattt tayaattcaa caygcactca atttatcaca   360
tacgctcaat ctcgttataa tctcaatata acaatttatc a                       401
```

<210> SEQ ID NO 146
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 146

```
gtttattcta acctcaattg cgataaactc atctcttacc tctaagyagg ctcacatgtg     60
tagtcygaca acgatagtga cgtttctagc gatttcctaa gattcttcaa aattttccta   120
agattttcta acrtyagaga aaagagaaa ggattataac ctatatttca ctgtctccgt    180
ctccrtgcga gggacatttc actaactgaa gacattgttt cacaaatcct aaygagtggga  240 ttgtgagaaa atgagtttya aacctgattt ttaaatttca caatgattca atggttaatg   300
artccgagat catagttta atggracaag tttggatgta tgcaggaaga gcatcttgtg    360
agggacattg ttctcaccac agacattatt taaaaattcc a                       401
```

<210> SEQ ID NO 147
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 147

```
attcttcaaa attttcctaa gattttctaa crtyagagaa aaagagaaag gattataacc     60
tatatttcac tgtctccgtc tccrtgcgag ggacatttcw ctaactgaag acattgtttc   120
acaaatccta ayagtgggat tgtgagaaaa tgagtttyaa acctgatttt taaatttcac   180
aatgattcaa tggttaatga atccgagatc atagtttaa tggracaagt ttggatgtat    240
gcaggaagag catcttgtga gggacattgt tctcaccaca gacattattt aaaaattcca   300
acgatgggaa tgtgagaaaa tgagtttgga acttggtgtt caaatttcat gataattcaa   360
tgattaacga gtataggatc gtagttttac ctgataggtt t                       401
```

<210> SEQ ID NO 148
<211> LENGTH: 401

```
<212> TYPE: DNA
<213> ORGANISM: Artificial Sequence
<220> FEATURE:
<223> OTHER INFORMATION: Consensus Reference Sequence

<400> SEQUENCE: 148
tagaaatata ttatgtgtaa aatctgatct aatatrtcta tttatagata tsgtactcty     60
aatttattat ttactctakc ttttctttat tttattattt tatwaaaaaa attctatttt    120
tactccctat caaatgaata aataaaatat tctttttttat tttccttcaa aytattattt   180
taattaataa aattattttt cctaattttat ttaattataa aaatcttatt attttttcaaa 240 aactctatttt attttttaaat aaaatgcttt twaatttatt taaaaaaaga cgagatgtta  300
caaatgtttg aagcacactt tgcaatgtta taaatgttga cctcagacat caattgcaat   360
atacacacca taaaacaaca tatgaagtac acgtatgaga t                       401

<210> SEQ ID NO 149
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 149
gctcgaatat aatgaatcta aacatatatg aaaaatcagt aactgacctt ttcgacacag    60
tcacatgaac aaactcgcag caacaacgca tacactagta acagcagtca rcgcactctc   120
ttgagaaaat ttgatgtaaa tgtatttata actttgtgac aaatattttt tttccctcat   180
tccacacagg aataaaaagt atccaagtga gtgaaagaga tgaggaatag atagacwtct   240
ttctccttat tttaaaatcc caagaaacta attacctaga acatttgtaa caaaaactag   300 tgttaatttta tttccatttta tccctttttct ctctgcttta ttttrtgggaw gctataaaga 360 acgctcttct ctcctgaaaa ttgctmatttt aagaaattat t                      401

<210> SEQ ID NO 150
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 150
gtgaaagaga tgaggaatag atagacwtct ttctccttat tttaaaatcc caagaaacta    60
attacctaga acatttgtaa caaaaactag tgttaatttta tttccatttta tccctttttct 120 ctctgcttta ttttrtgggaw gctataaaga acgctcttct ctcctgaaaa ttgctmatttt 180 aagaaattat tttcgaagga acacatttta atctgttaga aatagccmaa aaaaaataga  240
cagaaaaatt actctaatttt tttttttttt tkgaatgatt gactagtcaa attaactcca  300
gtaaacaaac aagcagcggc gggttgaaca tgaataactt tcaatatgcc cctttgttaa   360
gctaaaagat taccctaaca tggaagttta tgctacatat a                      401

<210> SEQ ID NO 151
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 151
```

```
cattttgtca ttatactttg cacgaagtgg gtcattgtaa gtccacctgt attacaattc    60
aacaataaca agaatgtcga ataattttag tattttacag cagttaatat gtaagtataa   120
aatgctactt gcagtagaag aaacccttttt ttcaggggaa ggggaggtct ggactctgga  180
ggttagttgc acgttaagca aaatgaatcs ctatcatcaa tgtgttaaca aatccaaaat   240
tcttggtaag ggagaaatat cggacagaaa aaaattaag atgtcagaaa gccaatgcag    300
aattttctca gcaaatacat tgaatgctgc cttaacatac taaaacccca ttattcgaaa   360
gatgattatc aatatttaat arcatgactg caagcctatc a                       401
```

<210> SEQ ID NO 152
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 152

```
attatacttt gcacgaagtg ggtcattgta agtccacctg tattacaatt caacaataac    60
aagaatgtcg aataatttta gtattttaca gcagttaata tgtaagtata aaatgctact   120
tgcagtagaa gaaacccttt tttcagggga aggggaggtc tggactctgg aggttagttg   180
cacgttaagc araatgaatc cctatcatca atgtgttaac aaatccaaaa ttcttggtaa    240
gggagaaata tcggacagaa aaaaaattaa gatgtcagaa agccaatgca gaattttctc   300
agcaaataca ttgaatgctg ccttaacata ctaaaacccc attattcgaa agatgattat   360
caatatttaa tarcatgact gcaagcctat caaccaacaa t                       401
```

<210> SEQ ID NO 153
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 153

```
gttagttgca cgttaagcar aatgaatcsc tatcatcaat gtgttaacaa atccaaaatt    60
cttggtaagg gagaaatatc ggacagaaaa aaaattaaga tgtcagaaag ccaatgcaga   120
attttctcag caaatacatt gaatgctgcc ttaacatact aaaacccccat tattcgaaag   180 atgattatca atatttaata acatgactgc aagcctatca accaacaata catgaaaaaa   240
ttctggtgtg ataaaaaaaa ttgtgtagac tccttttaat gtcataaaat cagaagtgtg   300
gcagaatcag tctaacatgt tacatcaaca ttgaaaacat aaacagattc aggactctgt   360
agataataaa tgtagcattt cagatattct cagaacagag a                       401
```

<210> SEQ ID NO 154
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 154

```
aacccaaaag tactatgaaa acagatgagc ataactcatg agcatgcact tttgtcaaga    60
tctcaaacca tatcaagggc tgctaataaa caactcattt aaattgtgag ttgtgacatg   120
caatatgatc ccttcttact gtccagctaa attcacatag aagtcaaggg agtcagggta   180
aagttgacaa actaagaacg ctgtaaacaa taaacttcaa gccaagtaca tatttctaca   240
```

```
aaatgaatgc caaaaaaata aaataagatt tgtgagatgg cataattatg cttactctaa    300
atgaaatatg tcttttaact atattccttc caatcaactc tccctcttga acctcaatct    360
cacccacaat caaattccta aataagcaaa atgataggta c                        401
```

<210> SEQ ID NO 155
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 155

```
ttctcccagc ccaagcctaa ttccacccta ccttgtacac acccttctcg ggctaatgtt     60
ctctgtcttc ttacaacaag cccacatgca ctcctcccat gctctgctac agggttgaca    120
gttggttata tctctctcct aaaattgatc aagtgaacct tttgcctatc cttacataca    180
ccttattttg tgatcttggg ccttgrggcc tccatcasaa aaccattctt cataaaaact    240
ctcatttcac tcttctgatg actaatagca gaaaattttt tagataacaa gagaaaaaga    300
aatcttaaat gaacatttca ctattgrcat gagcatctca atatcatcac atgaatccga    360
gatcattttg gaccagtgcc atagcagatg aacttcataa g                        401
```

<210> SEQ ID NO 156
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 156

```
ccagcccaag cctaattcca ccctaccttg tacacaccct ctcgggctaa tgttctctg     60 tcttcttaca acaagcccac atgcactcct cccatgctct gctacagggt tgacagttgg   120
ttatatctct ctcctaaaat tgatcaagtg aaccttttgc ctatccttac atacacctta   180
ttttgtgatc ttgggycttg aggcctccat casaaaacca ttcttcataa aaactctcat   240
ttcactcttc tgatgactaa tagcagaaaa tttttttagat aacaagagaa aaagaaatct   300
taaatgaaca tttcactatt grcatgagca tctcaatatc atcacatgaa tccgagatca   360
ttttggacca gtgccatagc agatgaactt cataagtaaa t                        401
```

<210> SEQ ID NO 157
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 157

```
tttttctcag gataaaacaa caaaaaacta ataccaaaga atagaataaa caatctacca     60
ctattcttga aaccgaaaga tatagaacat aggagaaatt gaacttacgg gttattccaa    120
tcagtagtat cctcattgac aagatgggtc cacttggttc ttccactacg accaaagtgc    180
ttaacttgca taacctttgg caatattgtc ttgtccattt tatcctcccc agttggggca    240
gagaaatcac gagcgaaaat accatcagat ccaacggtgg cagctcggtc atcagattca    300
ttctggaaga aagcaccttt gtgatagtat ttctgcataa atctccattt ctgctttggt    360
ggtggagcag gtttgggatt cctcctttcc cactccctcc t                        401
```

<210> SEQ ID NO 158
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 158

```
tcatcagccc attcaggaac tttaccgggc caataacgct taactttagt ttggccaatt      60
ttacctctga gcttatccct aatggctatt acagtatcac taacacccgc tgtcaccgac     120
attgttcttc ctcaattgaa cgccaaaccc tatattgcac agatgcatag taaatcggta     180
aaatgtttgt ttacacagca agaaacaga agattccaga ttaaatagca agaaaataaa     240
taaatgaatc aagaaacaca gaaagatcaa tagtgaatga taaattttga tatgcgaaac     300
attggaaggg tttgtgttcs aaacactaac acttgaattg ttagagagaa tagaagaaaa     360
gttwgaagga cttacaatta cagcgaccgg aaggaaccct c                         401
```

<210> SEQ ID NO 159
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 159

```
ccctctctgt ctctgtcccg ttccaggcag cgcgtcgccc caccccagct tgttctgtga      60
acttttattt gatttacttt ctatagtatt tattttgtt tttatgagta tgtaaatgac     120
atctttatac gaatattatg ttttcattaa ataataataa taataaattt cttaaaatta     180
aatatatata cactaatgct aataaaaaaa ttgaacgaat atcatattta ttaaaactaa     240
tttttttata ctaaactaaa ataatttaa aatttattat tattattatt ataaagatat     300
ttaaatttta tattttggaa ttgtatatat aagataaaat acatttaagt ttcctaagtt     360
acaactttcg catcggttac attttamagg wtatatatat a                         401
```

<210> SEQ ID NO 160
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 160

```
atgtctttgt ccaaggcttg ctaacaaaaa aggagattgc aagatcaata aaataccttta     60 caataatgag agacaaaggg ttttcagtag atgctgctac cacagaaatt actatcaact     120
acttatctac taatgaagga gacaccagaa ttcgagaatt ttttttttcca aaaagatagc     180 aaatgccaag agtttcactt agacatttat tcaaatcctg actctcaatt catccatgtt     240
ccacaatcct ataggacccc atagagagaa ctggcatagg cttcagaact tacmatttgt     300
taaatatata aaatcattac cattcaagtg cwtccacctg acaatttatg tgattaggag     360
agttggtcct taacaggtat cacaaccttt aagaaattat g                         401
```

<210> SEQ ID NO 161
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 161

```
ttgatccttg ttgcttctct tcttcataat taacttatat ttgagcccaa ggtaaagtgg      60
gtttgtgcat tgtccrcact tcaagctcaa aaagctctgt tttaagggggg tcttagatat    120 aaatctttct tagctccacc aatcagctta agctgtgaat agaattgttc cttgacattt    180
ttagtggtaa gtattttcac atctgcttgc acatttattt tgatataacc tcaagttatt    240
aaaatagctt aaaaaaatag acctatatac aattagaaa ttgtgctgta tccttgcatt     300
tttatggaac tgagtaattt tttacttatg tatatttgcc ttcaagtaag tttaataatg    360
aagcaagttg cattagggat aagccaatca atattgctag t                        401
```

<210> SEQ ID NO 162
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 200
<223> OTHER INFORMATION: n = A,T,C or G

<400> SEQUENCE: 162

```
tgttatttta tattttgttt cctttcttgt gtattttact tttctgtttt aggaggattc      60
ctgatccttc tgcactgtac tcctttttctc tcctagttca ttgtttgtga tgggaawttt   120
ttttccatat ttattacctg ttaggagacg aaaatctaag atctaattta tggatgcttg    180
ctgtcctttc tgcaaacgtn attttttttt tttacttttg acagttttcc ccccatttaa    240
aataacagtt tgacttcatg gttcttggtt tgcagattga aatcactyta tgcactcatt    300
ttgttataac ttatgtgcga ggaagaccgc aaatagttca gcgatggatc atagaaggtt    360
agtcaaacat ttttttcttttg caatatctgc tcagcttgtt t                      401
```

<210> SEQ ID NO 163
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 113
<223> OTHER INFORMATION: n = A,T,C or G

<400> SEQUENCE: 163

```
ctctcctagt tcattgtttg tgatgggaaw ttttttttcca tatttattac ctgttaggag    60
acgaaaatct aagatctaat ttatggatgc ttgctgtcct ttctgcaaac gtnwtttttt   120
ttttttactt tgacagttt tcccccccatt taaaataaca gtttgacttc atggttcttg   180
gtttgcagat tgaaatcact ctatgcactc attttgttat aacttatgtg cgaggaagac    240
cgcaaatagt tcagcgatgg atcatagaag gttagtcaaa cattttttct ttgcaatatc    300
tgctcagctt gttttttgta attcaaattt tttagcatca taagttgttc gtttgaaatt    360
ttgaatgaat atttatctgt taagttatat ttcacttttc t                        401
```

<210> SEQ ID NO 164
<211> LENGTH: 401
<212> TYPE: DNA
<213> ORGANISM: Artificial Sequence
<220> FEATURE:

```
<223> OTHER INFORMATION: Consensus Reference Sequence
<220> FEATURE:
<221> NAME/KEY: misc_feature
<222> LOCATION: 229
<223> OTHER INFORMATION: n = A,T,C or G

<400> SEQUENCE: 164
aatatattta tctcagaata atgctttgac ttttacaatg ttcccctcac aaaattgatc      60
tctttaaaaa ataaaaaata aaactttgg agtttgtcca gcttggctcc aatcttaacc     120
aaagcagcat taaagctttg aagtatagag caaaagtaca ccatattagg ctaatcaatg    180
aaaaggtaca aagctcccgt cagattttga actagrcaga taactaagng agtgtttagt    240
ttggttgttt tttgatttta ttttcactga aaataraaaa cggtgatgaa aatgtgtttg    300
gtttgatttc tgaaaacatt ttcrgtaaaa atgaaaacag taaacaacta gaaaatgaaa    360
acaaaaaatt ttcgttttca gwattttcag ttgagaacag a                        401

<210> SEQ ID NO 165
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 48
<223> OTHER INFORMATION: n = A,T,C or G

<400> SEQUENCE: 165
aaaggtacaa agctcccgty agattttgaa ctagrcagat aactaagnga gtgtttagtt     60
tggttgtttt ttgatttat tttcactgaa aataraaaac ggtgatgaaa atgtgtttgg    120
tttgatttct gaaaacattt tcrgtaaaaa tgaaaacagt aaacaactag aaaatgaaaa    180
caaaaaattt tcgttttcag aattttcagt tgagaacaga aacctcattt tggttaaaat    240
gaaattgygg tgacaataaa tgtagttta arcaaatcta aaaatacaaa aagcaataa     300 gtcaatatat cataaatttt cagtattttt atttcatraa aacagaaaac aagaaatcaa    360
accaaacatr ttttcagaat ttaaatcttt tgaaaataaa a                        401

<210> SEQ ID NO 166
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 166
tctcttcaaa agccaagtcc ttggttagga cagtggtact taacatggtt aatgcaaatg     60
gtttgtwgca aattcataat agacctttca accagctttt ggctcatttt attgcattag    120
tcttatttgt tttggagaat ttctttatt tttttggtaa ctagcagatt tcttatcctc    180
ctcctagttg tgcttctctt atctctttaa tgaatttcct cctatgtaaa aagcaataga    240 aaagaaaac cagttttaaa aaaataaaat aaagaactaa attcaggta ccttcttcca    300 ttttgcaatt agattgcggt cagcatatcc ttgatctaaa cagaattcat acagttcttt    360
agaaatttcc ttcctccgat ggtatagatc aaatatgtag c                        401

<210> SEQ ID NO 167
<211> LENGTH: 401
<212> TYPE: DNA
<213> ORGANISM: Artificial Sequence
```

```
<220> FEATURE:
<223> OTHER INFORMATION: Consensus Reference Sequence

<400> SEQUENCE: 167
taagtaaatc tagaaaatat ataacttttg acaaaaaaat tatatcacta tttaaatata       60
tcttttttcc tttgtttctt atttcctaaa taaatttttt tattaaattt attaacaaaa      120
atttctcata attaacgaat gaggttaaaa ataataaaaa aatgayaaat ataataaaaa      180
caaattaaat ttaaagactt aaaacataat ttttktgtcw catgaaaata tttttttttat     240 tctaaacaaa ttgtttaaag ataatraaaa tatcattttt ttaaatccta waaatatacc      300
arataactat aattatttaa attaaatcac tctagcatat attttaata aatcaaatta       360 atatatacaa atattttaat ttactttaaa tttaaagata a                          401

<210> SEQ ID NO 168
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 168
acataatttt tktgtcwcat gaaaatattt ttttattct aaacaaattg tttaaagata        60
atraaaatat catttttta aatcctawaa ataccara taactataat tatttaaatt        120
aaatcactct agcatatatt tttaataaat caaattaata tatacaaata ttttaattta     180
ctttaaattt aaagataata cgataatata aatatagtaa aatttatag aattttttaaa     240 caatatttty catttatctt ttttttttct tttatctctc tagttgcatg gagcatgagc     300
caacttccta gtttattgta tattttcgtg ataatgttgt ggcatttgtt agacatttta    360
aaatattaaa tcttattaat tattttwaaa tcatatttat a                         401

<210> SEQ ID NO 169
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 169
gtttaaagat aatraaaata tcattttttt aaatcctawa aatataccar ataactataa      60
ttatttaaat taaatcactc tagcatatat ttttaataaa tcaaattaat atatacaaat     120
attttaattt actttaaatt taaagataat aygataatat aaatatagta aaattttata    180 gaattttttaa acaatatttt ccatttatct ttttttttttc ttttatctct ctagttgcat   240
ggagcatgag ccaacttcct agtttattgt atattttcgt gataatgttg tggcatttgt     300
tagacatttt aaaatattaa atcttattaa ttattttwaa atcatattta tatgaaaaat    360
atgatttttt atttaatctt tctagaaaaa tcttaatgta t                         401

<210> SEQ ID NO 170
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 170
tctctagttg catggagcat gagccaactt cctagtttat tgtatatttt cgtgataatg      60
```

```
ttgtggcatt tgttagacat tttaaaatat taaatcttat taattatttt waaatcatat    120
ttatatgaaa aatatgattt tttatttaat ctttctagaa aaatcttaat gtatccactt    180
ccaactttta catttaaaat cccattatat atttttttc taattaacct tctctaacaa     240
ttgttcaaca ctttcttcct aaacctctat ttcagtttct ctccctcttc ggtcttccca    300
ttgaattcca ggattttaca tacaaaaaat ttgwtagttt tgttgtcttg acaagttttc    360
ggaggatttg ttaaattcta aaggacttat gcactacgtt g                        401
```

<210> SEQ ID NO 171
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 171

```
cgtgatgtca ctcatctcat attatctatt ttgtgactaa ctcatgaatt tatgatagat     60
tgatgatcgg tgattttggc ctactacaat aacaatttta acttttaagg aataatcccg    120
accacttaaa ggtatattaa tatattaatt attttttct ccaatcttaa tttaatttgt     180
ttgatggtaa tgaatcagat aaacgatttt gggactgttg ttgttgttcc attttcagtt    240
ttttattttg tttatgacta gttgagtttg yaatcggttc ttgctcggtg attttagagg    300
ttttggacat gattttagag tatgttgtat tgtgtaaaac tttgttgcaa tctcgtgtgg    360
ttaaatgggt gttaggatgt gaaaatttta tgtctaaaat t                        401
```

<210> SEQ ID NO 172
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 172

```
aatacacttg tgcattcaaa tatccataat agttaataac aacaacttat tcaatatact     60
atattatcta gggtcactag attaaaccca cttctaaaaa aatcttaaaa catccaaatt    120
ttattaatac gttatcttga acatactttc ttctataaat gttaaaattt atttgaaaat    180
ttgaaatctt agaaggtctc atactttaat taataaaatat cttttataat tttmatgaa    240 tagtacaatc aagtgtgtta aaaaatattt tcttgaaact cctctaaatt taatgctaca    300
aaaattactt tttcttgctt tctcttcaaa cttagtgagc atttttgcac tcttaaatta    360
tgtttgtcaa aatatttgaa ttgattttta gttttttat t                         401
```

<210> SEQ ID NO 173
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 173

```
aataacaaca acttattcaa tatactatat tatctagggt cactagatta aacccacttc     60
taaaaaaatc ttaaaacatc caaatttat taatacgtta tcttgaacat actttcttct    120
ataaatgtta aaatttattt gaaaatttga atcttagaa ggtctcrtac tttaattaat    180
aaatatcttt tataatttt aatgaatagt acaatcaagt gtgttaaaaa atattttctt    240
gaaactcctc taaatttaat gctacaaaaa ttacttttc ttgctttctc ttcaaactta    300
```

```
gtgagcattt ttgcactctt aaattatgtt tgtcaaaata tttgaattga tttttagttt    360
ttttattaac agaaaagttt atttagttgt ttgataaga a                         401
```

<210> SEQ ID NO 174
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 174

```
acttttctt gctttctctt caaacttagt gagcattttt gcactcttaa attatgtttg     60
tcaaaatatt tgaattgatt tttagttttt ttattaacag aaaagtttat ttagttgttt   120
gataaagaag ttttttaaat aattttttaac atttttttaa acactacttc aagtaatatt  180
tttwaaaata ttatttattt cttcatatat tctyttttta tttattttta atatatttat   240
caaatttatt atttatcctt tttaagcaaa tcattatttt attattttwa agttatttta   300
tattttttaa ctatttcaaa aactaatttt atcacacact taattttaat aaattaattt   360
tttaacttcc aactaattta ttagttttca gctaatttta t                       401
```

<210> SEQ ID NO 175
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 175

```
tgattttct gcatctgaaa caatttgaaa tttcaaaatt tctctttct ttacgaggtc      60 atcaaagcac aaagctaaca aattccctag aagagggtgc ataaaactcc aacctgtttc   120
ctctgttttt tcccttgcaa ttattactct tttttattgr tagaaattga attrttgaar   180
tataaatgtg aaataaagtc ccacatccaa taaaaataaa aaaatttaac atcatataag   240
taaaaataac taaatcttaa agttttttaaa ttgctattct ctttcatgta aagataaaac   300
acataaatct aactcttaaa gtctcttgat tactattttt catctttcat gatataagtg   360
atgatttagc ctctagattt catggtgatt atagaagtgt a                       401
```

<210> SEQ ID NO 176
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 176

```
caagatagga ccttttact ttgttggtct attaatatcc aagttgttca tgcttatttt     60
cacacctaac attagcttat tcaagattct taataaaata ttagggaaaa tatcatgaaa   120 ctttatcaa aattgtttat ttgtcgttga cgttttttgga aacatctcaa tagtgacttg   180
ttactcaatc aatctttact agcactctca tacttggttt tcgttattcc tgttttcaaa   240
ccacatactt tgactaatgg actatgaatg aggctgcgta taaaaataca attggcgtat   300
tcgagatgca aattgtgtta ttggcctctt gtcctttcc agatcagtat tgagaagttc    360
aggcaaggct tgtattgaat ctgactctga cagatacata a                       401
```

<210> SEQ ID NO 177

<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 177

```
atacgacttt twcttgttgc cactctttac caacagcatt caagacgtac gttaggatat    60
tcaaatccaa tgcgtcactg aggaactttt gcactcattt tttcacgcaa aaacagagaa   120
tcatccagca cagagtcttg caaaaattga tgtgaaacaa gaatgctctg agcctaaatt   180
ggatcaatgt gcatgctaaa atttagaccc atatmktatk gggaagtttt tatcccttag   240
tcgcttttgt cttttttcctt tccttttttct aagcaacaaa ccatattgtt ttataatttg   300
ggcgaggtct aaattcgttt tatcattgta acaaaaacta agaaattaa agcaaacgat   360
ttcataggct atttgggagc tatgttttat gaggttaata a                       401
```

<210> SEQ ID NO 178
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 178

```
aaattcgttt tatcattgta acaaaaacta agaaattaa agcaaacgat ttcataggct    60
atttgggagc tatgttttat gaggttaata acaaatagg aatctcttga ttttaagaat   120
gaacaatttt ttttcacta tgaaaggagt cctgaacatt ataattggat tgggtgttaa   180
ggagagaaat agaaaggaga catttcactc gattggttca raaagaaata agaacgaaat   240
tgacaaattc tgtgggttca tttgggaaat tcttctccat tgttcatgat tggaaatgat   300
tttgtgtatc ttcttttttt ttcttaattt cttttttaaaa aatcaaataa ttttttttwaa   360
aataatttct ttattaaaat acttttactt taygataaat a                       401
```

<210> SEQ ID NO 179
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 179

```
acaaaaacta agaaattaa agcaaacgat ttcataggct atttgggagc tatgttttat    60
gaggttaata acaaatagg aatctcttga ttttaagaat gaacaatttt ttttcacta   120
tgaaaggagt cctgaacatt ataattggat tgggtgttaa ggagagaaat agaaaggaga   180
satttcactc gattggttca aaaagaaata agaacgaaat tgacaaattc tgtgggttca   240
tttgggaaat tcttctccat tgttcatgat tggaaatgat tttgtgtatc ttcttttttt   300
ttcttaattt cttttttaaaa aatcaaataa ttttttttwaa aataatttct ttattaaaat   360
acttttactt taygataaat actatgaatt aaaaagataa a                       401
```

<210> SEQ ID NO 180
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 180

```
cttaatttct ttttaaaaaa tcaaataatt tttttwaaaa taatttcttt attaaaatac       60
ttttacttta ygataaatac tatgaattaa aaagataaat atattctctt attttcttat      120
ttctcttcca aggattgtcg agatgggaga agattaacgt aaagaatttt tattttttta      180
ttaaaacagc gaaatatag ggtatatata taaaaggcac aaatgggtgc ccccaatcaa       240
ttacaaagtg gataaaagtc caacaaagat agtatacctc ggttacacca tattaacaaa     300
ggagagtaaa tatagtttaa ccaaggccaa aaacatcact cctagccaca ctccagtaaa     360
tatagtttaa cgtgaagaat ttgattcaac ttgtgagagc t                         401
```

<210> SEQ ID NO 181
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 181

```
aagaatttga ttcaacttgt gagagcttca ccccttaagt taattcacca tatagctcaa      60
atcggattag ttggagaact taattaccct gattgcccctt tcttaaaaat attgcagaag    120
caccaaataa taccacaatg tgtcgatgtg tttccgaaac tagatgatag atgggtagga     180 attttttttat tttctttgat atattgaaaa ggcagaaaga aacacaaatt ttagtattta    240
ataaagcaaa atgcacacat cccccaaaca aaacaagcct tattcaaccc aaattggttt    300
catatcacag aaaccaacag gatgccgcct tcctccttac tggtcccacc cactcgaaca    360
aaagttstac agaaataaaa atggctacaa ttcttctacc a                         401
```

<210> SEQ ID NO 182
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 182

```
agagcctgaa gggcacagat gggatcaatc tcggtcacga tgacacgagc accagcctgc     60
ttcattgcag cagcacaacc cttgccaaca tcaccatatc cagccacaac agccacctttt   120 ccagcaatca taacatcggt agccctcatg agaccatcag ggagagagtg acggcaccca    180
tacaagttgt caaactgtta aaaaaccaca gattaaaagg ttaaacaaac aaaacacaag    240
caacaaagca aaatccaatt ataatcaact agatccatga ccagctagta taatgtcctc    300
aaaatccaat cacccacttc ttactttcaa taccctaatc aataaacaac ccgtcacaaa    360
agactcggtt tggatcaatg tttgcaaaac caattttgaa t                        401
```

<210> SEQ ID NO 183
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 183

```
aacaaacaaa acacaagcaa caaagcaaaa tccaattata atcaactaga tccatgacca     60
gctagtataa tgtcctcaaa atccaatcac ccacttctta ctttcaatac cctaatcaat   120
aaacaacccg tcacaaaaga ctcggtttgg atcaatgttt gcaaaaccaa ttttgaatga    180
```

```
aaacgatttc gagttaaaat agatttygaa acaacatgat ttatgtttga acattttttt    240
attttaaaac caaaaacagt agtaaaattc agtataattt attttatcct atccaaaagt    300
agcttcaaat caaaatgtgc actcagaatc aattccttat ttgtgtaata aaacatgtga    360
ccatttacct aaagtcacgt tagcaagcaa cttactaatg t                        401
```

<210> SEQ ID NO 184
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 184

```
caaaacacaa gcaacaaagc aaaatccaat tataatcaac tagatccatg accagctagt     60
ataatgtcct caaaatccaa tcacccactt cttactttca ataccctaat caataaacaa    120
cccgtcacaa aagactcggt ttggatcaat gtttgcaaaa ccaattttga atgaaaacga    180
tttcgagtta aaatwgattt cgaaacaaca tgatttatgt ttgaacattt ttttatttta    240
aaaccaaaaa cagtagtaaa attcagtata atttatttta tcctatccaa aagtagcttc    300
aaatcaaaat gtgcactcag aatcaattcc ttatttgtgt aataaaacat gtgaccattt    360
acctaaagtc acgttagcaa gcaacttact aatgttctga c                        401
```

<210> SEQ ID NO 185
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 185

```
amtatgaaaa attatacttc aaacaagtct ctcataagaa tgtttatggt ctcatacaga     60
tgaatatttt cacttcgaat acacgtaaaa ctaaatgaa ttcacacaag tgattaaaga    120
tctaaaacta acttttgtct tcttttttt atagatgtgg gtttcattct ctatcatgcc    180
actaaaacta tcatctaata gattctttga catctaagga ctaattgaat aaatacaatt    240
aagtaaaatt gtctatgatt taggcctgtg gaataatcct tgagtaagcc tttattgaca    300
tcgctaacaa gtagcatgtc attaaggttt cattcgatgg tattgatcag gcctctataa    360
aattttgtac attttaatat gcatcaaatg agcatackgg t                        401
```

<210> SEQ ID NO 186
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 186

```
atakattctt tgacatctaa ggactaattg aataaataca attaagtaaa attgtctatg     60
atttaggcct gtggaataat ccttgagtaa gcctttattg acatcgctaa caagtagcat    120
gtcattaagg tttcattcga tggtattgat caggcctcta taaaattttg tacattttaa    180
tatgcatcaa atgagcatac gggtaaagat ttcggtgctc aagttaatag ttggtaaagt    240
aaaagcatta tatgtaagat tttcatgtac ttgktaaagc taagggacta tcggagattg    300
ttgataagca tttaaaaaac tctcaacaat cttctatctg cctataaagt tttctyaaaa    360
agcatttaaa aaatttatag gttaattaga gatttgttag g                        401
```

<210> SEQ ID NO 187
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 187

| ctctataaaa | ttttgtacat | tttaatatgc | atcaaatgag | catackggta | aagatttcgg | 60 |
| tgctcaagtt | aatagttggt | aaagtaaaag | cattatatgt | aagattttca | tgtacttgkt | 120 |
| aaagctaagg | gactatcgga | gattgttgat | aagcatttaa | aaaactctca | acaatcttct | 180 |
| atctgcctat | aaagttttct | caaaaagcat | ttaaaaaatt | tataggttaa | ttagagattt | 240 |
| gttaggtagg | ttaacataca | tgtaaagatt | tttctttttt | tggaaaatac | atgtaaagag | 300 |
| ttttgtaaaa | gtagaacttg | tgaatacgtg | atttataaga | caattcatat | tcctcccaat | 360 |
| caggtaattt | tgtgcaaaaa | gtcttattaa | gttggtgtgt | a | | 401 |

<210> SEQ ID NO 188
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 188

| atattgtaaa | acacaaaata | tttatattcc | aatcttmaat | gttttttattt | gacattataa | 60 |
| atatttaaag | gatagaatca | atgttaatca | agttaacata | aaaaataaaa | aattacatag | 120 |
| cattcaacat | gtaggtatca | aatctatgtt | ataaaatgtt | tattagatag | agaaaaatat | 180 |
| ttgctaaaat | ttwgataatt | atgctatgtt | tatatgttga | atgatgggta | aaataaaatg | 240 |
| acgcataatt | aagtaacata | agtaaaataa | aaattaagtt | taattttttat | gaattatcaa | 300 |
| tataaaaaaa | taaaatatat | tcctaacatt | tctctttcct | ctattttaca | ttcattttat | 360 |
| tttcttaatt | ttttttcattt | tgatatcctt | taatataata | a | | 401 |

<210> SEQ ID NO 189
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 189

| cccggtcaaa | atataggttt | aacaattagt | caattactat | ataaataggt | tttgtatttg | 60 |
| aatatgttag | taaaaagtag | ttttaatata | tcttattcca | gtaaaattat | caattactttt | 120 |
| taataataaa | gtcatacaaa | tttgtataaa | actatttttcc | ccctacgata | aaagttgttt | 180 |
| cgaaaaaaaa | gtaagttgga | aaaatttatt | gaagtgatga | aaactatttt | tatggttatt | 240 |
| ttttatcaca | caaattaatt | ttggaatctt | ataattagaa | atggttgaat | ttatatattg | 300 |
| gttaacttta | ttttcttatt | tcgtccacag | taatgaattg | tttcaaacaa | aaaaaaaatc | 360 |
| aattaatata | tattttataa | ttttactatt | gaaaaatacc | t | | 401 |

<210> SEQ ID NO 190
<211> LENGTH: 401
<212> TYPE: DNA
<213> ORGANISM: Artificial Sequence
<220> FEATURE:

<223> OTHER INFORMATION: Consensus Reference Sequence

<400> SEQUENCE: 190

```
agcataatca caattattga gaagatattt ttattttatt tttaccgaat cgtcgcacga      60
ctcggcgtgt tgcaaccgca ttaaatcttt gtgttggtct caccctgtct ttttgtggat     120
gatcgatcct cttggattgg tttttataaa actcaacttc ccatcggtgt tctttagtaa     180
ttggagtatc tttggatgtt cgttacattt tatgataaat ttaaatgatc cacaatcact     240
aactcaattt tgcaaagcag gattctgaat gttttgtaa atctcgtttt gtcctaaaag      300
ttcgtctata acaataaaac aaacatgcac ttggttgttt ttaaaattgt ctcaaaactc     360
tgttataaag aaataagacc taaagatatt ttttacaaat t                         401
```

<210> SEQ ID NO 191
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 191

```
atatccttag attaatttat tttsttgata aaaaaaawkg ataaaaattt ccatgcttta      60
aatttgtcat tggtccatct gatcgactct atacatcaaa cttgagtgtt atttgcatac     120
aaaaggaaaa catcagagac atgacagagt aggttgcatt ggtgtttagt tgacctgatt     180
aagaagttac acacaaagtg ctcctctatc tcctcttcaa ggtcctccta cctatagtct     240
tcttgtacct cttattatat ggattaatta gtgtagaatt atttcaactt aattaataat     300
tttgaattta agtcatgaga atgagtatca aaayttttc acctataaaa atcgaatrtg      360
cttcaaataa gattgtctct aataaataat atgtgtttaa t                         401
```

<210> SEQ ID NO 192
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 192

```
aaacctatgt cggttggttc ctcttaaag aaagagaat aaaataaca agaaaaaaa         60
agtcgccttc catttcattc gcattcatag taaagagtg agcgatcccg ggaaatgaat      120
taatatacga ctaaaagat ttgagaatta taataattaa taattaataa ttcttttca      180
aaagtaaagt acagtactgc aggaaacatg agcatgttca tagattaaaa tttaaaagaa     240
tattatcagt aacaaaaaaa taaaattaa cccatgcatc caagaaagaa atacycatgt      300
gcttcagttg tccgctgtct gagatgtggt gaccttttt caaatgatca taatagttac      360
ttcataatga cgacatgcat caaactattt tttcttcaaa a                         401
```

<210> SEQ ID NO 193
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 193

```
tatcccccat gttaatgaag caaggtgtgg gggaaggaaa gagtcagcat cagtgaagta      60
gagagggggg ttggtgattt tggtgggaat aaattggcta tattgccccc accaacctcg     120
```

```
ttgctaccaa ataccaacaa cactgactca ctgagaattg ggaaagaaac ttaaaaccaa      180
gtcttgcagt gacgtacatg cagtgtgtgc atcacacatt caggtttcca gtcaaattgt      240
agaacaaatg aatttcttgc tttaacttaa gttgaagttt aagaagtgaa gctgatgctt      300
gtttttgaat gaaaagcctt tgatagtttg atgtaagcat tttccaaatt taactcttcc      360
catgcttgac agagccaatt aagctaactg gtttgataac a                         401
```

<210> SEQ ID NO 194
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 194

```
cacccctcat tagaggctta ggattttttt gagtcctaga acacacatct tatctcaata       60
atgatttcta tcattgccag aattacaatt aaaaactaaa atataatcaa ttagattgaa      120
ttgaacttct acagacccca aaggcactcg atgcattttc actgtatgtg gtttgtcttt      180
ctgtactata ctgcacgctt agcaaaataa tcagtaacac atgttaagag agcttgcact      240
ttatttttat cttgttgacg ggtttgttgt cattgaaaac acattatatt cagaggaatt      300
tgactcaaca tgttcaaccc accaattatc acatttaaac aaatytaaat caatcgcaaa      360
tcatatatat tcagaatttt acatattaaa tatttcatat c                         401
```

<210> SEQ ID NO 195
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 195

```
aataacatgg ttatgttgaa acaaaagaa aaaaatatca aatttaattc atgaatcttt        60
caactaatta aaaaatgacc aatcctaact agttgcagaa gctattaatt aaattttaa       120 aaaagtatat ctttctctct tatgactcac ataatttata ktccctatac tcaaagtctc     180
acataattta tactacaaaa acttaggttt aatttcgtac ctattgttaa tgtttcctaa     240
tcgaaattag aatttcaccc cgataattaa aagtttacat taaaaaatta yataaattac     300
cgaaataaaa ctcaaaattt agtcaaacaa taatgtaagc actaagcagc aactaagaag     360
ctataaacaa agttttgata aatagttaaa tttatcctcc a                         401
```

<210> SEQ ID NO 196
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 196

```
aagtggggaa ctgtcgatcc atggtgctgg cagcaaccgt aacatgccag ggtgcgagat       60
tttccgcagt ggcttccgcg ggcccactgt tgccagcaga gcaaaccacc acaacgccac      120
gcttggccgc atggaaggat ccgatggcaa cactatcctt gaaaaacgtg gaggaagagc      180
caccgagcga gacggagagg acatcgacgc cgtcgtggat ggcgaggtcg aaggccgcca      240
agatatcagc gtcgaagcac tcctcgcctc cgacgggggg ccagcagacc ttgtaggctg      300
```
ccacacgtgc cattggtgag ccacccttgg ctgttccctg gccctggccg aagacgctga    360
cacgtgcgac catgttcccg ccagctgtgg atagggtgtg g                        401

<210> SEQ ID NO 197
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 197
tgccattggt gagccaccct tggctgttcc ctggccctgg ccgaagacgc tgacacgtgc    60
gaccatgttc ccgccagctg tggatagggt gtgggtcccg tggccctcgt tgtcacgtgg    120
cgagtcaaag gaggagttca gtgggcccgc cactgaggcg tagcccttgt tgaagtacct    180
tgcccctatt agcttcctgc attcaacatc tccacttaac gtttctttaa tttwtcaaaa    240
caaaatcatt gaaagattgg tctggttggt gtgaaaacac tagtactata aagaataag    300 ataacgaaag aaacatgtct gcgttcaaag gagtgcttaa ccctttcatt gtagtattca    360
cctaataaag agtgccaatt taaaggcata tgactacaga a                        401

<210> SEQ ID NO 198
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 198
gccgggcaac cgctactacg gcggcaatga atacatcgac cagatcgaaa acctctgccg    60
ctcacgcgcc ctccaagcct tccacctcga cgcccaatcc tggggcgtca acgtccagcc    120
ctactccggc tccccggcca acttcgccgc ctacaccgcc gtcctcaacc cccacgaccg    180
catcatgggg ctagatctcc gctccggcgg ccacctcacc cacggctact acacctccgg    240
cggaaagaag atctccgcca cctccatttta cttcgagagt ctcccttaca aggtaaactc    300
caccaccggc tacatcgact aygaccgctt ggaagaaaaa gccctagact tcaggccaaa    360
actcataatc tgcggtggca gcgcgtaccc tcgcgattgg g                        401

<210> SEQ ID NO 199
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 199
ccgttgcgct tggaaaatac ttgatgggga aagggtacag ccttgtcact ggcggaacgg    60
agaaccatct tgttttgtgg gatctgagac ctcttggatt gactggtaat atatatagga    120
ttggatctct accttctggt tttgatttgt tacaaatgtc tataaatctg acttgttcgt    180
tgtgtgattg ttttgcaggg tataaggtgg agaaactctg tgatctctgt aacattactg    240
ttaacaagaa cgctgttttt ggtgatagca gtgccttggc ccctggtgga gtgcgaattg    300
gtaacgatct tacttctctt ttatatgcta caatacaaat cttgctttac taactcaatt    360
ggaaacaaga tctcatttat aagattataa aaatgatttc c                        401

<210> SEQ ID NO 200
<211> LENGTH: 401

-continued

```
<212> TYPE: DNA
<213> ORGANISM: Artificial Sequence
<220> FEATURE:
<223> OTHER INFORMATION: Consensus Reference Sequence

<400> SEQUENCE: 200
catatcgcat cacaggaata attgtgcggg gatgcaagac attggcacca aaataagact    60
gtacaacaga caatttgcaa gttaatctcc ttaattttac aagcagaagg agcattgagg   120
ctttccagca tctaactcac catttcccaa gcctcttgat aagacagtgt cttcaaaatc   180
acagcctcac taactgcata cgatattatt gtttatattt aatcaaaaca tcatgttatg   240
gcagtcaaac acaacacaaa agaatcatca atatgtcaga gctagaactc cctctggtta   300
ctaaaaacca attctcatga tccagtccac tcattgttta actcagagac agagtacgaa   360
gcataacaaa cctttctag gatctgcact atacacacca t                        401

<210> SEQ ID NO 201
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 201
taggatgttt ttcaaataca ctcttttctc gctgtttaaa aaaaaaaata cactctcttc    60
taataattaa aagttattaa aaatcataaa tttgaatgga tctcattttt cattgagtaa   120
ctctctctcg tgattttata ttatctctgt gcttttatt ttttatttt aaaaaatatg    180 taaaaaccaa gaaacataat taatgtgstt catcttaata aaacacttct ttcatcctta   240
aatataagac ttttataatt aattcacact tattaataaa attacaaaga cttttataat   300
taattcacac ttattaataa aattgctcga tttagttagt aattaacatt atatttgttt   360
gtaattttaa tattttttaa gattatcttt aaaattattc a                       401

<210> SEQ ID NO 202
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 202
tttttcaaat acactctttt ctcgctgttt aaaaaaaaaa atacactctc ttctaataat    60
taaaagttat taaaaatcat aaatttgaat ggatctcatt tttcattgag taactctctc   120
tcgtgatttt atattatctc tgtgcttttt attttttatt tttaaaaaat atgtaaaaac   180
caagaaacat aatwaatgtg gttcatctta ataaaacact tctttcatcc ttaaatataa   240
gacttttata attaattcac acttattaat aaaattacaa agacttttat aattaattca   300
cacttattaa taaaattgct cgatttagtt agtaattaac attatatttg tttgtaattt   360
taatattttt taagattatc tttaaaatta ttcagactaa a                       401

<210> SEQ ID NO 203
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 203
```

```
tctttaaaat tattcagact aaatatatat ttttttcatt taattatttt ctacccaaac    60
aattaacata tgaaaagaga ataatagtag tcgagtttta attttaaaat taaatccttc   120
aattctccaa tcctcccacg aaagagaaaa tgacaattca tagcaattrt tatttataga   180
ctacaacaac tagggtatt ctagtaaaaa gaaaacaag taatgcaaga aagaagtctt   240
atacaaaaga acaaagaatt ttttaaataa tgtcttatat tcatagacga aagaaacaat   300
tgatccttta tcatttttat taaacaataa atgcatagat gtaaataaat taaagattag   360
aaaaaagtaa gaacataatt ggcaaaaaaa taattaatgt c                       401
```

<210> SEQ ID NO 204
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 204

```
taaaaaaga aacgtggga gagtgcaatt aggataaagg gattggatta cttgaagaaa    60
aaaaraataa aggggttaga aaaagaccct ctagaagtat acgacagcct aaattgaaat   120
tgggatacat agtttggact gtaatagaat tgtggatctg tttgctcgtt ttatttcaaa   180
ataaaacaaa ataaagaact gctagcatra caacaaaaag tactaatttt taatctcaak   240
gatcrgaact ttgcrtttct ttcccgtatc ttgtcgaatt ttyattgtaa gaaatattct   300
ttgtgggttc agttattcac cattattatt tcagagggag cgatgggwgg aattataata   360
cttcttcatc agattcaatt ttgataaaga aaatcattca a                       401
```

<210> SEQ ID NO 205
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 205

```
aagaaaaaaa raataaaggg gttagaaaaa gaccctctag aagtatacga cagcctaaat    60
tgaaattggg atacatagtt tggactgtaa tagaattgtg gatctgtttg ctcgttttat   120
ttcaaaataa aacaaaataa agaactscta gcatracaac aaaaagtact aatttttaat   180
ctcaakgatc rgaactttgc gtttcttttcc cgtatcttgt cgaattttya ttgtaagaaa   240
tattctttgt gggttcagtt attcaccatt attatttcag agggagcgat gggwggaatt   300
ataatacttc ttcatcagat tcaattttga taaagaaaat cattcaaata agagacttta   360
ttatcttcaa aaagctaagt acggaagatg ccaaaaagaa a                       401
```

<210> SEQ ID NO 206
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 206

```
ttggatcatt taatttatga ggtgtgtgat tttgtttcct agttttaat tttgcaaatt    60 ggatcattta agtattacag gaatccaatt tactcaattg aattctgaaa gatcaaaatt   120
aaataaatgc aatacctaag agacaaaaaa taattaatct attttttaa agaaaatact   180 actatcagat atggaagcac taacaaaacc agtccaggag agacatcagc acctacctac   240
```

```
gcaccccaaa atcagataca actttaagct tacaacatca cctatagtaa cctaatattg    300
ctcaaaatgg aagcaaccat tccacaacca atacaacaaa caaaatcaat aaatttacta    360
caaactagtc gaaccgtacc tcgttaatgc cataaaccta g                        401
```

<210> SEQ ID NO 207
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 207

```
actaagctac acaaactgaa tcacgtctaa gacgctctaa aaacaaaatc aggaggcagg     60
ttccgcaaaa taggactgga taatgatgtt gaagcagtaa tttctatcaa aattaacagg    120
aaaaactcta aaaaatcag ccccrggaga aatttatata tattttttgt agataaaaat    180
ttaaattagg ggaagacacg tcttcttgta aaactacaag aaaaattaac aacatcagca    240
ttataaaatt tatacatcgc ataacaatat gcaaaatcca aaaatcaata aacctaaatt    300
attgctggta taactatttg actaaatgtg ccattgttgs ccagagaata ttaaaatgta    360
atgaaataaa gtattttaaa ttaattgact aagaattggc a                        401
```

<210> SEQ ID NO 208
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 208

```
gccccrggag aaatttatat atattttttg tagataaaaa tttaaattag gggaagacac     60
gycttcttgt aaaactacaa gaaaaattaa caacatcagc attataaaat ttatacatcg    120
cataacaata tgcaaaatcc aaaaatcaat aaacctaaat tattgctggt ataactattt    180
gactaaatgt gccattgttg gccagagaat attaaaatgt aatgaaataa agtattttaa    240
attaattgac taagaattgg catggctatg agaaatcatg cactaattga gcaaagatat    300
gatatatttt ttatacttgt cctaacaatg tactcccact aattaagtta ctaattgagc    360
actccataat ttttttggaa agatgttctt tggacactgt g                        401
```

<210> SEQ ID NO 209
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 209

```
tcatgtctac caagtccgac taacttwtcc gtccatcaac cattttttaa ctgagaattg     60
gtatgatatc aagagttaag agttgtgact gtatttggaa aaatatttct taaaataaaa    120
tgatattcaa aaaatatatt tttaatagtt ttttctgctg attttcagtc tataattaaa    180
cgaatttaga tactctatat taaaaaagag aaaatcattt tttcaataac agtcccaaaa    240
cttttaaatt aaaaaaaata aagtaaaatt tatcttttat tttgaattaa atcaagacat    300
actactatac ctgatcagtc ctggatcgaa ttctcccaac caaatcaact cgccataaat    360
accctcttat atccagttaa ttaatggtcc atctcgtttt g                        401
```

<210> SEQ ID NO 210
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 210

```
aaagagaaaa tcattttttc aataacagtc ccaaaactttt taaattaaaa aaaataaagt      60
aaaatttatc ttttattttg aattaaatca agacatacta ctatacctga tcagtcctgg     120
atcgaattct cccaaccaaa tcaactcgcc ataaatatccc tcttatatcc agttaattaa    180
tggtccatct cgttttgaaa ttttttttaac catgaagttt tttttttagtt acatgaggaa   240
aagaaagaca agggacaacc aaaaaaacta cacgtactac taaattaagg cagatcacac    300
tgccactccc tctgcacaaa aactggtggc ctctgccaga ccacagcatc agaactcaga    360
agcattggtt gcatcagagt tttgttatgg tgtatttaga a                        401
```

<210> SEQ ID NO 211
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 211

```
ccaatcccga cacaaccagc tcgaaatttt ccgcaccgca gaatgtcgtg attcttgtgg      60
caaccagagt tgttgttctt gctagctcta tattcttctc ctgtgtggca gtattgcatc    120
aatgctacca tgcagtgtct aacaagacta tatcatatat ttatgatagt ctctaatcaa    180
tttttgaaaa aattagagtc ttaatatttta tacatctcat tttcttataa ttcacttgca   240
tcttatttca ttttttcccc tatcatataa catatcatat ttattacatt ctctctatttt  300
ttatttttat ttctctctcc atctctcttc tcttttcacc ctaaaatggg ggtgaacact    360
caacatgttt tgaaaaatta ttattagatt aatatgtatt g                        401
```

<210> SEQ ID NO 212
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 212

```
gggtcatcct ttcacttgtt tggtctacac cacactcttg tcttgggtcg ctgaggtggc      60
gcgtgagttt cacctcccaa cagcgatgct gtggactcaa ccagctacga tactcgacat    120
cttctattac tactttcacg aacacggtga atacatcaaa gacaaaatca agaccccctc    180
gtgtttcatt gaattaccag gattgccatt gttgcttgca ccacgggacc taccctcytt   240
tttattgggt tcaaaccta ctattgactc tttcattgtc ccaatgtttg aaaagatgtt    300
ttatgatctt gacgtggaga caaagcccag aatacttgtc aacaccttcg aagccttgga   360
agcggaggct ctcagagccg ttgataagtt caacatgatc c                        401
```

<210> SEQ ID NO 213
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 213

```
ttgtcttggg tcgctgaggt ggcgcgtgag tttcacctcc caacagcgat gctgtggact    60
caaccagcta cgatactcga catcttctat tactactttc acgaacacgg tgaatacatc   120
aaagacaaaa tcaagaccc  tcgtgtttc  attgaattac cagsattgcc attgttgctt   180
gcaccacggg acctaccctc tttttattg  ggttcaaacc ctactattga ctctttcatt   240
gtcccaatgt tgaaaagat  gttttatgat cttgacgtgg agacaaagcc cagaatactt   300
gtcaacacct tcgaagcctt ggaagcggag gctctcagag ccgttgataa gttcaacatg   360
atcccaatcg gccgttgat  tccctcggct tcttggatgg                         401
```

<210> SEQ ID NO 214
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 214

```
tcccaatcgg gccgttgatt ccctcggctt tcttggatgg gaaagatmct aatgatactt    60
catttggcgg tgacatcttc cgcctctcta atggttgcag cgaatggttg gactcgaagc   120
cagagatgtc ggtggtttat gtctcgtttg gtagcctttg cgtgttgcct aagacgcaaa   180
tggaggaact tgcacgtgcg ttattagatt gtggaagtcc tttcctgtgg gtcattaaag   240
aaaaagaaaa taagtcacaa gtggaaggaa aagaggagct gagctgcata gaggaattgg   300
aacagaaggg gaagatagta aactggtgtt ctcaagtgga ggttctttca catggttctg   360
tgggttgttt tgttacacac tgtggttgga attcaaccat g                       401
```

<210> SEQ ID NO 215
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 215

```
aaatgaagaa attaggcggt gtttggaaga ggtgatgggg agtggagaga aaggacaaga    60
attgagaaac aatgcagaaa agtggagggg actggccagg gaagctgtca aggaaggtgg   120
ctcttcggat aagaatctaa gggcttttttt agatgatgtt gaagtttgac catatggctg   180
tcacatcagc ttttccgttt tgaattttc  ctgtccgttt cattttctt  ttctattatt   240
gcatttgcat gactgagaat caagtgaaat tcttctata  ttagtttgaa atttaaaaat   300
atctaaatga gccatgactc catgagtagt aattttgtgt tataattgat atatatattt   360
tctcttaagt agtggccaaa aatttaatct ttatgtagat g                       401
```

<210> SEQ ID NO 216
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 216

```
atgcatctgg atctggtttc cctattcata tttccaaagc ttgcatgctt tctggtttcc    60
ttgccaatca ctgcatggaa caatcttacc atcatagggc atgcttcttt ttttaagctc   120
```

| | |
|---|---|
| gcttgtggtc ttctttggt acatatgctc ccctcccccc tttttgttta ttttgtttt | 180 |
| atggttcata atagagttta ttgatgaaat agccaaatca tagaattagt aaaatatcat | 240 |
| gtacaaggtc aaaatagtat ttttagtaac catcttttt ttctcgtacc ttacatagaa | 300 |
| gctgactcaa tgataaagga aacctaaaaa ttagtttwaa aaaaaccttt tggccttttt | 360 |
| gacatmatat atgatatttt tgtcaaaata tgagactttt t | 401 |

<210> SEQ ID NO 217
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 217

| | |
|---|---|
| ggtacatatg ctcccctccc cccttttgt ttattttgt tttatggttc ataatagagt | 60 |
| ttaytgatga aatagccaaa tcatagaatt agtaaaatat catgtacaag gtcaaaatag | 120 |
| tattttagt aaccatcttt ttttctcgt accttacata gaagctgact caatgataaa | 180 |
| ggaaaccta aaaattagttt taaaaaaacc ttttggcctt tttgacatma tatatgatat | 240 |
| ttttgtcaaa atatgagact tttttttat aaaaactaat aaaaaaatat ttttattgg | 300 |
| taaacctaga acttaaattt tagttatttt attcttagas aaaccttacc taacaaataa | 360 |
| tttaattcaa atatttgcct ttcattctat tttatttcac c | 401 |

<210> SEQ ID NO 218
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 218

| | |
|---|---|
| atatgagact ttttttat aaaaactaat aaaaaaatat ttttattgg taaacctaga | 60 |
| acttaaattt tagttatttt attcttagas aaaccttacc taacaaataa tttaattcaa | 120 |
| atatttgcct ttcattctat tttatttcac cttaacaact tccctggcca caacatgttg | 180 |
| gatctcagta aaaattgatg gtgtaagatc attccattac gaagagatgc atggcctatt | 240 |
| attctttctc catccaagaa aaaaatacat ttattcttgc ttcctgttaa aacataaaaa | 300 |
| gacgttttac cttagtatga taaccttcat aaatagttaa atatagcatt gtcttgaact | 360 |
| ttgaaataaa ttatgtttaa ttagaactta taactataag t | 401 |

<210> SEQ ID NO 219
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 219

| | |
|---|---|
| atatgtcaag tattataata aatatttaat tatataaata aataattta ttcttaaata | 60 |
| taaacattta caaagttaaa gtaacaaaaa agtaagtttt taattctctt aataatgtca | 120 |
| tatcctaatt tcgtactagg actatcattc gtcaacgttt tgattctcca ttgtcaaatt | 180 |
| gaattgttcg acaccagttg ttrtgtaaga cggaagatta ttcgacattt cagtaaagaa | 240 |
| tgcaaaaaat gcccaatgg aaggacaaaa ggatcatttt raggcttttt cagacccctg | 300 |
| actcgctcag gctagtctct ggctcaccta ggcccctaaa tagtttaggg gtgaagtaac | 360 | tagctcgyct ggacgagcaa ggttacttca ggttgaagca a        401

<210> SEQ ID NO 220
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 220
atgtcaagta ttataataaa tatttaatta tataaataaa taattttatt cttaaatata     60
aacatttaca aagttaaagt aacaaaaaag taagttttta attctcttaa taatgtcata    120
tcctaatttc gtactaggac tatcattcgt caacgttttg attctccatt gtcaaattga    180
attgttcgac accagttgyt gtgtaagacg aagattatt cgacatttca gtaaagaatg     240
caaaaatgc ccaaatggaa ggacaaaagg atcattttra ggcttttca gaccccctgac    300
tcgctcaggc tagtctctgg ctcacctagg cccctaaata gtttaggggt gaagtaacta    360
gctcgyctgg acgagcaagg ttacttcagg ttgaagcaac a                        401

<210> SEQ ID NO 221
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 221
gtaacaaaaa agtaagtttt taattctctt aataatgtca tatcctaatt tcgtactagg     60
actatcattc gtcaacgttt tgattctcca ttgtcaaatt gaattgttcg acaccagttg    120
ytrtgtaaga cggaagatta ttcgacattt cagtaaagaa tgcaaaaaat gcccaaatgg    180
aaggacaaaa ggatcatttt gaggcttttt cagaccccctg actcgctcag gctagtctct    240
ggctcaccta ggcccctaaa tagtttaggg gtgaagtaac tagctcgyct ggacgagcaa    300
ggttacttca ggttgaagca acarctcgct tgggtgagct ccagatcaac taagtcccct    360
catttcctat aaataggcat gaggggctga agaaagggt t                         401

<210> SEQ ID NO 222
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 222
ccattgtcaa attgaattgt tcgacaccag ttgytrtgta agacggaaga ttattcgaca     60
tttcagtaaa gaatgcaaaa aatgcccaaa tggaaggaca aaaggatcat tttraggctt    120
tttcagaccc ctgactcgct caggctagtc tctggctcac ctaggcccct aaatagttta    180
ggggtgaagt aactagctcg tctggacgag caaggttact tcaggttgaa gcaacarctc    240
gcttgggtga gctccagatc aactaagtcc cctcatttcc tataaatagg catgaggggc    300
tgaaagaaag ggttcarcct tcaratattg aaaggattta gtgaaatttg aagaaaagaa    360
gaaraaataa aggaaaaaca aggtcgaggt gctaccgaat c                        401

<210> SEQ ID NO 223
<211> LENGTH: 401
<212> TYPE: DNA

<213> ORGANISM: Artificial Sequence
<220> FEATURE:
<223> OTHER INFORMATION: Consensus Reference Sequence

<400> SEQUENCE: 223

| | | | | | |
|---|---|---|---|---|---|
| tgtaagacgg | aagattattc | gacatttcag | taaagaatgc | aaaaaatgcc | caaatggaag | 60 |
| gacaaaagga | tcattttrag | gcttttttcag | acccctgact | cgctcaggct | agtctctggc | 120 |
| tcacctaggc | ccctaaatag | tttaggggtg | aagtaactag | ctcgyctgga | cgagcaaggt | 180 |
| tacttcaggt | tgaagcaaca | gctcgcttgg | gtgagctcca | gatcaactaa | gtcccctcat | 240 |
| ttcctataaa | taggcatgag | gggctgaaag | aaagggttca | rccttcarat | attgaaagga | 300 |
| tttagtgaaa | tttgaagaaa | agaagaaraa | ataaaggaaa | aacaaggtcg | aggtgctacc | 360 |
| gaatcacgat | cgtaatcgat | tttcacatcg | ttcttcgttc | g | | 401 |

<210> SEQ ID NO 224
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 224

| | | | | | |
|---|---|---|---|---|---|
| cagacccctg | actcgctcag | gctagtctct | ggctcaccta | ggcccctaaa | tagtttaggg | 60 |
| gtgaagtaac | tagctcgyct | ggacgagcaa | ggttacttca | ggttgaagca | acarctcgct | 120 |
| tgggtgagct | ccagatcaac | taagtcccct | catttcctat | aaataggcat | gagggggctga | 180 |
| aagaaagggt | tcarccttca | gatattgaaa | ggatttagtg | aaatttgaag | aaaagaagaa | 240 |
| raaataaagg | aaaaacaagg | tcgaggtgct | accgaatcac | gatcgtaatc | gatttcaca | 300 |
| tcgttcttcg | ttcgtcatcc | ggttagtatt | tattttaagt | atttcaattc | aatctatgca | 360 |
| cccataaggg | tcttctttgt | cgattcatgc | atcttcatct | c | | 401 |

<210> SEQ ID NO 225
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 225

| | | | | | |
|---|---|---|---|---|---|
| tgtaatctat | tttcttttgg | taaagtgagt | tttgaccggt | catttacgtc | accaaacatc | 60 |
| ttttaattag | tttgaagttt | aataagtgaa | atcaagttaa | atcaacatg | taaccgagct | 120 |
| ttttatccgc | aaaattcact | taaatccgtt | caaggtccaa | ggccttaatg | gtctcttta | 180 |
| tttttgttgg | ttcgaatgaa | ttttcaaaa | gtttaaaatc | aactcgacac | gcaatttttct | 240 |
| tgttttaaga | actatgtagg | tctgagtttc | tcatcgcamt | tgaggatacg | taggagcaag | 300 |
| ggcaacgcct | ttgtcgaccc | gaaaaaataa | agaagcataa | aaagggaaaa | taagtaatat | 360 |
| tgaagtcacg | ttttttgcaca | ttcgattaaa | ggttgtcrtc | c | | 401 |

<210> SEQ ID NO 226
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 226

| | | | | | |
|---|---|---|---|---|---|
| gaayttttca | aaagtttaaa | atcaactcga | cacgcaattt | tcttgttttta | agaactatgt | 60 |

```
aggtctgagt ttctcatcgc amttgaggat acgtaggagc aagggcaacg cctttgtcga    120
cccgaaaaaa taagaagca taaaaaggga aataagtaa tattgaagtc acgttttgc      180 acattcgatt aaaggttgtc gtcccctgtg acgaayacgt ggggtgttaa tacctttttc   240
gctcgtaaat aactcccgta cccttatttt caaaattcgc akatccccct ttttggtttt   300
tctaacgttt tcctcgaata aacgttggtg gcgactcccg cgtgttttc ttttggaag    360 acgcatcctt gagtctcgcc tcacccctcc cgtcgaaggg t                       401
```

<210> SEQ ID NO 227
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 227

```
mttgaggata cgtaggagca agggcaacgc ctttgtcgac ccgaaaaaat aaagaagcat    60
aaaaagggaa aataagtaat attgaagtca cgttttgca cattcgatta aaggttgtcr   120
tcccctgtga cgaayacgtg gggtgttaat accttttttcg ctcgtaaata actcccgtac  180 ccttatttc aaaattcgca tatccccctt tttggttttt ctaacgtttt cctcgaataa   240
acgttggtgg cgactcccgc gtgttttct ttttggaaga cgcatccttg agtctcgcct   300 caccctccc gtcgaagggt aggttgcaac agataataat aaaaaaattc aaccatgata   360
ttcgcaacaa taaattaaat gcacacatac atatatatag t                       401
```

<210> SEQ ID NO 228
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 228

```
gaattagtgt gagtctcaga ttcttcaaat ggtctatgag ttcatattca tgcagtaayg    60
tctcactgct tttcttatca tatatgaaag tattcaaaat ctcttcttca tcctagatgg   120
aggtatctat aacttcatct ccatcccaaa tgaaggtgtc tcgtacatat tcaattctca   180
aaataaaaca taaattgtca ttacttccta aaggatgata accaattcac acatatttat   240
aaaatatcat ttcaaataac tatcaaataa atactttaat tccatataca ctaattaata   300
acttgsaagg tcataccctta gttatagcat cacgtaagtc aatttataat taactatgaa   360
ataaaacata cacacaaatt aaaatatatt ttagttgcta t                       401
```

<210> SEQ ID NO 229
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 229

```
cttcatccta gatggaggta tctataactt catctccatc ccaaatgaag gtgtctcgta    60
catattcaat tctcaaaata aaacataaat tgtcaytact tcctaaagga tgataaccaa   120
ttcacacata tttataaaat atcatttcaa ataactatca aataaatact ttaattccat   180
atacactaat taataacttg gaaggtcata ccttagttat agcatcacgt aagtcaattt   240
```

```
ataattaact atgaaataaa acatacacac aaattaaaat atattttagt tgctatatat    300
gatagctaaa cacaaaatcc aaacaagctg attgatgaat tttcaaataa attttaagat    360
tgaatatgca actagtgaat atttgtacat tgtaataacct t                      401

<210> SEQ ID NO 230
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 230
atctagtttc tatcgtgcat atttgttgaa gttaaacaca agatccaagy aagcacatat     60
gatgcattat aattgcacta aaatttgaat atagtttcta tatatcgtgc atgtttgttg    120
gctctccttg acaagcatat ctatttaatt tatacaagta gtaaataaaa tgataagact    180
aaatgatgag ttcacatata ttttatttgt actcwtatat atatatatat atataattct    240
tggatgaaaa ggaccccgaa gatacttcct tgggtggtga cttgttaccg gtttcaaatg    300
gttacgttga gtggcttgac tcaaaggaag acaagtccgt ggtttacatt tcatttggga    360
gctactttgt gttgtctaag agacaaacgg aggaaattgc a                       401

<210> SEQ ID NO 231
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 231
caggtggagg ttcagtgggt tgttttgtga cgcactgtgg ttggaattcg accatggaga     60
gctaggtttc gggggtgccc atggtggtgt ttcctcagtg gtcgtaccaa agacaaatg    120 ctaaactgat agaaaatgtg tggaagatag gggtgagggt ggatcatgag gatgggaaag    180
tagaaggaga aagagattaa caagtgttcg gaagaggtga tggggagtgg agagttgaga    240
atgaatgtaa agaaatggaa gggttttggcc agggaggcag ccaaggaagg tggtccttca    300
gatttcttga tgccatgacg ttgcagaatc gataatcaat gcacgtgttt gccaaataat    360
tgacttggat tcccgtgttc tcagttcttc catgctaaat t                       401

<210> SEQ ID NO 232
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 232
aggtggtcct tcagatttct tgatgccatg acgttgcaga atcgataatc aatgcacgtg     60
tttgccaaat aattgacttg gattcccgtg ttctcagttc ttccatgcta aattattctt    120
tttctgcttc twtttctttt tccaatcaat tgattctatg tttaagattt ttattattta    180
gaacaattaa attattattg ttttaagaga tagtattatt ttaagtttaa atgtatattt    240
tttattcata attatatctc tatttaatct ggtatactcc ttaaaattac ttttatttaa    300
ttatgttttt ttttaaaata atcaaattat tcaatcttat tgataagtgg tttgtatcaa    360
atgctcacct aaaaaagata aatagactcc caaatattag a                       401
```

<210> SEQ ID NO 233
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 233

```
agataattaa tttcttttaa atggatgtag gaagagacta aattattact aatcttattg      60
ctttatattt tttatagtta tctttccact cctacagtac gaaacacatg taataaatca     120
gtgccattaa catacaactc gacctaattg taatttgtag taacttagat agtttagatt     180
ttttttttgt tatggtatta tgtatttcat aaaaatttat attaattttc ttttgaaaaa     240
tattatacwt catattgtct tcttgccttt gtaaataaaa agtgttaaaa tatcaatact     300
yatgtttatt tgaacaagtg agatgcatgt aatcrctatc attatttagg aatgytaatg     360
aacctacttg ttgcactaat taagcytgtt tcaacctgta a                         401
```

<210> SEQ ID NO 234
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 234

```
tattgtcttc ttgcctttgt aaaataaaag tgttaaaata tcaatactya tgtttatttg      60
aacaagtgag atgcatgtaa tcrctatcat tatttaggaa tgytaatgaa cctacttgtt    120
gcactaatta agcytgtttc aacctgtaaa aaaagtctg tttcaaaatt atttttttatg    180 cattttactt aaaaaaatta tacctaatga attttgaata ttgatttgat ttttttaaga    240
gaatatattt ttgagttata tatatatata ttagtagtcc tacctcgttc taatatttta    300
tattttttta ataaaatata caaattttta aacaatttg tattaaggaa aaattaatca     360
ttttattmtt ataattatac aaaatttagc tttgaatgac c                         401
```

<210> SEQ ID NO 235
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 235

```
aatgaaagtt tgaatataaa aggttacttt gtttaaactt aaaaaaaaat tctaaaaaat      60
attttttaag aagtaaatat gatttattta ttaacaagac attttctat ttttaagaaa     120 aaaatacata aaaaataatt attttattaa aaaatgatcc aaacccttca tcattaatgt     180
taatgattaa tctattaatt catgtttaat ttattatatt ataattataa tagattatac     240
aaaaagcaat tatacgattt aatgtttat atatttaatt ttatatttaa ratgtggaag     300
atgcgttagc aagtattaag atattgacta aaaagaaaa ttaaaaata tataattaaa      360 actaaagcat tttctataaa taaaaaatat aagactttt t                         401
```

<210> SEQ ID NO 236
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 236

```
ttaacaagac attttctat ttttaagaaa aaaatacata aaaataatt attttattaa      60
aaaatgatcc aaaccttca tcattaatgt taatgattaa tctattaatt matgtttaat    120
ttattatatt ataattataa tagattatac aaaaagcaat tatacgattt aatgttttat   180
atatttaatt ttatatttaa gatgtggaag atgcgttagc aagtattaag atattgacta   240
aaaaagaaaa ttaaaaaata tataattaaa actaaagcat ttctataaa taaaaaatat    300
aagactttt ttttacatga catataaaac ttactctatt caatattaaa attgttaaag    360
atttaactgg tatatactaa tagtgtaaat atattttaca c                        401
```

<210> SEQ ID NO 237
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 237

```
tcamatattg attcatcatg tagtgaaaaa ctaatcwctt ttactcaacc taasctgtat    60
cgatgytaat cattgctctt agtacattga ttataaaaaa aatactagaa agataaagtt   120
tttgttagaa atcatttgcg agtatatttt aaaataattg aagaatacat ttttatgcat   180
tatatagtta aagtgttttt tttttccttt tttcacttcc tctattttaa ccactatttt   240
ctttctacac amaaaaaaaa atccatcatt tttcttttat ccttttaaca aattttggtt   300
ttggacagtr aacacacaca aaatatatat ttytcttcta atatgatttg ttttattttt   360
gatgccaata tgttatgatt gtttgataat gtaaaaaata t                        401
```

<210> SEQ ID NO 238
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 238

```
aasctgtatc gatgytaatc attgctctta gtacattgat tataaaaaaa atactagaaa    60
gataaagttt ttgttagaaa tcatttgcga gtatatttta aaataattga agaatacatt   120
ttatgcatt atatagttaa agtgtttttk ttttccttt ttcacttcct ctattttaac    180
cactatttc tttctacaca caaaaaaaaa tccatcattt ttcttttatc cttttaacaa    240
attttggttt tggacagtra acacacacaa aatatatatt tytcttctaa tatgatttgt   300
tttatttttg atgccaatat gttatgattg tttgataatg taaaaaatat tasactaata   360
atgcgtagta ctagyaatta acctcatttt twaaatagtt a                        401
```

<210> SEQ ID NO 239
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 239

```
aagataaagt ttttgttaga aatcatttgc gagtatattt taaaataatt gaagaataca    60
ttttatgca ttatatagtt aaagtgtttt tkttttcctt ttttcacttc ctctattta   120
accactattt tctttctaca camaaaaaaa aatccatcat ttttctttta ccttttaac    180
```

```
aaattttggt tttggacagt gaacacacac aaaatatata tttytcttct aatatgattt    240
gttttatttt tgatgccaat atgttatgat tgtttgataa tgtaaaaaat attasactaa    300
taatgcgtag tactagyaat taacctcatt tttwaaatag ttaaaagaac ttgctcattc    360
attattaatt tttcattaaa aatattgtac cggccacttt a                       401
```

<210> SEQ ID NO 240
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 240

```
catttgcgag tatattttaa ataaattgaa gaatacattt ttatgcatta tatagttaaa     60 gtgttttkt tttccttttt tcacttcctc tattttaacc actattttct ttctacacam    120 aaaaaaaat ccatcatttt tcttttatcc ttttaacaaa ttttggtttt ggacagtraa    180
cacacacaaa atatatattt ttcttctaat atgatttgtt ttatttttga tgccaatatg    240
ttatgattgt ttgataatgt aaaaaatatt asactaataa tgcgtagtac tagyaattaa    300
cctcattttt waaatagtta aaagaacttg ctcattcatt attaatttt cattaaaaat    360 attgtaccgg ccactttaat ttattttcaa atgctattaa a                       401
```

<210> SEQ ID NO 241
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 241

```
gtagtactag yaattaacct cattttwaa atagttaaaa gaacttgctc attcattatt     60 aattttcat taaaaatatt gtaccggcca ctttaattta ttttcaaatg ctattaaaat    120
aaagcaatga gttaatgaca ttaattaaga aatgcattta aaattttatt aatattaagg    180
atcttgttaa ttaatgtttt tccccacaa gtcttctctt tcaaaggcct aatgtacatt    240
aggacactaa atgtcacccc tttaaatgaa tattcaaaca ttgattcatc acttagtgaa    300
aarttaatct cttccacttg actcaaccgg tgctgatgtt aaccattgct cttaatattg    360
gttataaaaa ataataaaaa gataaagttt tgttagaaa t                        401
```

<210> SEQ ID NO 242
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 242

```
acccaacggt gcttgtgaac acctttgaag ctttggaaga agaagcgttg agggccattg     60
ataagatcaa catgatcccc atcgggccgt tgattccttc tgcgttcttg gacgggaatg    120
acccaactga tacttcgttt ggtggggaca tttttcaagt ctcaaatgat tacgttgaat    180
ggcttgactc aaaggaagag gattcggtgg tttacgtttc atttggtagc tactttgagc    240
tttctaagag acaaatggag gaaattgcac gtgggttatt agattgtgga cgtccattyt    300
tgtgggtcgt tagagaaaag gtaattaatg gaaaaaaga agaggaggag gagctttgtt    360
```

```
gtttcagaga ggaattggag aagtggggga agatagtgac a              401
```

<210> SEQ ID NO 243
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 243

```
tctgcgttct tggacgggaa tgacccaact gatacttcgt ttggtgggga cattttttcaa    60
gtctcaaatg attacgttga atggcttgac tcaaaggaag agrattcggt ggtttacgtt   120
tcatttggta gctactttga gctttctaag agacaaatgg aggaaattgc acgtgggtta   180
ttagattgtg gacgtccatt tttgtgggtc gttagagaaa aggtaattaa tggaaaaaaa   240
gaagaggagg aggagctttg ttgtttcaga gaggaattgg agaagtgggg gaagatagtg   300
acatggtgtt ctcaggtgga ggttctttcg cattcttctg tgggttgttt tttaacacac   360
tgtgggtgga attcgaccat ggaaagcctt gtttctgggg t                       401
```

<210> SEQ ID NO 244
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 244

```
gcgaaagaag gtggctcttc agagaagaat ctgagggcat tgtggatga tgttagacaa     60
aaatttatgc atacacatgt gggtgaatat taattaagtt cgtctctaac tagctagtag   120
taagctgtaa tgtgttattg tatgcttatg atgcatggct caaacattg aaagatgaac    180
tgaaaaaatt aagaaattat cagtcagtta ataaaaatgt gcgaaaatgg aatatcttca   240
ataataacat gtgcgtrttg ctaaaaaatg agttgttgtc acgttagatg gtggatgcca   300
tataactgtc caatatgttg cccaattcgt caggaaaaga taaatatttt gataaagatt   360
attattacat tgttgcttta tactcccttc ctttcttttt a                       401
```

<210> SEQ ID NO 245
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 245

```
tgaaatgtca atcaaaatat acaacagtat gtgcatggat tcttgatgac aataattcca    60
aaccacaaa tatgtattta taatcatctt aaaagctcta gtgagacact tagckgtaca   120
aattaaattt tttaaatcgt tgggcaaaga atcatcagca aatgtagttt tttttttttt   180
ttgagaaatc acccaatgta ttcaattgcg gaagsaggag cttgtcattc cagtagtcca   240
attttttcagt tatacttttg atttttatag ggtaagtact aagtaaccta gctagtttct   300
taatctcatg atctcttggc ttatyttttt tttttttwaa tttgtgcttg agtcactata   360
catatttact tggttgtcga acaaaattaa aatytcttcg t                       401
```

<210> SEQ ID NO 246
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 246

```
aaatatacaa cagtatgtgc atggattctt gatgacaata attccaaaac cacaaatatg    60
tatttataat catcttaaaa gctctagtga gacacttagc kgtacaaatt aaattttta    120
aatcgttggg caaagaatca tcagcaaatg tagtttttt tttttttga gaaatcaccc    180
aatgtaktca attgcggaag gaggagcttg tcattccagt agtccaattt ttcagttata    240
cttttgattt ttatagggta agtactaagt aacctagcta gtttcttaat ctcatgatct    300
cttggcttat yttttttt tttwaatttg tgcttgagtc actatacata tttacttggt    360
tgtcgaacaa aattaaaaty tcttcgtacc taaacaaaac c    401
```

<210> SEQ ID NO 247
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 247

```
caatgtaktc aattgcggaa gsaggagctt gtcattccag tagtccaatt tttcagttat    60
acttttgatt tttatagggt aagtactaag taacctagct agtttcttaa tctcatgatc    120
tcttggctta tyttttttt ttttwaattt gtgcttgagt cactatacat atttacttgg    180
ttgtcgaaca aaattaaaat tcttcgtac ctaaacaaaa cctaacttaa agtcccagac    240
taattcaaca ataatcaact caattttttt tttttgcat gttacatttc atacattaac    300
tgttgagcta ctttatgggt tccctcccgt gtagggtttg tttaatgata ttagcttgaa    360
gttttcactc ttttgatctt caagaagagt taaaggtgga c    401
```

<210> SEQ ID NO 248
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 248

```
gcaacttgag gctgaactcg gtcgtgcggt caagcaagac atttctgtgt acgtagctgt    60
acaataatat acaatgaatt agaataataa cagattatgt ggcattaatt attacagcag    120
caactcattc cttgattctg ggaattagca atttcttcca gcttatatat ataccagcat    180
ctcaatcctt gattgtacga tataattttg caatttgatc caaatttatt acagctagtt    240
aggatactac tcgtcttaca attttgaca aggttttgtc agcaatgttg aggatgttta    300
agctgaacac cgtccgagaa gtaaaatact attaaaggag gctaaaggra tatattggat    360
tagaattta aaagattatt ttaatataaa aggttatatg a    401
```

<210> SEQ ID NO 249
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 249

```
caatttcttc cagcttatat atataccagc atctcaatcc ttgattgtac gayataattt    60
```

```
tgcaatttga tccaaattta ttacagctag ttaggatact actcgtctta caattttttga    120 caaggttttg tcagcaatgt tgaggatgtt taagctgaac accgtccgag aagtaaaata    180
ctattaaagg aggctaaagg gatatattgg attagaattt taaaagatta ttttaatata    240
aaaggttata tgaattttaa aaatkatgta gaagtattat gacttattat attttttttac    300 aarattttta taatagtttt aattttaata aatttatatg ataagaattt aaaagactta    360
aattttttta aaaaaattta taaratttaa aagaattata t                         401

<210> SEQ ID NO 250
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 250
atttgatcca aatttattac agctagttag gatactactc gtcttacaat ttttgacaag     60
gttttgtcag caatgttgag gatgtttaag ctgaacaccg tccgagaagt aaaatactat    120
taaaggaggc taaaggrata tattggatta gaattttaaa agattatttt aatataaaag    180
gttatatgaa ttttaaaaat tatgtagaag tattatgact tattatattt ttttacaara    240
tttttataat agtttaatt ttaataaatt tatgataa gaatttaaaa gacttaaatt       300
tttttaaaaa aatttataar atttaaaaga attatatgaa ttttaaaat cacattcaaa    360 attacaataa ttaatgaaga aaataacaaa aaataatgag a                         401

<210> SEQ ID NO 251
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 251 tagtttttaat tttaataaat ttatatgata agaatttaaa agacttaaat tttttttaaaa    60 aaatttataa ratttaaaag aattatatga attttttaaaa tcacattcaa aattacaata    120
attaatgaag aaaataacaa aaaataatga gatttggata aaaaaagtaa atcaaaaca    180 attttttttaa tctttcaata gcatattgat tctaaactta tattctccta tattaacctt    240
tcatgcaata atatcttctc attctyactt ttgaatttga acaataratt taaaattata    300
cattgatttt ctgattttt taattagtct aattatttca taataaatat aatgacatgt    360
tatggaatgc aataataaat atatactaaa aaagagtaat a                         401

<210> SEQ ID NO 252
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 252
tataarattt aaaagaatta tatgaatttt taaaatcaca ttcaaaatta caataattaa     60
tgaagaaaat aacaaaaaat aatgagattt ggataaaaaa agtaaaatca aacaattttt    120 tttaatctttt caatarcata ttgattctaa ctttatattc tcctatatta acctttcatg    180
caataatatc ttctcattct tacttttgaa tttgaacaat aratttaaaa ttatacattg    240
attttctgat tttttttaatt agtctaatta tttcataata aatataatga catgttatgg    300
```

```
aatgcaataa taaatatata ctaaaaaaga gtaataagag tgtgaaattg gtayrasagt    360
tattaagtca tgtggataat gaaattaaga gtaacattta t                        401
```

<210> SEQ ID NO 253
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 253

```
atgaattttt aaaatcacat tcaaaattac aataattaat gaagaaaata acaaaaaata    60
atgagatttg gataaaaaaa gtaaaatcaa acaattttt ttaatctttc aatarcatat    120
tgattctaac tttatattct cctatattaa cctttcatgc aataatatct tctcattcty   180
acttttgaat ttgaacaata gatttaaaat tatacattga ttttctgatt ttttaatta    240 gtctaattat ttcataataa atataatgac atgttatgga atgcaataat aaatatatac   300 taaaaagag taataagagt gtgaaattgg tayrasagtt attaagtcat gtggataatg    360
aaattaagag taacatttat gaaaatatta tattgagcaa g                        401
```

<210> SEQ ID NO 254
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 254

```
atattctcct atattaacct ttcatgcaat aatatcttct cattctyact tttgaatttg    60
aacaatarat ttaaaattat acattgattt tctgattttt ttaattagtc taattatttc   120
ataataaata taatgacatg ttatggaatg caataataaa tatatactaa aaagagtaa    180 taagagtgtg aaattggtay gasagttatt aagtcatgtg gataatgaaa ttaagagtaa   240
catttatgaa aatattatat tgagcaagtt ataaacataa tcamtaaaac tcatcataag    300 aaaaaaaca tgattagtct tgacacataa gataaacatt aatttaattt aaaaaacaaa    360 graaaagtg tagaggggag acatatattt gacatttttt a                         401
```

<210> SEQ ID NO 255
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 255

```
attctcctat attaaccttt catgcaataa tatcttctca ttctyacttt tgaatttgaa    60
caatarattt aaaattatac attgattttc tgatttttt aattagtcta attatttcat    120
aataaatata atgacatgtt atggaatgca ataataaata tactaaaa agagtaata      180 agagtgtgaa attggtayra gagttattaa gtcatgtgga taatgaaatt aagagtaaca   240
tttatgaaaa tattatattg agcaagttat aaacataatc amtaaaactc atcataagaa   300 aaaaacatg attagtcttg acacataaga taaacattaa tttaatttaa aaacaaagr    360 aaaaagtgta gagggagac atatatttga catttttat t                         401
```

<210> SEQ ID NO 256

-continued

```
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 256
atatactaaa aaagagtaat aagagtgtga aattggtayr asagttatta agtcatgtgg    60
ataatgaaat taagagtaac atttatgaaa atattatatt gagcaagtta taaacataat   120
camtaaaact catcataaga aaaaaaacat gattagtctt gacacataag ataaacatta   180
atttaattta aaaaacaaag gaaaagtgt agagggggaga catatatttg acatttttta    240
tttcaaaaga ataagagaaa tatatatggt gcttgcatct tgawgaacat taaatagata   300
araagatatg tgtgataaaa gaaaaaaaaa agtgtggtaa tcaatagaaa aaaaaaagag   360
waaaatcatt caaatcattc aatagaaaag tgtggggttg t                      401

<210> SEQ ID NO 257
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 257
tatgaaaata ttatattgag caagttataa acataatcam taaaactcat cataagaaaa    60
aaaacatgat tagtcttgac acataagata aacattaatt taatttaaaa aacaaagraa   120
aaagtgtaga ggggagacat atatttgaca ttttttattt caaagaata agagaaatat    180 atatggtgct tgcatcttga tgaacattaa atagataara agatatgtgt gataaaagaa   240 aaaaaaagt gtggtaatca atagaaaaaa aaaagagwaa aatcattcaa atcattcaat   300
agaaaagtgt ggggttgttt aattgatgtt ttatattaaa aaattagatg aaattcatcc   360
aaatcattct taaaaaataa tgcatcaaaa tttgtatatt t                      401

<210> SEQ ID NO 258
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 258
agcaagttat aaacataatc amtaaaactc atcataagaa aaaaaacatg attagtcttg    60
acacataaga taaacattaa tttaatttaa aaacaaagr aaaaagtgta gaggggagac   120
atatatttga catttttat ttcaaaagaa taagagaaat atatatgtg cttgcatctt    180 gawgaacatt aaatagataa gaagatatgt gtgataaaag aaaaaaaaaa gtgtggtaat   240
caatagaaaa aaaaagagw aaatcattc aaatcattca atagaaaagt gtggggttgt    300
ttaattgatg tttatattaaaaaattaga tgaaattcat ccaaatcatt cttaaaaaat    360
aatgcatcaa aatttgtata ttttttaaata ttaaaagact t                     401

<210> SEQ ID NO 259
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 259
```
tggtaatcaa tagaaaaaaa aaagagwaaa atcattcaaa tcattcaata gaaaagtgtg    60
gggttgttta attgatgttt tatattaaaa aattagatga aattcatcca aatcattctt   120
aaaaaataat gcatcaaaat ttgtatattt ttaaatatta aaagactttt ttataagtta   180
taaaaaatta taattgaata tcacmaaatt ttattatttt tcttaaaaaa tcttawatgt   240
tttaattgaa taccataaga cttttttata taaaaahtat tttaaaatct tttmaaatct   300
taatcyaata tatccactaa gttatyaaag gctaggagga aacaagtgga scatgagaca   360
atacatatat aggggggaat atatggaaat tgaaaaaaaa a                       401

<210> SEQ ID NO 260
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 260
aatcaataga aaaaaaaaag agwaaaatca ttcaaatcat tcaatagaaa agtgtggggt    60
tgtttaattg atgttttata ttaaaaaatt agatgaaatt catccaaatc attcttaaaa   120
aataatgcat caaaatttgt atatttttaa atattaaaag acttttttat aagttataaa   180
aaattataat tgaataycac caaattttat tattttcctt aaaaaatctt awatgtttta   240
attgaatacc ataagacttt tttatataaa aahtatttta aaatcttttm aaatcttaat   300
cyaatatatc cactaagtta tyaaaggcta ggaggaaaca agtggascat gagacaatac   360
atatataggg gggaatatat ggaaattgaa aaaaaaaga t                        401

<210> SEQ ID NO 261
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 261
tagatgaaat tcatccaaat cattcttaaa aaataatgca tcaaaatttg tatatttta    60 aatattaaaa gacttttta taagttataa aaaattataa ttgaataycac cmaaatttta   120 ttattttcct aaaaaatct tawatgttt aattgaatac cataagactt ttttatataa   180
aaahtatttt aaaatctttt caaatcttaa tcyaatatat ccactaagtt atyaaaggct   240
aggaggaaac aagtggasca tgagacaata catatatagg ggggaatata tggaaattga   300
aaaaaaaaag atgtgaaaaa taataaatct caatagaaaa tgaaggaagc ataaatgaaa   360
taaaagtgaa atcaggtgat gagataaaaa acaattgtst a                       401

<210> SEQ ID NO 262
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 262
ataatgcatc aaaatttgta tattttttaaa tattaaaaga cttttttata agttataaaa    60
aattataatt gaataycacm aaattttatt attttctta aaaaatctta watgttttaa   120
ttgaatacca taagactttt ttatataaaa ahtatttta aatctttma aatcttaatc    180

```
yaatatatcc actaagttat taaaggctag gaggaaacaa gtggascatg agacaataca    240
tatatagggg ggaatatatg gaaattgaaa aaaaaaagat gtgaaaaata taaatctca     300 atagaaaatg aaggaagcat aaatgaaata aaagtgaaat caggtgatga gataaaaaac    360
aattgtstaa aaaaattgac gataagtcta aataaataa a                        401
```

<210> SEQ ID NO 263
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 263

```
ttmaaatctt aatcyaatat atccactaag ttatyaaagg ctaggaggaa acaagtggas    60
catgagacaa tacatatata gggggggaata tatggaaatt gaaaaaaaaa agatgtgaaa   120
aataataaat ctcaatagaa aatgaaggaa gcataaatga aataaaagtg aaatcaggtg    180
atgagataaa aaacaattgt gtaaaaaaat tgacgataag tctataataa ataaaaagtg    240
aggtcatata catattcccg atttctataa aaaaaaatga atatttgaaa atcaattcat    300
tttcaatytt taaaaaataa ataaaaaaga attgaagttg tatatcaatc tatggagaat    360
taattcaaaa aatgatttat agaagttagc aatagaaaaa t                       401
```

<210> SEQ ID NO 264
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 264

```
aaaagatgtg aaaaataata atctcaata gaaaatgaag gaagcataaa tgaaataaaa     60
gtgaaatcag gtgatgagat aaaaaacaat tgtstaaaaa aattgacgat aagtctataa   120
taaataaaaa gtgaggtcat atacatattc ccgatttcta taaaaaaaaa tgaatatttg   180
aaaatcaatt cattttcaat tttaaaaaa taaataaaaa agaattgaag ttgtatatca   240
atctatggag aattaattca aaaatgatt tatagaagtt agcaatagaa aaatacgtac    300
taacattata agaaagagaa aatattttaa gagataaata gcaaataat atttatttaa    360 stgaatgagt atcttaaacc atatatcaaa atttacaaca c                       401
```

<210> SEQ ID NO 265
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 265

```
taaaaaaaaa tgaatatttg aaaatcaatt cattttcaat ytttaaaaaa taaataaaaa    60
agaattgaag ttgtatatca atctatggag aattaattca aaaatgatt tatagaagtt    120 agcaatagaa aaatacgtac taacattata agaaagagaa aatattttaa gagataaata   180 gcaaataat atttatttaa gtgaatgagt atcttaaacc atatatcaaa atttacaaca    240
cattaaaatg aaaaatctta aaagaagga acaacaaaac ttttttatgaa aattataacc   300 aaaaaaaaat aaaaattaat ataagcttta acatttctttt tgttgaagta ctaatatataaa 360 gcttaacatg atagctagga taagcactat cctatggcca c                       401
```

<210> SEQ ID NO 266
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 266
ttttggtaaa cagatttaat ttgatgtaaa tcatattaac ataattaata ttaggtattt    60
taataatttt ttattatttt atttgtattg ttcattawtt gttraataat atataagata   120
aaaaacattt tgtcatttat ctttatccta tcttattttt tatcttgtct aatatcatat   180
ttttaacaaa tcaaatwggg tgtaagtgtt tgataaattt tttcaaacaa attacaaatg   240
ttaatatatt ttatttttc aacaaktaat atgttaatct taataaacaa attcacattt    300 tattttttcat ttaccaaaat agatatatta tttttaaata ttgtttgaaa taaataatt t  360 ataattaatt waaaaaaata awaatttcat ttcgtaacat a                       401

<210> SEQ ID NO 267
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 267
attttttatt attttatttg tattgttcat tawttgttra ataatatata agataaaaaa    60
cattttgtca tttatctta tcctatctta ttttttatct tgtctaatat catatttta    120 acaaatcaaa twgggkgtaa gtgtttgata aattttttca aacaaattac aaatgttaat   180
atattttatt ttttcaacaa ttaatatgtt aatcttaata aacaaattca cattttattt   240
ttcatttacc aaaatagata tattattttt aaatattgtt tgaaataaat aatttataat   300
taattwaaaa aaataawaat ttcatttcgt aacatatttt tcacattgaa ataaacatgt   360
acgacacaca tatatacata catatatata tatatatata t                       401

<210> SEQ ID NO 268
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 268
aaaaataatt catattaata taccaactta agaaagctgt taaatatatt aaaaaaagga    60
aatatgttat tattaaatca aattttcatc agttaacaac caacatttta atctaatta    120 gttgtttaaa caaatttgt atgtattata aattttaat attattttta ttttttaaaaa   180 taaaaaacag tgaaaacaat caaccttgca ttatcatata tagtcaatta aaaaaaagga   240
atgagtgaag gggaaaaagt ggaggaaaag gtaatggatt caattccttc cattaatatt   300
ttaaacaaaa attaataaat taacatattg gtaaaaaata taatattaat ttcttgaaaa   360
tttgtatcca gtagtacaac attataaatt attttttagg t                       401

<210> SEQ ID NO 269
<211> LENGTH: 401
<212> TYPE: DNA
<213> ORGANISM: Artificial Sequence
<220> FEATURE:

<223> OTHER INFORMATION: Consensus Reference Sequence

<400> SEQUENCE: 269

```
ttctgccaat ggaagggtat ccaatgcgat tcatccagcc acgtgaccag cataagcctc    60
gcttcgcakt ccctcaccgg aacactcccc tcggatctca attccctctc tcaactccgc   120
actctctccc tccaagacaa ttccctcacc ggcaccctcc cttctctctc caacctttct   180
ttcctccaaa ccgtctactt caaccgcaac aacttctcct ccgtgtcccc caccgcyttc   240
gcctccctaa cctccctcca aaccctcagc ctcggctcca accctgctct ccaaccctgg   300
tccttcccca ccgacctcac ttcctcctct aacctaatcg acctcgacct cgccaccgta   360
tccctcaccg gtcccttgcc ggacattttc gacaaattcc c                       401
```

<210> SEQ ID NO 270
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 270

```
agccacgtga ccagcataag cctcgcttcg caktccctca ccggaacact cccctcggat    60
ctcaattccc tctctcaact ccgcactctc tccctccaag acaattccct caccggcacc   120
ctcccttctc tctccaacct ttctttcctc caaaccgtct acttmaaccg caacaacttc   180
tcctccgtgt cccccaccgc tttcgcctcc ctaacctccc tccaaaccct cagcctcggc   240
tccaaccctg ctctccaacc ctggtccttc cccaccgacc tcacttcctc ctctaaccta   300
atcgacctcg acctcgccac cgtatccctc accggtccct gccggacat tttcgacaaa   360
ttcccttccc ttcaacacct tcgcctctct tacaacaacc t                       401
```

<210> SEQ ID NO 271
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 271

```
gttcccgctt cattgacaag tcttcctagt ttgaagaaag tttctctgga taataatgag    60
cttcaggggc ctgtgcccgt gtttgggaaa ggtgtgaatg ttactctcga tgggattaat   120
agttttgtc ttgatactcc tgggaattgt gatcccaggg tgatggtttt gctgcagatt   180
gccgaggcat tcgggtatcc gattcggtyg gcagagtcgt ggaagggaa tgatccgtgt   240
gatggttgga actatgttgt gtgtgctgcc ggaaagatta ttactgtcaa tttcgagaaa   300
cagggtttgc agggtaccat ctcccctgca tttgccaatt tgactgactt gaggactttg   360
tttctcaatg gcaataattt gatcggttct atacctgata g                       401
```

<210> SEQ ID NO 272
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 272

```
aaggttgctg attttgggtt ggttaaaaat gcaccagatg ggaagtattc tgttgagaca    60
cggttggctg gaacatttgg atatcttgca cctgagtatg caggtacaga aagcctttga   120
```

```
ttttagttttt gtacaattgt gccttaattt tgaagttcat attttatatg ctcgtatttg      180
gtggttatag ctgttggtta ttacttcaat atcatgcttc ggtgttcagc aaatttaagt      240
agttcaccag agtaatcgct cacatacaaa aaaaaagtag aaagagttga agggaaaata      300
attgatactc aattcctaga tacatggcta cttcaaaatt ctttgtggct atttctttgc      360
aatgttatat tttgctcttt tcacgtgttt tgttgagttg g                          401

<210> SEQ ID NO 273
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 273
ggagcaatgg aaacctacta gccatgatga agaagaggaa gacggctctg gcggtgacct       60
tcatatgagc cttcctcaag ctctacgaag gtggcaagcc aacgaaggca cttcctcaat      120
atttaatgac atttccatct cacaaaccca atcaagcatc tcctctaaac ctgcagggtt      180
tgcagactcc tttgattcaa tggattgccg ttaaccgaat tgataaacga acaactatc       240 caagggcatc ttagtccata tgatagtgga aggtttagtt gagaataccc aagaaaacca      300
gaggttgtaa agctgttttg atctattagc atcgccaatt tctttgtaat tatttattat      360
tgttcaaaat gtcattttta tggtgttctt aaaatctcct c                          401

<210> SEQ ID NO 274
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 274
caagatttgt aagagaaaac ttcttggctc tatatttaas aacaaaaaat ctaagakraa       60
atgggattka atggaaatga tcggtcgcaa gcatatctaa atttgacagg aaatccataa      120
atgacttgac caccattaac aagataaata ttgtgtgaga tctttaaaar tgaagatttt      180
acgggtttaa cagattaaaa tcttttacaa tttaatatca cattcttttg aacacatgaa      240
cacttattga tgatagttac attccatgct tgctttcctt gcactttatt ttttgttgga      300
aattgatcta yggagagatc tttcaaggaa cattggctat agctgacatg atgatwgrag      360
gaaaaattac aaacaataat ttatacaaat tttatgtttc a                          401

<210> SEQ ID NO 275
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 275
tamaatagaa gaaaccagta tcttgacttc ttgagaaatg aggacaagga gcaaaactat       60
gctaagaatc ttgatggctg aaccasccat ttcagaaaat gtaaatacaa gcttcgattc      120
tcgaattgca tagctcttat atgtcgcgtt atttataaat gaattgttgt aatttgtaaa      180
acaatatgtt ttacgtttcg tgtgaagaat atcrcattta tgaatgactg aattttttaag      240 acaatgaaac tgaagttaaa gaaacataaa ttactctaaa aaaaattaaa tacagtgaaa      300
```

```
ttgtatagat ttgataaata ttttttttaat agttgatatg attttgtttt gttaggagaa    360
agctatcatt ttgttctcct atagttatst ttagyaagtt a                         401
```

<210> SEQ ID NO 276
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 276

```
accagtatct tgacttcttg agaaatgagg acaaggagca aaactatgct aagaatcttg    60
atggctgaac casccatttc agaaaatgta atacaagct tcgattctcg aattgcatag    120
ctcttatatg tcgcgttatt tataaatgaa ttgttgtaat ttgtaaaaca atatgtttta   180
cgtttcgygt gaagaatatc gcatttatga atgactgaat ttttaagaca atgaaactga   240
agttaaagaa acataaatta ctctaaaaaa aattaaatac agtgaaattg tatagatttg   300
ataaatattt ttttaatagt tgatatgatt ttgttttgtt aggagaaagc tatcattttg   360
ttctcctata gttatsttta gyaagttatt ttaattaaat t                       401
```

<210> SEQ ID NO 277
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 277

```
ttttacgttt cgygtgaaga atatcrcatt tatgaatgac tgaattttta agacaatgaa    60
actgaagtta agaaacata aattactcta aaaaaatta atacagtga aattgtatag      120 atttgataaa tattttttta atagttgata tgattttgtt ttgttaggag aaagctatca   180
ttttgttctc ctatagttat gtttagyaag ttatttttaat taaatttttt tattaattaa   240
aagatttatt tgactatttg ataaataatt ttttaagta attttttaatg tttctctagt   300 atyttttagt attttttttaa aatattattt aaaataacat ttttaaaaca ctaattttta   360 attttttaacc ttttaatttt attctcttta tatcttaaaa t                      401
```

<210> SEQ ID NO 278
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 278

```
gtttcgygtg aagaatatcr catttatgaa tgactgaatt tttaagacaa tgaaactgaa    60
gttaaagaaa cataaattac tctaaaaaaa attaaataca gtgaaattgt atagatttga   120
taaatatttt ttttaatagtt gatatgattt tgttttgtta ggagaaagct atcattttgt   180
tctcctatag ttatstttag taagttattt taattaaatt ttttttattaa ttaaaagatt   240 tatttgacta tttgataaat aatttttttta agtaatttt aatgtttctc tagtatytttt   300 tagtattttt ttaaaatatt atttaaaata cattttttta aacactaatt tttaattttt   360 aacctttttaa ttttattctc tttatatctt aaaatattta t                      401
```

<210> SEQ ID NO 279
<211> LENGTH: 401

```
<212> TYPE: DNA
<213> ORGANISM: Artificial Sequence
<220> FEATURE:
<223> OTHER INFORMATION: Consensus Reference Sequence

<400> SEQUENCE: 279
taacttttca gtttactttt gcaaataaya tatttctttc ctggmatatk acaaagctaa      60
acaatatttc ttgagtgttt aattgtttta aattgaaata ggaagtgagc atttmctaat     120
atcttagctc gaaacatctc tttcatcttt gttgaagtaa acctctgtat ggtaaaatta     180
agaggagaaa gaaaaatgaa gtggagtaag gtcttgtttg aaattatttt ttaatttcaa     240
aacttgtttt caatataatt tttagctttg ttatatttta aaaataaaat aaaaagaaaa     300
aayatttgtt aaaattcaaa atagatttt ttttaaaaaa atgttcataa aatatcagca      360
tytgtcaatt gcatgtttat gaggtaaaaa attgctttat t                         401

<210> SEQ ID NO 280
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 280
aagtgagcat ttmctaatat cttagctcga aacatctctt tcatctttgt tgaagtaaac      60
ctctgtatgg taaaattaag aggagaaaga aaatgaast ggagtaaggt cttgtttgaa     120 attattttt aatttcaaaa cttgttttca atataatttt tagctttgtt atattttaaa      180
aataaaataa aagaaaaaa tatttgttaa aattcaaaaa tagattttt ttaaaaaaat       240 gttcataaaa tatcagcaty tgtcaattgc atgtttatga ggtaaaaaat tgctttattt     300
atgaaaatat ttaggatcca aaacaagagt aggaaagtaa tttttaaaag acattttttt     360
ccagcactgc aattgtagga acaagtttta aaatacaaat g                         401

<210> SEQ ID NO 281
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 281
cctctgtatg gtaaaattaa gaggagaaag aaaaatgaas tggagtaagg tcttgtttga      60
aattattttt taatttcaaa acttgttttc aatataattt ttagctttgt tatattttaa     120
aaataaaata aaagaaaaa ayatttgtta aaattcaaaa atagattttt tttaaaaaaa      180
tgttcataaa atatcagcat tgtcaattg catgtttatg aggtaaaaaa ttgctttatt     240
tatgaaaata tttaggatcc aaaacaagag taggaaagta attttttaaaa gacattttttt   300 tccagcactg caattgtagg aacaagtttt aaaatacaaa tgycttgaaa atctttctaa     360
tacttaatgg aaaatattaa ataaaaataa aaataaaaat a                         401

<210> SEQ ID NO 282
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 282
```

```
taggaaagta attttaaaa gacattttt tccagcactg caattgtagg aacaagtttt    60
aaaatacaaa tgycttgaaa atctttctaa tacttaatgg aaaatattaa ataaaaataa   120
aaataaaaat aaaaatattt aatgttttaa aaactttaaa aacattcaaa tactttcttt   180
atttaataag aggaggatga tgggattaga attattcaat ttttttatat taaaatataa   240
cgaatccata acaaatttac agtagtactt tgtttcataa aaaaatactg attggatgaa   300
gcagakagga gagaggaaga tgtcagtaag tcataaatgt gccattaata catttaataa   360 ctttttttt ttacaaaagg gagaaaggct tacatttaaa t                       401
```

<210> SEQ ID NO 283
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 283

```
tttttttttt tacaaaaggg agaaaggctt acatttaaat tgctattact tttttaaac    60 gaaaagggg tgaaacgccc aaaataaatc atcataaata agataataag ataaggaagg   120
agaaaataaa tttaaatatt gatcacaaat aaattttgya taaatacaaa taaaatataa   180
gataataaat atcgatcaat tcgtgaaaca atttgcggaa gagcaaaatt tgagaaaaaa   240
aatcgaagaa rcaaaattcg cgatattata aaacttaga gataaaaaaa aattcatgat   300
aaataataca gtatattata attttaatct ttagttttta atacaactgt aaaaaaaatt   360
catgataaat aatatattat aattataatc tttagtttta a                      401
```

<210> SEQ ID NO 284
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 284

```
aacttttgt tagtaacaga aagtgtaaac tggtttggag aaaatgtgag agatggcagg    60
atactatgag taactagttg gattggaaaa tgttgtatcc agctgtaaat tacccattcc   120
attattggaa ggaaatattc cgcatgagcc aaactatgcg aaaatgacat ggtgaaaatt   180
gataaaggta agaaaaagt ggagctcaga aaggtgttat tcttcatcaa gaagagctat   240
ttccaaagca actatrttac ttgtgcaact ctttatttt tgtacatata ctactattat   300
tattacttgt gctactctga taaatagaaa gtagaaaaca aagaagtggt attgattgat   360
gttacgtaag ttacataaaa gtttgatgcg tattgattga t                      401
```

<210> SEQ ID NO 285
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 285

```
acaaagcaat ggatccagga ctcatatatg atatcaccac tgaggattat gtccaattcc    60
tatgttccat ggatcacagt agtgcatcca ttagcaaagt gactaagacc accacaagtt   120
gtaagaaagg aaatcaccaa gcactgaacc tcaaccttcc ttccatatca gtgccaaacc   180
tgaagagggc tgcaacagta ttgagaacag tgacaaacgt gggaaatatt actgcagtct   240
```

```
rcaaagctct agtgaaagtt ccacatggca taaaagttag agttgaacct caaactttga    300
gtttcaattc agrtgtacga atccttaact ttaktgtcag ttttctgtca actmaaaaat    360
ttcatggaga ttacaaattt gggagcctaa catggacaga t                        401
```

<210> SEQ ID NO 286
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 286

```
taatattttt tcttttaaa atacagawgg aagtacaaga ataaaaagtg gttcaacttc    60
catgaataaa aatggtctttt acatgatttg cacttaatct aaataaccaa gcacaaaata   120
tatcaaaywt gtgtatattt tcagtttagt attaattatt aatgactagc aatagaattt    180
agatttatag agacaataca gttagtaaat tttattttag aaattatttt aaaatattct    240
aataattaaa ttactctttt gtttttacat tgcaagtgca agcatctayg tgcaaaagga    300
gggtacgata ctcaacaata gataaatttg cacaacatca tcagtctttg ttyttcttt     360 tcttttttac tttagatacg taaggcagta acaacatacg a                        401
```

<210> SEQ ID NO 287
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 287

```
gacaaaagat aagagaaaca agcttacatt actcaacgt tataagaagc aaataaccta     60
cgaagaaaat caagataaat aaatagatgg tacaaatttg catgtgttcg gatatccatc   120
gacatcattc atttcgatca aaattcacgt tttggacata aaagcaattc ttcgtcgctt   180
cagataatgc gtgtcgtgga gcagaggatg caaaaccata catgcagaaa attatgcttg   240
cagaatgaca cwtacgatgg agcaccaaga tatgaggcaa gtcgtaaaat atcactaaat   300
attccaccag cggtgacttg agcaccagct cctggcccac gaactatcag aggctgatcc   360
ttataccttc gtgttgtaaa tgcaataatg ttatctgacc c                        401
```

<210> SEQ ID NO 288
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 288

```
ctgttattga ttgatsaatc acttattact atctgatgga agatgagttt tatataatag    60
agttaccttg tcctgcaagc ttacaataga aamttcagct gyctacagct attaagacta   120
actaaacttc agttaagcca atattaattg tgttttacta tttaagtcct agtttacaat   180
ttctcctata tttttatttc tattacttgt ttcgaaagca atcatctgaa ttttctctat   240
cttcttgtat aatgataaga accttgggag atctacacca caaaaactag tcattgtagt   300
ttggagagcc aaggacctta tacatcctaa acttcaaatg tgagactcaa gtctcatacc   360
ttgcaattgg atcctaacat tccatcttgc tttgcagcca c                        401
```

<210> SEQ ID NO 289
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 289

```
aaatgtagaa tgataaatct tcagtctgat atcactaaag agagtcaagt cttaacaatt      60
gaacagaaac atgcatttgg ttttagaaga attggattta gcacctgaga aagacgccca     120
ttatccaaag cttgacgaaa tctagattgc aatgcctcag caacagcttt tacttctttc     180
tcgggcacag caaagcatac tgaatgctca ctactagcct acataaatac tgttaatgat     240
taatgccatt tcttatatat carcgtggac aactagaaaa attgaaaaaa gttataagtg     300
cacctgagat atcatgataa cattagctcc aacatctttt actgcaccaa aaatagcact     360
ggcagtacct ggaacaccag ccattccagt tctgcaaaaa a                         401
```

<210> SEQ ID NO 290
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 290

```
ttaatgccat ttcttatata tcarcgtgga caactagaaa aattgaaaaa agttataagt      60
gcacctgaga tatcatgata acattagctc caacatcttt tactgcacca aaatagcac     120
tggcagtacc tggaacacca gccattccag ttctgcaaaa aagcatcaaa gaaaaattta     180
ttggaatcta caacttggac tattaatatt ggttaaagaa aaccttaaat taaatagaaa     240
tcctcgtgca gcaaaaaatg ccaactattc atcatgtaac acaactgcaa ttcatgactc     300
accctcgac gtttacaagt gccaagttgt ctatggttgc aaatcctttg acaaaatttt     360
gcaggttctg gctatcttca tgatcattaa cagaaggatg g                         401
```

<210> SEQ ID NO 291
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 291

```
cttgtggata aggtcataca tcatatctgt cacctttgac attgcagaaa caaccaccaa      60
tttcctctcc gaatcatcct taagaattat gtcygcaaca tttttttatt ctctgagagt     120
tcccacacag gttccaccaa atttgtgaac agaccaagtt tctcctttgg gtagttgttt     180
ttcctccaag gacacattcg gtgaaacatc tgctagcaaa tatagaaagg acaaaaaaac     240
ataagttact gtatttgtct attagagttc taaggttgac ttgatggtaa aaggagaagg     300
gagagaggga aaggtcgtgg gtgggttcaa ttttctccgc taacaaaaaa ctaacaatta     360
acaactaata tttgctgata ataaaaaaaa ctrtattcgt c                         401
```

<210> SEQ ID NO 292
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 292

| gaagggagag agggaaaggt cgtgggtggg ttcaattttc tccgctaaca aaaaactaac | 60 |
| aattaacaac taatatttgc tgataataaa aaaaactrta ttcgtctatt tcaaaacata | 120 |
| accataagag taagtcgtaa cctgtaaatg aagcacgtac agatgtactc ggtgcctctc | 180 |
| ttccccgtgg taaagtaaga cccttcctga dacagaaacc attgtatcgt cgtgaatcag | 240 |
| tatatagcaa acacaaaaa tccaattaat ctcatgggga gaatatcatt taaactgcca | 300 |
| aaattccgaa aacactctaa tctctgcaaa ggataaatat acaaaaagga aaaaaaaag | 360 |
| tacagaatat actgcttgta gaacaaccaa tcatctaaga g | 401 |

<210> SEQ ID NO 293
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 293

| ttgagttgaa ataatgaaat gaaatggatc ataatccatc atcatcttcc attatgtttc | 60 |
| atttcaactt ttacaaatca aacaatccaa cacctttttcc ttccactcca tccttcttca | 120 |
| ttccatactc tacaaccaat caaaacatat tcgaaggttt ccatgtatgt agaattataa | 180 |
| ataggttgaa caaaatttta ttgrgtaggt tgaamagaat tatttggtay tattattcgt | 240 |
| acgcccctaa ccatgtgttt ggatgaagaa tttaaaaatt tctaagaaat ttaaattcat | 300 |
| aacattttaa ttgccttgat tttaattcct ttccttttgt aaatatttg tttggatgag | 360 |
| gtaattcaaa ttcttgtatt ttaatttct tstttggaca a | 401 |

<210> SEQ ID NO 294
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 294

| aatgataaca aattgtacat attatagact aaaatgacaa taattttaat ctaaacaatt | 60 |
| tatttatatt tttttaattt tatgatgtgt taaattgtga cagtgcccta caattttaaa | 120 |
| gaacgtacaa aataattatt tattcaaaat tttaaacata acattacctt tccctacaac | 180 |
| gtcccccga tagtgtcatc ggtaggactc ttgcttcaga acaaaacgcg agtccatata | 240 |
| aggcaactgc aattttttta attagtcttc cgtttgtttc gggggctaat ggggaattat | 300 |
| agcaagtgtg akaattttct atgcttttaa actaaaatct acatatttat aaaaatataa | 360 |
| aagtaaaaaa aaaatgccac ggatagttca gtcaaagata a | 401 |

<210> SEQ ID NO 295
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 295

| aattttaaag aacgtacaaa ataattattt attcaaaatt ttaaacataa cattacctttt | 60 |
| ccctacaacg tcccccgat agtgtcatcr gtaggactct tgcttcagaa caaaacgcga | 120 |

```
gtccatataa ggcaactgca attttttttaa ttagtcttcc gtttgtttcg ggggctaatg      180
gggaattata gcaagtgtga taattttcta tgcttttaaa ctaaaatcta catatttata      240
aaaatataaa agtaaaaaaa aaatgccacg gatagttcag tcaagataa  ttcgaaatca      300 tagtaaatat taaatgattg gattttacaa catstatttg aaaagagtcat cataaaactt     360 aataccacay tttaaccmaa aactttaaaa gtcaacttta t                          401
```

<210> SEQ ID NO 296  
<211> LENGTH: 401  
<212> TYPE: DNA  
<213> ORGANISM: Artificial Sequence  
<220> FEATURE:  
<223> OTHER INFORMATION: Consensus Reference Sequence

<400> SEQUENCE: 296

```
ccaatcctat tatgttaccc aagatgycgt wagttctcta ggtggttttt tcraaacaaa       60
aaaaawttat ttgtaataaa ataaataata ttacttcatt ctcatgtctt tttatattta      120
aggttattat taagaaatat ttgatgaaaa taaacattgt tcaccctcgt agcctccgtt      180
atggcgagag tgcctctcat ttgcgttccr aacagcccta gcttrcacca taatgggttg     240
tgtcaccctc gtagccttcc ytgcattctc attatcataa acgaygccgc tttgggagac     300
gccttccatg tctatrccac ccttcagagc ataggcccca ccatcttgag cttgtgggyt    360
gtcggactag ggycgctctc taaagycacc accgctgtag c                         401
```

<210> SEQ ID NO 297  
<211> LENGTH: 401  
<212> TYPE: DNA  
<213> ORGANISM: Artificial Sequence  
<220> FEATURE:  
<223> OTHER INFORMATION: Consensus Reference Sequence

<400> SEQUENCE: 297

```
gagagtgcct ctcatytgcg ttccraacag ccctagcttr caccataatg ggttgtgtca      60
ccctcgtagc cttccytgca ttctcattat cataaacgay gccgctttgg gagacgcctt     120
ccatgtctat rccacccttc agagcatagg ccccaccatc ttgagcttgt gggytgtcgg     180
actagggycg ctctctaaag tcaccaccgc tgtagcggtg gcgctcgccg cgtttgtggt     240
ggttctttcc trgcctcaga gcacaaattt gatagctaaa cgcatatcat tgggtcagat     300
agtaccacca tgttgaaatt ragaggaaag aagtttttaaa aaccctaatt tgaggaagaa    360
gaagcaagtg aagaagaaaa tatttgacaa cttttttaaaa t                         401
```

<210> SEQ ID NO 298  
<211> LENGTH: 401  
<212> TYPE: DNA  
<213> ORGANISM: Artificial Sequence  
<220> FEATURE:  
<223> OTHER INFORMATION: Consensus Reference Sequence

<400> SEQUENCE: 298

```
gttgtgtcac cctcgtagcc ttccytgcat tctcattatc ataaacgayg ccgctttggg       60
agacgccttc catgtctatr ccacccttca gagcataggc ccaccatct tgagcttgtg      120 ggytgtcgga ctagggycgc tctctaaagy caccaccgct gtagcggtgg cgctcgccgc     180
gtttgtggtg gttctttcct ggcctcagag cacaaatttg atagctaaac gcatatcatt     240
gggtcagata gtaccaccat gttgaaattr agaggaaaga gtttttaaaa  accctaattt    300
gaggaagaag aagcaagtga agaagaaaat atttgacaac ttttttaaaat ttgcatcaaa    360
```

```
gtccagctta catgtcataa tctaggacaa tttgwcacgt t                         401

<210> SEQ ID NO 299
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 299
ccatgtctat rccacccttc agagcatagg ccccaccatc ttgagcttgt gggytgtcgg      60
actagggycg ctctctaaag ycaccaccgc tgtagcggtg gcgctcgccg cgtttgtggt     120
ggttctttcc trgcctcaga gcacaaattt gatagctaaa cgcatatcat tgggtcagat     180
agtaccacca tgttgaaatt gagaggaaag aagttttaaa aaccctaatt tgaggaagaa     240
gaagcaagtg aagaagaaaa tatttgacaa cttttttaaaa tttgcatcaa agtccagctt    300
acatgtcata atctaggaca atttgwcacg ttagataatc tatgtgacay taaaattatt     360
aaaaatatat ctcattaatg gygttayttt taaatttaac g                         401

<210> SEQ ID NO 300
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 300
tgcatcaaag tccagcttac atgtcataat ctaggacaat tgwcacgtt agataatcta       60 tgtgacayta aaattattaa aaatatatct cattaatggy gttaytttta aatttaacgg     120
caaakactat tttrtaaaat ttatgcaaaa atagagacta ttttttacat ttaaaaaag     180 ataaagacta atttgcaaaa ggaatcaaaa gttagaaatc aaaataccta tttayttaaw    240
aaaaaaaaca tcatgcgtta gttataacct taacttctaa tttttttgcta acgcccaaaa    300 aaactaagaa ttcgaatcag aagtaggyag aatagkcaat ttggttctta aaagtgtatg     360
gaaggaaaaa wtttcctttg acttttttaaa ttggaacacg t                        401

<210> SEQ ID NO 301
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 301
aaaatttatg caaaaataga gactattttt tacatttaaa aaagataaa gactaatttg       60 caaaargaat caaagttag aaatcaaaat acctatttay ttaawaaaaa aaacatcatg      120
cgttagttat aaccttaact tctaattttt tgctaacgcc caaaaaaact aagaattcga     180
atcagaagta ggyagaatag tcaatttggt tcttaaaagt gtatggaagg aaaaawtttc     240 ctttgactttt ttaaattgga acacgtcttg atttttttcc cttgttgccc aaaagcagtc    300
ttattattca tccgttggga attttgtgtt tt aatttcgct gatmaaaaaa ttgagaattt   360
tatgtctgct ttgtgaatta ccattttwtc ggaacctgca t                         401

<210> SEQ ID NO 302
<211> LENGTH: 401
<212> TYPE: DNA
```

<213> ORGANISM: Artificial Sequence
<220> FEATURE:
<223> OTHER INFORMATION: Consensus Reference Sequence

<400> SEQUENCE: 302

```
tagaagkaat aattttgttt tggcttgttg aattggaaaa tgttacagtc ccggtcattc      60
tttttatttt tatatgttta tttattttg tccaaatagc agggtcatat tcaaaacttg     120
ggttttactt tcaagctttg gaacaatgtt agtgtaattt gtgacttttg ataaagccaa    180
agaagtaact ttcgttctta ttttcatgtg acttgtaaca agttacaagt cagtaatata    240
acctataact twytcttcat crtctgcttc ttcttttgat cataatatct gttaagtgat    300
ctttcataga gagagagaga gagagatgga gaggtgtgac aaggtgatga accaacgcaa    360
catgcatgat tgtcctaaaa caggtcctgg ctatccttca c                        401
```

<210> SEQ ID NO 303
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 303

```
tctgaaaagg ccaattcagc ttcattggag gaatagatag gcattaggca gagagatcaa     60
gataggtttc tcaagttgtt gttacaaaca ttttatatga catgatactg ggaacaagtg    120
acatgtagaa atatctatct ctttctagtg ctatgcatga agacttggtg cagcttaaac    180
aatttctgtc aaaacgtgta ttttggtgat tttatatata tatattggtg atgaatattc    240
aattcaatgc aggaacagga agggataagc ctgactttct ggccacagtg gatgtggatc    300
caagctctcc aacgtattca aaagttatcc ataggttacc tgtaccttat ttaggtgatg    360
aactgcacca ttttgggtgg aattcatgca gctcttgcta t                        401
```

<210> SEQ ID NO 304
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 304

```
gtgatgaact gcaccatttt gggtggaatt catgcagctc ttgctatgga gatccatcag     60
cagttcggcg atatctgatt ctaccttcac tggtgtaaga tactaaacag ccactttgga    120
ttttacttgc acgcatatgc gcatgcayac acacacataa caaacactga caaggttcaa    180
gaacttcact ggtgtaagac gtcggttttc ttgaaacgaa atccttatta agtcagattt    240
accatatttc agatcaggcc gcatttatgt ggttgacaca agatcaaatc caaggtctcc    300
atctttgcac aaagttgttg agccagaaga catcataagt aagactggat tagcttatgc    360
acacacatct cattgtcttg cttctggtga cgtcatgatc t                        401
```

<210> SEQ ID NO 305
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 305

```
ctggtaccaa ccacagcata agactatgat tagctcatca tggggtgctc ctgctgcttt     60
```

```
caccaaaggt tttaacttac agcatgtctc tgatggtctt tatgggaggc atctacatgt    120
atacagctgg cctgggggtg aactgagaca acattggac cttggtgagt caggggttct    180
acccttggag gtacattgct taataaataa ttctggagtt atttccwcca attataagca    240
ctttatgtta atgtacttgt gatttaatca taaatatgtt tgtcctttgc tacattttt    300 ctctctagcc tgtacttgtg aagtaatatg ttaaaggtgg cataatttgt aagcaacttg    360
tcctaaatgc aggtaaggtt tctgcatgat ccttctaaag a                        401
```

<210> SEQ ID NO 306
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 306

```
tgattagctc atcatggggt gctcctgctg ctttcaccaa aggttttaac ttacagcatg     60
tctctgatgg tctttatggg aggcatctac atgtatacag ctggcctggg ggtgaactga    120
gacaaacatt ggaccttggt gagtcagggg ttctacccct tggaggtacat tgctyaataa    180 ataattctgg agttatttcc tccaattata agcactttat gttaatgtac ttgtgattta    240
atcataaata tgtttgtcct tgctacatt ttttctctct agcctgtact tgtgaagtaa     300
tatgttaaag gtggcataat ttgtaagcaa cttgtcctaa atgcaggtaa ggtttctgca    360
tgatccttct aaagatacag gtttcgtkgg gtgtgcattg t                        401
```

<210> SEQ ID NO 307
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 307

```
gtcaagtaac atggtacggt ttttcaagac cgaggatgaa tcatggagtc atgaggtaca     60 caaaaggat atagtaaaaa atcaatgcct aaatttagg agaatcatga catctcatta    120
atcagaaggt ttacattcag ctattctatt tttatttcat tcctataatt ttgggattcc    180
tggttcttgg aatttccttt ttaattttct tcacctttc tatatattgt atctgtgctc    240
atatgaaata atagagatga tataattttc atactctact ctactcatag atatccatac    300
tcattttrta ttgtcatctg gtatgcgttt gtgcagcttc aaccaaggta taatgatcaa    360
taatacttac acactagact gactttgcag gttgcaatat c                        401
```

<210> SEQ ID NO 308
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 308

```
tgacatctca ttaatcagaa ggtttacatt cagctattct attttttattt cattcctata     60 attttgggat tcctggttct tggaatttcc tttwtaattt tcttcacctt tctatatat    120 tgtatctgtg ctcatatgaa ataatagaga tgatataatt tcatactct actctactca    180 tagatatcca tactcatttt gtattgtcat ctggtatgcg tttgtgcagc ttcaaccaag    240
```

-continued gtataatgat caataatact tacacactag actgactttg caggttgcaa tatcagtgaa    300
accattgaaa gtgcaaaact ggattcttcc agaaatgcct gggcttataa ctgattttct    360
gatatctctt gatgatcggt ttctgtactt tgtgaattgg c                         401

<210> SEQ ID NO 309
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 309
tagacaatat aacattgagg accctaaaaa tcctgtactg actggccaag tatgggttgg     60
gggactactt cagaaaggaa gccctatagt agcaataacc gaagatggta atacttggca    120
atctgatgtt ccagacatcc aggtttgtgc agtttaactt ttgaaattag tgattctagt    180
gtcatgcttg ttgatttctc ccatgtttgg agttgattgg ttcttagatg tactagatat    240
aatagacttg tgcattacat tggtgccttc aaacttttg tcacttttgt attttatctt    300
gtgttatgct taaacgtggt aaataattgc actttaaatt ttgacccttt agtggttgaa    360
ggtgaagaga tcaaaatttt taatttcagg gaaataagtt g                         401

<210> SEQ ID NO 310
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 310
aaaatggtgg tctgaaaatt aaccctaatt tctttgttga ctttggagct gagcctgggg     60
gtccctgcct tgcccatgag atgagatatc ctggtggtga ctgcacttca gatatatgga    120
tttaatagct atgctacttg aggccaggct acaagcaata tccatgtgaa taaaatcctt    180
agtcctagaa tgaatcgagg tgggctaatg ttataaataa ataatagttg catatgtatg    240
atggttgcat tgtaataaag ttatattgtc atgtagttttt cmgtactttc tcatttacat    300
catcctaaac agtgttctct rtgaaataaa tcttgctcac ctacaaaatt tgggtcttct    360
gattgagtaa atctctattg gagtaacatt ctagattaat g                         401

<210> SEQ ID NO 311
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 311
tgagatatcc tggtggtgac tgcacttcag atatatggat ttaatagcta tgctacttga     60
ggccaggcta caagcaatat ccatgtgaat aaaatcctta gtcctagaat gaatcgaggw    120
gggctaatgt tataaataaa taatagttgc atatgtatga tggttgcatt gtaataaagt    180
tatattgtca tgtagttttc cgtactttct catttacatc atcctaaaca gtgttctctr    240
tgaaataaat cttgctcacc tacaaaattt gggtcttctg attgagtaaa tctctattgg    300
agtaacattc tagattaatg gccttacttg ggattctatg attttcattc acatcatgaa    360
tgtgctgcac cttctacgtt gcttgttccc atttgaatgy a                         401

```
<210> SEQ ID NO 312
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 312
tttaatagct atgctacttg aggccaggct acaagcaata tccatgtgaa taaaatcctt      60
agtcctagaa tgaatcgagg wgggctaatg ttataaataa ataatagttg catatgtatg     120
atggttgcat tgtaataaag ttatattgtc atgtagtttt cmgtactttc tcatttacat     180
catcctaaac agtgttctct gtgaaataaa tcttgctcac ctacaaaatt tgggtcttct     240
gattgagtaa atctctattg gagtaacatt ctagattaat ggccttactt gggattctat     300
gattttcatt cacatcatga atgtgctgca ccttctacgt tgcttgttcc catttgaatg     360
yatttgaaat cacaacccaa ccaaatcatt tcaatatgat g                         401

<210> SEQ ID NO 313
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 313
cmgtactttc tcatttacat catcctaaac agtgttctct rtgaaataaa tcttgctcac      60
ctacaaaatt tgggtcttct gattgagtaa atctctattg gagtaacatt ctagattaat     120
ggccttactt gggattctat gattttcatt cacatcatga atgtgctgca ccttctacgt     180
tgcttgttcc catttgaatg tatttgaaat cacaacccaa ccaaatcatt tcaatatgat     240
gtacttctta acaaatcaat gcacaaataa ttttaatcat aaattcagaa cttatgcagt     300
gaatattctc gttgttaagt tataagggggc gggggaatc ttatatatgt gattttggt      360 atatgaacgt ttggtttgtg aattgtgatt gtcagatggt a                         401

<210> SEQ ID NO 314
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 314
acaacagagg atgctccagg atatgcaaat gcagaaaatg aagtcttcag ttcgttcaat      60
gggaagaata aggaaatcat atacctattt ttcatctttt atatttatgc agtcgtctat     120
gatgaattga tgagtgtttt cctggccatg tgtgttgttt tggcttctgc tttgtaaaca     180
caagataata atacaggcac cataataaac tgtataatga catgaagatc aatatctttc     240
tttgaagcta agaaaaattg ttatagcatg tagctacttt tgttgtccca caaatgtgtg     300
gcatggagca attttttaat atattcaaaa tatttatttt gtggactcga cagtctacat     360
ctattttatg aagtgtagtg aatccaacat caaaccccctt t                        401

<210> SEQ ID NO 315
<211> LENGTH: 401
<212> TYPE: DNA
<213> ORGANISM: Artificial Sequence
<220> FEATURE:
<223> OTHER INFORMATION: Consensus Reference Sequence
```

<400> SEQUENCE: 315

| acttttgttg tcccacaaat gtgtggcatg gagcaatttt ttaatatatt caaaatattt | 60 |
| attttgtgga ctcgacagtc tacatctatt ttatgaagtg tagtgaatcc aacatcaaac | 120 |
| ccctttgtcc cactttacaa aaaccctctg atcatttgaa cctcctaaat gaatacaaac | 180 |
| tgtgtccata aaaaaaaatt gttgtgtcct acgtgcaaaa aaaaaaaaaa aamttcacta | 240 |
| ccctatttg tttttatcat gttaaatata tgaaaataaa ttattgccaa gtccaaattg | 300 |
| tttgctacta ttgaagcctg catttgtctc gatgtaaaat agtagtactt atccaaacac | 360 |
| agtatcaggt tgaagcaaac tagttcatat tattgatgag a | 401 |

<210> SEQ ID NO 316
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 316

| ccaccacaac tgtatgttga ggtccattgt ctgatagaag actgagagtt taggtggggc | 60 |
| aacttcgagg aatatgtacc aaatatttta gatgtatgat tatatcaaca cacacacctt | 120 |
| tgcctctgtt ctctcctttt tcttttgcca tgataatacc cttcctataa tcctattcac | 180 |
| ccaacgccac atttgttttc ttgtatactt aaatgtgtgt taagggtaag ggcttcaaat | 240 |
| aagaaactta gctaaaacag ttaagtaact atttactccc atcattttgc acaaattttt | 300 |
| atgaacttag attttaccaa aggagggaca aaactaagaa ccaaaaaawt atcatcatat | 360 |
| tcagawgcca caaccaacca catgttttct atacatattt t | 401 |

<210> SEQ ID NO 317
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 317

| attttgcaca aatttttatg aacttagatt ttaccaaagg agggacaaaa ctaagaacca | 60 |
| aaaaawtatc atcatattca gawgccacaa ccaaccacat gttttctata catattttt | 120 |
| caatatgggg tactaacaaa aaagtcttat ttggtatgga atttttaatt actctatatt | 180 |
| tatagtatac aatatacttg gacatatta gaattttatc ttccaagagc aacctaatct | 240 |
| cagttatctc atacatatgc aatcgcttat tagcagagta aatcagwagt cttcacagaa | 300 |
| aagagaaaaa aaatcatctg tagcacatgg aaaataacat aatttccttg ttgtccaaaa | 360 |
| ggtttggtga agtgcgctct atcagcttat cactaatgca a | 401 |

<210> SEQ ID NO 318
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 318

| gcttcttagt ggagagtgga agrwagggta catccaatcc aagacacaga acagaagaat | 60 |
| ggcctcaaaa tcatccacca tyaracttgt ttgtttctgc tacttcatgc tcttcagctc | 120 |
| tatgcatttc accagctgca ccgtgctctc attgaaaagt catgcaagca catgcaatgg | 180 |

```
ttccatagct gaatgcaatc gagaagatga gctgttgatg gagtctgaaa taagccgaag    240
gtttctggag cagaagagat catacatttc caatggagct ttacagagag acaaaccagt    300
ttgtaatggt ggtggctctg gtgaagctta tagtaaaact ggagggtgtc ttcctccccc    360
ctcaaatcct caaagtagag gctgctctaa gtattatcgt t                        401

<210> SEQ ID NO 319
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 319
aggaaagatc tatgattgta ttaattatcc gtttcttgtc atctccaatc tttctttgtt     60
ccattatgct rgatggaatt tgattttttc ttcttttttt tttgggtgaa atgttttkgt    120
aatgcacata atgcaaccat aaggtataaa tcctcttaca cattctacct cgatatacat    180
atttaaataa taaaatatat gaaaatatag aattatataa aatgagattt tattttaaac    240 ataaagagt tcacrtgggt aaagtattca cattcacttt actattayca aataaaattt    300
gtsagaaaca ttttcggctc aacatcatgc aattaaacca gaaacttatg tctcaatgtc    360
ayattctaty agatcatttt attcygacat cctccaacat a                        401

<210> SEQ ID NO 320
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 320
ttcttctttt tttttgggt gaaatgtttt kgtaatgcac ataatgcaac cataaggtat     60
aaatcctctt acacattcta cctcgatata catatttaaa taataaaata tatraaaata    120
tagaattata taaatgaga ttttatttta aacatataag agttcacrtg ggtaaagtat    180
tcacattcac tttactatta tcaaataaaa tttgtsagaa acattttcgg ctcaacatca    240
tgcaattaaa ccagaaactt atgtctcaat gtcayattct atyagatcat tttattcyga    300
catcctccaa cataagattt cttaaagcaa tccatctagt catttgcttc cacaaacaca    360
aggttcgaga tcatcacaag atccaaacac aaacagcaya c                        401

<210> SEQ ID NO 321
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 321
tgggtgaaat gttttkgtaa tgcacataat gcaaccataa ggtataaatc ctcttacaca    60
ttctacctcg atatacatat ttaaataata aaatatatra aaatatagaa ttatataaaa    120
tgagatttta ttttaaacat ataagagttc acrtgggtaa agtattcaca ttcactttac    180
tattaycaaa taaaatttgt gagaaacatt tcggctcaa catcatgcaa ttaaaccaga    240
aacttatgtc tcaatgtcay attctatyag atcattttat tcygacatcc tccaacataa    300
gatttcttaa agcaatccat ctagtcattt gcttccacaa acacaaggtt cgagatcatc    360
```
acaagatcca aacacaaaca gcayacargg aatgagttat c                401

<210> SEQ ID NO 322
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 322
taycaaataa aatttgtsag aaacattttc ggctcaacat catgcaatta aaccagaaac    60
ttatgtctca atgtcayatt ctatyagatc attttattcy gacatcctcc aacataagat   120
ttcttaaagc aatccatcta gtcatttgct tccacaaaca caaggttcga gatcatcaca   180
agatccaaac acaaacagca tacarggaat gagttatcac attcccaact aatagagaga   240
aacgagacaa tatgtagata tacatattat ataaatgaaa tatarctyac tyaaacatag   300
ctcacatcat tccatcactt atcgtgtaac atcacatctc aacactacac atctcacaca   360
ttttcacatt atttacgtrc tcaaggatcg aaacacaata t                401

<210> SEQ ID NO 323
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 323
yagatcattt tattcygaca tcctccaaca taagatttct taaagcaatc catctagtca    60
tttgcttcca caaacacaag gttcgagatc atcaagat ccaaacacaa acagcayaca   120
rggaatgagt tatcacattc caactaata gagagaaacg agacaatatg tagatataca   180
tattatataa atgaaatata gctyactyaa acatagctca catcattcca tcacttatcg   240
tgtaacatca catctcaaca ctacacatct cacacatttt cacattattt acgtrctcaa   300
ggatcgaaac acaatatcac tcaaccaatc aatatcgayc aatrcacaag cgttatgcaa   360
caaatatact aagacttaat cctatatgta atgtggtatc a                401

<210> SEQ ID NO 324
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 324
atcattttat tcygacatcc tccaacataa gatttcttaa agcaatccat ctagtcattt    60
gcttccacaa acacaaggtt cgagatcatc acaagatcca aacacaaaca gcayacargg   120
aatgagttat cacattccca actaatagag agaaacgaga caatatgtag atatacatat   180
tatataaatg aaatatarct tactyaaaca tagctcacat cattccatca cttatcgtgt   240
aacatcacat ctcaacacta cacatctcac acattttcac attatttacg trctcaagga   300
tcgaaacaca atatcactca accaatcaat atcgaycaat rcacaagcgt tatgcaacaa   360
atatactaag acttaatcct atatgtaatg tggtatcatg t                401

<210> SEQ ID NO 325
<211> LENGTH: 401
<212> TYPE: DNA
<213> ORGANISM: Artificial Sequence

```
<220> FEATURE:
<223> OTHER INFORMATION: Consensus Reference Sequence

<400> SEQUENCE: 325
atcattccat cacttatcgt gtaacatcac atctcaacac tacacatctc acacattttc      60
acattattta cgtrctcaag gatcgaaaca caatatcact caaccaatca atatcgayca     120
atrcacaagc gttatgcaac aaatatacta agacttaatc ctatatgtaa tgtggtatca     180
tgtyagtgaa aaatctcatc gggcgcctag aagtatatga caagataaac cacacactgg     240
taagtcaggt cactctcayt agataaaatc ataaggagat tagttagggt cactctrttt     300
tgcgagaaca cttcaatcat acgaaatcaa cataggtttc aaggaacatt caaaccgagt     360
atatttaccc ctaaggccta cactctaaag agtccgttag g                         401

<210> SEQ ID NO 326
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 326
gataaaccac acactggtaa gtcaggtcac tctcaytaga taaaatcata aggagattag      60
ttagggtcac tctrttttgc gagaacactt caatcatacg aaatcaacat aggtttcaag     120
gaacattcaa accgagtata tttacccta aggcctacac tctaaagagt ccgttaggac     180
ctctccctct tgattcaggt tcaacctaga aaatatttta gcaccyagac tctatttatg     240
aactgtacaa aacacycgac tcctcaattg ttctcaaaat aattttatct catcgcgcct     300
caaagtgatt aaactcgtcg agttyccaca atggttctca tcacaatact cgtcgcacat     360
taactcatcg ttctgaaagg gtcttatagt cgtgtggtgg t                         401

<210> SEQ ID NO 327
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 327
attagttagg gtcactctrt tttgcgagaa cacttcaatc atacgaaatc aacataggtt      60
tcaaggaaca ttcaaaccga gtatatttac ccctaaggcc tacactctaa agagtccgtt     120
aggacctctc cctcttgatt caggtycaac ctagaaaata ttttagcacc yagactctat     180
ttatgaactg tacaaaacac tcgactcctc aattgttctc aaaataattt tatctcatcg     240
cgcctcaaag tgattaaact cgtcgagtty ccacaatggt tctcatcaca atactcgtcg     300
cacattaact catcgttctg aaagggtctt atagtcgtgt ggtggtaygg tacataactc     360
aaaactccat gcacacaata tttcaataca catgtatttt a                         401

<210> SEQ ID NO 328
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 328
attcaaaccg agtatattta ccectaaggc ctacactcta aagagtccgt taggacctct      60
```

```
cctcttgat tcaggtycaa cctagaaaat attttagcac cyagactcta tttatgaact      120
gtacaaaaca cycgactcct caattgttct caaaataatt ttatctcatc gcgcctcaaa      180
gtgattaaac tcgtcgagtt tccacaatgg ttctcatcac aatactcgtc gcacattaac      240
tcatcgttct gaaagggtct tatagtcgtg tggtggtayg gtacataact caaaactcca      300
tgcacacaat atttcaatac acatgtattt tayaattcaa caygcactca atttatcaca      360
tacgctcaat ctcgttataa tctcaatata acaatttatc a                         401

<210> SEQ ID NO 329
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 329
gtttattcta acctcaattg cgataaactc atctcttacc tctaagyagg ctcacatgtg       60
tagtcygaca acgatagtga cgtttctagc gatttcctaa gattcttcaa aattttccta      120
agattttcta acrtyagaga aaaagagaaa ggattataac ctatatttca ctgtctccgt      180
ctccrtgcga gggacatttc tctaactgaa gacattgttt cacaaatcct aayagtggga      240
ttgtgagaaa atgagtttya aacctgatttt ttaaatttca caatgattca atggttaatg      300
artccgagat catagtttta atggracaag tttggatgta tgcaggaaga gcatcttgtg      360
agggacattg ttctcaccac agacattatt taaaaattcc a                         401

<210> SEQ ID NO 330
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 330
attcttcaaa attttcctaa gattttctaa crtyagagaa aaagagaaag gattataacc       60
tatatttcac tgtctccgtc tccrtgcgag ggacatttcw ctaactgaag acattgtttc      120
acaaatccta ayagtgggat tgtgagaaaa tgagtttyaa acctgatttt taaatttcac      180
aatgattcaa tggttaatga gtccgagatc atagttttaa tggracaagt ttggatgtat      240
gcaggaagag catcttgtga gggacattgt tctcaccaca gacattattt aaaaattcca      300
acgatgggaa tgtgagaaaa tgagtttgga acttggtgtt caaatttcat gataattcaa      360
tgattaacga gtataggatc gtagttttac ctgataggtt t                         401

<210> SEQ ID NO 331
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 331
tagaaatata ttatgtgtaa aatctgatct aatatrtcta tttatagata tsgtactcty       60
aatttattat ttactctakc ttttcttttat tttattattt tatwaaaaaa attctatttt      120
tactccctat caaatgaata aataaaaatat tcttttttat tttccttcaa aytattattt      180
taattaataa aattatttttt tctaatttat ttaattataa aaatcttatt attttttcaaa      240 aactctattt attttttaaat aaaatgcttt twaatttatt taaaaaaaga cgagatgtta      300
```

| | |
|---|---|
| caaatgtttg aagcacactt tgcaatgtta taaatgttga cctcagacat caattgcaat | 360 |
| atacacacca taaaacaaca tatgaagtac acgtatgaga t | 401 |

<210> SEQ ID NO 332
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 332

| | |
|---|---|
| gctcgaatat aatgaatcta aacatatatg aaaaatcagt aactgacctt ttcgacacag | 60 |
| tcacatgaac aaactcgcag caacaacgca tacactagta acagcagtca rcgcactctc | 120 |
| ttgagaaaat ttgatgtaaa tgtatttata actttgtgac aaatattttt tttccctcat | 180 |
| tccacacagg aataaaaagt gtccaagtga gtgaaagaga tgaggaatag atagacwtct | 240 |
| ttctccttat tttaaaatcc caagaaacta attacctaga acatttgtaa caaaaactag | 300 |
| tgttaattta tttccattta tccctttcct ctctgcttta tttrtgggaw gctataaaga | 360 |
| acgctcttct ctcctgaaaa ttgctmattt aagaaattat t | 401 |

<210> SEQ ID NO 333
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 333

| | |
|---|---|
| gtgaaagaga tgaggaatag atagacwtct ttctccttat tttaaaatcc caagaaacta | 60 |
| attacctaga acatttgtaa caaaaactag tgttaattta tttccattta tccctttcct | 120 |
| ctctgcttta tttrtgggaw gctataaaga acgctcttct ctcctgaaaa ttgctmattt | 180 |
| aagaaattat tttcgaagga ccacatttta atctgttaga aatagccmaa aaaaaataga | 240 |
| cagaaaaatt actctaattt ttttttttttt tkgaatgatt gactagtcaa attaactcca | 300 |
| gtaaacaaac aagcagcggc gggttgaaca tgaataactt tcaatatgcc cctttgttaa | 360 |
| gctaaaagat taccctaaca tggaagttta tgctacatat a | 401 |

<210> SEQ ID NO 334
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 334

| | |
|---|---|
| cattttgtca ttatactttg cacgaagtgg gtcattgtaa gtccacctgt attacaattc | 60 |
| aacaataaca agaatgtcga ataattttag tattttacag cagttaatat gtaagtataa | 120 |
| aatgctactt gcagtagaag aaacccttttt ttcaggggaa ggggaggtct ggactctgga | 180 |
| ggttagttgc acgttaagca gaatgaatcs ctatcatcaa tgtgttaaca aatccaaaat | 240 |
| tcttggtaag ggagaaatat cggacagaaa aaaaattaag atgtcagaaa gccaatgcag | 300 |
| aattttctca gcaaatacat tgaatgctgc cttaacatac taaaacccca ttattcgaaa | 360 |
| gatgattatc aatatttaat arcatgactg caagcctatc a | 401 |

<210> SEQ ID NO 335

<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 335

```
attatacttt gcacgaagtg ggtcattgta agtccacctg tattacaatt caacaataac    60
aagaatgtcg aataatttta gtattttaca gcagttaata tgtaagtata aaatgctact   120
tgcagtagaa gaaacccttt tttcagggga aggggaggtc tggactctgg aggttagttg   180
cacgttaagc araatgaatc gctatcatca atgtgttaac aaatccaaaa ttcttggtaa   240
gggagaaata tcggacagaa aaaaaattaa gatgtcagaa agccaatgca gaattttctc   300
agcaaataca ttgaatgctg ccttaacata ctaaaacccc attattcgaa agatgattat   360
caatatttaa tarcatgact gcaagcctat caaccaacaa t                      401
```

<210> SEQ ID NO 336
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 336

```
gttagttgca cgttaagcar aatgaatcsc tatcatcaat gtgttaacaa atccaaaatt    60
cttggtaagg gagaaatatc ggacagaaaa aaaattaaga tgtcagaaag ccaatgcaga   120
attttctcag caaatacatt gaatgctgcc ttaacatact aaaacccat tattcgaaag    180
atgattatca atatttaata gcatgactgc aagcctatca accaacaata catgaaaaaa   240
ttctggtgtg ataaaaaaaa ttgtgtagac tccttttaat gtcataaaat cagaagtgtg   300
gcagaatcag tctaacatgt tacatcaaca ttgaaaacat aaacagattc aggactctgt   360
agataataaa tgtagcattt cagatattct cagaacagag a                      401
```

<210> SEQ ID NO 337
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 337

```
aacccaaaag tactatgaaa acagatgagc ataactcatg agcatgcact tttgtcaaga    60
tctcaaacca tatcaagggc tgctaataaa caactcattt aaattgtgag ttgtgacatg   120
caatatgatc ccttcttact gtccagctaa attcacatag aagtcaaggg agtcagggta   180
aagttgacaa actaagaacg ttgtaaacaa taaacttcaa gccaagtaca tatttctaca   240
aaatgaatgc caaaaaaata aaataagatt tgtgagatgg cataattatg cttactctaa   300
atgaaatatg tcttttaact atattccttc caatcaactc tccctcttga acctcaatct   360
cacccacaat caaattccta ataagcaaa atgataggta c                       401
```

<210> SEQ ID NO 338
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 338

```
ttctcccagc caagcctaa ttccacccta ccttgtacac acccttctcg ggctaatgtt      60
ctctgtcttc ttacaacaag cccacatgca ctcctcccat gctctgctac agggttgaca    120
gttggttata tctctctcct aaaattgatc aagtgaacct tttgcctatc cttacataca    180
ccttattttg tgatcttggg tcttgrggcc tccatcasaa aaccattctt cataaaaact    240
ctcatttcac tcttctgatg actaatagca gaaaattttt tagataacaa gagaaaaaga    300
aatcttaaat gaacatttca ctattgrcat gagcatctca atatcatcac atgaatccga    360
gatcattttg gaccagtgcc atagcagatg aacttcataa g                         401
```

<210> SEQ ID NO 339
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 339

```
ccagcccaag cctaattcca ccctaccttg tacacaccct tctcgggcta atgttctctg     60
tcttcttaca acaagcccac atgcactcct cccatgctct gctacagggt tgacagttgg    120
ttatatctct ctcctaaaat tgatcaagtg aaccttttgc ctatccttac atacacctta    180
ttttgtgatc ttgggycttg gggcctccat casaaaacca ttcttcataa aaactctcat    240
ttcactcttc tgatgactaa tagcagaaaa tttttagat aacaagagaa aagaaatct     300 taaatgaaca tttcactatt grcatgagca tctcaatatc atcacatgaa tccgagatca    360
ttttggacca gtgccatagc agatgaactt cataagtaaa t                         401
```

<210> SEQ ID NO 340
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 340

```
tttttctcag gataaaacaa caaaaaacta ataccaaaga atagaataaa caatctacca     60
ctattcttga aaccgaaaga tatagaacat aggagaaatt gaacttacgg gttattccaa    120
tcagtagtat cctcattgac aagatgggtc cacttggttc ttccactacg accaaagtgc    180
ttaacttgca taacctttgg taatattgtc ttgtccattt tatcctcccc agttggggca    240
gagaaatcac gagcgaaaat accatcagat ccaacggtgg cagctcggtc atcagattca    300
ttctggaaga aagcaccttt gtgatagtat ttctgcataa atctccattt ctgctttggt    360
ggtggagcag gtttgggatt cctcctttcc cactccctcc t                         401
```

<210> SEQ ID NO 341
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 341

```
tcatcagccc attcaggaac tttaccgggc aataacgct taactttagt ttggccaatt      60
ttacctctga gctatcccct aatggctatt acagtatcac taacaccgc tgtcaccgac    120 attgttcttc ctcaattgaa cgccaaaccc tatattgcac agatgcatag taaatcggta    180
```

```
aaatgtttgt tacacagca cagaaacaga agattccaga ttaaatagca agaaaataaa      240
taaatgaatc aagaaacaca gaaagatcaa tagtgaatga taaattttga tatgcgaaac      300
attggaaggg tttgtgttcs aaacactaac acttgaattg ttagagagaa tagaagaaaa      360
gttwgaagga cttacaatta cagcgaccgg aaggaaccct c                          401

<210> SEQ ID NO 342
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 342
ccctctctgt ctctgtcccg ttccaggcag cgcgtcgccc cacccagct tgttctgtga       60 acttttattt gatttacttt ctatagtatt tattttgtt tttatgagta tgtaaatgac      120
atctttatac gaatattatg ttttcattaa ataataataa taataaattt cttaaaatta    180
aatatatata cactaatgct cataaaaaaa ttgaacgaat atcatattta ttaaaactaa     240 ttttttata ctaaactaaa ataatttaa aatttattat tattattatt ataaagatat      300
ttaaatttta tattttggaa ttgtatatat aagataaaat acatttaagt ttcctaagtt    360
acaactttcg catcggttac atttttamagg wtatatatat a                       401

<210> SEQ ID NO 343
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 343
atgtctttgt ccaaggcttg ctaacaaaaa aggagattgc aagatcaata aaataccttta    60 caataatgag agacaaaggg ttttcagtag atgctgctac cacagaaatt actatcaact    120
acttatctac taatgaagga gacaccagaa ttcgagaatt ttttttttcca aaaagatagc  180 aaatgccaag agtttcactt ggacatttat tcaaatcctg actctcaatt catccatgtt    240
ccacaatcct ataggacccc atagagagaa ctggcatagg cttcagaact tacmatttgt   300
taaatatata aaatcattac cattcaagtg cwtccacctg acaatttatg tgattaggag    360
agttggtcct taacaggtat cacaacccttt aagaaattat g                       401

<210> SEQ ID NO 344
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 344
ttgatccttg ttgcttctct tcttcataat taacttatat ttgagcccaa ggtaaagtgg      60
gtttgtgcat tgtccrcact tcaagctcaa aaagctctgt tttaagggg tcttagatat     120 aaatctttct tagctccacc aatcagctta agctgtgaat agaattgttc cttgacattt    180
ttagtggtaa gtattttcac ctctgcttgc acatttattt tgatataacc tcaagttatt   240
aaaatagctt aaaaaaatag acctatatac aatttagaaa ttgtgctgta tccttgcatt    300
tttatggaac tgagtaattt tttacttatg tatatttgcc ttcaagtaag tttaataatg    360
aagcaagttg cattagggat aagccaatca atattgctag t                        401
```

<210> SEQ ID NO 345
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 200
<223> OTHER INFORMATION: n = A,T,C or G

<400> SEQUENCE: 345

```
tgttatttta tattttgttt cctttcttgt gtattttact tttctgtttt aggaggattc    60
ctgatccttc tgcactgtac tccttttctc tcctagttca ttgtttgtga tgggaawttt   120
ttttccatat ttattacctg ttaggagacg aaaatctaag atctaattta tggatgcttg   180
ctgtcctttc tgcaaacgtn tttttttttt tttacttttg acagttttcc ccccatttaa   240
aataacagtt tgacttcatg gttcttggtt tgcagattga aatcactyta tgcactcatt   300
ttgttataac ttatgtgcga ggaagaccgc aaatagttca gcgatggatc atagaaggtt   360
agtcaaacat tttttctttg caatatctgc tcagcttgtt t                       401
```

<210> SEQ ID NO 346
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 113
<223> OTHER INFORMATION: n = A,T,C or G

<400> SEQUENCE: 346

```
ctctcctagt tcattgtttg tgatgggaaw ttttttttcca tatttattac ctgttaggag    60
acgaaaatct aagatctaat ttatggatgc ttgctgtcct ttctgcaaac gtnwttttt   120 tttttttactt tgacagtttt tcccccatt taaaataaca gtttgacttc atggttcttg   180
gtttgcagat tgaaatcact ttatgcactc attttgttat aacttatgtg cgaggaagac   240
cgcaaatagt tcagcgatgg atcatagaag gttagtcaaa cattttttct ttgcaatatc   300
tgctcagctt gttttttgta attcaaattt tttagcatca taagttgttc gtttgaaatt   360
ttgaatgaat atttatctgt taagttatat ttcactttc t                        401
```

<210> SEQ ID NO 347
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 229
<223> OTHER INFORMATION: n = A,T,C or G

<400> SEQUENCE: 347

```
aatatattta tctcagaata atgctttgac ttttacaatg ttcccctcac aaaattgatc    60
tctttaaaaa ataaaaaata aaaactttgg agtttgtcca gcttggctcc aatcttaacc   120
aaagcagcat taaagctttg aagtatagag caaaagtaca ccatattagg ctaatcaatg   180
aaaaggtaca aagctcccgt tagattttga actagrcaga taactaagng agtgtttagt   240
```

```
ttggttgttt tttgatttta ttttcactga aaataraaaa cggtgatgaa aatgtgtttg      300
gtttgatttc tgaaaacatt ttcrgtaaaa atgaaaacag taaacaacta gaaaatgaaa      360
acaaaaaatt ttcgttttca gwattttcag ttgagaacag a                         401
```

<210> SEQ ID NO 348
<211> LENGTH: 401
<212> TYPE: DNA
<213> ORGANISM: Artificial Sequence
<220> FEATURE:
<223> OTHER INFORMATION: Consensus Reference Sequence
<220> FEATURE:
<221> NAME/KEY: misc_feature
<222> LOCATION: 48
<223> OTHER INFORMATION: n = A,T,C or G

<400> SEQUENCE: 348

```
aaaggtacaa agctcccgty agattttgaa ctagrcagat aactaagnga gtgtttagtt       60
tggttgtttt ttgattttat tttcactgaa aataraaaac ggtgatgaaa atgtgtttgg      120
tttgatttct gaaaacattt tcrgtaaaaa tgaaaacagt aaacaactag aaaatgaaaa      180
caaaaaattt tcgttttcag tattttcagt tgagaacaga aacctcattt tggttaaaat      240
gaaattgygg tgacaataaa tgtagtttta arcaaatcta aaaatacaaa aagacaataa      300
gtcaatatat cataaatttt cagtattttt atttcatraa aacagaaaac aagaaatcaa      360
accaaacatr ttttcagaat ttaaatcttt tgaaaataaa a                         401
```

<210> SEQ ID NO 349
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 349

```
tctcttcaaa agccaagtcc ttggttagga cagtggtact taacatggtt aatgcaaatg       60
gtttgtwgca aattcataat agacctttca accagctttt ggctcatttt attgcattag      120
tcttatttgt tttggagaat ttcttttatt tttttggtaa ctagcagatt tcttatcctc      180
ctcctagttg tgcttctctt ttctctttaa tgaatttcct cctatgtaaa aagcaataga      240 aaagaaaac cagttttaaa aaaataaat aaaagaacta atttcaggta ccttcttcca       300
ttttgcaatt agattgcggt cagcatatcc ttgatctaaa cagaattcat acagttcttt      360
agaaatttcc ttcctccgat ggtatagatc aaatatgtag c                         401
```

<210> SEQ ID NO 350
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 350

```
taagtaaatc tagaaaatat ataacttttg acaaaaaaat tatatcacta tttaaatata       60
tcttttttcc tttgtttctt atttcctaaa taaattttt tattaaattt attaacaaaa      120
atttctcata attaacgaat gaggttaaaa ataataaaaa aatgayaaat ataataaaaa      180
caaattaaat ttaaagactt gaaacataat ttttktgtcw catgaaaata ttttttttat      240
tctaaacaaa ttgtttaaag ataatraaaa tatcattttt ttaaatccta waaatatacc      300
arataactat aattatttaa attaaatcac tctagcatat attttaata aatcaaatta      360
```

```
atatatacaa atatttaat ttactttaaa tttaaagata a                         401
```

<210> SEQ ID NO 351
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 351

```
acataatttt tktgtcwcat gaaaatattt tttttattct aaacaaattg tttaaagata     60
atraaaatat catttttta aatcctawaa ataaccara taactataat tatttaaatt     120
aaatcactct agcatatatt tttaataaat caaattaata tatacaaata ttttaattta   180
ctttaaattt aaagataata tgataatata aatatagtaa aatttatag aattttaaa     240
caatatttty catttatctt ttttttttct tttatctctc tagttgcatg gagcatgagc   300
caacttccta gtttattgta tattttcgtg ataatgttgt ggcatttgtt agacatttta   360
aaatattaaa tcttattaat tattttwaaa tcatatttat a                       401
```

<210> SEQ ID NO 352
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 352

```
gtttaaagat aatraaaata tcatttttt aaatcctawa aatataccar ataactataa     60
ttatttaaat taaatcactc tagcatatat ttaataaa tcaaattaat atatacaaat    120
attttaattt actttaaatt taaagataat aygataatat aaatatagta aaattttata   180
gaattttaa acaatatttt tcatttatct ttttttttc ttttatctct ctagttgcat    240
ggagcatgag ccaacttcct agtttattgt atattttcgt gataatgttg tggcatttgt   300
tagacatttt aaaatattaa atcttattaa ttattttwaa atcatattta tatgaaaaat   360
atgattttt atttaatctt tctagaaaaa tcttaatgta t                        401
```

<210> SEQ ID NO 353
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 353

```
tctctagttg catggagcat gagccaactt cctagtttat tgtatatttt cgtgataatg     60
ttgtggcatt tgttagacat tttaaaatat taaatcttat taattatttt waaatcatat   120
ttatatgaaa aatatgattt tttatttaat ctttctagaa aaatcttaat gtatccactt   180
ccaacttta catttaaaat tccattatat atttttttc taattaacct tctctaacaa    240
ttgttcaaca ctttcttcct aaacctctat ttcagtttct ctccctcttc ggtcttccca   300
ttgaattcca ggatttaca tacaaaaaat ttgwtagttt tgttgtcttg acaagttttc   360
ggaggatttg ttaaattcta aaggacttat gcactacgtt g                       401
```

<210> SEQ ID NO 354
<211> LENGTH: 401
<212> TYPE: DNA

<213> ORGANISM: Artificial Sequence
<220> FEATURE:
<223> OTHER INFORMATION: Consensus Reference Sequence

<400> SEQUENCE: 354

| | | | | | |
|---|---|---|---|---|---|
| cgtgatgtca | ctcatctcat | attatctatt | ttgtgactaa | ctcatgaatt | tatgatagat | 60 |
| tgatgatcgg | tgattttggc | ctactacaat | aacaatttta | acttttaagg | aataatcccg | 120 |
| accactttaa | ggtatattaa | tatattaatt | atttttttct | ccaatcttaa | tttaatttgt | 180 |
| ttgatggtaa | tgaatcagat | caacgatttt | gggactgttg | ttgttgttcc | attttcagtt | 240 |
| ttttattttg | tttatgacta | gttgagtttg | yaatcggttc | ttgctcggtg | attttagagg | 300 |
| ttttggacat | gattttagag | tatgttgtat | tgtgtaaaac | tttgttgcaa | tctcgtgtgg | 360 |
| ttaaatgggt | gttaggatgt | gaaaatttta | tgtctaaaat | t | | 401 |

<210> SEQ ID NO 355
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 355

| | | | | | |
|---|---|---|---|---|---|
| aatacacttg | tgcattcaaa | tatccataat | agttaataac | aacaacttat | tcaatatact | 60 |
| atattatcta | gggtcactag | attaaaccca | cttctaaaaa | aatcttaaaa | catccaaatt | 120 |
| ttattaatac | gttatcttga | acatactttc | ttctataaat | gttaaaattt | atttgaaaat | 180 |
| ttgaaatctt | agaaggtctc | gtactttaat | taataaaatat | cttttataat | ttttmatgaa | 240 |
| tagtacaatc | aagtgtgtta | aaaaatattt | tcttgaaact | cctctaaatt | taatgctaca | 300 |
| aaaattactt | tttcttgctt | tctcttcaaa | cttagtgagc | atttttgcac | tcttaaatta | 360 |
| tgtttgtcaa | aatatttgaa | ttgattttta | gttttttttat | t | | 401 |

<210> SEQ ID NO 356
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 356

| | | | | | |
|---|---|---|---|---|---|
| aataacaaca | acttattcaa | tatactatat | tatctagggt | cactagatta | aacccacttc | 60 |
| taaaaaaatc | ttaaaacatc | caaattttat | taatacgtta | tcttgaacat | actttcttct | 120 |
| ataaatgtta | aaatttattt | gaaaatttga | aatcttagaa | ggtctcrtac | tttaattaat | 180 |
| aaatatcttt | tataattttt | catgaatagt | acaatcaagt | gtgttaaaaa | atattttctt | 240 |
| gaaactcctc | taaatttaat | gctacaaaaa | ttactttttc | ttgctttctc | ttcaaactta | 300 |
| gtgagcattt | ttgcactctt | aaattatgtt | tgtcaaaata | tttgaattga | ttttagttt | 360 |
| ttttattaac | agaaaagttt | atttagttgt | ttgataaaga | a | | 401 |

<210> SEQ ID NO 357
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 357

| | | | | | |
|---|---|---|---|---|---|
| acttttctt | gctttctctt | caaacttagt | gagcattttt | gcactcttaa | attatgtttg | 60 |

```
tcaaaatatt tgaattgatt tttagttttt ttattaacag aaaagtttat ttagttgttt        120
gataaagaag ttttttaaat aatttttaac attttttttaa acactacttc aagtaatatt       180
tttwaaaata ttatttattt tttcatatat tctyttttta tttattttta atatatttat       240
caaatttatt atttatcctt tttaagcaaa tcattattttt attattttwa agttatttta      300
tattttttaa ctatttcaaa aactaatttt atcacacact taattttaat aaattaattt       360
tttaacttcc aactaattta ttagttttca gctaatttta t                            401

<210> SEQ ID NO 358
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 358 tgattttttct gcatctgaaa caatttgaaa tttcaaaatt tctctttttct ttacgaggtc      60 atcaaagcac aaagctaaca aattccctag aagagggtgc ataaaactcc aacctgtttc      120
ctctgttttt tcccttgcaa ttattactct tttttattgr tagaaattga attrttgaar      180
tataaatgtg aaataaagtc tcacatccaa taaaaataaa aaaatttaac atcatataag      240
taaaaataac taaatcttaa agttttttaaa ttgctattct ctttcatgta aagataaaac     300
acataaatct aactcttaaa gtctcttgat tactattttt catctttcat gatataagtg      360
atgatttagc ctctagattt catggtgatt atagaagtgt a                           401

<210> SEQ ID NO 359
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 359
caagatagga ccttttact ttgttggtct attaatatcc aagttgttca tgcttatttt       60
cacacctaac attagcttat tcaagattct taataaaata ttagggaaaa tatcatgaaa      120
cttttatcaa aattgtttat ttgtcgttga cgtttttgga aacatctcaa tagtgacttg      180
ttactcaatc aatctttact ggcactctca tacttggttt tcgttattcc tgttttcaaa      240
ccacatactt tgactaatgg actatgaatg aggctgcgta taaaaataca attggcgtat     300
tcgagatgca aattgtgtta ttggcctctt gtccttttcc agatcagtat tgagaagttc     360
aggcaaggct tgtattgaat ctgactctga cagatacata a                          401

<210> SEQ ID NO 360
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 360
atacgacttt twcttgttgc cactctttac caacagcatt caagacgtac gttaggatat       60
tcaaatccaa tgcgtcactg aggaactttt gcactcattt tttcacgcaa aaacagagaa     120
tcatccagca cagagtcttg caaaaattga tgtgaaacaa gaatgctctg agcctaaatt      180
ggatcaatgt gcatgctaaa gtttagaccc atatmktatk gggaagtttt tatcccttag      240
```

```
tcgcttttgt cttttccctt tcctttttct aagcaacaaa ccatattgtt ttataatttg    300
ggcgaggtct aaattcgttt tatcattgta acaaaaacta aagaaattaa agcaaacgat    360
ttcataggct atttgggagc tatgttttat gaggttaata a                        401
```

<210> SEQ ID NO 361
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 361

```
aaattcgttt tatcattgta acaaaaacta aagaaattaa agcaaacgat ttcataggct    60
atttgggagc tatgttttat gaggttaata acaaaatagg aatctcttga ttttaagaat    120
gaacaatttt tttttcacta tgaaaggagt cctgaacatt ataattggat tgggtgttaa    180
ggagagaaat agaaaggaga gatttcactc gattggttca raaagaaata agaacgaaat    240
tgacaaattc tgtgggttca tttgggaaat tcttctccat tgttcatgat tggaaatgat    300
tttgtgtatc ttcttttttt ttcttaattt cttttaaaa atcaaataa ttttttwaa     360 ataatttct ttattaaaat acttttactt taygataaat a                        401
```

<210> SEQ ID NO 362
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 362

```
acaaaaacta aagaaattaa agcaaacgat ttcataggct atttgggagc tatgttttat    60
gaggttaata acaaaatagg aatctcttga ttttaagaat gaacaatttt tttttcacta    120
tgaaaggagt cctgaacatt ataattggat tgggtgttaa ggagagaaat agaaaggaga    180
satttcactc gattggttca gaaagaaata agaacgaaat tgacaaattc tgtgggttca    240
tttgggaaat tcttctccat tgttcatgat tggaaatgat tttgtgtatc ttcttttttt    300
ttcttaattt cttttaaaa atcaaataa ttttttwaa aataatttct ttattaaaat       360
acttttactt taygataaat actatgaatt aaaaagataa a                       401
```

<210> SEQ ID NO 363
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 363

```
cttaatttct ttttaaaaaa tcaaataatt ttttwaaaa taatttcttt attaaaatac    60
ttttacttta ygataaatac tatgaattaa aaagataaat atattctctt attttcttat    120
ttctcttcca aggattgtcg agatgggaga agattaacgt aaagaatttt tatttttta    180 ttaaaacagc gaaatatag tgtatatata taaaaggcac aaatgggtgc ccccaatcaa    240
ttacaaagtg gataaaagtc caacaaagat agtatacctc ggttacacca tattaacaaa    300
ggagagtaaa tatagtttaa ccaaggccaa aaacatcact cctagccaca ctccagtaaa    360
tatagtttaa cgtgaagaat ttgattcaac ttgtgagagc t                        401
```

<210> SEQ ID NO 364
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 364

```
aagaatttga ttcaacttgt gagagcttca ccccttaagt taattcacca tatagctcaa      60
atcggattag ttggagaact taattaccct gattgccctt tcttaaaaat attgcagaag     120
caccaaataa taccacaatg tgtcgatgtg tttccgaaac tagatgatag atgggtagga     180 attttttat tttctttgat gtattgaaaa ggcagaaaga aacacaaatt ttagtattta      240
ataaagcaaa atgcacacat cccccaaaca aaacaagcct tattcaaccc aaattggttt     300
catatcacag aaaccaacag gatgccgcct tcctccttac tggtcccacc cactcgaaca     360
aaagttstac agaaataaaa atggctacaa ttcttctacc a                         401
```

<210> SEQ ID NO 365
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 365

```
agagcctgaa gggcacagat gggatcaatc tcggtcacga tgacacgagc accagcctgc      60
ttcattgcag cagcacaacc cttgccaaca tcaccatatc cagccacaac agccaccttt     120
ccagcaatca taacatcggt agccctcatg agaccatcag ggagagagtg acggcaccca     180
tacaagttgt caaactgtta caaaaccaca gattaaaagg ttaaacaaac aaaacacaag     240
caacaaagca aaatccaatt ataatcaact agatccatga ccagctagta taatgtcctc     300
aaaatccaat cacccacttc ttactttcaa taccctaatc aataaacaac ccgtcacaaa     360
agactcggtt tggatcaatg tttgcaaaac caattttgaa t                         401
```

<210> SEQ ID NO 366
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 366

```
aacaaacaaa acacaagcaa caaagcaaaa tccaattata atcaactaga tccatgacca      60
gctagtataa tgtcctcaaa atccaatcac ccacttctta ctttcaatac cctaatcaat     120
aaacaacccg tcacaaaaga ctcggtttgg atcaatgttt gcaaaaccaa ttttgaatga     180
aaacgatttc gagttaaaat tgatttygaa acaacatgat ttatgtttga acatttttt     240 attttaaaac caaaaacagt agtaaaattc agtataattt attttatcct atccaaaagt     300
agcttcaaat caaaatgtgc actcagaatc aattccttat ttgtgtaata aaacatgtga     360
ccatttacct aaagtcacgt tagcaagcaa cttactaatg t                         401
```

<210> SEQ ID NO 367
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 367

```
caaaacacaa gcaacaaagc aaaatccaat tataatcaac tagatccatg accagctagt    60
ataatgtcct caaaatccaa tcacccactt cttactttca atacccrtaat caataaacaa  120
cccgtcacaa aagactcggt ttggatcaat gttttgcaaaa ccaattttga atgaaaacga  180
tttcgagtta aaatwgattt tgaaacaaca tgatttatgt ttgaacattt ttttatttta  240
aaaccaaaaa cagtagtaaa attcagtata atttatttta tcctatccaa aagtagcttc  300
aaatcaaaat gtgcactcag aatcaattcc ttatttgtgt aataaaacat gtgaccattt  360
acctaaagtc acgttagcaa gcaacttact aatgttctga c                      401
```

<210> SEQ ID NO 368
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 368

```
amtatgaaaa attatacttc aaacaagtct ctcataagaa tgtttatggt ctcatacaga    60
tgaatatttt cacttcgaat acacgtaaaa ctaatatgaa ttcacacaag tgattaaaga  120
tctaaaacta acttttgtct tcttttttt atagatgtgg gtttcattct ctatcatgcc  180
actaaaacta tcatctaata tattctttga catctaagga ctaattgaat aaatacaatt  240
aagtaaaatt gtctatgatt taggcctgtg gaataatcct tgagtaagcc tttattgaca  300
tcgctaacaa gtagcatgtc attaaggttt cattcgatgg tattgatcag gcctctataa  360
aattttgtac attttaatat gcatcaaatg agcatackgg t                      401
```

<210> SEQ ID NO 369
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 369

```
atakattctt tgacatctaa ggactaattg aataaataca attaagtaaa attgtctatg    60
atttaggcct gtggaataat ccttgagtaa gcctttattg acatcgctaa caagtagcat  120
gtcattaagg tttcattcga tggtattgat caggcctcta taaaattttg tacattttaa  180
tatgcatcaa atgagcatac tggtaaagat ttcggtgctc aagttaatag ttggtaaagt  240
aaaagcatta tatgtaagat tttcatgtac ttgktaaagc taagggacta tcggagattg  300
ttgataagca tttaaaaaac tctcaacaat cttctatctg cctataaagt tttctyaaaa  360
agcatttaaa aaatttatag gttaattaga gatttgttag g                      401
```

<210> SEQ ID NO 370
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 370

```
ctctataaaa ttttgtacat tttaatatgc atcaaatgag catackggta aagatttcgg    60
tgctcaagtt aatagttggt aaagtaaaag cattatatgt aagattttca tgtacttgkt  120
aaagctaagg gactatcgga gattgttgat aagcatttaa aaaactctca acaatcttct  180
```

```
atctgcctat aaagtttct taaaaagcat ttaaaaaatt tataggttaa ttagagattt      240
gttaggtagg ttaacataca tgtaaagatt tttctttttt tggaaaatac atgtaaagag      300
ttttgtaaaa gtagaacttg tgaatacgtg atttataaga caattcatat tcctcccaat      360
caggtaattt tgtgcaaaaa gtcttattaa gttggtgtgt a                          401
```

<210> SEQ ID NO 371
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 371

```
atattgtaaa acacaaaata tttatattcc aatcttmaat gtttttattt gacattataa       60
atatttaaag gatagaatca atgttaatca agttaacata aaaaataaaa aattacatag      120
cattcaacat gtaggtatca aatctatgtt ataaaatgtt tattagatag agaaaaatat      180
ttgctaaaat ttwgataatt gtgctatgtt tatatgttga atgatgggta aaataaaatg      240
acgcataatt aagtaacata agtaaaataa aaattaagtt taattttat gaattatcaa       300 tataaaaaaa taaaatatat tcctaacatt tctctttcct ctattttaca ttcatttat       360 tttcttaatt tttttcattt tgatatcctt taatataata a                          401
```

<210> SEQ ID NO 372
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 372

```
cccggtcaaa atataggttt aacaattagt caattactat ataaataggt tttgtatttg       60
aatatgttag taaaaagtag ttttaatata tcttattcca gtaaaattat caattacttt      120
taataataaa gtcatacaaa tttgtataaa actattttcc ccctacgata aaagttgttt      180
cgaaaaaaaa gtaagttgga gaaatttatt gaagtgatga aaactatttt tatggttatt      240
ttttatcaca caaattaatt ttggaatctt ataattagaa atggttgaat ttatatattg      300 gttaactta ttttcttatt tcgtccacag taatgaattg tttcaaacaa aaaaaaaatc       360
aattaatata tattttataa ttttactatt gaaaaatacc t                          401
```

<210> SEQ ID NO 373
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 373

```
agcataatca caattattga gaagatattt ttattttatt tttaccgaat cgtcgcacga       60
ctcggcgtgt tgcaaccgca ttaaatcttt gtgttggtct caccctgtct ttttgtggat      120
gatcgatcct cttggattgg ttttataaa actcaacttc ccatcggtgt tctttagtaa      180
ttggagtatc tttggatgtt tgttacattt tatgataaat ttaaatgatc cacaatcact      240
aactcaattt tgcaaagcag gattctgaat gttttttgtaa atctcgtttt gtcctaaaag      300
ttcgtctata acaataaaac aaacatgcac ttggttgttt ttaaaattgt ctcaaaactc      360
```
tgttataaag aaataagacc taaagatatt ttttacaaat t                401

<210> SEQ ID NO 374
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 374
atatccttag attaatttat tttsttgata aaaaaaawkg ataaaaattt ccatgcttta    60
aatttgtcat tggtccatct gatcgactct atacatcaaa cttgagtgtt atttgcatac   120
aaaaggaaaa catcagagac atgacagagt aggttgcatt ggtgtttagt tgacctgatt   180
aagaagttac acacaaagtg ttcctctatc tcctcttcaa ggtcctccta cctatagtct   240
tcttgtacct cttattatat ggattaatta gtgtagaatt atttcaactt aattaataat   300
tttgaattta agtcatgaga atgagtatca aaayttttc acctataaaa atcgaatrtg    360
cttcaaataa gattgtctct aataaataat atgtgtttaa t                       401

<210> SEQ ID NO 375
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 375
aaacctatgt cggttggttc ctctttaaag aaaagagaat aaaataaca aagaaaaaaa    60
agtcgccttc catttcattc gcattcatag taaaagagtg agcgatcccg ggaaatgaat   120
taatatacga ctaaaaagat ttgagaatta taataattaa taattaataa ttcttttca    180
aaagtaaagt acagtactgc tggaaacatg agcatgttca tagattaaaa tttaaagaa    240
tattatcagt aacaaaaaaa taaaaattaa cccatgcatc caagaaagaa atacycatgt   300
gcttcagttg tccgctgtct gagatgtggt gaccttttt caaatgatca taatagttac   360
ttcataatga cgacatgcat caaactattt tttcttcaaa a                       401

<210> SEQ ID NO 376
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 376 tatccccccat gttaatgaag caaggtgtgg gggaaggaaa gagtcagcat cagtgaagta    60
gagagggggg ttggtgattt tggtgggaat aaattggcta tattgccccc accaacctcg   120
ttgctaccaa ataccaacaa cactgactca ctgagaattg ggaaagaaac ttaaaaccaa   180
gtcttgcagt gacgtacatg tagtgtgtgc atcacacatt caggtttcca gtcaaattgt   240
agaacaaatg aatttcttgc tttaacttaa gttgaagttt aagaagtgaa gctgatgctt   300
gttttttgaat gaaaagcctt tgatagtttg atgtaagcat tttccaaatt taactcttcc   360
catgcttgac agagccaatt aagctaactg gtttgataac a                       401

<210> SEQ ID NO 377
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 377

```
cacccctcat tagaggctta ggattttttt gagtcctaga acacacatct tatctcaata    60
atgatttcta tcattgccag aattacaatt aaaaactaaa atataatcaa ttagattgaa   120
ttgaacttct acagacccca aaggcactcg atgcattttc actgtatgtg gtttgtcttt   180
ctgtactata ctgcacgctt ggcaaaataa tcagtaacac atgttaagag agcttgcact   240
ttatttttat cttgttgacg ggtttgttgt cattgaaaac acattatatt cagaggaatt   300
tgactcaaca tgttcaaccc accaattatc acatttaaac aaatytaaat caatcgcaaa   360
tcatatatat tcagaatttt acatattaaa tatttcatat c                       401
```

<210> SEQ ID NO 378
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 378

```
aataacatgg ttatgttgaa acaaaagaa aaaatatca aatttaattc atgaatcttt      60
caactaatta aaaatgacc aatcctaact agttgcagaa gctattaatt aaattttaa    120
aaaagtatat ctttctctct tatgactcac ataatttata ktccctatac tcaaagtctc   180
acataattta tactacaaaa tcttaggttt aatttcgtac ctattgttaa tgtttcctaa   240
tcgaaattag aatttcaccc cgataattaa aagtttacat taaaaaatta yataaattac   300
cgaaataaaa ctcaaaattt agtcaaacaa taatgtaagc actaagcagc aactaagaag   360
ctataaacaa agttttgata aatagttaaa tttatcctcc a                       401
```

<210> SEQ ID NO 379
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 379

```
aagtggggaa ctgtcgatcc atggtgctgg cagcaaccgt aacatgccag ggtgcgagat    60
tttccgcagt ggcttccgcg ggcccactgt tgccagcaga gcaaaccacc acaacgccac   120
gcttggccgc atggaaggat ccgatggcaa cactatcctt gaaaaacgtg gaggaagagc   180
caccgagcga gacggagagg gcatcgacgc cgtcgtggat ggcgaggtcg aaggccgcca   240
agatatcagc gtcgaagcac tcctcgcctc cgacgggggg ccagcagacc ttgtaggctg   300
ccacacgtgc cattggtgag ccacccttgg ctgttccctg gccctggccg aagacgctga   360
cacgtgcgac catgttcccg ccagctgtgg atagggtgtg g                       401
```

<210> SEQ ID NO 380
<211> LENGTH: 401
<212> TYPE: DNA
<213> ORGANISM: Artificial Sequence
<220> FEATURE:
<223> OTHER INFORMATION: Consensus Reference Sequence

<400> SEQUENCE: 380

```
tgccattggt gagccaccct tggctgttcc ctggccctgg ccgaagacgc tgacacgtgc    60
```

-continued

```
gaccatgttc ccgccagctg tggatagggt gtgggtcccg tggccctcgt tgtcacgtgg      120
cgagtcaaag gaggagttca gtgggcccgc cactgaggcg tagcccttgt tgaagtacct      180
tgcccctatt agcttcctgc gttcaacatc tccacttaac gtttctttaa tttwtcaaaa      240
caaaatcatt gaaagattgg tctggttggt gtgaaaacac tagtactata aaagaataag      300
ataacgaaag aaacatgtct gcgttcaaag gagtgcttaa ccctttcatt gtagtattca      360
cctaataaag agtgccaatt taaaggcata tgactacaga a                          401
```